(12) United States Patent
Kreider et al.

(10) Patent No.: US 6,815,420 B2
(45) Date of Patent: Nov. 9, 2004

(54) METHODS OF USING CHEMOKINE BETA-6

(75) Inventors: Brent L. Kreider, Bedford, MA (US); Steven M. Ruben, Olney, MD (US); Henrik S Olsen, Gaithersburg, MD (US)

(73) Assignee: Human Genome Sciences, INC, Rockville, MD (US)

( * ) Notice: Subject to any disclaimer, the term of this patent is extended or adjusted under 35 U.S.C. 154(b) by 0 days.

(21) Appl. No.: 10/054,967

(22) Filed: Jan. 25, 2002

(65) Prior Publication Data

US 2003/0059874 A1 Mar. 27, 2003

Related U.S. Application Data

(62) Division of application No. 09/419,281, filed on Oct. 15, 1999, now Pat. No. 6,379,926, which is a division of application No. 08/995,156, filed on Dec. 19, 1997, now Pat. No. 6,028,169.
(60) Provisional application No. 60/042,269, filed on Mar. 31, 1997.

(51) Int. Cl.$^7$ ............................................. A61K 38/16
(52) U.S. Cl. ............................................. 514/12; 514/2
(58) Field of Search ........................ 514/2, 12; 424/85.1

(56) References Cited

U.S. PATENT DOCUMENTS 5,350,836 A * 9/1994 Kopchick et al.

* cited by examiner

Primary Examiner—Elizabeth Kemmerer
(74) Attorney, Agent, or Firm—Human Genome Sciences, INC

(57) ABSTRACT

Human chemokine β-6 agonist and antagonist polypeptides and DNA encoding such polypeptides and a procedure for producing such polypeptides by recombinant techniques are disclosed. The chemokine β-6 antagonists of the present invention may be employed to treat rheumatoid arthritis, lung inflammation, allergy, asmtha, infectious diseases and to prevent inflammation and atherosclerosis. The chemokine β-6 agonists may be employed to myeloprotect patients undergoing chemotherapy.

26 Claims, 29 Drawing Sheets

```
  1 ATGGCAGGCCTGATGACCATAGTAACCAGCCTTCTGTTCCTTGGTGTCTGTGCCCACCAC  60
    M  A  G  L  M  T  I  V  T  S  L  L  F  L  G  V  C  A  H  H

61 ATCATCCCTACGGGCTCTGTGGTCATACCCTATCCCTGCTGCATGTTCTTTGTTTCCAAG 120
    I  I  P  T  G  S  V  V  I  P  S  P  C  C  M  F  F  V  S  K

121 AGAATTCCTGAGAACCGAGTGGTCAGCTACCAGCTGTCCAGCAGGAGCACATGCCTCAAG 180
    R  I  P  E  N  R  V  V  S  Y  Q  L  S  S  R  S  T  C  L  K

181 GCAGGAGTGATCTTCACCACCAAGAAGGGCCAGCAGTTCTGTGGCGACCCCAAGCAGGAG 240
    A  G  V  I  F  T  T  K  K  G  Q  Q  F  C  G  D  P  K  Q  E

241 TGGGTCCAGAGGTACATGAAGAACCTGGACGCCAAGCAGAAGAAGGCTTCCCCTAGGGCC 300
    W  V  Q  R  Y  M  K  N  L  D  A  K  Q  K  K  A  S  P  R  A

301 AGGGCAGTGGCTGTCAAGGGCCCTGTCCAGAGATATCCTGGCAACCAAACCAGCTGCTAA 360
    R  A  V  A  V  K  G  P  V  Q  R  Y  P  G  N  Q  T  T  C  *
```

FIG.1

Percent Similarity: 52.128    Percent Identity: 36.170

HMSAF34.aa x HuMCP1.aa..

```
  5 MTIVTSLLFLGVCAHHIIPTG.....SVVIPSPCCMFFVSKRIPENRVVS 49
    |.: ..|| | :.|  ·:|| |     .: | .||  |..::|. .|:.|
  1 MKVSAALLCLLLIAATFIPQGLAQPDAINAPVTCCYNFTNRKISVQRLAS 50

50 YQLSSRSTCLKGGVIFTTKKGQQFCGDPKQEWVQRYMKNLDAKQKKASP 98
    |.  ..|.| |::|||.|  :.::|:||||.|||  |.:|| .  ....
 51 YRRITSSKCPKEAVIFKTIVAKEICADPKQKWVQDSMDHLDKQTQTPKT 99
```

FIG.2

```
                                      -35         Operator 1
1  AAGCTTAAAAAACTGCAAAAAATAGT TTGACT TGTGAGCGGATAACAAT -10              Operator 2
50  TAAGAT GTACCCA ATTGTGAGCGGATAACAAT TTCACACATTAA

S/D
94  A GAGGAG AAATTA CATATG
```

FIG. 22

SEQUENCE LISTING (1) GENERAL INFORMATION:

(iii) NUMBER OF SEQUENCES: 114

(2) INFORMATION FOR SEQ ID NO: 1:

(i) SEQUENCE CHARACTERISTICS:
      (A) LENGTH: 360 base pairs
      (B) TYPE: nucleic acid
      (C) STRANDEDNESS: single
      (D) TOPOLOGY: linear (ii) MOLECULE TYPE: DNA (genomic)

(ix) FEATURE:
             (A) NAME/KEY: CDS
             (B) LOCATION: 1..357

(ix) FEATURE:
             (A) NAME/KEY: sig_peptide
             (B) LOCATION: 1..79

(ix) FEATURE:
             (A) NAME/KEY: mat_peptide
             (B) LOCATION: 79..357

(xi) SEQUENCE DESCRIPTION: SEQ ID NO: 1:

```
ATG GCA GGC CTG ATG ACC ATA GTA ACC AGC CTT CTG TTC CTT GGT GTC       48
Met Ala Gly Leu Met Thr Ile Val Thr Ser Leu Leu Phe Leu Gly Val
-26 -25             -20                 -15

TGT GCC CAC CAC ATC ATC CCT ACG GGC TCT GTG GTC ATA CCC TCT CCC       96
Cys Ala His His Ile Ile Pro Thr Gly Ser Val Val Ile Pro Ser Pro
-10              -5                   1                   5

TGC TGC ATG TTC TTT GTT TCC AAG AGA ATT CCT GAG AAC CGA GTG GTC      144
Cys Cys Met Phe Phe Val Ser Lys Arg Ile Pro Glu Asn Arg Val Val
             10                  15                  20

AGC TAC CAG CTG TCC AGC AGG AGC ACA TGC CTC AAG GCA GGA GTG ATC      192
Ser Tyr Gln Leu Ser Ser Arg Ser Thr Cys Leu Lys Ala Gly Val Ile
         25                  30                  35

TTC ACC ACC AAG AAG GGC CAG CAG TTC TGT GGC GAC CCC AAG CAG GAG      240
Phe Thr Thr Lys Lys Gly Gln Gln Phe Cys Gly Asp Pro Lys Gln Glu
     40                  45                  50

TGG GTC CAG AGG TAC ATG AAG AAC CTG GAC GCC AAG CAG AAG AAG GCT      288
Trp Val Gln Arg Tyr Met Lys Asn Leu Asp Ala Lys Gln Lys Lys Ala
 55                  60                  65                  70

TCC CCT AGG GCC AGG GCA GTG GCT GTC AAG GGC CCT GTC CAG AGA TAT      336
Ser Pro Arg Ala Arg Ala Val Ala Val Lys Gly Pro Val Gln Arg Tyr
                 75                  80                  85

CCT GGC AAC CAA ACC ACC TGC TAA                                      360
Pro Gly Asn Gln Thr Thr Cys
             90
```

(2) INFORMATION FOR SEQ ID NO: 2:

(i) SEQUENCE CHARACTERISTICS:
             (A) LENGTH: 119 amino acids
             (B) TYPE: amino acid
             (D) TOPOLOGY: linear (ii) MOLECULE TYPE: protein (xi) SEQUENCE DESCRIPTION: SEQ ID NO: 2:

```
Met Ala Gly Leu Met Thr Ile Val Thr Ser Leu Leu Phe Leu Gly Val
-26 -25             -20                 -15

Cys Ala His His Ile Ile Pro Thr Gly Ser Val Val Ile Pro Ser Pro
-10              -5                   1                   5

Cys Cys Met Phe Phe Val Ser Lys Arg Ile Pro Glu Asn Arg Val Val
             10                  15                  20

Ser Tyr Gln Leu Ser Ser Arg Ser Thr Cys Leu Lys Ala Gly Val Ile
         25                  30                  35

Phe Thr Thr Lys Lys Gly Gln Gln Phe Cys Gly Asp Pro Lys Gln Glu
     40                  45                  50

Trp Val Gln Arg Tyr Met Lys Asn Leu Asp Ala Lys Gln Lys Lys Ala
 55                  60                  65                  70
```

```
Ser Pro Arg Ala Arg Ala Val Ala Val Lys Gly Pro Val Gln Arg Tyr
             75                  80                  85

Pro Gly Asn Gln Thr Thr Cys
             90
```

(2) INFORMATION FOR SEQ ID NO: 3:

(i) SEQUENCE CHARACTERISTICS:
        (A) LENGTH: 26 base pairs
        (B) TYPE: nucleic acid
        (C) STRANDEDNESS: double
        (D) TOPOLOGY: linear (ii) MOLECULE TYPE: DNA (genomic)

(xi) SEQUENCE DESCRIPTION: SEQ ID NO: 3:

```
TCAGGATCCC CTACGGGCTC GTGGTC                                            26
```

(2) INFORMATION FOR SEQ ID NO: 4:

(i) SEQUENCE CHARACTERISTICS:
        (A) LENGTH: 26 base pairs
        (B) TYPE: nucleic acid
        (C) STRANDEDNESS: double
        (D) TOPOLOGY: linear (ii) MOLECULE TYPE: DNA (genomic)

(xi) SEQUENCE DESCRIPTION: SEQ ID NO: 4:

```
TGACCGGCAG CAAAATGAGA TCTCGC                                            26
```

(2) INFORMATION FOR SEQ ID NO: 5:

(i) SEQUENCE CHARACTERISTICS:
        (A) LENGTH: 99 amino acids
        (B) TYPE: amino acid
        (D) TOPOLOGY: linear (ii) MOLECULE TYPE: protein (xi) SEQUENCE DESCRIPTION: SEQ ID NO: 5:

```
Met Lys Val Ser Ala Ala Leu Leu Cys Leu Leu Leu Ile Ala Ala Thr
1               5                   10                  15

Phe Ile Pro Gln Gly Leu Ala Gln Pro Asp Ala Ile Asn Ala Pro Val
             20                  25                  30

Thr Cys Cys Tyr Asn Phe Thr Asn Arg Lys Ile Ser Val Gln Arg Leu
         35                  40                  45

Ala Ser Tyr Arg Arg Ile Thr Ser Ser Lys Cys Pro Lys Glu Ala Val
     50                  55                  60

Ile Phe Lys Thr Ile Val Ala Lys Glu Ile Cys Ala Asp Pro Lys Gln
65                  70                  75                  80

Lys Trp Val Gln Asp Ser Met Asp His Leu Asp Lys Gln Thr Gln Thr
                 85                  90                  95

Pro Lys Thr
```

(2) INFORMATION FOR SEQ ID NO: 6:

(i) SEQUENCE CHARACTERISTICS:
        (A) LENGTH: 285 base pairs
        (B) TYPE: nucleic acid
        (C) STRANDEDNESS: double
        (D) TOPOLOGY: linear (ii) MOLECULE TYPE: cDNA (xi) SEQUENCE DESCRIPTION: SEQ ID NO: 6:

```
ATGGTGGTTA TACCTTCTCC GTGCTGCATG TTCTTTGTTA GCAAGCGCAT TCCTGAAAAC      60

CGTGTGGTCA GCTACCAGCT GTCCAGCCGC AGCACCTGCC TGAAAGCTGG CGTGATCTTC     120

ACCACCAAAA AGGGCCAGCA GTTCTGTGGC GACCCGAAAC AAGAGTGGGT CCAGCGTTAC     180

ATGAAAAACC TGGACGCCAA ACAGAAGAAA GCTTCCCCTC GTGCCCGCGC AGTGGCTGTC     240

AAAGGCCCTG TTCAGCGTTA TCCGGGCAAC CAAACCACCT GCTAA                     285
```

(2) INFORMATION FOR SEQ ID NO: 7:

(i) SEQUENCE CHARACTERISTICS:
        (A) LENGTH: 96 base pairs
        (B) TYPE: nucleic acid
        (C) STRANDEDNESS: single
        (D) TOPOLOGY: linear (ii) MOLECULE TYPE: cDNA (xi) SEQUENCE DESCRIPTION: SEQ ID NO: 7:

```
GACTCCATGG TGGTTATACC TTCTCCGTGC TGCATGTTCT TTGTTAGCAA GCGCATTCCT      60

GAAAACCGTG TGGTCAGCTA CCAGCTGTCC AGCCGC                                96
```

(2) INFORMATION FOR SEQ ID NO: 8:

(i) SEQUENCE CHARACTERISTICS:
        (A) LENGTH: 97 base pairs
        (B) TYPE: nucleic acid
        (C) STRANDEDNESS: single
        (D) TOPOLOGY: linear (ii) MOLECULE TYPE: cDNA (xi) SEQUENCE DESCRIPTION: SEQ ID NO: 8:

```
GTTTCGGGTC GCCACAGAAC TGCTGGCCCT TTTTGGTGGT GAAGATCACG CCAGCTTTCA      60

GGCAGGTGCT GCGGCTGGAC AGCTGGTAGC TGACCAC                               97
```

(2) INFORMATION FOR SEQ ID NO: 9:

(i) SEQUENCE CHARACTERISTICS:
        (A) LENGTH: 98 base pairs
        (B) TYPE: nucleic acid
        (C) STRANDEDNESS: single
        (D) TOPOLOGY: linear (ii) MOLECULE TYPE: cDNA (xi) SEQUENCE DESCRIPTION: SEQ ID NO: 9:

```
AAGGGCCAGC AGTTCTGTGG CGACCCGAAA CAAGAGTGGG TCCAGCGTTA CATGAAAAAC      60

CTGGACGCCA AACAGAAGAA AGCTTCCCCT CGTGCCCG                              98
```

(2) INFORMATION FOR SEQ ID NO: 10:

(i) SEQUENCE CHARACTERISTICS:
        (A) LENGTH: 99 base pairs
        (B) TYPE: nucleic acid
        (C) STRANDEDNESS: single
        (D) TOPOLOGY: linear (ii) MOLECULE TYPE: cDNA (xi) SEQUENCE DESCRIPTION: SEQ ID NO: 10:

```
AGTCAGATCT TTAGCAGGTG GTTTGGTTGC CCGGATAACG CTGAACAGGG CCTTTGACAG      60

CCACTGCGCG GGCACGAGGG GAAGCTTTCT TCTGTTTGG                             99
```

(2) INFORMATION FOR SEQ ID NO: 11:

(i) SEQUENCE CHARACTERISTICS:
        (A) LENGTH: 34 base pairs
        (B) TYPE: nucleic acid
        (C) STRANDEDNESS: single
        (D) TOPOLOGY: linear (ii) MOLECULE TYPE: cDNA (xi) SEQUENCE DESCRIPTION: SEQ ID NO: 11:

GACGGATCCC CATATGGTGG TTATACCTTC TCCG                                    34

(2) INFORMATION FOR SEQ ID NO: 12:

(i) SEQUENCE CHARACTERISTICS:
        (A) LENGTH: 32 base pairs
        (B) TYPE: nucleic acid
        (C) STRANDEDNESS: single
        (D) TOPOLOGY: linear (ii) MOLECULE TYPE: cDNA (xi) SEQUENCE DESCRIPTION: SEQ ID NO: 12:

GACTGGTACC TTAGCAGGTG GTTTGGTTGC CC                                      32

(2) INFORMATION FOR SEQ ID NO: 13:

(i) SEQUENCE CHARACTERISTICS:
        (A) LENGTH: 36 base pairs
        (B) TYPE: nucleic acid
        (C) STRANDEDNESS: single
        (D) TOPOLOGY: linear (ii) MOLECULE TYPE: cDNA (xi) SEQUENCE DESCRIPTION: SEQ ID NO: 13:

GACTGGTACC TTATCAACGA GGGGAAGCTT TCTTCT                                36

(2) INFORMATION FOR SEQ ID NO: 14:

(i) SEQUENCE CHARACTERISTICS:
        (A) LENGTH: 37 base pairs
        (B) TYPE: nucleic acid
        (C) STRANDEDNESS: single
        (D) TOPOLOGY: linear (ii) MOLECULE TYPE: cDNA (xi) SEQUENCE DESCRIPTION: SEQ ID NO: 14:

GACTGGTACC CTATCAAGCC ACTGCGCGGG CACGAGG                             37

(2) INFORMATION FOR SEQ ID NO: 15:

(i) SEQUENCE CHARACTERISTICS:
        (A) LENGTH: 34 base pairs
        (B) TYPE: nucleic acid
        (C) STRANDEDNESS: single
        (D) TOPOLOGY: linear (ii) MOLECULE TYPE: cDNA (xi) SEQUENCE DESCRIPTION: SEQ ID NO: 15:

GACTCATATG GTTATACCTT CTCCGTGCTG CATG                                    34

(2) INFORMATION FOR SEQ ID NO: 16:

(i) SEQUENCE CHARACTERISTICS:
    (A) LENGTH: 31 base pairs
    (B) TYPE: nucleic acid
    (C) STRANDEDNESS: single
    (D) TOPOLOGY: linear (ii) MOLECULE TYPE: cDNA (xi) SEQUENCE DESCRIPTION: SEQ ID NO: 16:

GACTCATATG ATACCTTCTC CGTGCTGCAT G                                    31

(2) INFORMATION FOR SEQ ID NO: 17:

(i) SEQUENCE CHARACTERISTICS:
        (A) LENGTH: 31 base pairs
        (B) TYPE: nucleic acid
        (C) STRANDEDNESS: single
        (D) TOPOLOGY: linear (ii) MOLECULE TYPE: cDNA (xi) SEQUENCE DESCRIPTION: SEQ ID NO: 17:

GACTCATATG CCTTCTCCGT GCTGCATGTT C                                    31

(2) INFORMATION FOR SEQ ID NO: 18:

(i) SEQUENCE CHARACTERISTICS:
        (A) LENGTH: 32 base pairs
        (B) TYPE: nucleic acid
        (C) STRANDEDNESS: single
        (D) TOPOLOGY: linear (ii) MOLECULE TYPE: cDNA (xi) SEQUENCE DESCRIPTION: SEQ ID NO: 18:

GACTCATATG TCTCCGTGCT GCATGTTCTT TG                                   32

(2) INFORMATION FOR SEQ ID NO: 19:

(i) SEQUENCE CHARACTERISTICS:
        (A) LENGTH: 29 base pairs
        (B) TYPE: nucleic acid
        (C) STRANDEDNESS: single
        (D) TOPOLOGY: linear (ii) MOLECULE TYPE: cDNA (xi) SEQUENCE DESCRIPTION: SEQ ID NO: 19:

GACTCATATG CCGTGCTGCA TGTTCTTTG                                       29

(2) INFORMATION FOR SEQ ID NO: 20:

(i) SEQUENCE CHARACTERISTICS:
        (A) LENGTH: 30 base pairs
        (B) TYPE: nucleic acid
        (C) STRANDEDNESS: single
        (D) TOPOLOGY: linear (ii) MOLECULE TYPE: cDNA (xi) SEQUENCE DESCRIPTION: SEQ ID NO: 20:

GACTCATATG TGCTGCATGT TCTTTGTTAG                                      30

(2) INFORMATION FOR SEQ ID NO: 21:

(i) SEQUENCE CHARACTERISTICS:
        (A) LENGTH: 4256 base pairs
        (B) TYPE: nucleic acid
        (C) STRANDEDNESS: double (D) TOPOLOGY: linear (ii) MOLECULE TYPE: DNA (genomic)

(xi) SEQUENCE DESCRIPTION: SEQ ID NO: 21:

```
AAGCTTAAAA AACTGCAAAA AATAGTTTGA CTTGTGAGCG GATAACAATT AAGATGTACC      60
CAATTGTGAG CGGATAACAA TTTCACACAT TAAAGAGGAG AAATTACATA TGGTGGTTAT     120
ACCTTCTCCG TGCTGCATGT TCTTTGTTAG CAAGCGCATT CCTGAAAACC GTGTGGTCAG     180
CTACCAGCTG TCCAGCCGCA GCACCTGCCT GAAAGCTGGC GTGATCTTCA CCACCAAAAA     240
GGGCCAGCAG TTCTGTGGCG ACCCGAAACA AGAGTGGGTC CAGCGTTACA TGAAAAACCT     300
GGACGCCAAA CAGAAGAAAG CTTCCCCTCG TGCCCGCGCA GTGGCTGTCA AAGGCCCTGT     360
TCAGCGTTAT CCGGGCAACC AAACCACCTG CTAAGGTACC TAAGTGAGTA GGGCGTCCGA     420
TCGACGGACG CCTTTTTTTT GAATTCGTAA TCATGGTCAT AGCTGTTTCC TGTGTGAAAT     480
TGTTATCCGC TCACAATTCC ACACAACATA CGAGCCGGAA GCATAAAGTG TAAAGCCTGG     540
GGTGCCTAAT GAGTGAGCTA ACTCACATTA ATTGCGTTGC GCTCACTGCC CGCTTTCCAG     600
TCGGGAAACC TGTCGTGCCA GCTGCATTAA TGAATCGGCC AACGCGCGGG GAGAGGCGGT     660
TTGCGTATTG GGCGCTCTTC CGCTTCCTCG CTCACTGACT CGCTGCGCTC GGTCGTTCGG     720
CTGCGGCGAG CGGTATCAGC TCACTCAAAG GCGGTAATAC GGTTATCCAC AGAATCAGGG     780
GATAACGCAG GAAAGAACAT GTGAGCAAAA GGCCAGCAAA AGGCCAGGAA CCGTAAAAAG     840
GCCGCGTTGC TGGCGTTTTT CCATAGGCTC CGCCCCCCTG ACGAGCATCA CAAAAATCGA     900
CGCTCAAGTC AGAGGTGGCG AAACCCGACA GGACTATAAA GATACCAGGC GTTTCCCCCT     960
GGAAGCTCCC TCGTGCGCTC TCCTGTTCCG ACCCTGCCGC TTACCGGATA CCTGTCCGCC    1020
TTTCTCCCTT CGGGAAGCGT GGCGCTTTCT CATAGCTCAC GCTGTAGGTA TCTCAGTTCG    1080
GTGTAGGTCG TTCGCTCCAA GCTGGGCTGT GTGCACGAAC CCCCCGTTCA GCCCGACCGC    1140
TGCGCCTTAT CCGGTAACTA TCGTCTTGAG TCCAACCCGG TAAGACACGA CTTATCGCCA    1200
CTGGCAGCAG CCACTGGTAA CAGGATTAGC AGAGCGAGGT ATGTAGGCGG TGCTACAGAG    1260
TTCTTGAAGT GGTGGCCTAA CTACGGCTAC ACTAGAAGAA CAGTATTTGG TATCTGCGCT    1320
CTGCTGAAGC CAGTTACCTT CGGAAAAAGA GTTGGTAGCT CTTGATCCGG CAAACAAACC    1380
ACCGCTGGTA GCGGTGGTTT TTTTGTTTGC AAGCAGCAGA TTACGCGCAG AAAAAAAGGA    1440
TCTCAAGAAG ATCCTTTGAT CTTTTCTACG GGGTCTGACG CTCAGTGGAA CGAAAACTCA    1500
CGTTAAGGGA TTTTGGTCAT GAGATTATCG TCGACAATTC GCGCGCGAAG GCGAAGCGGC    1560
ATGCATTTAC GTTGACACCA TCGAATGGTG CAAAACCTTT CGCGGTATGG CATGATAGCG    1620
CCCGGAAGAG AGTCAATTCA GGGTGGTGAA TGTGAAACCA GTAACGTTAT ACGATGTCGC    1680
AGAGTATGCC GGTGTCTCTT ATCAGACCGT TTCCCGCGTG GTGAACCAGG CCAGCCACGT    1740
TTCTGCGAAA ACGCGGGAAA AAGTGGAAGC GGCGATGGCG GAGCTGAATT ACATTCCCAA    1800
CCGCGTGGCA CAACAACTGG CGGGCAAACA GTCGTTGCTG ATTGGCGTTG CCACCTCCAG    1860
TCTGGCCCTG CACGCGCCGT CGCAAATTGT CGCGGCGATT AAATCTCGCG CCGATCAACT    1920
GGGTGCCAGC GTGGTGGTGT CGATGGTAGA ACGAAGCGGC GTCGAAGCCT GTAAAGCGGC    1980
GGTGCACAAT CTTCTCGCGC AACGCGTCAG TGGGCTGATC ATTAACTATC CGCTGGATGA    2040
CCAGGATGCC ATTGCTGTGG AAGCTGCCTG CACTAATGTT CCGGCGTTAT TCTTGATGT     2100
CTCTGACCAG ACACCCATCA ACAGTATTAT TTTCTCCCAT GAAGACGGTA CGCGACTGGG    2160
CGTGGAGCAT CTGGTCGCAT TGGGTCACCA GCAAATCGCG CTGTTAGCGG GCCCATTAAG    2220
```

```
TTCTGTCTCG GCGCGTCTGC GTCTGGCTGG CTGGCATAAA TATCTCACTC GCAATCAAAT      2280

TCAGCCGATA GCGGAACGGG AAGGCGACTG GAGTGCCATG TCCGGTTTTC AACAAACCAT      2340

GCAAATGCTG AATGAGGGCA TCGTTCCCAC TGCGATGCTG GTTGCCAACG ATCAGATGGC      2400

GCTGGGCGCA ATGCGCGCCA TTACCGAGTC CGGGCTGCGC GTTGGTGCGG ATATCTCGGT      2460

AGTGGGATAC GACGATACCG AAGACAGCTC ATGTTATATC CCGCCGTTAA CCACCATCAA      2520

ACAGGATTTT CGCCTGCTGG GGCAAACCAG CGTGGACCGC TTGCTGCAAC TCTCTCAGGG      2580

CCAGGCGGTG AAGGGCAATC AGCTGTTGCC CGTCTCACTG GTGAAAAGAA AAACCACCCT      2640

GGCGCCCAAT ACGCAAACCG CCTCTCCCCG CGCGTTGGCC GATTCATTAA TGCAGCTGGC      2700

ACGACAGGTT TCCCGACTGG AAAGCGGGCA GTGAGCGCAA CGCAATTAAT GTAAGTTAGC      2760

GCGAATTGTC GACCAAAGCG CCATCGTGC CTCCCCACTC CTGCAGTTCG GGGCATGGA       2820

TGCGCGGATA GCCGCTGCTG GTTTCCTGGA TGCCGACGGA TTTGCACTGC CGGTAGAACT      2880

CCGCGAGGTC GTCCAGCCTC AGGCAGCAGC TGAACCAACT CGCGAGGGGA TCGAGCCCGG      2940

GGTGGGCGAA GAACTCCAGC ATGAGATCCC CGCGCTGGAG GATCATCCAG CCGGCGTCCC      3000

GGAAAACGAT TCCGAAGCCC AACCTTTCAT AGAAGGCGGC GGTGGAATCG AAATCTCGTG      3060

ATGGCAGGTT GGGCGTCGCT TGGTCGGTCA TTTCGAACCC CAGAGTCCCG CTCAGAAGAA      3120

CTCGTCAAGA AGGCGATAGA AGGCGATGCG CTGCGAATCG GGAGCGGCGA TACCGTAAAG      3180

CACGAGGAAG CGGTCAGCCC ATTCGCCGCC AAGCTCTTCA GCAATATCAC GGGTAGCCAA      3240

CGCTATGTCC TGATAGCGGT CCGCCACACC CAGCCGGCCA CAGTCGATGA ATCCAGAAAA      3300

GCGGCCATTT TCCACCATGA TATTCGGCAA GCAGGCATCG CCATGGGTCA CGACGAGATC      3360

CTCGCCGTCG GGCATGCGCG CCTTGAGCCT GGCGAACAGT TCGGCTGGCG CGAGCCCCTG      3420

ATGCTCTTCG TCCAGATCAT CCTGATCGAC AAGACCGGCT TCCATCCGAG TACGTGCTCG      3480

CTCGATGCGA TGTTTCGCTT GGTGGTCGAA TGGGCAGGTA GCCGGATCAA GCGTATGCAG      3540

CCGCCGCATT GCATCAGCCA TGATGGATAC TTTCTCGGCA GGAGCAAGGT GAGATGACAG      3600

GAGATCCTGC CCCGGCACTT CGCCCAATAG CAGCCAGTCC CTTCCCGCTT CAGTGACAAC      3660

GTCGAGCACA GCTGCGCAAG GAACGCCCGT CGTGGCCAGC CACGATAGCC GCGCTGCCTC      3720

GTCCTGCAGT TCATTCAGGG CACCGGACAG GTCGGTCTTG ACAAAAAGAA CCGGGCGCCC      3780

CTGCGCTGAC AGCCGGAACA CGGCGGCATC AGAGCAGCCG ATTGTCTGTT GTGCCCAGTC      3840

ATAGCCGAAT AGCCTCTCCA CCCAAGCGGC CGGAGAACCT GCGTGCAATC CATCTTGTTC      3900

AATCATGCGA AACGATCCTC ATCCTGTCTC TTGATCAGAT CTTGATCCCC TGCGCCATCA      3960

GATCCTTGGC GGCAAGAAAG CCATCCAGTT TACTTTGCAG GGCTTCCCAA CCTTACCAGA      4020

GGGCGCCCCA GCTGGCAATT CCGGTTCGCT TGCTGTCCAT AAAACCGCCC AGTCTAGCTA      4080

TCGCCATGTA AGCCCACTGC AAGCTACCTG CTTTCTCTTT GCGCTTGCGT TTTCCCTTGT      4140

CCAGATAGCC CAGTAGCTGA CATTCATCCG GGGTCAGCAC CGTTTCTGCG GACTGGCTTT      4200

CTACGTGTTC CGCTTCCTTT AGCAGCCCTT GCGCCCTGAG TGCTTGCGGC AGCGTG         4256
```

(2) INFORMATION FOR SEQ ID NO: 22:

(i) SEQUENCE CHARACTERISTICS:
        (A) LENGTH: 112 base pairs
        (B) TYPE: nucleic acid
        (C) STRANDEDNESS: double
        (D) TOPOLOGY: linear (ii) MOLECULE TYPE: cDNA -continued (xi) SEQUENCE DESCRIPTION: SEQ ID NO: 22:

AAGCTTAAAA AACTGCAAAA AATAGTTTGA CTTGTGAGCG GATAACAATT AAGATGTACC    60

CAATTGTGAG CGGATAACAA TTTCACACAT TAAAGAGGAG AAATTACATA TG          112

(2) INFORMATION FOR SEQ ID NO: 23:

(i) SEQUENCE CHARACTERISTICS:
        (A) LENGTH: 45 amino acids
        (B) TYPE: amino acid
        (D) TOPOLOGY: linear (ii) MOLECULE TYPE: protein (xi) SEQUENCE DESCRIPTION: SEQ ID NO: 23:

Pro Ser Pro Cys Cys Met Phe Phe Val Ser Lys Arg Ile Pro Glu Asn
1               5                   10                  15

Arg Val Val Ser Tyr Gln Leu Ser Ser Arg Ser Thr Cys Leu Lys Ala
            20                  25                  30

Gly Val Ile Phe Thr Thr Lys Lys Gly Gln Gln Phe Cys
        35                  40                  45

(2) INFORMATION FOR SEQ ID NO: 24:

(i) SEQUENCE CHARACTERISTICS:
        (A) LENGTH: 46 amino acids
        (B) TYPE: amino acid
        (D) TOPOLOGY: linear (ii) MOLECULE TYPE: protein (xi) SEQUENCE DESCRIPTION: SEQ ID NO: 24:

Pro Ser Pro Cys Cys Met Phe Phe Val Ser Lys Arg Ile Pro Glu Asn
1               5                   10                  15

Arg Val Val Ser Tyr Gln Leu Ser Ser Arg Ser Thr Cys Leu Lys Ala
            20                  25                  30

Gly Val Ile Phe Thr Thr Lys Lys Gly Gln Gln Phe Cys Gly
        35                  40                  45

(2) INFORMATION FOR SEQ ID NO: 25:

(i) SEQUENCE CHARACTERISTICS:
        (A) LENGTH: 47 amino acids
        (B) TYPE: amino acid
        (D) TOPOLOGY: linear (ii) MOLECULE TYPE: protein (xi) SEQUENCE DESCRIPTION: SEQ ID NO: 25:

Pro Ser Pro Cys Cys Met Phe Phe Val Ser Lys Arg Ile Pro Glu Asn
1               5                   10                  15

Arg Val Val Ser Tyr Gln Leu Ser Ser Arg Ser Thr Cys Leu Lys Ala
            20                  25                  30

Gly Val Ile Phe Thr Thr Lys Lys Gly Gln Gln Phe Cys Gly Asp
        35                  40                  45

(2) INFORMATION FOR SEQ ID NO: 26:

(i) SEQUENCE CHARACTERISTICS:
        (A) LENGTH: 48 amino acids
        (B) TYPE: amino acid
        (D) TOPOLOGY: linear (ii) MOLECULE TYPE: protein (xi) SEQUENCE DESCRIPTION: SEQ ID NO: 26:

Pro Ser Pro Cys Cys Met Phe Phe Val Ser Lys Arg Ile Pro Glu Asn
1               5                   10                  15

Arg Val Val Ser Tyr Gln Leu Ser Ser Arg Ser Thr Cys Leu Lys Ala
            20                  25                  30

Gly Val Ile Phe Thr Thr Lys Lys Gly Gln Gln Phe Cys Gly Asp Pro
        35                  40                  45

(2) INFORMATION FOR SEQ ID NO: 27:

(i) SEQUENCE CHARACTERISTICS:
        (A) LENGTH: 49 amino acids
        (B) TYPE: amino acid
        (D) TOPOLOGY: linear (ii) MOLECULE TYPE: protein (xi) SEQUENCE DESCRIPTION: SEQ ID NO: 27:

Pro Ser Pro Cys Cys Met Phe Phe Val Ser Lys Arg Ile Pro Glu Asn
1               5                   10                  15

Arg Val Val Ser Tyr Gln Leu Ser Ser Arg Ser Thr Cys Leu Lys Ala
            20                  25                  30

Gly Val Ile Phe Thr Thr Lys Lys Gly Gln Gln Phe Cys Gly Asp Pro
        35                  40                  45

Lys (2) INFORMATION FOR SEQ ID NO: 28:

(i) SEQUENCE CHARACTERISTICS:
        (A) LENGTH: 50 amino acids
        (B) TYPE: amino acid
        (D) TOPOLOGY: linear (ii) MOLECULE TYPE: protein (xi) SEQUENCE DESCRIPTION: SEQ ID NO: 28:

Pro Ser Pro Cys Cys Met Phe Phe Val Ser Lys Arg Ile Pro Glu Asn
1               5                   10                  15

Arg Val Val Ser Tyr Gln Leu Ser Ser Arg Ser Thr Cys Leu Lys Ala
            20                  25                  30

Gly Val Ile Phe Thr Thr Lys Lys Gly Gln Gln Phe Cys Gly Asp Pro
        35                  40                  45

Lys Gln
    50

(2) INFORMATION FOR SEQ ID NO: 29:

(i) SEQUENCE CHARACTERISTICS:
        (A) LENGTH: 51 amino acids
        (B) TYPE: amino acid
        (D) TOPOLOGY: linear (ii) MOLECULE TYPE: protein (xi) SEQUENCE DESCRIPTION: SEQ ID NO: 29:

Pro Ser Pro Cys Cys Met Phe Phe Val Ser Lys Arg Ile Pro Glu Asn
1               5                   10                  15

Arg Val Val Ser Tyr Gln Leu Ser Ser Arg Ser Thr Cys Leu Lys Ala
            20                  25                  30

Gly Val Ile Phe Thr Thr Lys Lys Gly Gln Gln Phe Cys Gly Asp Pro
        35                  40                  45

Lys Gln Glu
    50

(2) INFORMATION FOR SEQ ID NO: 30:

(i) SEQUENCE CHARACTERISTICS:
        (A) LENGTH: 52 amino acids
        (B) TYPE: amino acid
        (D) TOPOLOGY: linear (ii) MOLECULE TYPE: protein (xi) SEQUENCE DESCRIPTION: SEQ ID NO: 30:

Pro Ser Pro Cys Cys Met Phe Phe Val Ser Lys Arg Ile Pro Glu Asn
1               5                   10                  15

Arg Val Val Ser Tyr Gln Leu Ser Ser Arg Ser Thr Cys Leu Lys Ala
            20                  25                  30

Gly Val Ile Phe Thr Thr Lys Lys Gly Gln Gln Phe Cys Gly Asp Pro
            35                  40                  45

Lys Gln Glu Trp
    50

(2) INFORMATION FOR SEQ ID NO: 31:

(i) SEQUENCE CHARACTERISTICS:
        (A) LENGTH: 53 amino acids
        (B) TYPE: amino acid
        (D) TOPOLOGY: linear (ii) MOLECULE TYPE: protein (xi) SEQUENCE DESCRIPTION: SEQ ID NO: 31:

Pro Ser Pro Cys Cys Met Phe Phe Val Ser Lys Arg Ile Pro Glu Asn
1               5                   10                  15

Arg Val Val Ser Tyr Gln Leu Ser Ser Arg Ser Thr Cys Leu Lys Ala
            20                  25                  30

Gly Val Ile Phe Thr Thr Lys Lys Gly Gln Gln Phe Cys Gly Asp Pro
            35                  40                  45

Lys Gln Glu Trp Val
    50

(2) INFORMATION FOR SEQ ID NO: 32:

(i) SEQUENCE CHARACTERISTICS:
        (A) LENGTH: 54 amino acids
        (B) TYPE: amino acid
        (D) TOPOLOGY: linear (ii) MOLECULE TYPE: protein (xi) SEQUENCE DESCRIPTION: SEQ ID NO: 32:

Pro Ser Pro Cys Cys Met Phe Phe Val Ser Lys Arg Ile Pro Glu Asn
1               5                   10                  15

Arg Val Val Ser Tyr Gln Leu Ser Ser Arg Ser Thr Cys Leu Lys Ala
            20                  25                  30

Gly Val Ile Phe Thr Thr Lys Lys Gly Gln Gln Phe Cys Gly Asp Pro
            35                  40                  45

Lys Gln Glu Trp Val Gln
    50

(2) INFORMATION FOR SEQ ID NO: 33:

(i) SEQUENCE CHARACTERISTICS:
    (A) LENGTH: 55 amino acids
    (B) TYPE: amino acid
    (D) TOPOLOGY: linear (ii) MOLECULE TYPE: protein (xi) SEQUENCE DESCRIPTION: SEQ ID NO: 33:

Pro Ser Pro Cys Cys Met Phe Phe Val Ser Lys Arg Ile Pro Glu Asn
1               5                   10                  15

Arg Val Val Ser Tyr Gln Leu Ser Ser Arg Ser Thr Cys Leu Lys Ala
            20                  25                  30

Gly Val Ile Phe Thr Thr Lys Lys Gly Gln Gln Phe Cys Gly Asp Pro
        35                  40                  45

Lys Gln Glu Trp Val Gln Arg
    50                  55

(2) INFORMATION FOR SEQ ID NO: 34:

(i) SEQUENCE CHARACTERISTICS:
        (A) LENGTH: 56 amino acids
        (B) TYPE: amino acid
        (D) TOPOLOGY: linear (ii) MOLECULE TYPE: protein (xi) SEQUENCE DESCRIPTION: SEQ ID NO: 34:

Pro Ser Pro Cys Cys Met Phe Phe Val Ser Lys Arg Ile Pro Glu Asn
1               5                   10                  15

Arg Val Val Ser Tyr Gln Leu Ser Ser Arg Ser Thr Cys Leu Lys Ala
            20                  25                  30

Gly Val Ile Phe Thr Thr Lys Lys Gly Gln Gln Phe Cys Gly Asp Pro
        35                  40                  45

Lys Gln Glu Trp Val Gln Arg Tyr
    50                  55

(2) INFORMATION FOR SEQ ID NO: 35:

(i) SEQUENCE CHARACTERISTICS:
        (A) LENGTH: 57 amino acids
        (B) TYPE: amino acid
        (D) TOPOLOGY: linear (ii) MOLECULE TYPE: protein (xi) SEQUENCE DESCRIPTION: SEQ ID NO: 35:

Pro Ser Pro Cys Cys Met Phe Phe Val Ser Lys Arg Ile Pro Glu Asn
1               5                   10                  15

Arg Val Val Ser Tyr Gln Leu Ser Ser Arg Ser Thr Cys Leu Lys Ala
            20                  25                  30

Gly Val Ile Phe Thr Thr Lys Lys Gly Gln Gln Phe Cys Gly Asp Pro
        35                  40                  45

Lys Gln Glu Trp Val Gln Arg Tyr Met
    50                  55

(2) INFORMATION FOR SEQ ID NO: 36:

(i) SEQUENCE CHARACTERISTICS:
        (A) LENGTH: 58 amino acids
        (B) TYPE: amino acid
        (D) TOPOLOGY: linear (ii) MOLECULE TYPE: protein (xi) SEQUENCE DESCRIPTION: SEQ ID NO: 36:

Pro Ser Pro Cys Cys Met Phe Phe Val Ser Lys Arg Ile Pro Glu Asn
1               5                   10                  15

Arg Val Val Ser Tyr Gln Leu Ser Ser Arg Ser Thr Cys Leu Lys Ala
            20                  25                  30

Gly Val Ile Phe Thr Thr Lys Lys Gly Gln Gln Phe Cys Gly Asp Pro
            35                  40                  45

Lys Gln Glu Trp Val Gln Arg Tyr Met Lys
    50                  55

(2) INFORMATION FOR SEQ ID NO: 37:

(i) SEQUENCE CHARACTERISTICS:
        (A) LENGTH: 59 amino acids
        (B) TYPE: amino acid
        (D) TOPOLOGY: linear (ii) MOLECULE TYPE: protein (xi) SEQUENCE DESCRIPTION: SEQ ID NO: 37:

Pro Ser Pro Cys Cys Met Phe Phe Val Ser Lys Arg Ile Pro Glu Asn
1               5                   10                  15

Arg Val Val Ser Tyr Gln Leu Ser Ser Arg Ser Thr Cys Leu Lys Ala
            20                  25                  30

Gly Val Ile Phe Thr Thr Lys Lys Gly Gln Gln Phe Cys Gly Asp Pro
            35                  40                  45

Lys Gln Glu Trp Val Gln Arg Tyr Met Lys Asn
    50                  55

(2) INFORMATION FOR SEQ ID NO: 38:

(i) SEQUENCE CHARACTERISTICS:
        (A) LENGTH: 60 amino acids
        (B) TYPE: amino acid
        (D) TOPOLOGY: linear (ii) MOLECULE TYPE: protein (xi) SEQUENCE DESCRIPTION: SEQ ID NO: 38:

Pro Ser Pro Cys Cys Met Phe Phe Val Ser Lys Arg Ile Pro Glu Asn
1               5                   10                  15

Arg Val Val Ser Tyr Gln Leu Ser Ser Arg Ser Thr Cys Leu Lys Ala
            20                  25                  30

Gly Val Ile Phe Thr Thr Lys Lys Gly Gln Gln Phe Cys Gly Asp Pro
            35                  40                  45

Lys Gln Glu Trp Val Gln Arg Tyr Met Lys Asn Leu
    50                  55                  60

(2) INFORMATION FOR SEQ ID NO: 39:

(i) SEQUENCE CHARACTERISTICS:
        (A) LENGTH: 61 amino acids
        (B) TYPE: amino acid
        (D) TOPOLOGY: linear (ii) MOLECULE TYPE: protein (xi) SEQUENCE DESCRIPTION: SEQ ID NO: 39:

Pro Ser Pro Cys Cys Met Phe Phe Val Ser Lys Arg Ile Pro Glu Asn
1               5                   10                  15

Arg Val Val Ser Tyr Gln Leu Ser Ser Arg Ser Thr Cys Leu Lys Ala
            20                  25                  30

```
Gly Val Ile Phe Thr Thr Lys Lys Gly Gln Gln Phe Cys Gly Asp Pro
            35                  40                  45

Lys Gln Glu Trp Val Gln Arg Tyr Met Lys Asn Leu Asp
 50                  55                  60
```

(2) INFORMATION FOR SEQ ID NO: 40:

(i) SEQUENCE CHARACTERISTICS:
        (A) LENGTH: 62 amino acids
        (B) TYPE: amino acid
        (D) TOPOLOGY: linear (ii) MOLECULE TYPE: protein (xi) SEQUENCE DESCRIPTION: SEQ ID NO: 40:

```
Pro Ser Pro Cys Cys Met Phe Phe Val Ser Lys Arg Ile Pro Glu Asn
 1               5                  10                  15

Arg Val Val Ser Tyr Gln Leu Ser Ser Arg Ser Thr Cys Leu Lys Ala
            20                  25                  30

Gly Val Ile Phe Thr Thr Lys Lys Gly Gln Gln Phe Cys Gly Asp Pro
            35                  40                  45

Lys Gln Glu Trp Val Gln Arg Tyr Met Lys Asn Leu Asp Ala
 50                  55                  60
```

(2) INFORMATION FOR SEQ ID NO: 41:

(i) SEQUENCE CHARACTERISTICS:
        (A) LENGTH: 63 amino acids
        (B) TYPE: amino acid
        (D) TOPOLOGY: linear (ii) MOLECULE TYPE: protein (xi) SEQUENCE DESCRIPTION: SEQ ID NO: 41:

```
Pro Ser Pro Cys Cys Met Phe Phe Val Ser Lys Arg Ile Pro Glu Asn
 1               5                  10                  15

Arg Val Val Ser Tyr Gln Leu Ser Ser Arg Ser Thr Cys Leu Lys Ala
            20                  25                  30

Gly Val Ile Phe Thr Thr Lys Lys Gly Gln Gln Phe Cys Gly Asp Pro
            35                  40                  45

Lys Gln Glu Trp Val Gln Arg Tyr Met Lys Asn Leu Asp Ala Lys
 50                  55                  60
```

(2) INFORMATION FOR SEQ ID NO: 42:

(i) SEQUENCE CHARACTERISTICS:
        (A) LENGTH: 64 amino acids
        (B) TYPE: amino acid
        (D) TOPOLOGY: linear (ii) MOLECULE TYPE: protein (xi) SEQUENCE DESCRIPTION: SEQ ID NO: 42:

```
Pro Ser Pro Cys Cys Met Phe Phe Val Ser Lys Arg Ile Pro Glu Asn
 1               5                  10                  15

Arg Val Val Ser Tyr Gln Leu Ser Ser Arg Ser Thr Cys Leu Lys Ala
            20                  25                  30

Gly Val Ile Phe Thr Thr Lys Lys Gly Gln Gln Phe Cys Gly Asp Pro
            35                  40                  45

Lys Gln Glu Trp Val Gln Arg Tyr Met Lys Asn Leu Asp Ala Lys Gln
 50                  55                  60
```

(2) INFORMATION FOR SEQ ID NO: 43:

(i) SEQUENCE CHARACTERISTICS:
        (A) LENGTH: 65 amino acids
        (B) TYPE: amino acid
        (D) TOPOLOGY: linear (ii) MOLECULE TYPE: protein (xi) SEQUENCE DESCRIPTION: SEQ ID NO: 43:

```
Pro Ser Pro Cys Cys Met Phe Phe Val Ser Lys Arg Ile Pro Glu Asn
1               5                   10                  15

Arg Val Val Ser Tyr Gln Leu Ser Ser Arg Ser Thr Cys Leu Lys Ala
            20                  25                  30

Gly Val Ile Phe Thr Thr Lys Lys Gly Gln Gln Phe Cys Gly Asp Pro
            35                  40                  45

Lys Gln Glu Trp Val Gln Arg Tyr Met Lys Asn Leu Asp Ala Lys Gln
        50                  55                  60

Lys
65
```

(2) INFORMATION FOR SEQ ID NO: 44:

(i) SEQUENCE CHARACTERISTICS:
        (A) LENGTH: 66 amino acids
        (B) TYPE: amino acid
        (D) TOPOLOGY: linear (ii) MOLECULE TYPE: protein (xi) SEQUENCE DESCRIPTION: SEQ ID NO: 44:

```
Pro Ser Pro Cys Cys Met Phe Phe Val Ser Lys Arg Ile Pro Glu Asn
1               5                   10                  15

Arg Val Val Ser Tyr Gln Leu Ser Ser Arg Ser Thr Cys Leu Lys Ala
            20                  25                  30

Gly Val Ile Phe Thr Thr Lys Lys Gly Gln Gln Phe Cys Gly Asp Pro
            35                  40                  45

Lys Gln Glu Trp Val Gln Arg Tyr Met Lys Asn Leu Asp Ala Lys Gln
        50                  55                  60

Lys Lys
65
```

(2) INFORMATION FOR SEQ ID NO: 45:

(i) SEQUENCE CHARACTERISTICS:
        (A) LENGTH: 67 amino acids
        (B) TYPE: amino acid
        (D) TOPOLOGY: linear (ii) MOLECULE TYPE: protein (xi) SEQUENCE DESCRIPTION: SEQ ID NO: 45:

```
Pro Ser Pro Cys Cys Met Phe Phe Val Ser Lys Arg Ile Pro Glu Asn
1               5                   10                  15

Arg Val Val Ser Tyr Gln Leu Ser Ser Arg Ser Thr Cys Leu Lys Ala
            20                  25                  30

Gly Val Ile Phe Thr Thr Lys Lys Gly Gln Gln Phe Cys Gly Asp Pro
            35                  40                  45

Lys Gln Glu Trp Val Gln Arg Tyr Met Lys Asn Leu Asp Ala Lys Gln
        50                  55                  60

Lys Lys Ala
```

(2) INFORMATION FOR SEQ ID NO: 46:

(i) SEQUENCE CHARACTERISTICS:
        (A) LENGTH: 68 amino acids
        (B) TYPE: amino acid
        (D) TOPOLOGY: linear (ii) MOLECULE TYPE: protein (xi) SEQUENCE DESCRIPTION: SEQ ID NO: 46:

```
Pro Ser Pro Cys Cys Met Phe Phe Val Ser Lys Arg Ile Pro Glu Asn
1               5                   10                  15

Arg Val Val Ser Tyr Gln Leu Ser Ser Arg Ser Thr Cys Leu Lys Ala
            20                  25                  30

Gly Val Ile Phe Thr Thr Lys Lys Gly Gln Gln Phe Cys Gly Asp Pro
        35                  40                  45

Lys Gln Glu Trp Val Gln Arg Tyr Met Lys Asn Leu Asp Ala Lys Gln
    50                  55                  60

Lys Lys Ala Ser
65
```

(2) INFORMATION FOR SEQ ID NO: 47:

(i) SEQUENCE CHARACTERISTICS:
        (A) LENGTH: 69 amino acids
        (B) TYPE: amino acid
        (D) TOPOLOGY: linear (ii) MOLECULE TYPE: protein (xi) SEQUENCE DESCRIPTION: SEQ ID NO: 47:

```
Pro Ser Pro Cys Cys Met Phe Phe Val Ser Lys Arg Ile Pro Glu Asn
1               5                   10                  15

Arg Val Val Ser Tyr Gln Leu Ser Ser Arg Ser Thr Cys Leu Lys Ala
            20                  25                  30

Gly Val Ile Phe Thr Thr Lys Lys Gly Gln Gln Phe Cys Gly Asp Pro
        35                  40                  45

Lys Gln Glu Trp Val Gln Arg Tyr Met Lys Asn Leu Asp Ala Lys Gln
    50                  55                  60

Lys Lys Ala Ser Pro
65
```

(2) INFORMATION FOR SEQ ID NO: 48:

(i) SEQUENCE CHARACTERISTICS:
        (A) LENGTH: 70 amino acids
        (B) TYPE: amino acid
        (D) TOPOLOGY: linear (ii) MOLECULE TYPE: protein (xi) SEQUENCE DESCRIPTION: SEQ ID NO: 48:

```
Pro Ser Pro Cys Cys Met Phe Phe Val Ser Lys Arg Ile Pro Glu Asn
1               5                   10                  15

Arg Val Val Ser Tyr Gln Leu Ser Ser Arg Ser Thr Cys Leu Lys Ala
            20                  25                  30

Gly Val Ile Phe Thr Thr Lys Lys Gly Gln Gln Phe Cys Gly Asp Pro
        35                  40                  45

Lys Gln Glu Trp Val Gln Arg Tyr Met Lys Asn Leu Asp Ala Lys Gln
    50                  55                  60
```

Lys Lys Ala Ser Pro Arg
65              70

(2) INFORMATION FOR SEQ ID NO: 49:

(i) SEQUENCE CHARACTERISTICS:
        (A) LENGTH: 71 amino acids
        (B) TYPE: amino acid
        (D) TOPOLOGY: linear (ii) MOLECULE TYPE: protein (xi) SEQUENCE DESCRIPTION: SEQ ID NO: 49:

Pro Ser Pro Cys Cys Met Phe Phe Val Ser Lys Arg Ile Pro Glu Asn
1               5                   10                  15

Arg Val Val Ser Tyr Gln Leu Ser Ser Arg Ser Thr Cys Leu Lys Ala
            20                  25                  30

Gly Val Ile Phe Thr Thr Lys Lys Gly Gln Gln Phe Cys Gly Asp Pro
            35                  40                  45

Lys Gln Glu Trp Val Gln Arg Tyr Met Lys Asn Leu Asp Ala Lys Gln
        50                  55                  60

Lys Lys Ala Ser Pro Arg Ala
65              70

(2) INFORMATION FOR SEQ ID NO: 50:

(i) SEQUENCE CHARACTERISTICS:
        (A) LENGTH: 72 amino acids
        (B) TYPE: amino acid
        (D) TOPOLOGY: linear (ii) MOLECULE TYPE: protein (xi) SEQUENCE DESCRIPTION: SEQ ID NO: 50:

Pro Ser Pro Cys Cys Met Phe Phe Val Ser Lys Arg Ile Pro Glu Asn
1               5                   10                  15

Arg Val Val Ser Tyr Gln Leu Ser Ser Arg Ser Thr Cys Leu Lys Ala
            20                  25                  30

Gly Val Ile Phe Thr Thr Lys Lys Gly Gln Gln Phe Cys Gly Asp Pro
            35                  40                  45

Lys Gln Glu Trp Val Gln Arg Tyr Met Lys Asn Leu Asp Ala Lys Gln
        50                  55                  60

Lys Lys Ala Ser Pro Arg Ala Arg
65              70

(2) INFORMATION FOR SEQ ID NO: 51:

(i) SEQUENCE CHARACTERISTICS:
        (A) LENGTH: 73 amino acids
        (B) TYPE: amino acid
        (D) TOPOLOGY: linear (ii) MOLECULE TYPE: protein (xi) SEQUENCE DESCRIPTION: SEQ ID NO: 51:

Pro Ser Pro Cys Cys Met Phe Phe Val Ser Lys Arg Ile Pro Glu Asn
1               5                   10                  15

Arg Val Val Ser Tyr Gln Leu Ser Ser Arg Ser Thr Cys Leu Lys Ala
            20                  25                  30

Gly Val Ile Phe Thr Thr Lys Lys Gly Gln Gln Phe Cys Gly Asp Pro
            35                  40                  45

```
Lys Gln Glu Trp Val Gln Arg Tyr Met Lys Asn Leu Asp Ala Lys Gln
 50                  55                  60

Lys Lys Ala Ser Pro Arg Ala Arg Ala
 65                  70
```

(2) INFORMATION FOR SEQ ID NO: 52:

(i) SEQUENCE CHARACTERISTICS:
        (A) LENGTH: 74 amino acids
        (B) TYPE: amino acid
        (D) TOPOLOGY: linear (ii) MOLECULE TYPE: protein (xi) SEQUENCE DESCRIPTION: SEQ ID NO: 52:

```
Pro Ser Pro Cys Cys Met Phe Phe Val Ser Lys Arg Ile Pro Glu Asn
 1               5                  10                  15

Arg Val Val Ser Tyr Gln Leu Ser Ser Arg Ser Thr Cys Leu Lys Ala
                 20                  25                  30

Gly Val Ile Phe Thr Thr Lys Lys Gly Gln Gln Phe Cys Gly Asp Pro
             35                  40                  45

Lys Gln Glu Trp Val Gln Arg Tyr Met Lys Asn Leu Asp Ala Lys Gln
 50                  55                  60

Lys Lys Ala Ser Pro Arg Ala Arg Ala Val
 65                  70
```

(2) INFORMATION FOR SEQ ID NO: 53:

(i) SEQUENCE CHARACTERISTICS:
        (A) LENGTH: 75 amino acids
        (B) TYPE: amino acid
        (D) TOPOLOGY: linear (ii) MOLECULE TYPE: protein (xi) SEQUENCE DESCRIPTION: SEQ ID NO: 53:

```
Pro Ser Pro Cys Cys Met Phe Phe Val Ser Lys Arg Ile Pro Glu Asn
 1               5                  10                  15

Arg Val Val Ser Tyr Gln Leu Ser Ser Arg Ser Thr Cys Leu Lys Ala
                 20                  25                  30

Gly Val Ile Phe Thr Thr Lys Lys Gly Gln Gln Phe Cys Gly Asp Pro
             35                  40                  45

Lys Gln Glu Trp Val Gln Arg Tyr Met Lys Asn Leu Asp Ala Lys Gln
 50                  55                  60

Lys Lys Ala Ser Pro Arg Ala Arg Ala Val Ala
 65                  70                  75
```

(2) INFORMATION FOR SEQ ID NO: 54:

(i) SEQUENCE CHARACTERISTICS:
        (A) LENGTH: 76 amino acids
        (B) TYPE: amino acid
        (D) TOPOLOGY: linear (ii) MOLECULE TYPE: protein (xi) SEQUENCE DESCRIPTION: SEQ ID NO: 54:

```
Pro Ser Pro Cys Cys Met Phe Phe Val Ser Lys Arg Ile Pro Glu Asn
 1               5                  10                  15

Arg Val Val Ser Tyr Gln Leu Ser Ser Arg Ser Thr Cys Leu Lys Ala
                 20                  25                  30

Gly Val Ile Phe Thr Thr Lys Lys Gly Gln Gln Phe Cys Gly Asp Pro
```

```
                    35                  40                  45
Lys Gln Glu Trp Val Gln Arg Tyr Met Lys Asn Leu Asp Ala Lys Gln
         50                  55                  60
Lys Lys Ala Ser Pro Arg Ala Arg Ala Val Ala Val
 65                  70                  75

(2) INFORMATION FOR SEQ ID NO: 55:

(i) SEQUENCE CHARACTERISTICS:
        (A) LENGTH: 77 amino acids
        (B) TYPE: amino acid
        (D) TOPOLOGY: linear (ii) MOLECULE TYPE: protein (xi) SEQUENCE DESCRIPTION: SEQ ID NO: 55:

Pro Ser Pro Cys Cys Met Phe Phe Val Ser Lys Arg Ile Pro Glu Asn
 1               5                  10                  15
Arg Val Val Ser Tyr Gln Leu Ser Ser Arg Ser Thr Cys Leu Lys Ala
                 20                  25                  30
Gly Val Ile Phe Thr Thr Lys Lys Gly Gln Gln Phe Cys Gly Asp Pro
                    35                  40                  45
Lys Gln Glu Trp Val Gln Arg Tyr Met Lys Asn Leu Asp Ala Lys Gln
         50                  55                  60
Lys Lys Ala Ser Pro Arg Ala Arg Ala Val Ala Val Lys
 65                  70                  75

(2) INFORMATION FOR SEQ ID NO: 56:

(i) SEQUENCE CHARACTERISTICS:
        (A) LENGTH: 78 amino acids
        (B) TYPE: amino acid
        (D) TOPOLOGY: linear (ii) MOLECULE TYPE: protein (xi) SEQUENCE DESCRIPTION: SEQ ID NO: 56:

Pro Ser Pro Cys Cys Met Phe Phe Val Ser Lys Arg Ile Pro Glu Asn
 1               5                  10                  15
Arg Val Val Ser Tyr Gln Leu Ser Ser Arg Ser Thr Cys Leu Lys Ala
                 20                  25                  30
Gly Val Ile Phe Thr Thr Lys Lys Gly Gln Gln Phe Cys Gly Asp Pro
                    35                  40                  45
Lys Gln Glu Trp Val Gln Arg Tyr Met Lys Asn Leu Asp Ala Lys Gln
         50                  55                  60
Lys Lys Ala Ser Pro Arg Ala Arg Ala Val Ala Val Lys Gly
 65                  70                  75

(2) INFORMATION FOR SEQ ID NO: 57:

(i) SEQUENCE CHARACTERISTICS:
        (A) LENGTH: 79 amino acids
        (B) TYPE: amino acid
        (D) TOPOLOGY: linear (ii) MOLECULE TYPE: protein (xi) SEQUENCE DESCRIPTION: SEQ ID NO: 57:

Pro Ser Pro Cys Cys Met Phe Phe Val Ser Lys Arg Ile Pro Glu Asn
 1               5                  10                  15
Arg Val Val Ser Tyr Gln Leu Ser Ser Arg Ser Thr Cys Leu Lys Ala
                 20                  25                  30
```

```
Gly Val Ile Phe Thr Thr Lys Lys Gly Gln Gln Phe Cys Gly Asp Pro
        35                  40                  45

Lys Gln Glu Trp Val Gln Arg Tyr Met Lys Asn Leu Asp Ala Lys Gln
 50                  55                  60

Lys Lys Ala Ser Pro Arg Ala Arg Ala Val Ala Val Lys Gly Pro
 65                  70                  75
```

(2) INFORMATION FOR SEQ ID NO: 58:

(i) SEQUENCE CHARACTERISTICS:
        (A) LENGTH: 80 amino acids
        (B) TYPE: amino acid
        (D) TOPOLOGY: linear (ii) MOLECULE TYPE: protein (xi) SEQUENCE DESCRIPTION: SEQ ID NO: 58:

```
Pro Ser Pro Cys Cys Met Phe Phe Val Ser Lys Arg Ile Pro Glu Asn
 1               5                  10                  15

Arg Val Val Ser Tyr Gln Leu Ser Ser Arg Ser Thr Cys Leu Lys Ala
                 20                  25                  30

Gly Val Ile Phe Thr Thr Lys Lys Gly Gln Gln Phe Cys Gly Asp Pro
        35                  40                  45

Lys Gln Glu Trp Val Gln Arg Tyr Met Lys Asn Leu Asp Ala Lys Gln
 50                  55                  60

Lys Lys Ala Ser Pro Arg Ala Arg Ala Val Ala Val Lys Gly Pro Val
 65                  70                  75                  80
```

(2) INFORMATION FOR SEQ ID NO: 59:

(i) SEQUENCE CHARACTERISTICS:
        (A) LENGTH: 81 amino acids
        (B) TYPE: amino acid
        (D) TOPOLOGY: linear (ii) MOLECULE TYPE: protein (xi) SEQUENCE DESCRIPTION: SEQ ID NO: 59:

```
Pro Ser Pro Cys Cys Met Phe Phe Val Ser Lys Arg Ile Pro Glu Asn
 1               5                  10                  15

Arg Val Val Ser Tyr Gln Leu Ser Ser Arg Ser Thr Cys Leu Lys Ala
                 20                  25                  30

Gly Val Ile Phe Thr Thr Lys Lys Gly Gln Gln Phe Cys Gly Asp Pro
        35                  40                  45

Lys Gln Glu Trp Val Gln Arg Tyr Met Lys Asn Leu Asp Ala Lys Gln
 50                  55                  60

Lys Lys Ala Ser Pro Arg Ala Arg Ala Val Ala Val Lys Gly Pro Val
 65                  70                  75                  80

Gln
```

(2) INFORMATION FOR SEQ ID NO: 60:

(i) SEQUENCE CHARACTERISTICS:
        (A) LENGTH: 82 amino acids
        (B) TYPE: amino acid
        (D) TOPOLOGY: linear (ii) MOLECULE TYPE: protein (xi) SEQUENCE DESCRIPTION: SEQ ID NO: 60:

```
Pro Ser Pro Cys Cys Met Phe Phe Val Ser Lys Arg Ile Pro Glu Asn
```

```
              1               5                  10                 15
Arg Val Val Ser Tyr Gln Leu Ser Ser Arg Ser Thr Cys Leu Lys Ala
                20                  25                  30

Gly Val Ile Phe Thr Thr Lys Lys Gly Gln Gln Phe Cys Gly Asp Pro
            35                  40                  45

Lys Gln Glu Trp Val Gln Arg Tyr Met Lys Asn Leu Asp Ala Lys Gln
    50                  55                  60

Lys Lys Ala Ser Pro Arg Ala Arg Ala Val Ala Val Lys Gly Pro Val
65                  70                  75                  80

Gln Arg (2) INFORMATION FOR SEQ ID NO: 61:

(i) SEQUENCE CHARACTERISTICS:
        (A) LENGTH: 83 amino acids
        (B) TYPE: amino acid
        (D) TOPOLOGY: linear (ii) MOLECULE TYPE: protein (xi) SEQUENCE DESCRIPTION: SEQ ID NO: 61:

Pro Ser Pro Cys Cys Met Phe Phe Val Ser Lys Arg Ile Pro Glu Asn
1               5                  10                  15

Arg Val Val Ser Tyr Gln Leu Ser Ser Arg Ser Thr Cys Leu Lys Ala
                20                  25                  30

Gly Val Ile Phe Thr Thr Lys Lys Gly Gln Gln Phe Cys Gly Asp Pro
            35                  40                  45

Lys Gln Glu Trp Val Gln Arg Tyr Met Lys Asn Leu Asp Ala Lys Gln
    50                  55                  60

Lys Lys Ala Ser Pro Arg Ala Arg Ala Val Ala Val Lys Gly Pro Val
65                  70                  75                  80

Gln Arg Tyr (2) INFORMATION FOR SEQ ID NO: 62:

(i) SEQUENCE CHARACTERISTICS:
        (A) LENGTH: 84 amino acids
        (B) TYPE: amino acid
        (D) TOPOLOGY: linear (ii) MOLECULE TYPE: protein (xi) SEQUENCE DESCRIPTION: SEQ ID NO: 62:

Pro Ser Pro Cys Cys Met Phe Phe Val Ser Lys Arg Ile Pro Glu Asn
1               5                  10                  15

Arg Val Val Ser Tyr Gln Leu Ser Ser Arg Ser Thr Cys Leu Lys Ala
                20                  25                  30

Gly Val Ile Phe Thr Thr Lys Lys Gly Gln Gln Phe Cys Gly Asp Pro
            35                  40                  45

Lys Gln Glu Trp Val Gln Arg Tyr Met Lys Asn Leu Asp Ala Lys Gln
    50                  55                  60

Lys Lys Ala Ser Pro Arg Ala Arg Ala Val Ala Val Lys Gly Pro Val
65                  70                  75                  80

Gln Arg Tyr Pro (2) INFORMATION FOR SEQ ID NO: 63:

(i) SEQUENCE CHARACTERISTICS:
        (A) LENGTH: 85 amino acids
```

(B) TYPE: amino acid
        (D) TOPOLOGY: linear (ii) MOLECULE TYPE: protein (xi) SEQUENCE DESCRIPTION: SEQ ID NO: 63:

Pro Ser Pro Cys Cys Met Phe Phe Val Ser Lys Arg Ile Pro Glu Asn
1               5                   10                  15

Arg Val Val Ser Tyr Gln Leu Ser Ser Arg Ser Thr Cys Leu Lys Ala
            20                  25                  30

Gly Val Ile Phe Thr Thr Lys Lys Gly Gln Gln Phe Cys Gly Asp Pro
        35                  40                  45

Lys Gln Glu Trp Val Gln Arg Tyr Met Lys Asn Leu Asp Ala Lys Gln
    50                  55                  60

Lys Lys Ala Ser Pro Arg Ala Arg Ala Val Ala Val Lys Gly Pro Val
65                  70                  75                  80

Gln Arg Tyr Pro Gly
                85

(2) INFORMATION FOR SEQ ID NO: 64:

(i) SEQUENCE CHARACTERISTICS:
        (A) LENGTH: 86 amino acids
        (B) TYPE: amino acid
        (D) TOPOLOGY: linear (ii) MOLECULE TYPE: protein (xi) SEQUENCE DESCRIPTION: SEQ ID NO: 64:

Pro Ser Pro Cys Cys Met Phe Phe Val Ser Lys Arg Ile Pro Glu Asn
1               5                   10                  15

Arg Val Val Ser Tyr Gln Leu Ser Ser Arg Ser Thr Cys Leu Lys Ala
            20                  25                  30

Gly Val Ile Phe Thr Thr Lys Lys Gly Gln Gln Phe Cys Gly Asp Pro
        35                  40                  45

Lys Gln Glu Trp Val Gln Arg Tyr Met Lys Asn Leu Asp Ala Lys Gln
    50                  55                  60

Lys Lys Ala Ser Pro Arg Ala Arg Ala Val Ala Val Lys Gly Pro Val
65                  70                  75                  80

Gln Arg Tyr Pro Gly Asn
                85

(2) INFORMATION FOR SEQ ID NO: 65:

(i) SEQUENCE CHARACTERISTICS:
        (A) LENGTH: 87 amino acids
        (B) TYPE: amino acid
        (D) TOPOLOGY: linear (ii) MOLECULE TYPE: protein (xi) SEQUENCE DESCRIPTION: SEQ ID NO: 65:

Pro Ser Pro Cys Cys Met Phe Phe Val Ser Lys Arg Ile Pro Glu Asn
1               5                   10                  15

Arg Val Val Ser Tyr Gln Leu Ser Ser Arg Ser Thr Cys Leu Lys Ala
            20                  25                  30

Gly Val Ile Phe Thr Thr Lys Lys Gly Gln Gln Phe Cys Gly Asp Pro
        35                  40                  45

Lys Gln Glu Trp Val Gln Arg Tyr Met Lys Asn Leu Asp Ala Lys Gln
    50                  55                  60

-continued

```
Lys Lys Ala Ser Pro Arg Ala Arg Ala Val Ala Val Lys Gly Pro Val
 65                  70                  75                  80

Gln Arg Tyr Pro Gly Asn Gln
                85
```

(2) INFORMATION FOR SEQ ID NO: 66:

(i) SEQUENCE CHARACTERISTICS:
        (A) LENGTH: 88 amino acids
        (B) TYPE: amino acid
        (D) TOPOLOGY: linear (ii) MOLECULE TYPE: protein (xi) SEQUENCE DESCRIPTION: SEQ ID NO: 66:

```
Pro Ser Pro Cys Cys Met Phe Phe Val Ser Lys Arg Ile Pro Glu Asn
 1               5                  10                  15

Arg Val Val Ser Tyr Gln Leu Ser Ser Arg Ser Thr Cys Leu Lys Ala
                20                  25                  30

Gly Val Ile Phe Thr Thr Lys Lys Gly Gln Gln Phe Cys Gly Asp Pro
            35                  40                  45

Lys Gln Glu Trp Val Gln Arg Tyr Met Lys Asn Leu Asp Ala Lys Gln
 50                  55                  60

Lys Lys Ala Ser Pro Arg Ala Arg Ala Val Ala Val Lys Gly Pro Val
 65                  70                  75                  80

Gln Arg Tyr Pro Gly Asn Gln Thr
                85
```

(2) INFORMATION FOR SEQ ID NO: 67:

(i) SEQUENCE CHARACTERISTICS:
        (A) LENGTH: 89 amino acids
        (B) TYPE: amino acid
        (D) TOPOLOGY: linear (ii) MOLECULE TYPE: protein (xi) SEQUENCE DESCRIPTION: SEQ ID NO: 67:

```
Pro Ser Pro Cys Cys Met Phe Phe Val Ser Lys Arg Ile Pro Glu Asn
 1               5                  10                  15

Arg Val Val Ser Tyr Gln Leu Ser Ser Arg Ser Thr Cys Leu Lys Ala
                20                  25                  30

Gly Val Ile Phe Thr Thr Lys Lys Gly Gln Gln Phe Cys Gly Asp Pro
            35                  40                  45

Lys Gln Glu Trp Val Gln Arg Tyr Met Lys Asn Leu Asp Ala Lys Gln
 50                  55                  60

Lys Lys Ala Ser Pro Arg Ala Arg Ala Val Ala Val Lys Gly Pro Val
 65                  70                  75                  80

Gln Arg Tyr Pro Gly Asn Gln Thr Thr
                85
```

(2) INFORMATION FOR SEQ ID NO: 68:

(i) SEQUENCE CHARACTERISTICS:
        (A) LENGTH: 90 amino acids
        (B) TYPE: amino acid
        (D) TOPOLOGY: linear (ii) MOLECULE TYPE: protein (xi) SEQUENCE DESCRIPTION: SEQ ID NO: 68:

```
Pro Ser Pro Cys Cys Met Phe Phe Val Ser Lys Arg Ile Pro Glu Asn
```

```
                  1               5                  10                 15
Arg Val Val Ser Tyr Gln Leu Ser Ser Arg Ser Thr Cys Leu Lys Ala
                 20                 25                 30

Gly Val Ile Phe Thr Thr Lys Lys Gly Gln Gln Phe Cys Gly Asp Pro
                 35                 40                 45

Lys Gln Glu Trp Val Gln Arg Tyr Met Lys Asn Leu Asp Ala Lys Gln
                 50                 55                 60

Lys Lys Ala Ser Pro Arg Ala Arg Ala Val Ala Val Lys Gly Pro Val
 65                 70                 75                 80

Gln Arg Tyr Pro Gly Asn Gln Thr Thr Cys
                 85                 90
```

(2) INFORMATION FOR SEQ ID NO: 69:

(i) SEQUENCE CHARACTERISTICS:
        (A) LENGTH: 46 amino acids
        (B) TYPE: amino acid
        (D) TOPOLOGY: linear (ii) MOLECULE TYPE: protein (xi) SEQUENCE DESCRIPTION: SEQ ID NO: 69:

```
Met Pro Ser Pro Cys Cys Met Phe Phe Val Ser Lys Arg Ile Pro Glu
 1               5                  10                 15

Asn Arg Val Val Ser Tyr Gln Leu Ser Ser Arg Ser Thr Cys Leu Lys
                 20                 25                 30

Ala Gly Val Ile Phe Thr Thr Lys Lys Gly Gln Gln Phe Cys
                 35                 40                 45
```

(2) INFORMATION FOR SEQ ID NO: 70:

(i) SEQUENCE CHARACTERISTICS:
        (A) LENGTH: 47 amino acids
        (B) TYPE: amino acid
        (D) TOPOLOGY: linear (ii) MOLECULE TYPE: protein (xi) SEQUENCE DESCRIPTION: SEQ ID NO: 70:

```
Met Pro Ser Pro Cys Cys Met Phe Phe Val Ser Lys Arg Ile Pro Glu
 1               5                  10                 15

Asn Arg Val Val Ser Tyr Gln Leu Ser Ser Arg Ser Thr Cys Leu Lys
                 20                 25                 30

Ala Gly Val Ile Phe Thr Thr Lys Lys Gly Gln Gln Phe Cys Gly
                 35                 40                 45
```

(2) INFORMATION FOR SEQ ID NO: 71:

(i) SEQUENCE CHARACTERISTICS:
        (A) LENGTH: 48 amino acids
        (B) TYPE: amino acid
        (D) TOPOLOGY: linear (ii) MOLECULE TYPE: protein (xi) SEQUENCE DESCRIPTION: SEQ ID NO: 71:

```
Met Pro Ser Pro Cys Cys Met Phe Phe Val Ser Lys Arg Ile Pro Glu
 1               5                  10                 15

Asn Arg Val Val Ser Tyr Gln Leu Ser Ser Arg Ser Thr Cys Leu Lys
                 20                 25                 30

Ala Gly Val Ile Phe Thr Thr Lys Lys Gly Gln Gln Phe Cys Gly Asp
                 35                 40                 45
```

(2) INFORMATION FOR SEQ ID NO: 72:

(i) SEQUENCE CHARACTERISTICS:
        (A) LENGTH: 49 amino acids
        (B) TYPE: amino acid
        (D) TOPOLOGY: linear (ii) MOLECULE TYPE: protein (xi) SEQUENCE DESCRIPTION: SEQ ID NO: 72:

Met Pro Ser Pro Cys Cys Met Phe Phe Val Ser Lys Arg Ile Pro Glu
1               5                   10                  15

Asn Arg Val Val Ser Tyr Gln Leu Ser Ser Arg Ser Thr Cys Leu Lys
            20                  25                  30

Ala Gly Val Ile Phe Thr Thr Lys Lys Gly Gln Gln Phe Cys Gly Asp
        35                  40                  45

Pro (2) INFORMATION FOR SEQ ID NO: 73:

(i) SEQUENCE CHARACTERISTICS:
        (A) LENGTH: 50 amino acids
        (B) TYPE: amino acid
        (D) TOPOLOGY: linear (ii) MOLECULE TYPE: protein (xi) SEQUENCE DESCRIPTION: SEQ ID NO: 73:

Met Pro Ser Pro Cys Cys Met Phe Phe Val Ser Lys Arg Ile Pro Glu
1               5                   10                  15

Asn Arg Val Val Ser Tyr Gln Leu Ser Ser Arg Ser Thr Cys Leu Lys
            20                  25                  30

Ala Gly Val Ile Phe Thr Thr Lys Lys Gly Gln Gln Phe Cys Gly Asp
        35                  40                  45

Pro Lys
    50

(2) INFORMATION FOR SEQ ID NO: 74:

(i) SEQUENCE CHARACTERISTICS:
        (A) LENGTH: 51 amino acids
        (B) TYPE: amino acid
        (D) TOPOLOGY: linear (ii) MOLECULE TYPE: protein (xi) SEQUENCE DESCRIPTION: SEQ ID NO: 74:

Met Pro Ser Pro Cys Cys Met Phe Phe Val Ser Lys Arg Ile Pro Glu
1               5                   10                  15

Asn Arg Val Val Ser Tyr Gln Leu Ser Ser Arg Ser Thr Cys Leu Lys
            20                  25                  30

Ala Gly Val Ile Phe Thr Thr Lys Lys Gly Gln Gln Phe Cys Gly Asp
        35                  40                  45

Pro Lys Gln
    50

(2) INFORMATION FOR SEQ ID NO: 75:

(i) SEQUENCE CHARACTERISTICS:
        (A) LENGTH: 52 amino acids
        (B) TYPE: amino acid
        (D) TOPOLOGY: linear (ii) MOLECULE TYPE: protein (xi) SEQUENCE DESCRIPTION: SEQ ID NO: 75:

Met Pro Ser Pro Cys Cys Met Phe Phe Val Ser Lys Arg Ile Pro Glu
1               5                   10                  15

Asn Arg Val Val Ser Tyr Gln Leu Ser Ser Arg Ser Thr Cys Leu Lys
            20                  25                  30

Ala Gly Val Ile Phe Thr Thr Lys Lys Gly Gln Gln Phe Cys Gly Asp
        35                  40                  45

Pro Lys Gln Glu
    50

(2) INFORMATION FOR SEQ ID NO: 76:

(i) SEQUENCE CHARACTERISTICS:
        (A) LENGTH: 53 amino acids
        (B) TYPE: amino acid
        (D) TOPOLOGY: linear (ii) MOLECULE TYPE: protein (xi) SEQUENCE DESCRIPTION: SEQ ID NO: 76:

Met Pro Ser Pro Cys Cys Met Phe Phe Val Ser Lys Arg Ile Pro Glu
1               5                   10                  15

Asn Arg Val Val Ser Tyr Gln Leu Ser Ser Arg Ser Thr Cys Leu Lys
            20                  25                  30

Ala Gly Val Ile Phe Thr Thr Lys Lys Gly Gln Gln Phe Cys Gly Asp
        35                  40                  45

Pro Lys Gln Glu Trp
    50

(2) INFORMATION FOR SEQ ID NO: 77:

(i) SEQUENCE CHARACTERISTICS:
        (A) LENGTH: 54 amino acids
        (B) TYPE: amino acid
        (D) TOPOLOGY: linear (ii) MOLECULE TYPE: protein (xi) SEQUENCE DESCRIPTION: SEQ ID NO: 77:

Met Pro Ser Pro Cys Cys Met Phe Phe Val Ser Lys Arg Ile Pro Glu
1               5                   10                  15

Asn Arg Val Val Ser Tyr Gln Leu Ser Ser Arg Ser Thr Cys Leu Lys
            20                  25                  30

Ala Gly Val Ile Phe Thr Thr Lys Lys Gly Gln Gln Phe Cys Gly Asp
        35                  40                  45

Pro Lys Gln Glu Trp Val
    50

(2) INFORMATION FOR SEQ ID NO: 78:

(i) SEQUENCE CHARACTERISTICS:
        (A) LENGTH: 55 amino acids
        (B) TYPE: amino acid
        (D) TOPOLOGY: linear (ii) MOLECULE TYPE: protein (xi) SEQUENCE DESCRIPTION: SEQ ID NO: 78:

Met Pro Ser Pro Cys Cys Met Phe Phe Val Ser Lys Arg Ile Pro Glu
1               5                   10                  15

Asn Arg Val Val Ser Tyr Gln Leu Ser Ser Arg Ser Thr Cys Leu Lys
            20                  25                  30

Ala Gly Val Ile Phe Thr Thr Lys Lys Gly Gln Gln Phe Cys Gly Asp
        35                  40                  45

Pro Lys Gln Glu Trp Val Gln
    50                  55

(2) INFORMATION FOR SEQ ID NO: 79:

(i) SEQUENCE CHARACTERISTICS:
        (A) LENGTH: 56 amino acids
        (B) TYPE: amino acid
        (D) TOPOLOGY: linear (ii) MOLECULE TYPE: protein (xi) SEQUENCE DESCRIPTION: SEQ ID NO: 79:

Met Pro Ser Pro Cys Cys Met Phe Phe Val Ser Lys Arg Ile Pro Glu
1               5                   10                  15

Asn Arg Val Val Ser Tyr Gln Leu Ser Ser Arg Ser Thr Cys Leu Lys
            20                  25                  30

Ala Gly Val Ile Phe Thr Thr Lys Lys Gly Gln Gln Phe Cys Gly Asp
        35                  40                  45

Pro Lys Gln Glu Trp Val Gln Arg
    50                  55

(2) INFORMATION FOR SEQ ID NO: 80:

(i) SEQUENCE CHARACTERISTICS:
        (A) LENGTH: 57 amino acids
        (B) TYPE: amino acid
        (D) TOPOLOGY: linear (ii) MOLECULE TYPE: protein (xi) SEQUENCE DESCRIPTION: SEQ ID NO: 80:

Met Pro Ser Pro Cys Cys Met Phe Phe Val Ser Lys Arg Ile Pro Glu
1               5                   10                  15

Asn Arg Val Val Ser Tyr Gln Leu Ser Ser Arg Ser Thr Cys Leu Lys
            20                  25                  30

Ala Gly Val Ile Phe Thr Thr Lys Lys Gly Gln Gln Phe Cys Gly Asp
        35                  40                  45

Pro Lys Gln Glu Trp Val Gln Arg Tyr
    50                  55

(2) INFORMATION FOR SEQ ID NO: 81:

(i) SEQUENCE CHARACTERISTICS:
        (A) LENGTH: 58 amino acids
        (B) TYPE: amino acid
        (D) TOPOLOGY: linear (ii) MOLECULE TYPE: protein (xi) SEQUENCE DESCRIPTION: SEQ ID NO: 81:

Met Pro Ser Pro Cys Cys Met Phe Phe Val Ser Lys Arg Ile Pro Glu
1               5                   10                  15

Asn Arg Val Val Ser Tyr Gln Leu Ser Ser Arg Ser Thr Cys Leu Lys
            20                  25                  30

Ala Gly Val Ile Phe Thr Thr Lys Lys Gly Gln Gln Phe Cys Gly Asp
        35                  40                  45

Pro Lys Gln Glu Trp Val Gln Arg Tyr Met
    50                  55

(2) INFORMATION FOR SEQ ID NO: 82:

(i) SEQUENCE CHARACTERISTICS:
        (A) LENGTH: 59 amino acids
        (B) TYPE: amino acid
        (D) TOPOLOGY: linear (ii) MOLECULE TYPE: protein (xi) SEQUENCE DESCRIPTION: SEQ ID NO: 82:

Met Pro Ser Pro Cys Cys Met Phe Phe Val Ser Lys Arg Ile Pro Glu
 1               5                  10                  15

Asn Arg Val Val Ser Tyr Gln Leu Ser Ser Arg Ser Thr Cys Leu Lys
            20                  25                  30

Ala Gly Val Ile Phe Thr Thr Lys Lys Gly Gln Gln Phe Cys Gly Asp
        35                  40                  45

Pro Lys Gln Glu Trp Val Gln Arg Tyr Met Lys
    50                  55

(2) INFORMATION FOR SEQ ID NO: 83:

(i) SEQUENCE CHARACTERISTICS:
        (A) LENGTH: 60 amino acids
        (B) TYPE: amino acid
        (D) TOPOLOGY: linear (ii) MOLECULE TYPE: protein (xi) SEQUENCE DESCRIPTION: SEQ ID NO: 83:

Met Pro Ser Pro Cys Cys Met Phe Phe Val Ser Lys Arg Ile Pro Glu
 1               5                  10                  15

Asn Arg Val Val Ser Tyr Gln Leu Ser Ser Arg Ser Thr Cys Leu Lys
            20                  25                  30

Ala Gly Val Ile Phe Thr Thr Lys Lys Gly Gln Gln Phe Cys Gly Asp
        35                  40                  45

Pro Lys Gln Glu Trp Val Gln Arg Tyr Met Lys Asn
    50                  55                  60

(2) INFORMATION FOR SEQ ID NO: 84:

(i) SEQUENCE CHARACTERISTICS:
        (A) LENGTH: 61 amino acids
        (B) TYPE: amino acid
        (D) TOPOLOGY: linear (ii) MOLECULE TYPE: protein (xi) SEQUENCE DESCRIPTION: SEQ ID NO: 84:

Met Pro Ser Pro Cys Cys Met Phe Phe Val Ser Lys Arg Ile Pro Glu
 1               5                  10                  15

Asn Arg Val Val Ser Tyr Gln Leu Ser Ser Arg Ser Thr Cys Leu Lys
            20                  25                  30

Ala Gly Val Ile Phe Thr Thr Lys Lys Gly Gln Gln Phe Cys Gly Asp
        35                  40                  45

Pro Lys Gln Glu Trp Val Gln Arg Tyr Met Lys Asn Leu
    50                  55                  60

(2) INFORMATION FOR SEQ ID NO: 85:

(i) SEQUENCE CHARACTERISTICS:

(A) LENGTH: 62 amino acids
        (B) TYPE: amino acid
        (D) TOPOLOGY: linear (ii) MOLECULE TYPE: protein (xi) SEQUENCE DESCRIPTION: SEQ ID NO: 85:

Met Pro Ser Pro Cys Cys Met Phe Phe Val Ser Lys Arg Ile Pro Glu
1               5                   10                  15

Asn Arg Val Val Ser Tyr Gln Leu Ser Ser Arg Ser Thr Cys Leu Lys
            20                  25                  30

Ala Gly Val Ile Phe Thr Thr Lys Lys Gly Gln Gln Phe Cys Gly Asp
        35                  40                  45

Pro Lys Gln Glu Trp Val Gln Arg Tyr Met Lys Asn Leu Asp
    50                  55                  60

(2) INFORMATION FOR SEQ ID NO: 86:

(i) SEQUENCE CHARACTERISTICS:
        (A) LENGTH: 63 amino acids
        (B) TYPE: amino acid
        (D) TOPOLOGY: linear (ii) MOLECULE TYPE: protein (xi) SEQUENCE DESCRIPTION: SEQ ID NO: 86:

Met Pro Ser Pro Cys Cys Met Phe Phe Val Ser Lys Arg Ile Pro Glu
1               5                   10                  15

Asn Arg Val Val Ser Tyr Gln Leu Ser Ser Arg Ser Thr Cys Leu Lys
            20                  25                  30

Ala Gly Val Ile Phe Thr Thr Lys Lys Gly Gln Gln Phe Cys Gly Asp
        35                  40                  45

Pro Lys Gln Glu Trp Val Gln Arg Tyr Met Lys Asn Leu Asp Ala
    50                  55                  60

(2) INFORMATION FOR SEQ ID NO: 87:

(i) SEQUENCE CHARACTERISTICS:
        (A) LENGTH: 64 amino acids
        (B) TYPE: amino acid
        (D) TOPOLOGY: linear (ii) MOLECULE TYPE: protein (xi) SEQUENCE DESCRIPTION: SEQ ID NO: 87:

Met Pro Ser Pro Cys Cys Met Phe Phe Val Ser Lys Arg Ile Pro Glu
1               5                   10                  15

Asn Arg Val Val Ser Tyr Gln Leu Ser Ser Arg Ser Thr Cys Leu Lys
            20                  25                  30

Ala Gly Val Ile Phe Thr Thr Lys Lys Gly Gln Gln Phe Cys Gly Asp
        35                  40                  45

Pro Lys Gln Glu Trp Val Gln Arg Tyr Met Lys Asn Leu Asp Ala Lys
    50                  55                  60

(2) INFORMATION FOR SEQ ID NO: 88:

(i) SEQUENCE CHARACTERISTICS:
        (A) LENGTH: 65 amino acids
        (B) TYPE: amino acid
        (D) TOPOLOGY: linear (ii) MOLECULE TYPE: protein (xi) SEQUENCE DESCRIPTION: SEQ ID NO: 88:

```
Met Pro Ser Pro Cys Cys Met Phe Phe Val Ser Lys Arg Ile Pro Glu
1               5                   10                  15

Asn Arg Val Val Ser Tyr Gln Leu Ser Ser Arg Ser Thr Cys Leu Lys
            20                  25                  30

Ala Gly Val Ile Phe Thr Thr Lys Lys Gly Gln Gln Phe Cys Gly Asp
            35                  40                  45

Pro Lys Gln Glu Trp Val Gln Arg Tyr Met Lys Asn Leu Asp Ala Lys
        50                  55                  60

Gln
65

(2) INFORMATION FOR SEQ ID NO: 89:

(i) SEQUENCE CHARACTERISTICS:
        (A) LENGTH: 66 amino acids
        (B) TYPE: amino acid
        (D) TOPOLOGY: linear (ii) MOLECULE TYPE: protein (xi) SEQUENCE DESCRIPTION: SEQ ID NO: 89:

Met Pro Ser Pro Cys Cys Met Phe Phe Val Ser Lys Arg Ile Pro Glu
1               5                   10                  15

Asn Arg Val Val Ser Tyr Gln Leu Ser Ser Arg Ser Thr Cys Leu Lys
            20                  25                  30

Ala Gly Val Ile Phe Thr Thr Lys Lys Gly Gln Gln Phe Cys Gly Asp
            35                  40                  45

Pro Lys Gln Glu Trp Val Gln Arg Tyr Met Lys Asn Leu Asp Ala Lys
        50                  55                  60

Gln Lys
65

(2) INFORMATION FOR SEQ ID NO: 90:

(i) SEQUENCE CHARACTERISTICS:
        (A) LENGTH: 67 amino acids
        (B) TYPE: amino acid
        (D) TOPOLOGY: linear (ii) MOLECULE TYPE: protein (xi) SEQUENCE DESCRIPTION: SEQ ID NO: 90:

Met Pro Ser Pro Cys Cys Met Phe Phe Val Ser Lys Arg Ile Pro Glu
1               5                   10                  15

Asn Arg Val Val Ser Tyr Gln Leu Ser Ser Arg Ser Thr Cys Leu Lys
            20                  25                  30

Ala Gly Val Ile Phe Thr Thr Lys Lys Gly Gln Gln Phe Cys Gly Asp
            35                  40                  45

Pro Lys Gln Glu Trp Val Gln Arg Tyr Met Lys Asn Leu Asp Ala Lys
        50                  55                  60

Gln Lys Lys
65

(2) INFORMATION FOR SEQ ID NO: 91:

(i) SEQUENCE CHARACTERISTICS:
        (A) LENGTH: 68 amino acids
        (B) TYPE: amino acid
        (D) TOPOLOGY: linear (ii) MOLECULE TYPE: protein
```

(xi) SEQUENCE DESCRIPTION: SEQ ID NO: 91:

Met Pro Ser Pro Cys Cys Met Phe Phe Val Ser Lys Arg Ile Pro Glu
1               5                   10                  15

Asn Arg Val Val Ser Tyr Gln Leu Ser Ser Arg Ser Thr Cys Leu Lys
            20                  25                  30

Ala Gly Val Ile Phe Thr Thr Lys Lys Gly Gln Gln Phe Cys Gly Asp
        35                  40                  45

Pro Lys Gln Glu Trp Val Gln Arg Tyr Met Lys Asn Leu Asp Ala Lys
    50                  55                  60

Gln Lys Lys Ala
65

(2) INFORMATION FOR SEQ ID NO: 92:

(i) SEQUENCE CHARACTERISTICS:
        (A) LENGTH: 69 amino acids
        (B) TYPE: amino acid
        (D) TOPOLOGY: linear (ii) MOLECULE TYPE: protein (xi) SEQUENCE DESCRIPTION: SEQ ID NO: 92:

Met Pro Ser Pro Cys Cys Met Phe Phe Val Ser Lys Arg Ile Pro Glu
1               5                   10                  15

Asn Arg Val Val Ser Tyr Gln Leu Ser Ser Arg Ser Thr Cys Leu Lys
            20                  25                  30

Ala Gly Val Ile Phe Thr Thr Lys Lys Gly Gln Gln Phe Cys Gly Asp
        35                  40                  45

Pro Lys Gln Glu Trp Val Gln Arg Tyr Met Lys Asn Leu Asp Ala Lys
    50                  55                  60

Gln Lys Lys Ala Ser
65

(2) INFORMATION FOR SEQ ID NO: 93:

(i) SEQUENCE CHARACTERISTICS:
        (A) LENGTH: 70 amino acids
        (B) TYPE: amino acid
        (D) TOPOLOGY: linear (ii) MOLECULE TYPE: protein (xi) SEQUENCE DESCRIPTION: SEQ ID NO: 93:

Met Pro Ser Pro Cys Cys Met Phe Phe Val Ser Lys Arg Ile Pro Glu
1               5                   10                  15

Asn Arg Val Val Ser Tyr Gln Leu Ser Ser Arg Ser Thr Cys Leu Lys
            20                  25                  30

Ala Gly Val Ile Phe Thr Thr Lys Lys Gly Gln Gln Phe Cys Gly Asp
        35                  40                  45

Pro Lys Gln Glu Trp Val Gln Arg Tyr Met Lys Asn Leu Asp Ala Lys
    50                  55                  60

Gln Lys Lys Ala Ser Pro
65              70

(2) INFORMATION FOR SEQ ID NO: 94:

(i) SEQUENCE CHARACTERISTICS:
        (A) LENGTH: 71 amino acids
        (B) TYPE: amino acid
        (D) TOPOLOGY: linear (ii) MOLECULE TYPE: protein (xi) SEQUENCE DESCRIPTION: SEQ ID NO: 94:

Met Pro Ser Pro Cys Cys Met Phe Phe Val Ser Lys Arg Ile Pro Glu
1               5                   10                  15

Asn Arg Val Val Ser Tyr Gln Leu Ser Ser Arg Ser Thr Cys Leu Lys
            20                  25                  30

Ala Gly Val Ile Phe Thr Thr Lys Lys Gly Gln Gln Phe Cys Gly Asp
                35                  40                  45

Pro Lys Gln Glu Trp Val Gln Arg Tyr Met Lys Asn Leu Asp Ala Lys
    50                  55                  60

Gln Lys Lys Ala Ser Pro Arg
65                  70

(2) INFORMATION FOR SEQ ID NO: 95:

(i) SEQUENCE CHARACTERISTICS:
        (A) LENGTH: 72 amino acids
        (B) TYPE: amino acid
        (D) TOPOLOGY: linear (ii) MOLECULE TYPE: protein (xi) SEQUENCE DESCRIPTION: SEQ ID NO: 95:

Met Pro Ser Pro Cys Cys Met Phe Phe Val Ser Lys Arg Ile Pro Glu
1               5                   10                  15

Asn Arg Val Val Ser Tyr Gln Leu Ser Ser Arg Ser Thr Cys Leu Lys
            20                  25                  30

Ala Gly Val Ile Phe Thr Thr Lys Lys Gly Gln Gln Phe Cys Gly Asp
                35                  40                  45

Pro Lys Gln Glu Trp Val Gln Arg Tyr Met Lys Asn Leu Asp Ala Lys
    50                  55                  60

Gln Lys Lys Ala Ser Pro Arg Ala
65                  70

(2) INFORMATION FOR SEQ ID NO: 96:

(i) SEQUENCE CHARACTERISTICS:
        (A) LENGTH: 73 amino acids
        (B) TYPE: amino acid
        (D) TOPOLOGY: linear (ii) MOLECULE TYPE: protein (xi) SEQUENCE DESCRIPTION: SEQ ID NO: 96:

Met Pro Ser Pro Cys Cys Met Phe Phe Val Ser Lys Arg Ile Pro Glu
1               5                   10                  15

Asn Arg Val Val Ser Tyr Gln Leu Ser Ser Arg Ser Thr Cys Leu Lys
            20                  25                  30

Ala Gly Val Ile Phe Thr Thr Lys Lys Gly Gln Gln Phe Cys Gly Asp
                35                  40                  45

Pro Lys Gln Glu Trp Val Gln Arg Tyr Met Lys Asn Leu Asp Ala Lys
    50                  55                  60

Gln Lys Lys Ala Ser Pro Arg Ala Arg
65                  70

(2) INFORMATION FOR SEQ ID NO: 97:

(i) SEQUENCE CHARACTERISTICS:
        (A) LENGTH: 74 amino acids (B) TYPE: amino acid
        (D) TOPOLOGY: linear (ii) MOLECULE TYPE: protein (xi) SEQUENCE DESCRIPTION: SEQ ID NO: 97:

Met Pro Ser Pro Cys Cys Met Phe Phe Val Ser Lys Arg Ile Pro Glu
1               5                   10                  15

Asn Arg Val Val Ser Tyr Gln Leu Ser Ser Arg Ser Thr Cys Leu Lys
            20                  25                  30

Ala Gly Val Ile Phe Thr Thr Lys Lys Gly Gln Gln Phe Cys Gly Asp
        35                  40                  45

Pro Lys Gln Glu Trp Val Gln Arg Tyr Met Lys Asn Leu Asp Ala Lys
    50                  55                  60

Gln Lys Lys Ala Ser Pro Arg Ala Arg Ala
65                  70

(2) INFORMATION FOR SEQ ID NO: 98:

(i) SEQUENCE CHARACTERISTICS:
        (A) LENGTH: 75 amino acids
        (B) TYPE: amino acid
        (D) TOPOLOGY: linear (ii) MOLECULE TYPE: protein (xi) SEQUENCE DESCRIPTION: SEQ ID NO: 98:

Met Pro Ser Pro Cys Cys Met Phe Phe Val Ser Lys Arg Ile Pro Glu
1               5                   10                  15

Asn Arg Val Val Ser Tyr Gln Leu Ser Ser Arg Ser Thr Cys Leu Lys
            20                  25                  30

Ala Gly Val Ile Phe Thr Thr Lys Lys Gly Gln Gln Phe Cys Gly Asp
        35                  40                  45

Pro Lys Gln Glu Trp Val Gln Arg Tyr Met Lys Asn Leu Asp Ala Lys
    50                  55                  60

Gln Lys Lys Ala Ser Pro Arg Ala Arg Ala Val
65                  70                  75

(2) INFORMATION FOR SEQ ID NO: 99:

(i) SEQUENCE CHARACTERISTICS:
        (A) LENGTH: 76 amino acids
        (B) TYPE: amino acid
        (D) TOPOLOGY: linear (ii) MOLECULE TYPE: protein (xi) SEQUENCE DESCRIPTION: SEQ ID NO: 99:

Met Pro Ser Pro Cys Cys Met Phe Phe Val Ser Lys Arg Ile Pro Glu
1               5                   10                  15

Asn Arg Val Val Ser Tyr Gln Leu Ser Ser Arg Ser Thr Cys Leu Lys
            20                  25                  30

Ala Gly Val Ile Phe Thr Thr Lys Lys Gly Gln Gln Phe Cys Gly Asp
        35                  40                  45

Pro Lys Gln Glu Trp Val Gln Arg Tyr Met Lys Asn Leu Asp Ala Lys
    50                  55                  60

Gln Lys Lys Ala Ser Pro Arg Ala Arg Ala Val Ala
65                  70                  75

(2) INFORMATION FOR SEQ ID NO: 100:

```
     (i) SEQUENCE CHARACTERISTICS:
         (A) LENGTH: 77 amino acids
         (B) TYPE: amino acid
         (D) TOPOLOGY: linear (ii) MOLECULE TYPE: protein (xi) SEQUENCE DESCRIPTION: SEQ ID NO: 100:

Met Pro Ser Pro Cys Cys Met Phe Phe Val Ser Lys Arg Ile Pro Glu
1               5                   10                  15

Asn Arg Val Val Ser Tyr Gln Leu Ser Ser Arg Ser Thr Cys Leu Lys
            20                  25                  30

Ala Gly Val Ile Phe Thr Thr Lys Lys Gly Gln Gln Phe Cys Gly Asp
        35                  40                  45

Pro Lys Gln Glu Trp Val Gln Arg Tyr Met Lys Asn Leu Asp Ala Lys
    50                  55                  60

Gln Lys Lys Ala Ser Pro Arg Ala Arg Ala Val Ala Val
65                  70                  75

(2) INFORMATION FOR SEQ ID NO: 101:

(i) SEQUENCE CHARACTERISTICS:
         (A) LENGTH: 78 amino acids
         (B) TYPE: amino acid
         (D) TOPOLOGY: linear (ii) MOLECULE TYPE: protein (xi) SEQUENCE DESCRIPTION: SEQ ID NO: 101:

Met Pro Ser Pro Cys Cys Met Phe Phe Val Ser Lys Arg Ile Pro Glu
1               5                   10                  15

Asn Arg Val Val Ser Tyr Gln Leu Ser Ser Arg Ser Thr Cys Leu Lys
            20                  25                  30

Ala Gly Val Ile Phe Thr Thr Lys Lys Gly Gln Gln Phe Cys Gly Asp
        35                  40                  45

Pro Lys Gln Glu Trp Val Gln Arg Tyr Met Lys Asn Leu Asp Ala Lys
    50                  55                  60

Gln Lys Lys Ala Ser Pro Arg Ala Arg Ala Val Ala Val Lys
65                  70                  75

(2) INFORMATION FOR SEQ ID NO: 102:

(i) SEQUENCE CHARACTERISTICS:
         (A) LENGTH: 79 amino acids
         (B) TYPE: amino acid
         (D) TOPOLOGY: linear (ii) MOLECULE TYPE: protein (xi) SEQUENCE DESCRIPTION: SEQ ID NO: 102:

Met Pro Ser Pro Cys Cys Met Phe Phe Val Ser Lys Arg Ile Pro Glu
1               5                   10                  15

Asn Arg Val Val Ser Tyr Gln Leu Ser Ser Arg Ser Thr Cys Leu Lys
            20                  25                  30

Ala Gly Val Ile Phe Thr Thr Lys Lys Gly Gln Gln Phe Cys Gly Asp
        35                  40                  45

Pro Lys Gln Glu Trp Val Gln Arg Tyr Met Lys Asn Leu Asp Ala Lys
    50                  55                  60

Gln Lys Lys Ala Ser Pro Arg Ala Arg Ala Val Ala Val Lys Gly
65                  70                  75
```

(2) INFORMATION FOR SEQ ID NO: 103:

(i) SEQUENCE CHARACTERISTICS:
        (A) LENGTH: 80 amino acids
        (B) TYPE: amino acid
        (D) TOPOLOGY: linear (ii) MOLECULE TYPE: protein (xi) SEQUENCE DESCRIPTION: SEQ ID NO: 103:

```
Met Pro Ser Pro Cys Cys Met Phe Phe Val Ser Lys Arg Ile Pro Glu
 1               5                  10                  15

Asn Arg Val Val Ser Tyr Gln Leu Ser Ser Arg Ser Thr Cys Leu Lys
            20                  25                  30

Ala Gly Val Ile Phe Thr Thr Lys Lys Gly Gln Gln Phe Cys Gly Asp
        35                  40                  45

Pro Lys Gln Glu Trp Val Gln Arg Tyr Met Lys Asn Leu Asp Ala Lys
    50                  55                  60

Gln Lys Lys Ala Ser Pro Arg Ala Arg Ala Val Ala Val Lys Gly Pro
65                  70                  75                  80
```

(2) INFORMATION FOR SEQ ID NO: 104:

(i) SEQUENCE CHARACTERISTICS:
        (A) LENGTH: 81 amino acids
        (B) TYPE: amino acid
        (D) TOPOLOGY: linear (ii) MOLECULE TYPE: protein (xi) SEQUENCE DESCRIPTION: SEQ ID NO: 104:

```
Met Pro Ser Pro Cys Cys Met Phe Phe Val Ser Lys Arg Ile Pro Glu
 1               5                  10                  15

Asn Arg Val Val Ser Tyr Gln Leu Ser Ser Arg Ser Thr Cys Leu Lys
            20                  25                  30

Ala Gly Val Ile Phe Thr Thr Lys Lys Gly Gln Gln Phe Cys Gly Asp
        35                  40                  45

Pro Lys Gln Glu Trp Val Gln Arg Tyr Met Lys Asn Leu Asp Ala Lys
    50                  55                  60

Gln Lys Lys Ala Ser Pro Arg Ala Arg Ala Val Ala Val Lys Gly Pro
65                  70                  75                  80

Val
```

(2) INFORMATION FOR SEQ ID NO: 105:

(i) SEQUENCE CHARACTERISTICS:
        (A) LENGTH: 82 amino acids
        (B) TYPE: amino acid
        (D) TOPOLOGY: linear (ii) MOLECULE TYPE: protein (xi) SEQUENCE DESCRIPTION: SEQ ID NO: 105:

```
Met Pro Ser Pro Cys Cys Met Phe Phe Val Ser Lys Arg Ile Pro Glu
 1               5                  10                  15

Asn Arg Val Val Ser Tyr Gln Leu Ser Ser Arg Ser Thr Cys Leu Lys
            20                  25                  30

Ala Gly Val Ile Phe Thr Thr Lys Lys Gly Gln Gln Phe Cys Gly Asp
        35                  40                  45

Pro Lys Gln Glu Trp Val Gln Arg Tyr Met Lys Asn Leu Asp Ala Lys
    50                  55                  60
```

-continued

```
Gln Lys Lys Ala Ser Pro Arg Ala Arg Ala Val Ala Val Lys Gly Pro
 65                  70                  75                  80

Val Gln (2) INFORMATION FOR SEQ ID NO: 106:

(i) SEQUENCE CHARACTERISTICS:
        (A) LENGTH: 83 amino acids
        (B) TYPE: amino acid
        (D) TOPOLOGY: linear (ii) MOLECULE TYPE: protein (xi) SEQUENCE DESCRIPTION: SEQ ID NO: 106:

Met Pro Ser Pro Cys Cys Met Phe Phe Val Ser Lys Arg Ile Pro Glu
  1               5                  10                  15

Asn Arg Val Val Ser Tyr Gln Leu Ser Ser Arg Ser Thr Cys Leu Lys
                 20                  25                  30

Ala Gly Val Ile Phe Thr Thr Lys Lys Gly Gln Gln Phe Cys Gly Asp
             35                  40                  45

Pro Lys Gln Glu Trp Val Gln Arg Tyr Met Lys Asn Leu Asp Ala Lys
 50                  55                  60

Gln Lys Lys Ala Ser Pro Arg Ala Arg Ala Val Ala Val Lys Gly Pro
 65                  70                  75                  80

Val Gln Arg (2) INFORMATION FOR SEQ ID NO: 107:

(i) SEQUENCE CHARACTERISTICS:
        (A) LENGTH: 84 amino acids
        (B) TYPE: amino acid
        (D) TOPOLOGY: linear (ii) MOLECULE TYPE: protein (xi) SEQUENCE DESCRIPTION: SEQ ID NO: 107:

Met Pro Ser Pro Cys Cys Met Phe Phe Val Ser Lys Arg Ile Pro Glu
  1               5                  10                  15

Asn Arg Val Val Ser Tyr Gln Leu Ser Ser Arg Ser Thr Cys Leu Lys
                 20                  25                  30

Ala Gly Val Ile Phe Thr Thr Lys Lys Gly Gln Gln Phe Cys Gly Asp
             35                  40                  45

Pro Lys Gln Glu Trp Val Gln Arg Tyr Met Lys Asn Leu Asp Ala Lys
 50                  55                  60

Gln Lys Lys Ala Ser Pro Arg Ala Arg Ala Val Ala Val Lys Gly Pro
 65                  70                  75                  80

Val Gln Arg Tyr (2) INFORMATION FOR SEQ ID NO: 108:

(i) SEQUENCE CHARACTERISTICS:
        (A) LENGTH: 85 amino acids
        (B) TYPE: amino acid
        (D) TOPOLOGY: linear (ii) MOLECULE TYPE: protein (xi) SEQUENCE DESCRIPTION: SEQ ID NO: 108:

Met Pro Ser Pro Cys Cys Met Phe Phe Val Ser Lys Arg Ile Pro Glu
  1               5                  10                  15

Asn Arg Val Val Ser Tyr Gln Leu Ser Ser Arg Ser Thr Cys Leu Lys
```

```
              20                  25                  30
Ala Gly Val Ile Phe Thr Thr Lys Lys Gly Gln Gln Phe Cys Gly Asp
            35                  40                  45

Pro Lys Gln Glu Trp Val Gln Arg Tyr Met Lys Asn Leu Asp Ala Lys
        50                  55                  60

Gln Lys Lys Ala Ser Pro Arg Ala Arg Ala Val Ala Val Lys Gly Pro
65                  70                  75                  80

Val Gln Arg Tyr Pro
                85

(2) INFORMATION FOR SEQ ID NO: 109:

(i) SEQUENCE CHARACTERISTICS:
        (A) LENGTH: 86 amino acids
        (B) TYPE: amino acid
        (D) TOPOLOGY: linear (ii) MOLECULE TYPE: protein (xi) SEQUENCE DESCRIPTION: SEQ ID NO: 109:

Met Pro Ser Pro Cys Cys Met Phe Phe Val Ser Lys Arg Ile Pro Glu
1               5                  10                  15

Asn Arg Val Val Ser Tyr Gln Leu Ser Ser Arg Ser Thr Cys Leu Lys
            20                  25                  30

Ala Gly Val Ile Phe Thr Thr Lys Lys Gly Gln Gln Phe Cys Gly Asp
        35                  40                  45

Pro Lys Gln Glu Trp Val Gln Arg Tyr Met Lys Asn Leu Asp Ala Lys
    50                  55                  60

Gln Lys Lys Ala Ser Pro Arg Ala Arg Ala Val Ala Val Lys Gly Pro
65                  70                  75                  80

Val Gln Arg Tyr Pro Gly
                85

(2) INFORMATION FOR SEQ ID NO: 110:

(i) SEQUENCE CHARACTERISTICS:
        (A) LENGTH: 87 amino acids
        (B) TYPE: amino acid
        (D) TOPOLOGY: linear (ii) MOLECULE TYPE: protein (xi) SEQUENCE DESCRIPTION: SEQ ID NO: 110:

Met Pro Ser Pro Cys Cys Met Phe Phe Val Ser Lys Arg Ile Pro Glu
1               5                  10                  15

Asn Arg Val Val Ser Tyr Gln Leu Ser Ser Arg Ser Thr Cys Leu Lys
            20                  25                  30

Ala Gly Val Ile Phe Thr Thr Lys Lys Gly Gln Gln Phe Cys Gly Asp
        35                  40                  45

Pro Lys Gln Glu Trp Val Gln Arg Tyr Met Lys Asn Leu Asp Ala Lys
    50                  55                  60

Gln Lys Lys Ala Ser Pro Arg Ala Arg Ala Val Ala Val Lys Gly Pro
65                  70                  75                  80

Val Gln Arg Tyr Pro Gly Asn
                85

(2) INFORMATION FOR SEQ ID NO: 111:

(i) SEQUENCE CHARACTERISTICS:
        (A) LENGTH: 88 amino acids
```

-continued

```
        (B) TYPE: amino acid
        (D) TOPOLOGY: linear (ii) MOLECULE TYPE: protein (xi) SEQUENCE DESCRIPTION: SEQ ID NO: 111:

Met Pro Ser Pro Cys Cys Met Phe Phe Val Ser Lys Arg Ile Pro Glu
1               5                   10                  15

Asn Arg Val Val Ser Tyr Gln Leu Ser Ser Arg Ser Thr Cys Leu Lys
            20                  25                  30

Ala Gly Val Ile Phe Thr Thr Lys Lys Gly Gln Gln Phe Cys Gly Asp
        35                  40                  45

Pro Lys Gln Glu Trp Val Gln Arg Tyr Met Lys Asn Leu Asp Ala Lys
    50                  55                  60

Gln Lys Lys Ala Ser Pro Arg Ala Arg Ala Val Ala Val Lys Gly Pro
65                  70                  75                  80

Val Gln Arg Tyr Pro Gly Asn Gln
                85

(2) INFORMATION FOR SEQ ID NO: 112:

(i) SEQUENCE CHARACTERISTICS:
        (A) LENGTH: 89 amino acids
        (B) TYPE: amino acid
        (D) TOPOLOGY: linear (ii) MOLECULE TYPE: protein (xi) SEQUENCE DESCRIPTION: SEQ ID NO: 112:

Met Pro Ser Pro Cys Cys Met Phe Phe Val Ser Lys Arg Ile Pro Glu
1               5                   10                  15

Asn Arg Val Val Ser Tyr Gln Leu Ser Ser Arg Ser Thr Cys Leu Lys
            20                  25                  30

Ala Gly Val Ile Phe Thr Thr Lys Lys Gly Gln Gln Phe Cys Gly Asp
        35                  40                  45

Pro Lys Gln Glu Trp Val Gln Arg Tyr Met Lys Asn Leu Asp Ala Lys
    50                  55                  60

Gln Lys Lys Ala Ser Pro Arg Ala Arg Ala Val Ala Val Lys Gly Pro
65                  70                  75                  80

Val Gln Arg Tyr Pro Gly Asn Gln Thr
                85

(2) INFORMATION FOR SEQ ID NO: 113:

(i) SEQUENCE CHARACTERISTICS:
        (A) LENGTH: 90 amino acids
        (B) TYPE: amino acid
        (D) TOPOLOGY: linear (ii) MOLECULE TYPE: protein (xi) SEQUENCE DESCRIPTION: SEQ ID NO: 113:

Met Pro Ser Pro Cys Cys Met Phe Phe Val Ser Lys Arg Ile Pro Glu
1               5                   10                  15

Asn Arg Val Val Ser Tyr Gln Leu Ser Ser Arg Ser Thr Cys Leu Lys
            20                  25                  30

Ala Gly Val Ile Phe Thr Thr Lys Lys Gly Gln Gln Phe Cys Gly Asp
        35                  40                  45

Pro Lys Gln Glu Trp Val Gln Arg Tyr Met Lys Asn Leu Asp Ala Lys
    50                  55                  60
```

-continued

```
Gln Lys Lys Ala Ser Pro Arg Ala Arg Ala Val Ala Val Lys Gly Pro
 65                  70                  75                  80

Val Gln Arg Tyr Pro Gly Asn Gln Thr Thr
                 85                  90
```

(2) INFORMATION FOR SEQ ID NO: 114:

(i) SEQUENCE CHARACTERISTICS:
        (A) LENGTH: 91 amino acids
        (B) TYPE: amino acid
        (D) TOPOLOGY: linear (ii) MOLECULE TYPE: protein (xi) SEQUENCE DESCRIPTION: SEQ ID NO: 114:

```
Met Pro Ser Pro Cys Cys Met Phe Phe Val Ser Lys Arg Ile Pro Glu
  1              5                  10                  15

Asn Arg Val Val Ser Tyr Gln Leu Ser Ser Arg Ser Thr Cys Leu Lys
                 20                  25                  30

Ala Gly Val Ile Phe Thr Thr Lys Lys Gly Gln Gln Phe Cys Gly Asp
                 35                  40                  45

Pro Lys Gln Glu Trp Val Gln Arg Tyr Met Lys Asn Leu Asp Ala Lys
     50                  55                  60

Gln Lys Lys Ala Ser Pro Arg Ala Arg Ala Val Ala Val Lys Gly Pro
 65                  70                  75                  80

Val Gln Arg Tyr Pro Gly Asn Gln Thr Thr Cys
                 85                  90
```

METHODS OF USING CHEMOKINE BETA-6

This application is a divisional of U.S. application Ser. No. 09/419,281, filed Oct. 15, 1999, now U.S. Pat. No. 6,379,926, which is a divisional of U.S. application Ser. No. 08/995,156, filed Dec. 19, 1997, now U.S. Pat. No. 6,028,169, which claims the benefit of U.S. Provisional Application No. 60/042,269, filed Mar. 31, 1997, all of which disclosures are herein incorporated by reference.

BACKGROUND OF THE INVENTION

1. Field of the Invention

The present invention relates to human chemokine β-6 agonist and antagonist polypeptides and DNA (RNA) encoding such polypeptides and a procedure for producing such polypeptides by recombinant techniques. The chemokine β-6 antagonists of the present invention may be employed to treat rheumatoid arthritis, lung inflammation, allergy, asthma, infectious diseases and to prevent inflammation and atherosclerosis. The chemokine β-6 agonists may be empoyled to myeloprotect patients undergoing chemotherapy. Chemokine β-6 (Ckβ-6) is also refered to herein as MPIF-2 and eotaxin-2.

2. Related Art

There are three forms of monocyte chemotactic protein, namely, MCP-1, MCP-2 and MCP-3. All of these proteins have been structurally and functionally characterized and have also been cloned and expressed. MCP-1 and MCP-2 have the ability to attract leukocytes (monocytes, and leukocytes), while MCP-3 also attracts eosinophils and T lymphocytes (Dahinderi, E., et al, *J. Exp. Med.* 179:751–756 (1994)).

Initially, human monocyte-specific attracting factor, was purified from a glioma cell line and a monocytic cell line. Matsushima, K., et al, *J. Exp. Med.* 169:1485–1490 (1989). This factor was originally designated glioma-derived chemotactic factor (GDCF) and monocyte chemotactic and activating factor (MCAF) by Matsushima, et al. This factor is now referred to as MCP-1. Subsequent cloning of the cDNA for MCP-1 showed it to be highly similar to the murine JE gene. The JE gene could be massively induced in murine fibroblasts by platelet-derived growth factor. Cochran, B. H., et al, *Cell* 33:939–947 (1983). Murine JE is highly similar to MCP-1. The MCP-1 protein is 62% identical to murine JE in a region of 68 shared N-terminal residues. It is widely accepted that JE and MCP-1 are species homologs.

A method of suppressing tumor formation in a vertebrate by administering JE/MCP-1 has been disclosed in PCT application WO-92/20372, along with methods of treating localized complications of malignancies and methods of combatting parasitic infection by administering JE/MCP-1. Expression of the JE/MCP-1 protein in malignant cells was found to suppress the cells ability to form tumors in vivo.

Human MCP-1 is a basic peptide of 76 amino acids with a predicted molecular mass of 8,700 daltons. MCP-1 is inducibly expressed mainly in monocytes, endothelial cells and fibroblasts. Leonard, E. J. and Yoshimura, T., *Immunol. Today* 11:97–101 (1990). The factors which induce this expression is IL-1, TNF or lipopolysaccharide treatment.

Other properties of MCP-1 include the ability to strongly activate mature human basophils in a pertussis toxin-sensitive manner. MCP-1 is a cytokine capable of directly inducing histamine release by basophils, (Bischoff, S. C., et al., *J. Exp. Med.* 175:1271–1275 (1992)). Furthermore, MCP-1 promotes the formation of leukotriene C4 by basophils pretreated with Interleukin 3, Interleukin 5, or granulocyte/macrophage colony-stimulating factor. MCP-1 induced basophil mediator release may play an important role in allergic inflammation and other pathologies expressing MCP-1.

Clones having a nucleotide sequence encoding a human monocyte chemotactic and activating factor (MCAF) reveal the primary structure of the MCAF polypeptide to be composed of a putative signal peptide sequence of 23 amino acid residues and a mature MCAF sequence of 76 amino acid residues. Furutani, Y. H., et al., *Biochem. Biophys. Res. Commu.* 159:249–55 (1989). The complete amino acid sequence of human glioma-derived monocyte chemotactic factor (GDCF-2) has also been determined. This peptide attracts human monocytes but not neutrophils. It was established that GDCF-2 comprises 76 amino acid residues. The peptide chain contains 4 half-cysteines, at positions 11, 12, 36 and 52, which create a pair of loops, clustered at the disulfide bridges. Further, the MCP-1 gene has been designated to human chromosome 17. Mehrabian, M. R., et al., *Genomics* 9:200–3 (1991).

Certain data suggests that a potential role for MCP-1 is mediating monocytic infiltration of the artery wall. Monocytes appear to be central to atherogenesis both as the progenitors of foam cells and as a potential source of growth factors mediating intimal hyperplasia Nelken, N. A., et al., *J. Clin. Invest.* 88:1121–7(1991). It has also been found that synovial production of MCP-1 may play an important role in the recruitment of mononuclear phagocytes during inflammation associated with rheumatoid arthritis and that synovial tissue macrophages are the dominant source of this cytokine. MCP-1 levels were found to be significantly higher in synovial fluid from rheumatoid arthritis patients compared to synovial fluid from osteoarthritis patients or from patients with other arthritides. Koch, A. E., et al., *J. Clin. Invest.* 90:772–9 (1992).

MCP-2 and MCP-3 are classified in a subfamily of proinflammatory proteins and are functionally related to MCP-1 because they specifically attract monocytes, but not neutrophils. Van Damme, J., et al., *J. Exp. Med.* 176:59–65 (1992). MCP-3 shows-71% and 58% amino acid homology to MCP-1 and MCP-2 respectively. MCP-3 is an inflammatory cytokine that regulates macrophage functions.

The transplantation of hemolymphopoietic stem cells has been proposed in the treatment of cancer and hematological disorders. Many studies demonstrate that transplantation of hematopoietic stem cells harvested from the peripheral blood has advantages over the transplantation of marrow-derived stem cells. Due to the low number of circulating stem cells, there is a need for induction of pluripotent marrow stem cell mobilization into the peripheral blood. Reducing the amount of blood to be processed to obtain an adequate amount of stem cells would increase the use of autotransplantation procedures and eliminate the risk of graph versus host reaction connected with allotransplantation. Presently, blood mobilization of marrow CD34$^+$ stem cells is obtained by the injection of a combination of agents, including antiblastic drugs and G-CSF or GM-CSF. Drugs which are capable of stem cell mobilization include IL-1, IL-7, IL-8, and NIP-1a Both IL-1 and IL-8 demonstrate proinflammatory activity that may be dangerous for good engrafting. IL-7 must be administered at high doses over a long duration and MIP-1a is not very active as a single agent and shows best activity when in combination with G-CSF.

SUMMARY OF THE INVENTION

In accordance with one aspect of the present invention, there is provided a novel full-length or mature polypeptide, as well as biologically active, diagnostically or therapeutically useful fragments, analogs and derivatives thereof. The polypeptide of the present invention is of human origin.

In accordance with another aspect of the present invention, there are provided isolated nucleic acid molecules encoding a polypeptide of the present invention including mRNAs, DNAs, cDNAs, genomic DNAs as well as analogs and biologically active and diagnostically or therapeutically useful fragments, analogs and derivatives thereof.

The present invention also provides isolated nucleic acid molecules comprising a polynucleotide encoding the Ckβ-6 polypeptide having the amino acid sequence shown in FIG. 1 (SEQ ID NO:2) or the amino acid sequence encoded by the cDNA clone deposited as ATCC Deposit No. 75703 on Mar. 10, 1994. The nucleotide sequence determined, at least in part, by sequencing the deposited Ckβ-6 clone, which is shown in FIG. 1 (SEQ ID NO: 1), contains an open reading frame encoding a polypeptide of 119 amino acid residues, with a leader of about 26 amino acid residues. The amino acid sequence of the mature Ckβ-6 protein is shown in FIG. 1, as amino acid residues 1–93 of SEQ ID NO:2.

Thus, one aspect of the invention provides an isolated nucleic acid molecule comprising a polynucleotide having a nucleotide sequence selected from the group consisting of: (a) a nucleotide sequence encoding an Ckβ-6 polypeptide having the complete amino acid sequence in FIG. 1 (SEQ ID NO:2); (b) a nucleotide sequence encoding an Ckβ-6 polypeptide having the complete amino acid sequence in FIG. 1 (SEQ ID NO:2) excepting the N-terminal methionine; (c) a nucleotide sequence encoding an Ckβ-6 polypeptide having the amino acid sequence at positions 1–93 in FIG. 1 (SEQ ID NO-2); (d) a nucleotide sequence encoding the Ckβ-6 polypeptide having the complete amino acid sequence encoded by the cDNA clone contained in ATCC Deposit No. 75703; (e) a nucleotide sequence encoding the Ckβ-6 polypeptide having the complete amino acid sequence encoded by the cDNA clone contained in ATCC Deposit No. 75703 excepting the N-terminal methionine; (f) a nucleotide sequence encoding the mature Ckβ-6 polypeptide having the amino acid sequence encoded by the cDNA clone contained in ATCC Deposit No. 75703; and (g) a nucleotide sequence complementary to any of the nucleotide sequences in (a), (b), (c), (d), (e) or (f) above.

The present invention further relates to variants of the hereinabove described polynucleotides which encode fragments, analogs and derivatives of the Ckβ-6 polypeptide having the deduced amino acid sequence of FIG. 1 (SEQ ID NO:2) or the polypeptides encoded by the cDNA of the deposited clone. The variants of the polynucleotides can be a naturally occurring allelic variant of the polynucleotides or a non-naturally ocurring variant of the polynucleotides.

Further embodiments of the invention include islolated nucleic acid molecules that comprise a polynucleotide having a nucleotide sequence at least 90% homologous or identical, and more preferably at least 95%, 96%, 97%, 98%, or 99% identical, to any of the nucleotide sequences in (a), (b), (c), (d), (e), (f) or (g), above, or a polynucleotide which hybridizes under stringent hybridization conditions to a polynucleotide in (a), (b), (c), (d), (e), (f) or (g), above. These polynucleotides which hybridize do not hybridize under stringent hybridization conditions to a polynucleotide having a nucleotide sequence consisting of only A residues or of only T residues.

The present invention also relates to recombinant vectors, which include the isolated nucleic acid molecules of the present invention, and to host cells containing the recombinant vectors, as well as to methods of making such vectors and host cells.

In accordance with yet a further aspect of the present invention, there is provided a process for producing such polypeptide by recombinant techniques comprising culturing recombinant prokaryotic and/or eukaryotic host cells, containing a nucleic acid sequence encoding a polypeptide of the present invention, under conditions promoting expression of said protein and subsequent recovery of said protein.

The invention further provides an isolated Ckβ-6 polypeptide having an amino acid sequence selected from the group consisting of: (a) the amino acid sequence of the Ckβ-6 polypeptide having the complete amino acid sequence, including the leader sequence shown in FIG. 1 (SEQ ID NO:2); (b) the amino acid sequence of the Ckβ-6 polypeptide having the complete amino acid sequence, including the leader sequence shown in FIG. 1, excepting the N-terminal methionine; (c) the amino acid sequence of the mature Ckβ-6 polypeptide (without the leader) having the amino acid sequence at positions 1–93 in FIG. 1 (SEQ ID NO:2); (d) the amino acid sequence of the Ckβ-6 polypeptide having the complete amino acid sequence, including the leader sequence, encoded by the cDNA clone contained in ATCC Deposit No. 75703; (e) the amino acid sequence of the Ckβ-6 polypeptide having the complete amino acid sequence, including the leader sequence, encoded by the cDNA clone contained in ATCC Deposit No. 75703, excepting the N-terminal methionine; and (f) the amino acid sequence of the mature Ckβ-6 polypeptide having the amino acid sequence encoded by the cDNA clone contained in ATCC Deposit No. 75703.

Polypeptides of the present invention also include homologous polypeptides having an amino acid sequence with at least 90% identity, and more preferably at least 95% identity to those described in (a), (b), (c), (d), (e) or (f) above, as well as polypeptides having an amino acid sequence at least 80% identical, more preferably at least 90% identical, and still more preferably 95%, 96%, 97%, 98% or 99% identical to those above.

An additional embodiment of this aspect of the invention relates to a peptide or polypeptide which has the amino acid sequence of an epitope bearing portion of an Ckβ-6 polypeptide having an amino acid sequence described in (a), (b), (c), (d), (e) or (f) above. Peptides or polypeptides having the amino acid sequence of an epitope bearing portion of an Ckβ-6 polypeptide of the invention include portions of an Ckβ-6 polypeptide with at least six or seven, preferably at least nine, and more preferably at least about 30 amino acids to about 50 amino acids, although epitope-bearing polypeptides of any length up to and including the entire amino acid sequence of a polypeptide of the invention described above also are included in the invention.

An additional nucleic acid embodiment of the invention relates to an isolated nucleic acid molecule comprising a polynucleotide which encodes the amino acid sequence of an epitope-bearing portion of an Ckβ-6 polypeptide having an amino acid sequence in (a), (b), (c), (d), (e) or (f), above.

The present invention also provides, in another aspect, pharmaceutical compositions comprising an Ckβ-6 polynucleotide, probe, vector, host cell, polypeptide, fragment, variant, derivative, epitope bearing portion, antibody, antagonist or agonist.

In accordance with yet a further aspect of the present invention, there is provided a process for utilizing such polypeptide, or polynucleotide encoding such polypeptide for therapeutic purposes, for example, for stem cell mobilization, myeloprotection and neuronal protection, to treat tumors, to promote wound healing, to combat parasitic infection and to regulate hematopoiesis.

An additional aspect of the invention is related to a method for treating an individual in need of an increased level of Ckβ-6 activity in the body comprising administering to such an individual a composition comprising a therapeutically effective amount of an isolated Ckβ-6 polypeptide of the invention or an agonist thereof.

A still further aspect of the invention is related to a method for treating an individual in need of a decreased level of Ckβ-6 activity in the body comprising, administering to such an individual a composition comprising a therapeutically effective amount of an Ckβ-6 antagonist. Preferred antagonists for use in the present invention are Ckβ-6 specific or CCR3 receptor specific antibodies.

In accordance with yet a further aspect of the present invention, there are provided antibodies against such polypeptides. In another embodiment, the invention provides an isolated antibody that binds specifically to an Ckβ-6 polypeptide having an amino acid sequence described in (a), (b), (c), (d), (e) or (f) above.

The invention further provides methods for isolating antibodies that bind specifically to an Ckβ-6 polypeptide having an amino acid sequence as described herein. Such antibodies are useful diagnostically or therapeutically as described below.

In accordance with another aspect of the present invention, there are provided agonists which mimic the polypeptide of the present invention and bind to receptors to elicit second messenger responses.

In accordance with yet another aspect of the present invention, there are provided antagonists to such polypeptides, which may be used to inhibit the action of such polypeptides, for example, in the treatment of rheumatoid arthritis, lung inflammation, histamine-mediated allergic reactions, infectious diseases, hyper-eosinophilic syndromes, silicosis, sarcoidosis and to prevent auto immune and chronic inflammation and atherosclerosis. Alternatively, such polypeptides can be used to inhibit production of IL-1 and TNFα, to treat aplastic anemia, myelodysplastic syndrome, asthma and arthritis.

In accordance with yet a further aspect of the present invention, there is also provided nucleic acid probes comprising nucleic acid molecules of sufficient length to specifically hybridize to a nucleic acid sequence of the present invention.

In accordance with still another aspect of the present invention, there are provided diagnostic assays for detecting diseases relating to underexpression or overexpression of the polypeptides and for detecting susceptibility to diseases related to mutations in the nucleic acid sequences encoding a polypeptide of the present invention.

In accordance with yet a further aspect of the present invention, there is provided a process for utilizing such polypeptides, or polynucleotides encoding such polypeptides, for in vitro purposes related to scientific research, for example, synthesis of DNA and manufacture of DNA vectors, for the purpose of developing therapeutics and diagnostics for the treatment of human disease.

The present invention also provides a screening method for identifying compounds capable of enhancing or inhibiting a cellular response induced by an Ckβ-6 polypeptide, which involves contacting cells which express the Ckβ-6 polypeptide with the candidate compound, assaying a cellular response, and comparing the cellular response to a standard cellular response, the standard being assayed when contact is made in absence of the candidate compound; whereby, an increased cellular response over the standard indicates that the compound is an agonist and a decreased cellular response over the standard indicates that the compound is an antagonist.

For a number of disorders, it is believed that significantly higher or lower levels of Ckβ-6 gene expression can be detected in certain tissues or bodily fluids (e.g., serum, plama, urine, synovial fluid or spinal fluid) taken from an individual having such a disorder, relative to a standard Ckβ-6 gene expression level; i.e., the Ckβ-6 expression level in tissue or bodily fluids from an individual not having the disorder, which involves: (a) assaying the Ckβ-6 gene expression level in cells or body fluid of an individual; (b) comparing the Ckβ-6 gene expression level with a standard Ckβ-6 gene expression level, whereby an increase or decrease in the assayed Ckβ-6 gene expression level compared to the standard expression level is indicative of a disorder. Such disorders include leukemia, chronic inflammation, autoimmune diseases, and solid tumors.

These and other aspects of the present invention should be apparent to those skilled in the art from the teachings herein.

BRIEF DESCRIPTION OF THE FIGURES

The following drawings are illustrative of embodiments of the invention and are not meant to limit the scope of the invention as encompassed by the claims.

FIG. 1 depicts the cDNA sequence (SEQ ID NO: 1) and corresponding determined amino acid sequence (SEQ ID NO:2) of Ckβ-6. The 119 amino acid sequence shown is the full length protein, with approximately the first 26 amino acids representing leader sequence (underlined) such that the mature form of the protein is 93 amino acids in length The standard one letter abbreviation for amino acids is used.

FIG. 2 illustrates a comparison of the amino acid sequence homology between the polypeptide of the present invention with human MCP-1 (SEQ ID NO:5). Ckβ-6 shows 36% identity and 52% similarity with human MCP-1 as determined by the computer program Bestfit.

Columns 3, 4 and 5 show the ratio of LPP-CFC/HPP-CFC found in the Lin-cells that were cultured with 5 ng/ml IL-3 and 100 ng/ml SCF (column 3), IL-3, SCF and 50 ng/ml Ckβ-6 (column 4) or IL-3, SCF and 50 ng/ml of an irrelevant protein (column 5). After 6 days, cultures were assayed for HPP-CFC and LPP-CFC. The panel B shows the cellularity after 6 days incubation.

Figure 6:
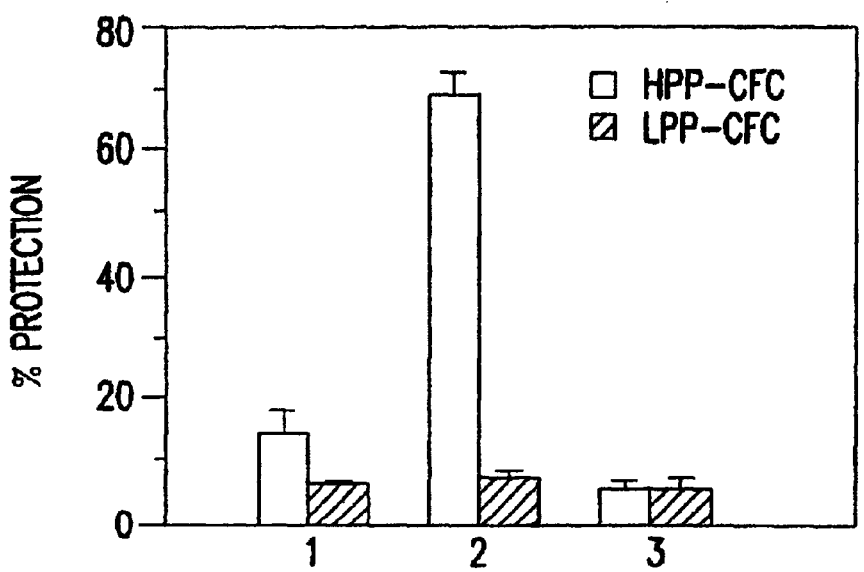

FIG. 6 illustrates that Ckβ-6 protects HPP-CFC but not LPP-CFC from the cytotoxic effect of cytosine arabinoside (Ara-C) in vitro.

Figure 7:
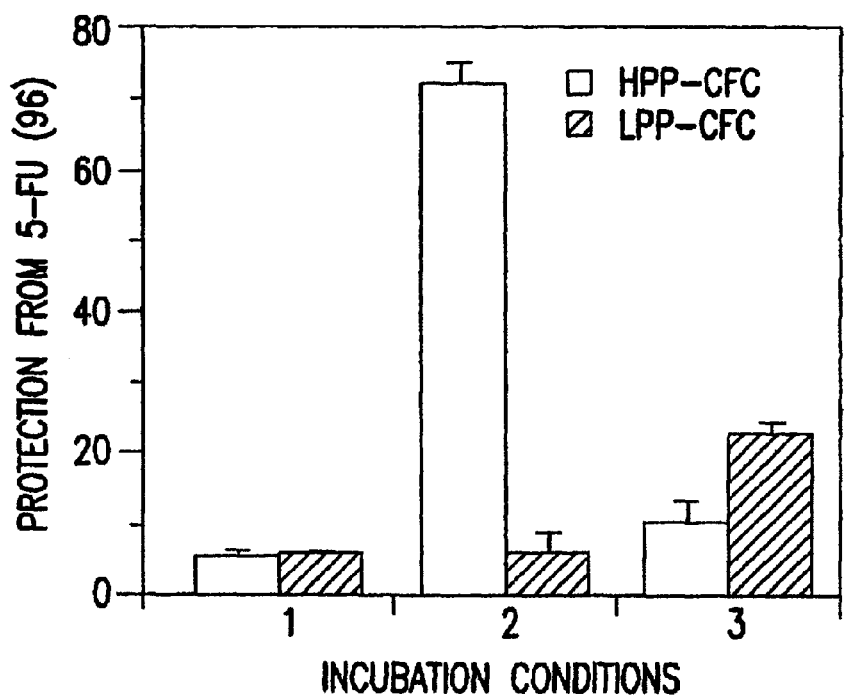

FIG. 7 illustrates that Ckβ-6 protects HPP-CFC but not LPP-CFC from the cytotoxic effect of 5-Fluorouracil (5-FU) in vitro.

Figure 8:
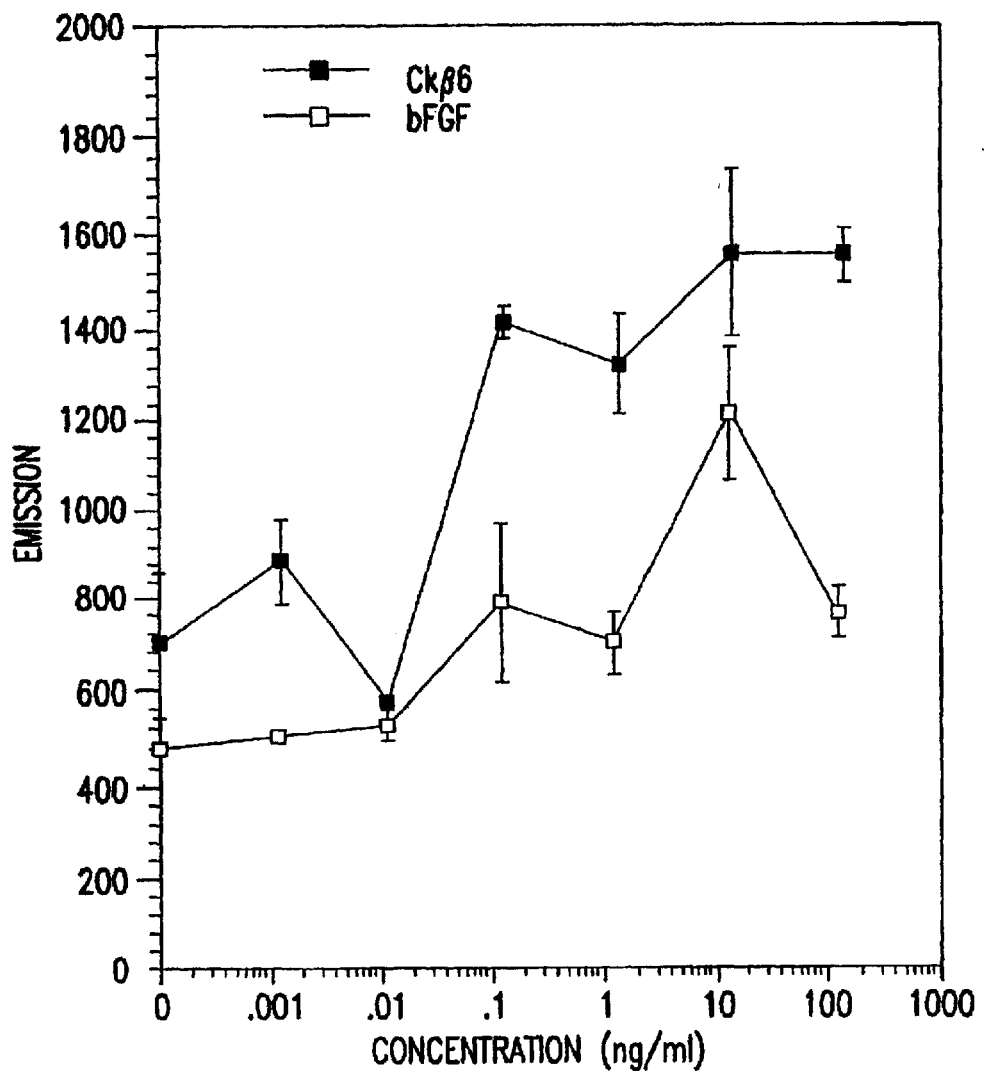

FIG. 8 illustrates the effect of Ckβ-6 and Basic FGF on Cortical Neuronal Survival.

Figure 9:
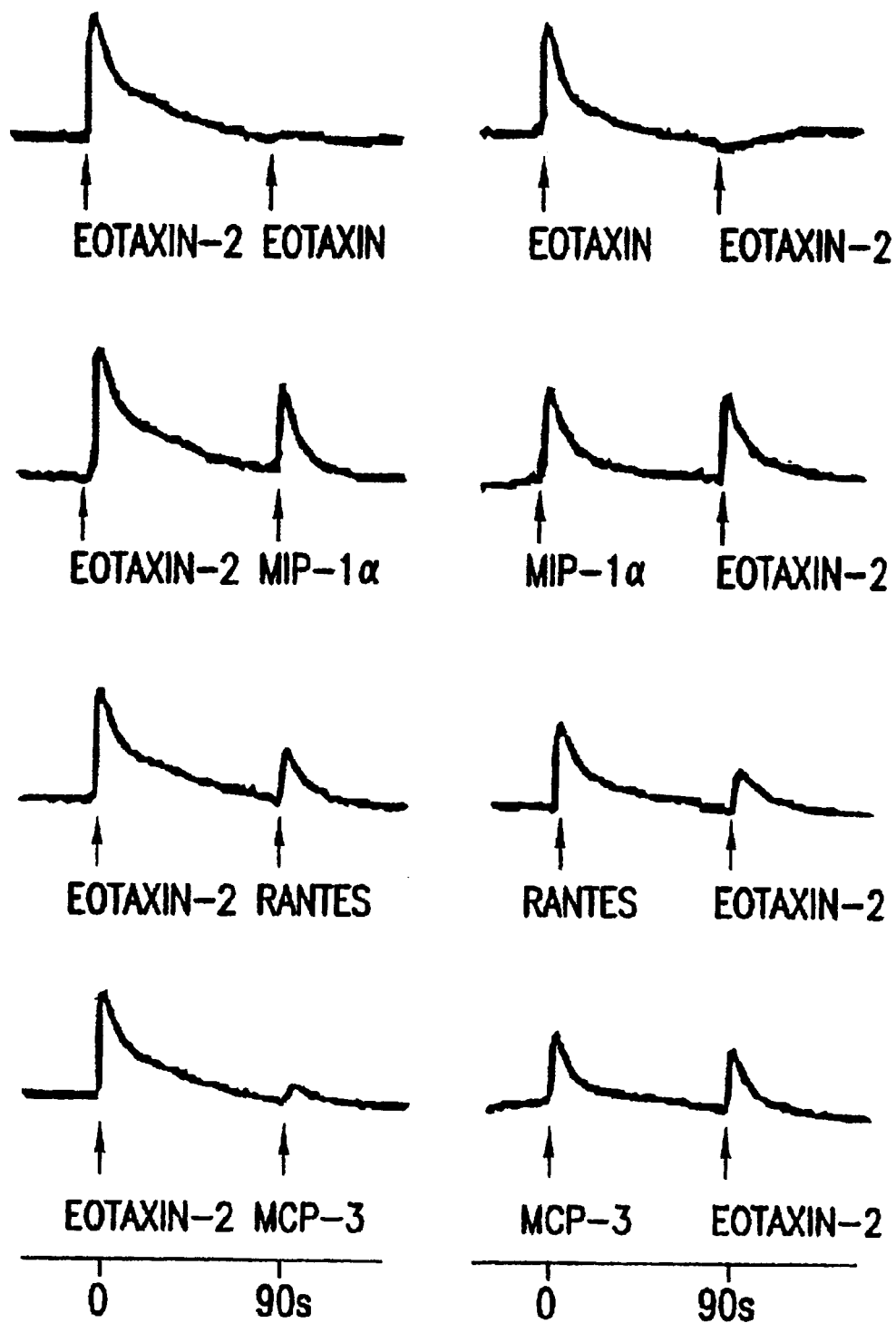

FIG. 9 illustrates the effect of Ckβ-6 and other chemokines on the release of calcium by human eosinophils.

Figure 10A:
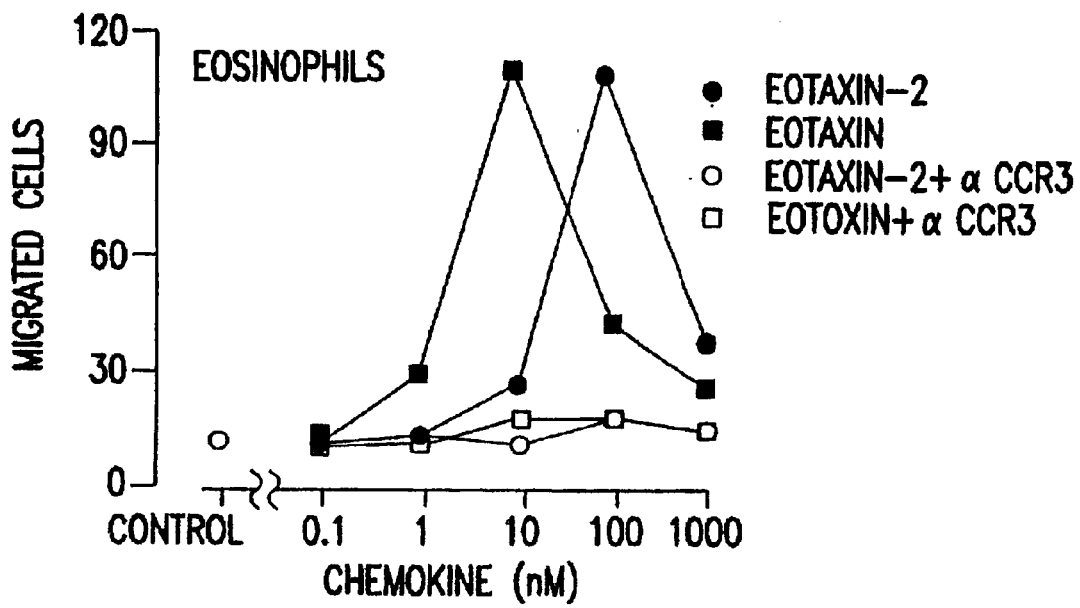
Figure 10B:
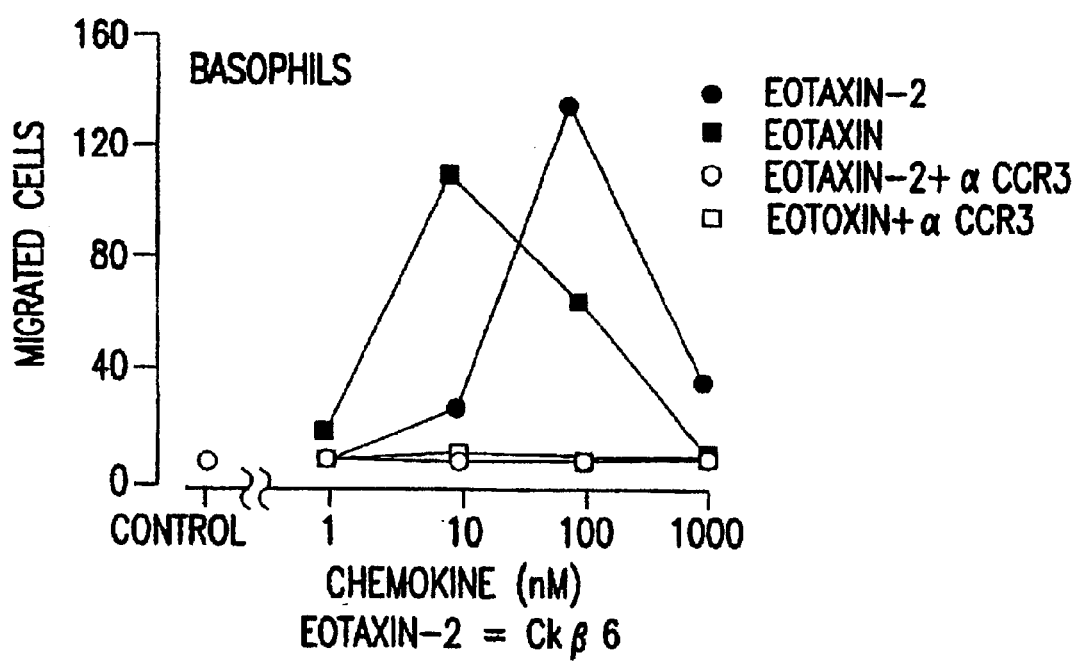
Figure 11A:
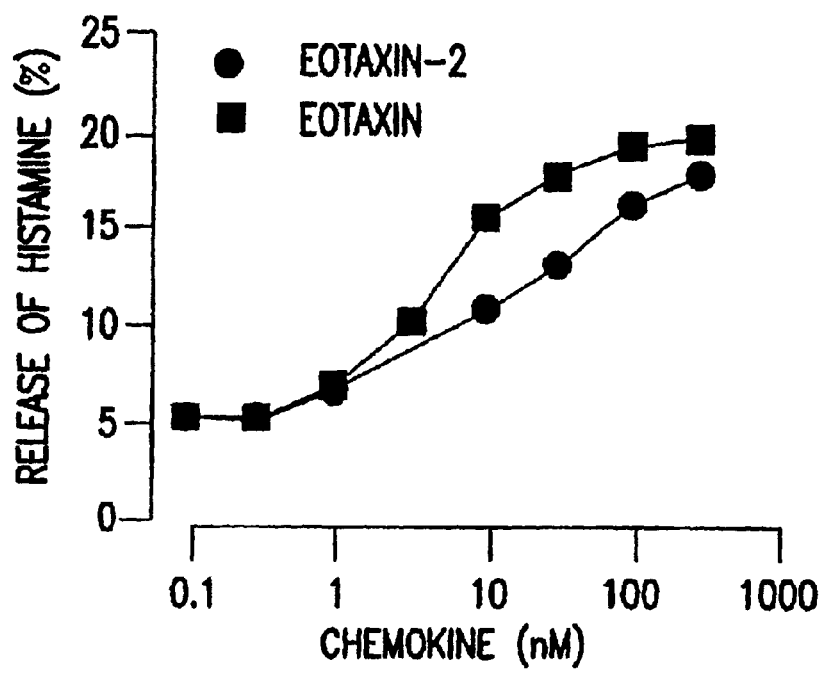
Figure 11B:
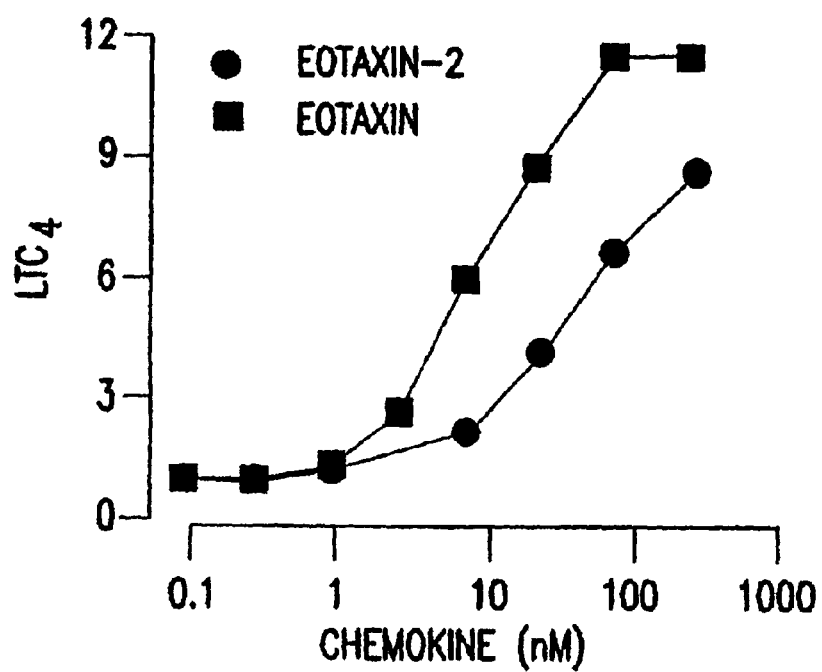
Figure 11C:
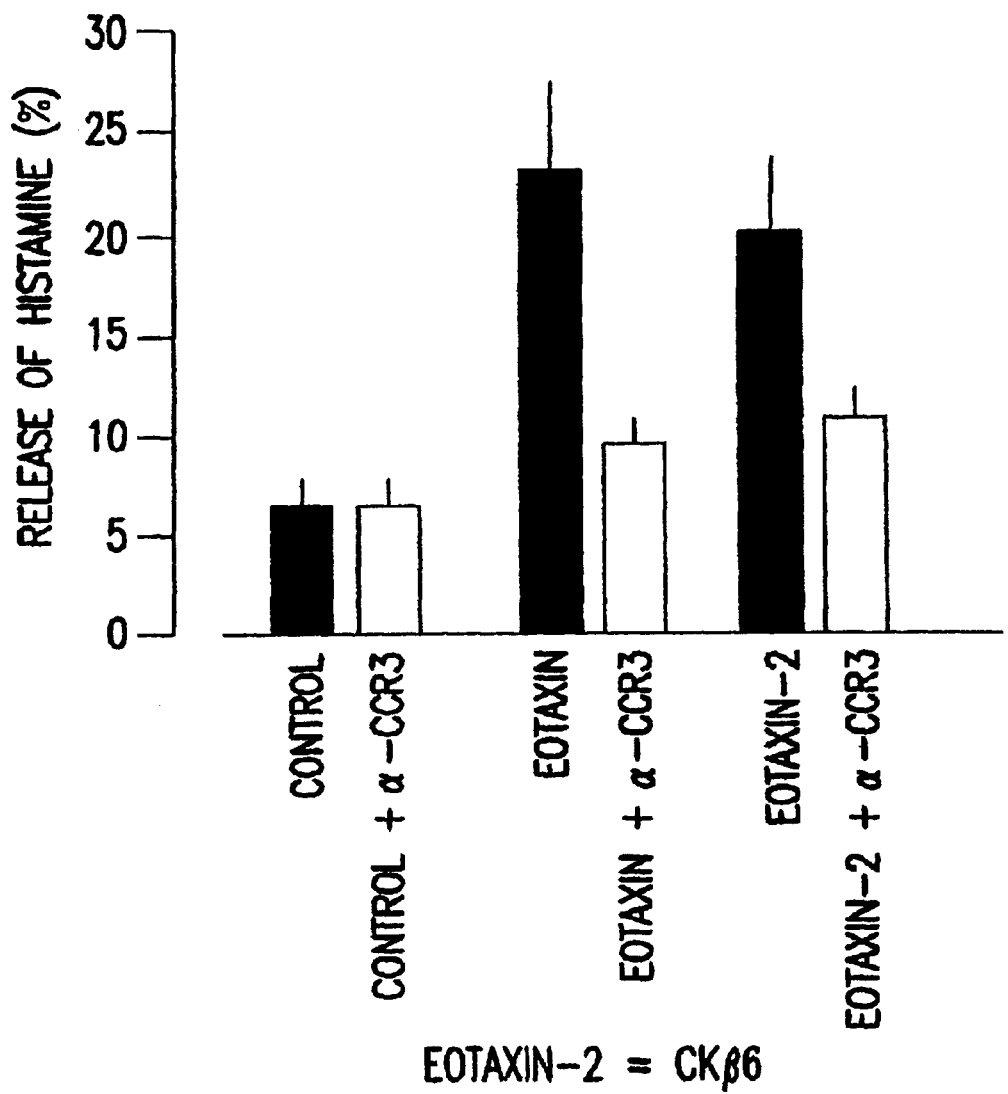
Figure 11D:
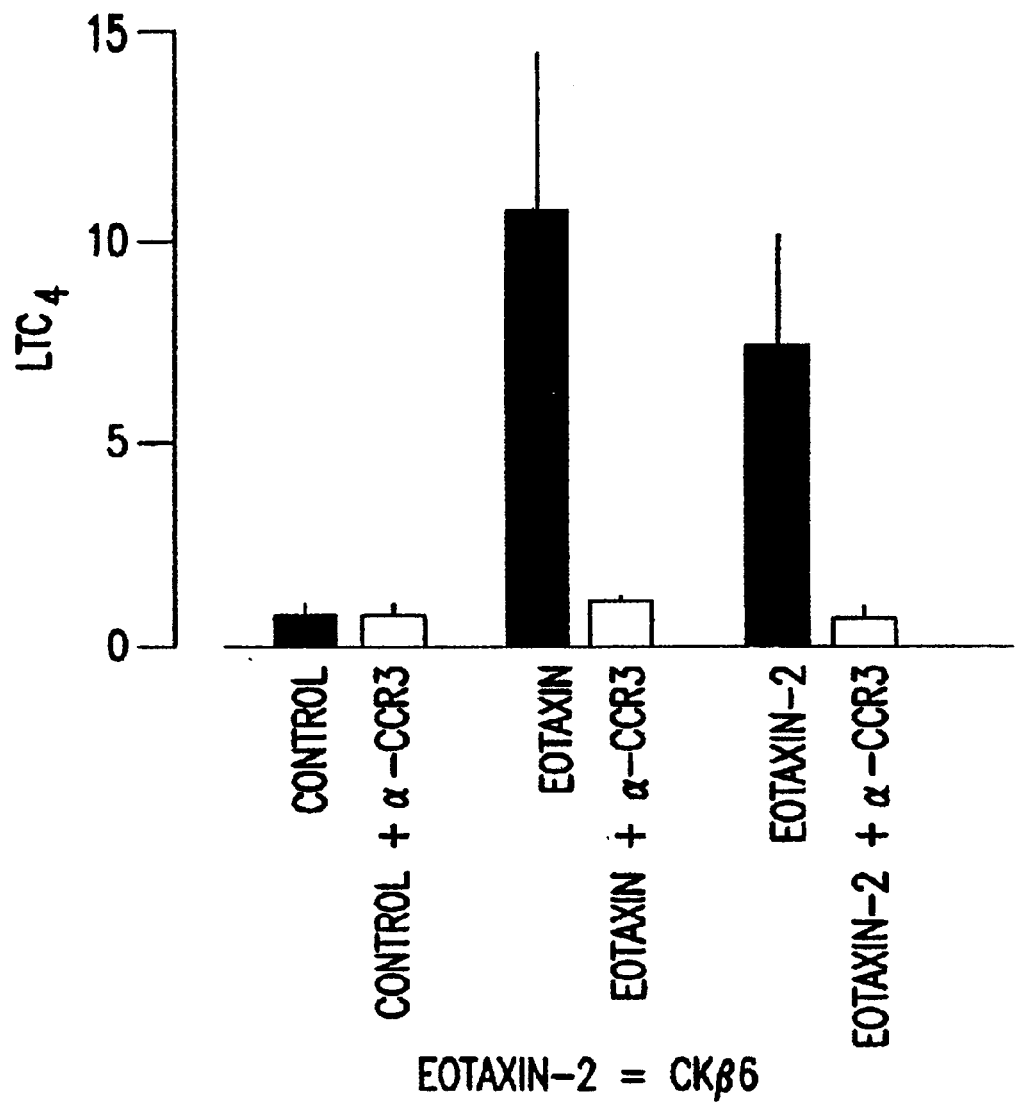

FIG. 10 illustrates the ability of Ckβ-6. to act as a chemoattractant for human eosinophils and basophils in-vitro. Also, illustrated is the ability of a monoclonal antibody directed against the CCR3 receptor (anti-CCR3) to block the migratory response of these cell types.

FIGS. 11A to 11D illustrate the effect of CKβ-6 on histamine and LTC4 release and the ability of anti-CCR3 to block such activity, as described in Example 11.

Figure 12:
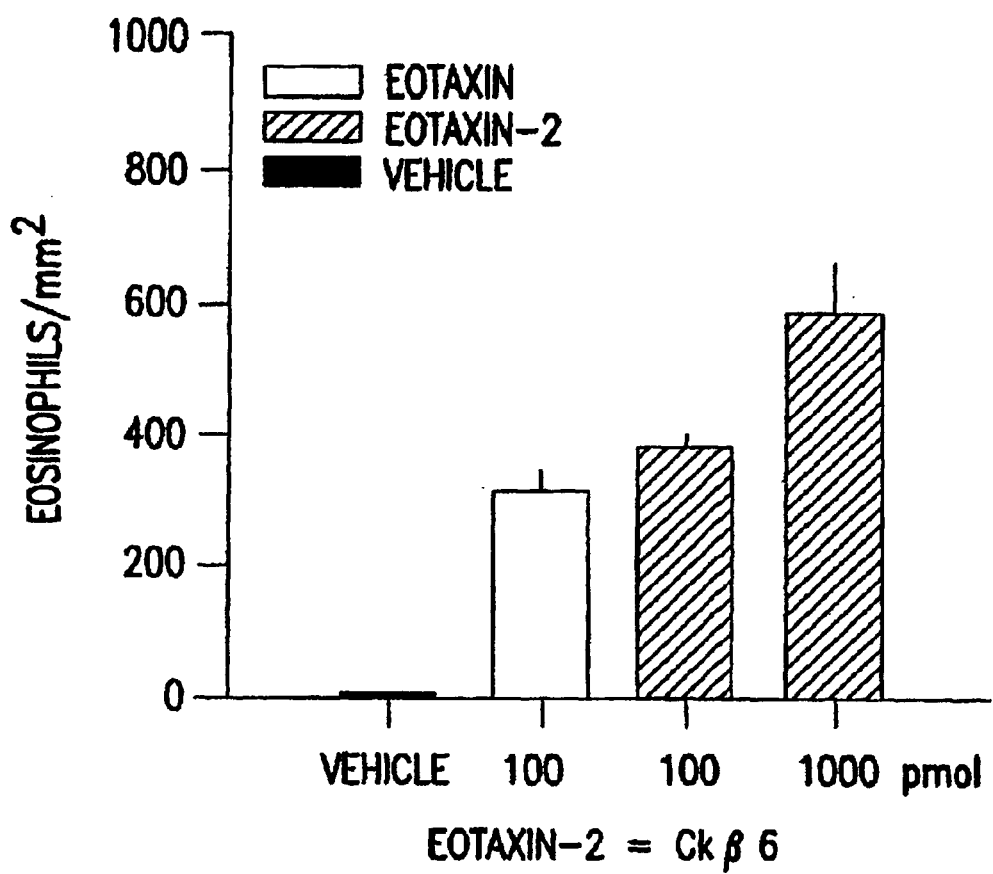

FIG. 12 illustrates the ability of Ckβ-6 to act as a chemoattractant in-vivo.

Figure 13:
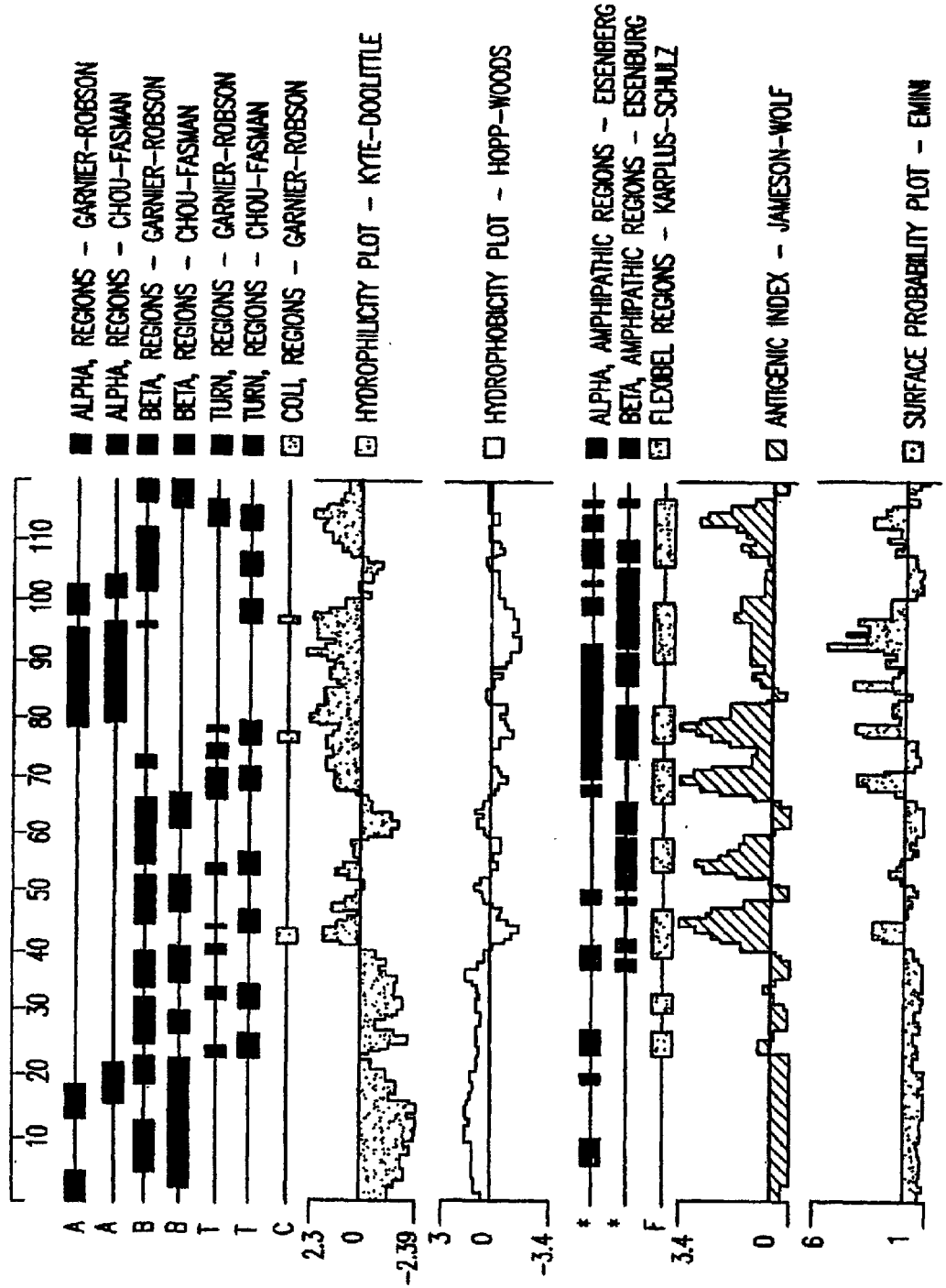

FIG. 13 shows an analysis of the Ckβ-6 amino acid sequence. Alpha, beta, turn and coil regions; hydrophilicity and hydrophobicity; amphipathic regions; flexible regions; antigenic index and surface probability are shown. In the "Antigenic Index—Jameson-Wolf" graph, the positive peaks indicate locations of the highly antigenic regions of the Ckβ-6 protein, i.e., regions from which epitope-bearing peptides of the invention can be obtained.

Figure 14A:
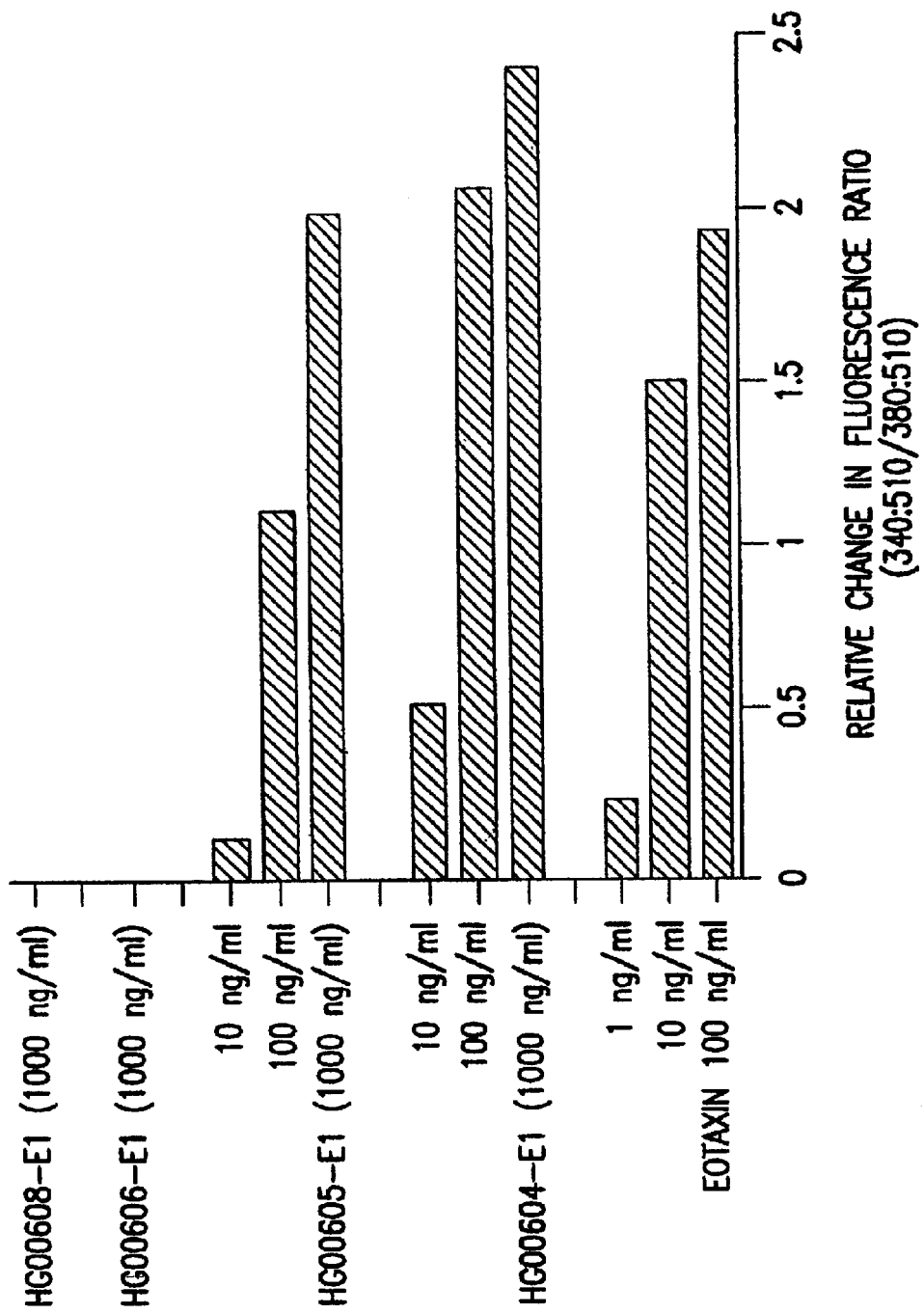
Figure 14B:
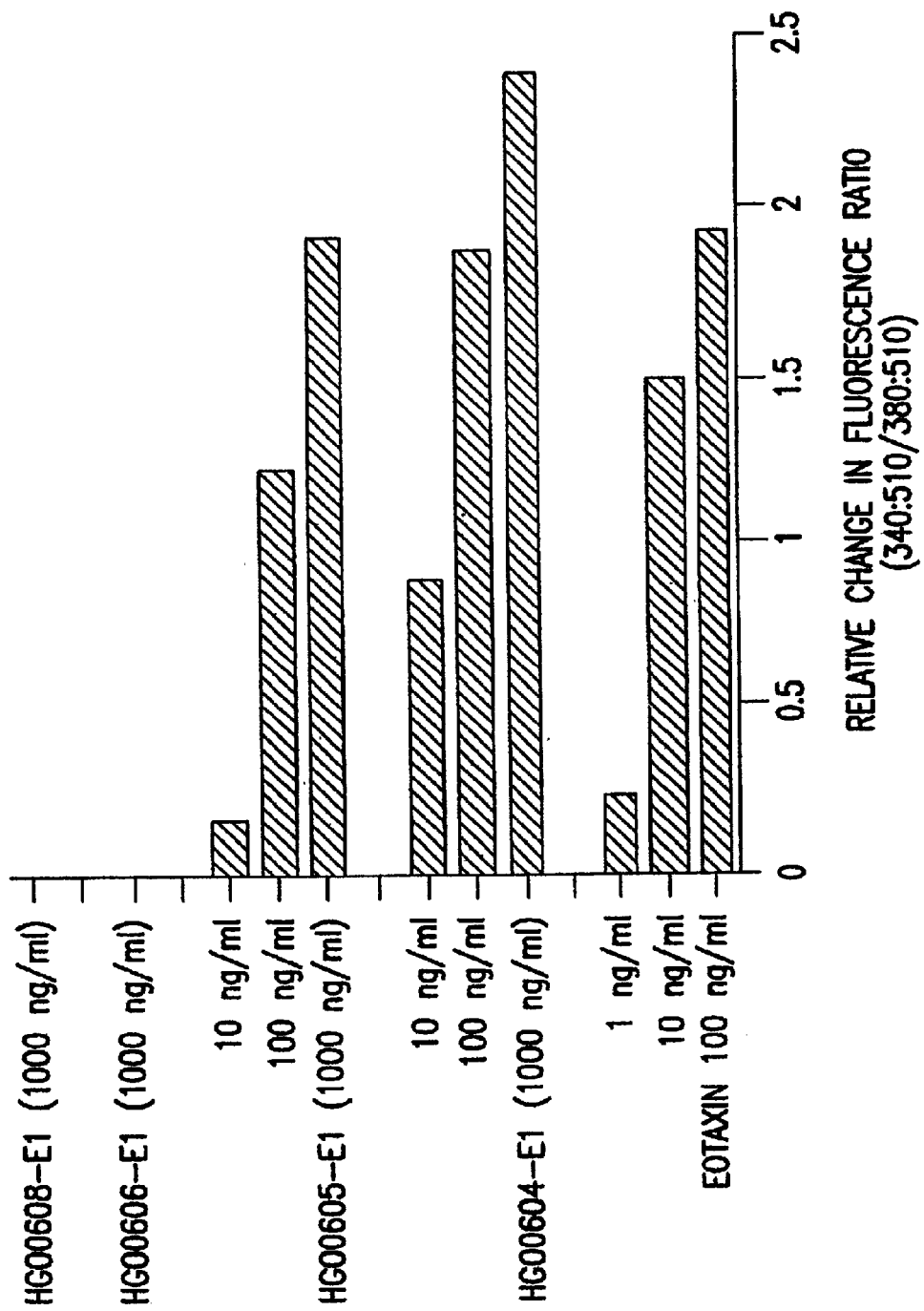

FIGS. 14A and 14B demonstrates that HG00604 and HG00605 are agonist for eosinophils but HG00606 and HG00608 are not. Eosinophils were used for calcium flux assays as described in Example 9. The various chemokines, including Eotaxin, were used at the concentrations indicated. Panel A and B show the results obtained with two individual donors.

Figure 15A:
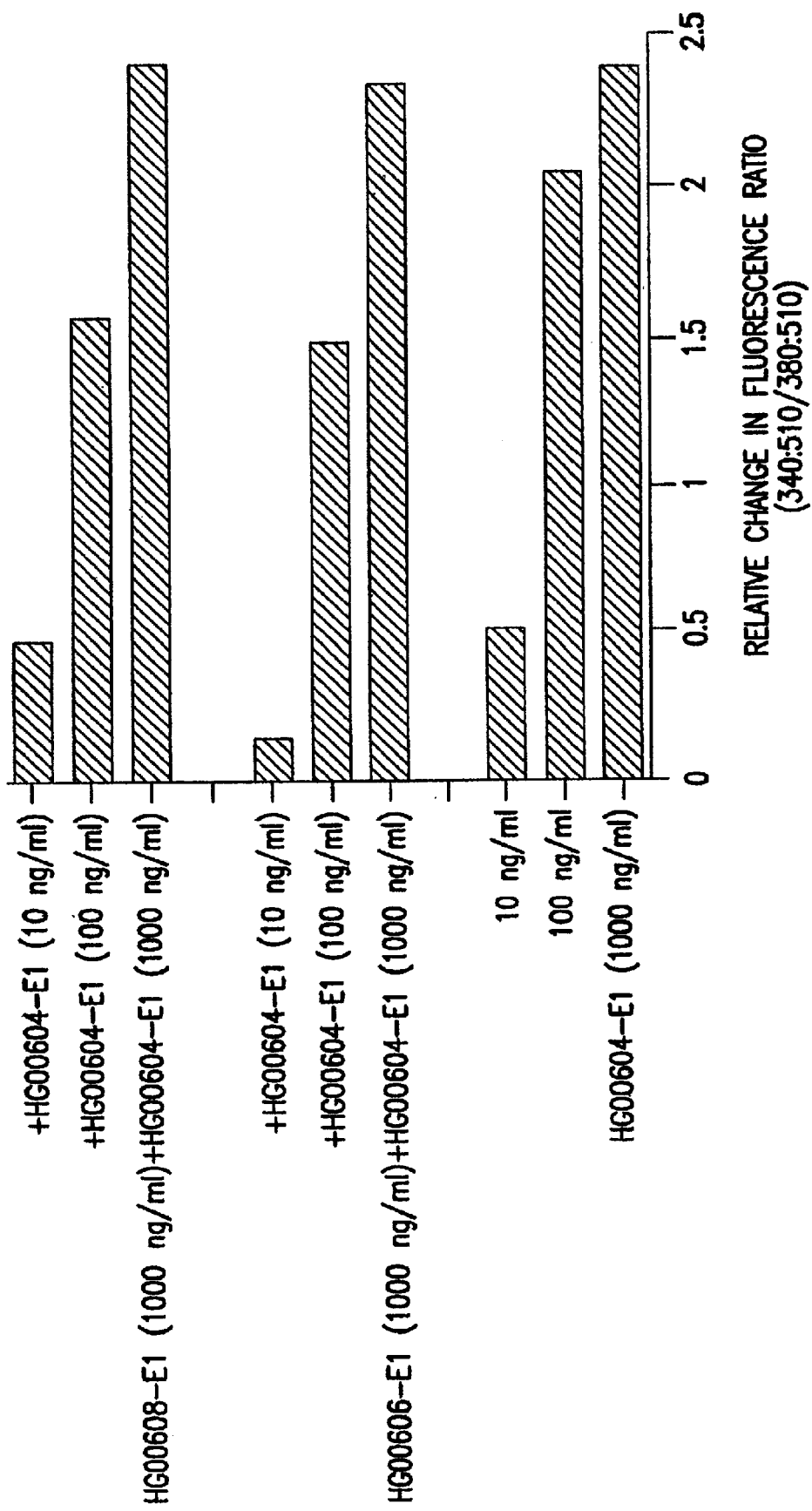

FIGS. 15A and B illustrates that HG00606 is an antagonist of HG00604 but HG00608 is not Eosinophils were used for calcium flux assays as described in Example 9. HG00604 was used in 10, 100, and 1000 ng/ml with or without 1000 ng/ml of HG00606 or HG00608. As shown, the presence of HG00606 reduced the calcium flux directed by 10 or 100 ng/ml of HG00604. Under the same conditions, HG00608 showed no effects. Panel A and B show the results obtained with two individual donors.

Figure 16A:
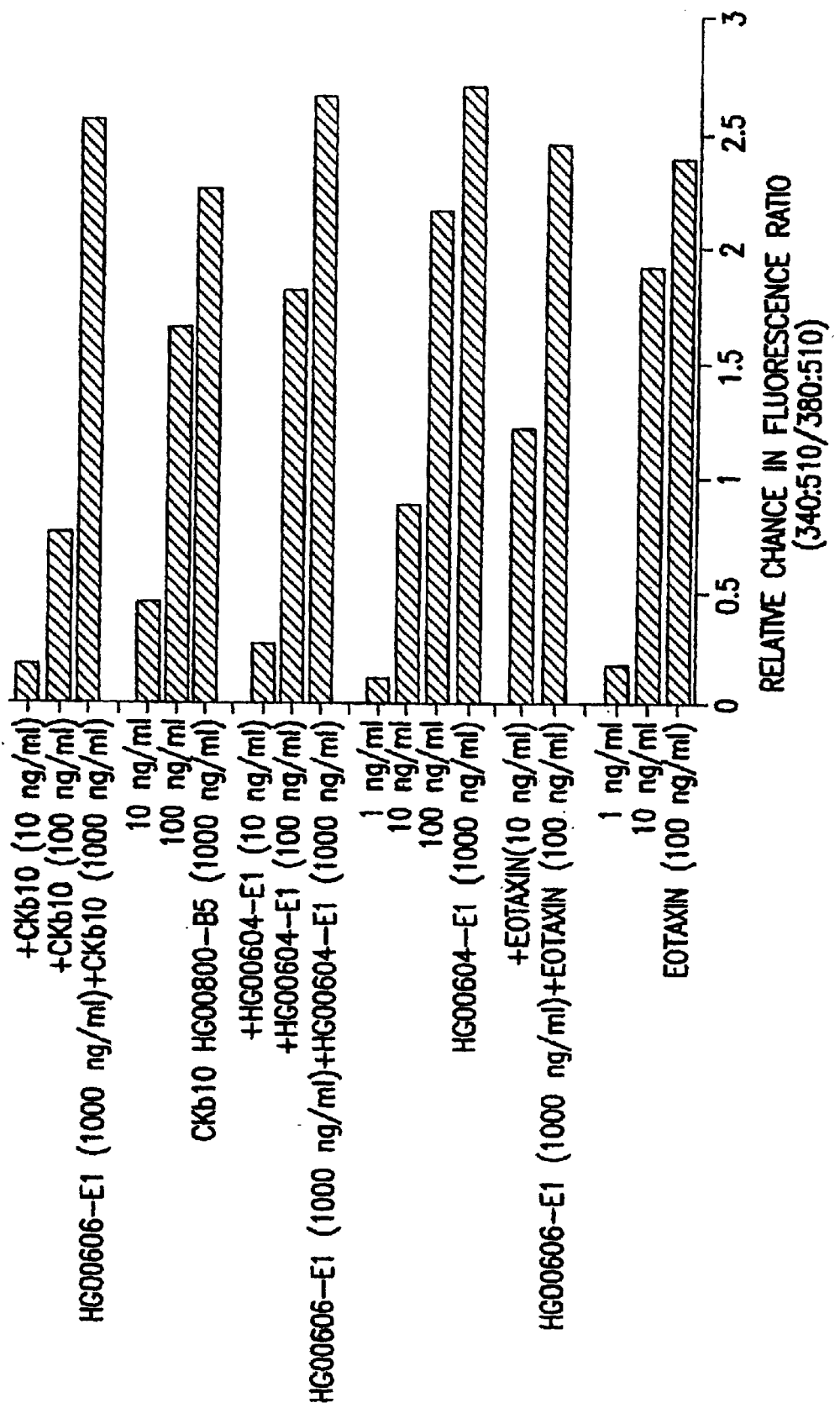
Figure 16B:
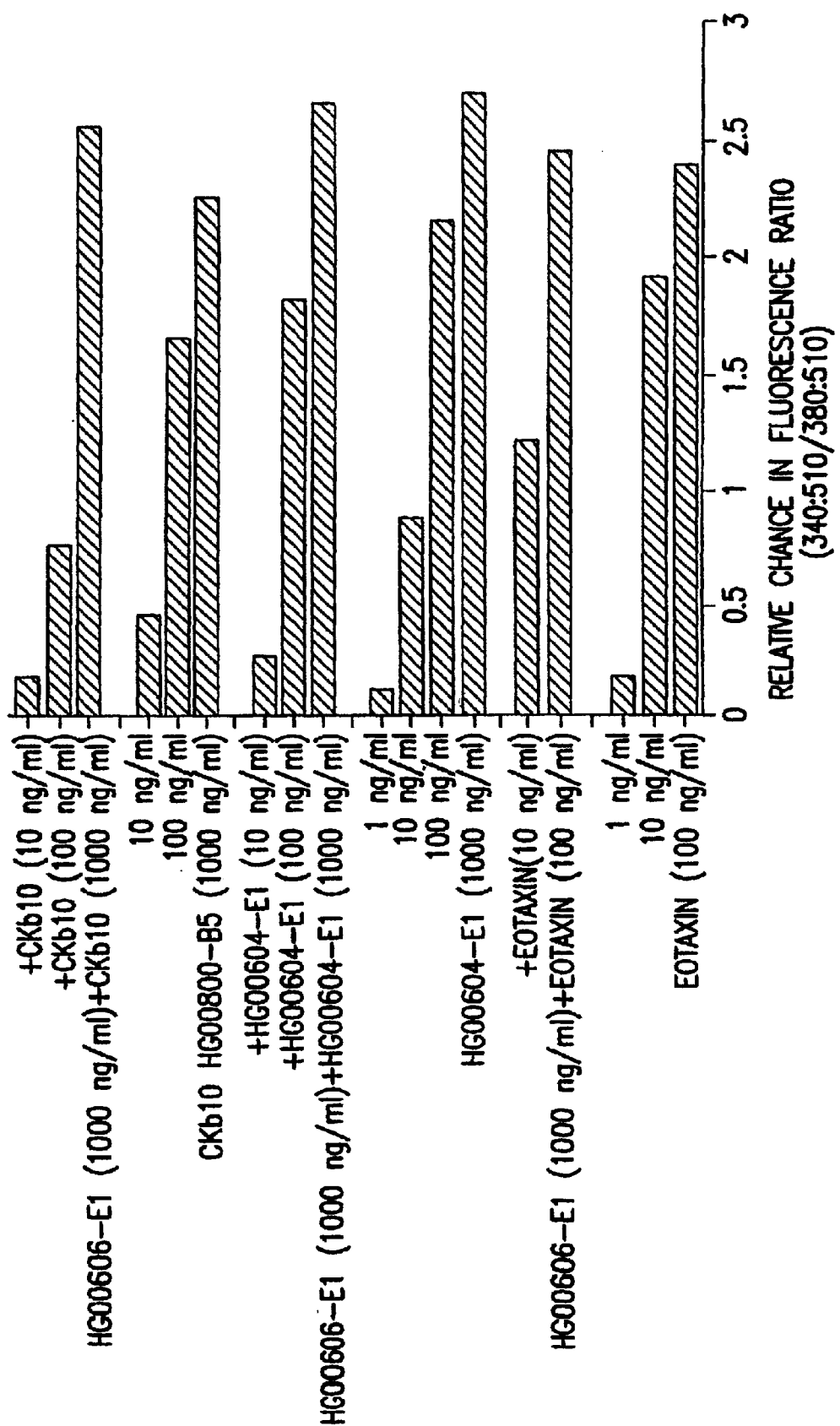

FIGS. 16A and 16B demonstrates that HG00606 is an antagonist of HG00604, Eotaxin and CkBeta-10. Eosinophils were used for calcium flux assays as described in Example 9. HG00604, eotaxin and CkBeta-10 was used at 10, 100, and 1000 ng/ml with or without 1000 ng/ml of HG00606. As shown the presence of HG00606 reduced the calcium flux directed by 10 or 100 ng/ml of HG00604 or CkBeta-10 and the calcium flux directed by 10 ng/ml of Eotaxin. Panel A and B show the results obtained with two individual donors.

Figure 17:
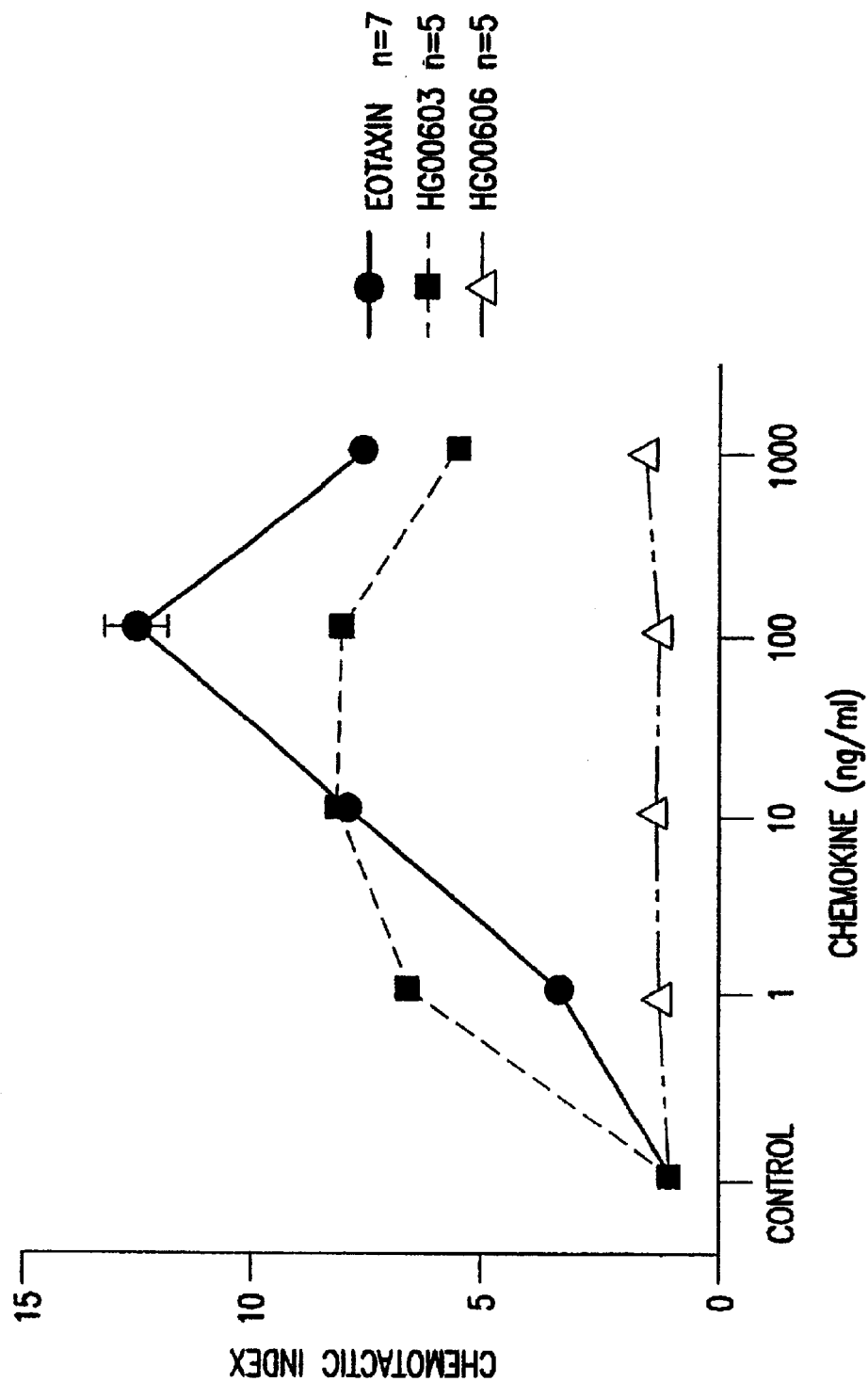

FIG. 17 illustrates that HG00603 but not HG00606 is chemotactic for eosinophils. Eosinophils were used for chemotaxis assays as described in Example 13. Chemotaxis in response to Eotaxin (closed circles), HG00603 (closed squares), or HG00606 (open triangles) is depicted as the chemotactic index and represents the average of 5 to 7 separate experiments where individual experiments were performed in triplicate.

Figure 18A:
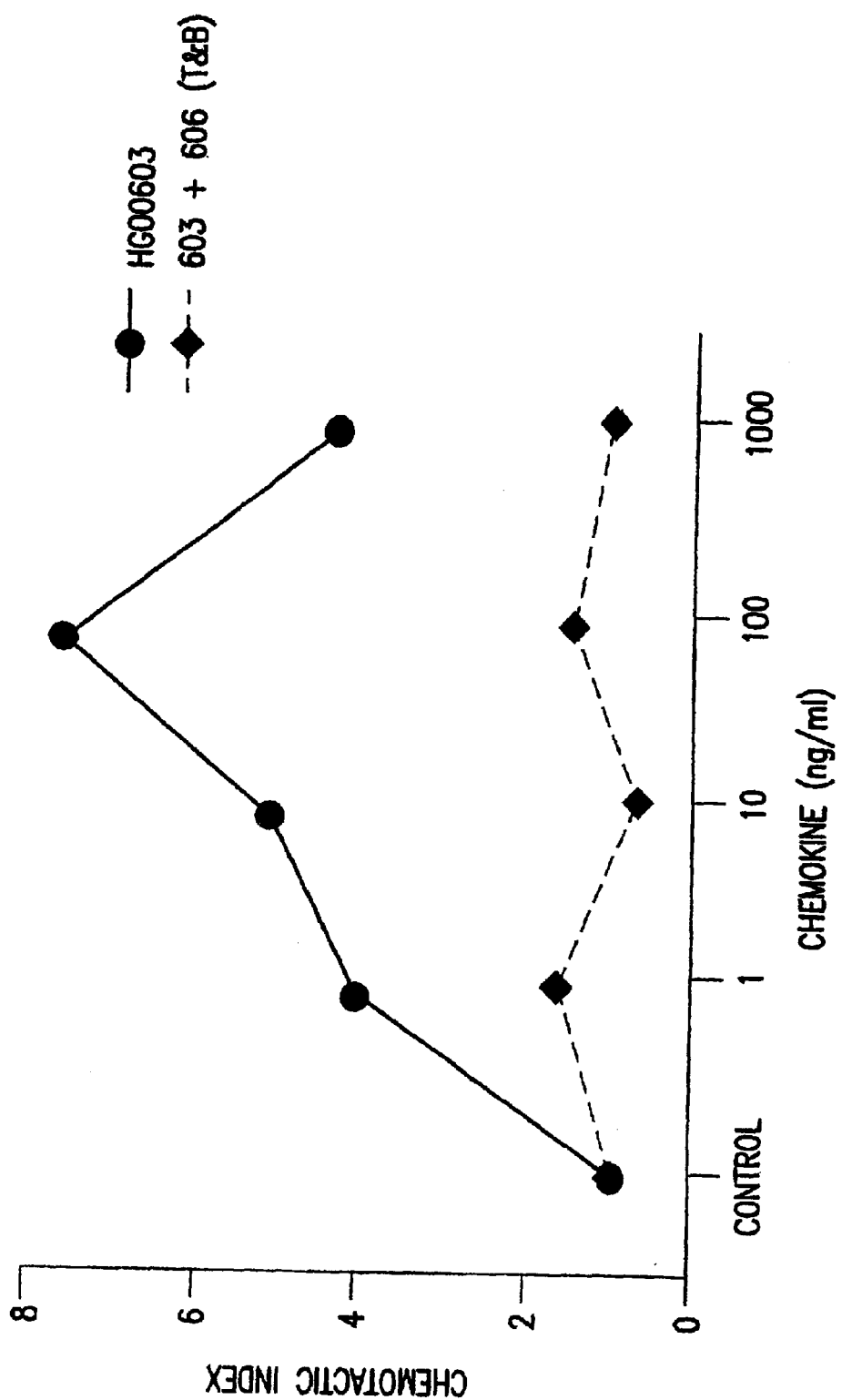
Figure 18B:
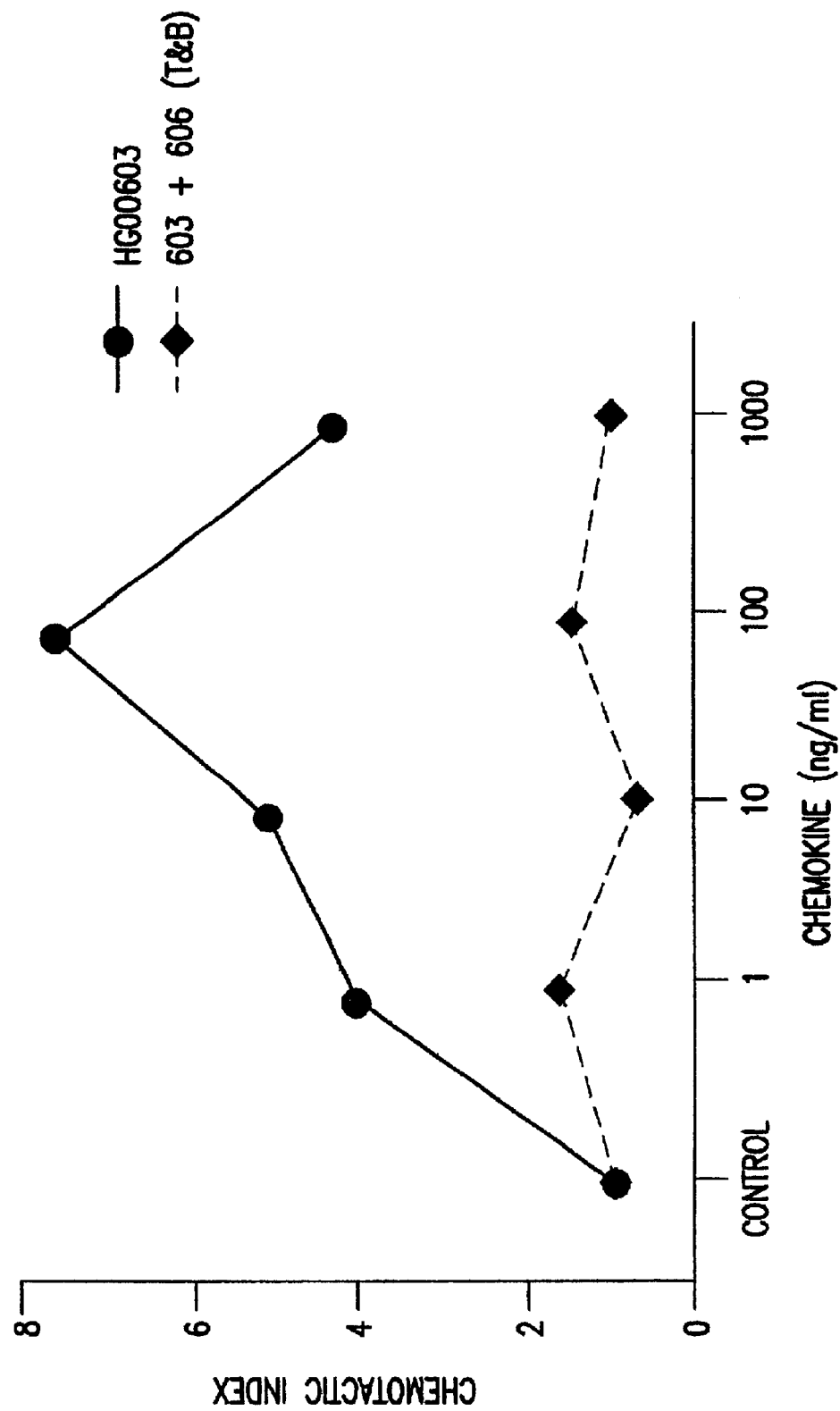

FIGS. 18A and 18B illustrates that HG00606 acts as an antagonist of HG00603. Eosinophils were used for chemotaxis assays as described in Example 13. Chemotaxis in response to HG00603 (closed circles) or HG00603+ HG00606 (closed diamonds) is depicted as the chemotactic index from one representative experiment performed in triplicate. HG00603 was added to the bottom well of the chemotaxis chamber at the concentration indicated along with 1000 ng/ml of HG00606 in both the bottom well and top part of the filter. Panel A and B show the results obtained with two individual donors.

Figure 19A:
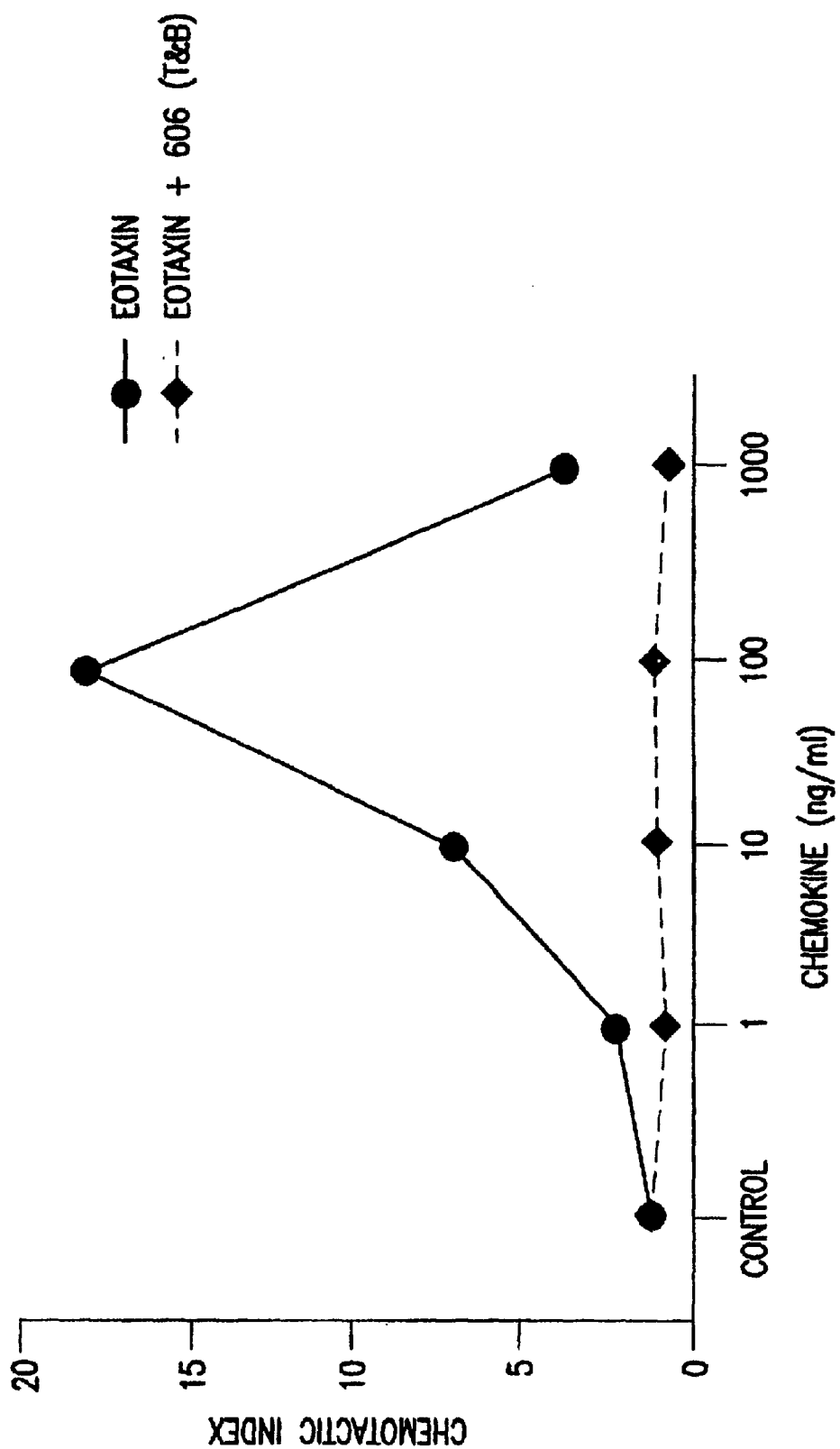
Figure 19B:
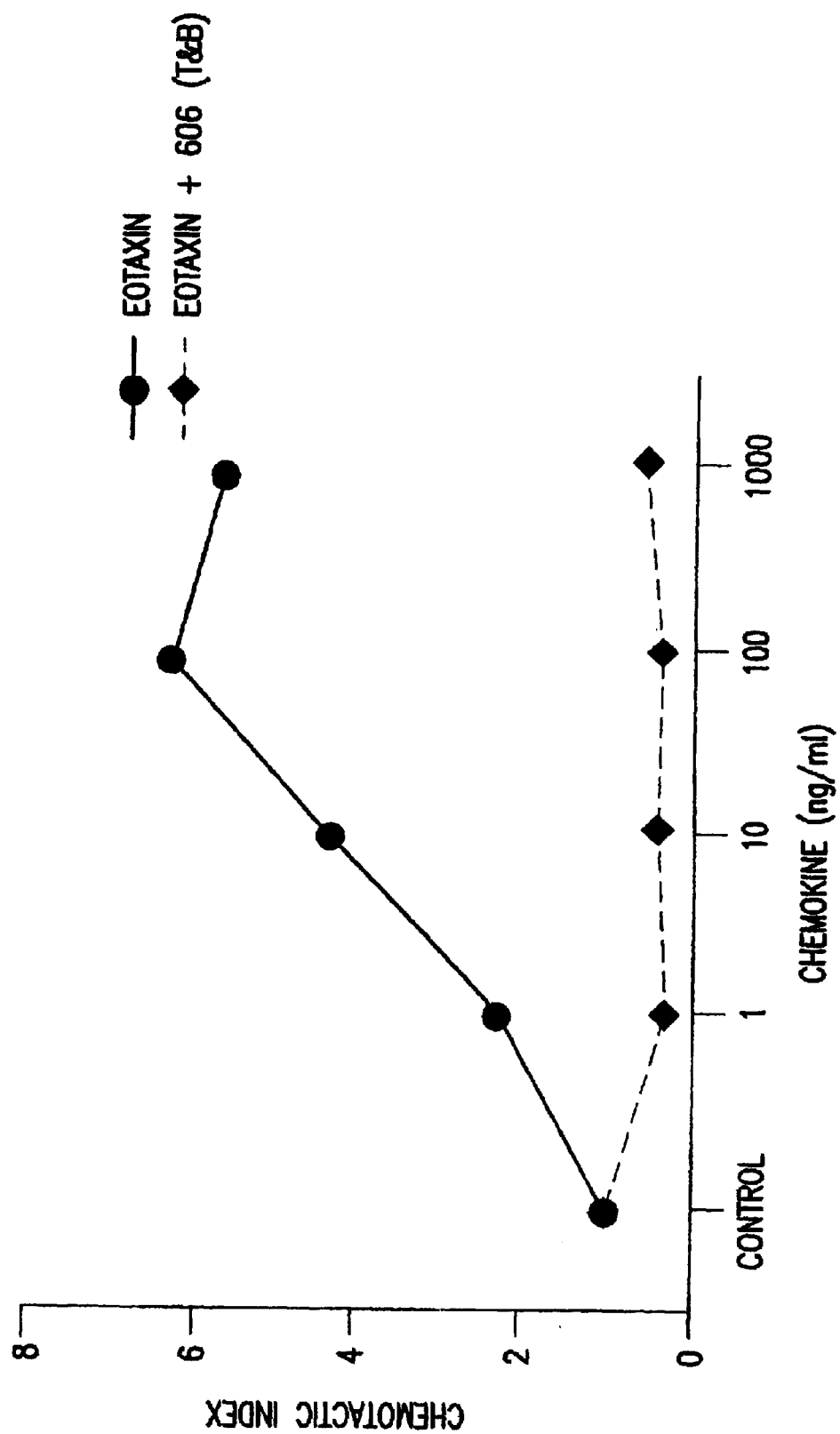

FIGS. 19A and 19B illustrates that HG00606 acts as an antagonist of Eotaxin. Eosinophils were used for chemotaxis assays as described in Example 13. Chemotaxis in response to Eotaxin (closed circles) or Eotaxin +HG00606 (closed diamonds) is depicted as the chemotactic index from one representative experiment performed in triplicate. Eotaxin was added to the bottom well of the chemotaxis chamber at the concentrations indicated along with 1000 ng/ml of HG00606 in both the bottom well and top part of the filter. Panel A and B show the results obtained with two individual donors.

Figure 20A:
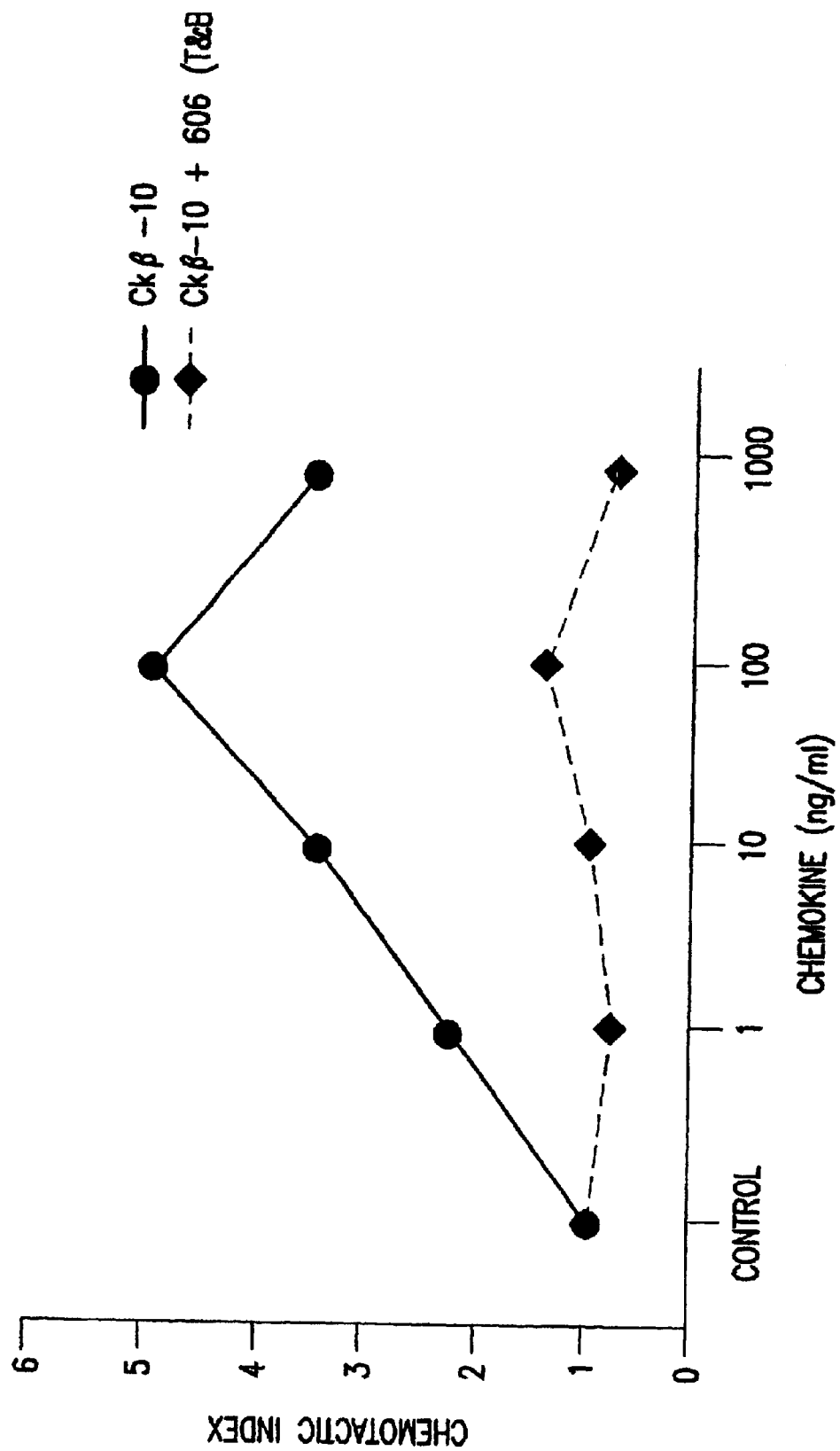
Figure 20B:
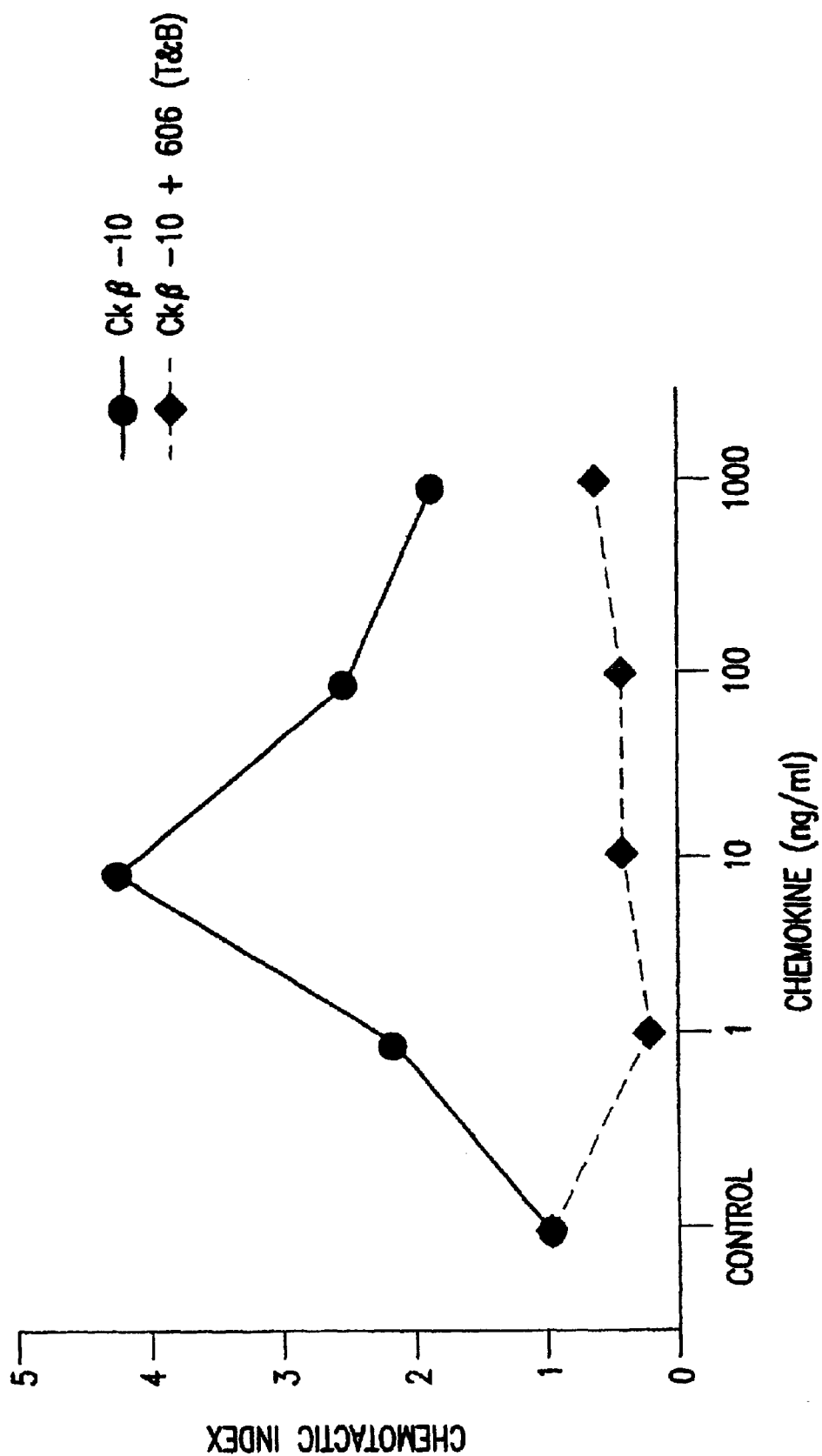

FIGS. 20A and 20B demonstrates that HG00606 acts as an antagonist of CkBeta-10. Eosinophils were used for chemotaxis assays as described in Example 13. Chemotaxis in response to CkBeta-10 (closed circles) or CkBeta-10+ HG00606 (closed diamonds) is depicted as the chemotactic index from one representative experiment performed in triplicate. CkBeta-10 was added to the bottom well of the chemotaxis chamber at the concentrations indicated along with 1000 ng/ml of HG00606 in both the bottom well and top part of the filter. Panel A and B show the results obtained with two individual donors.

Figure 21:
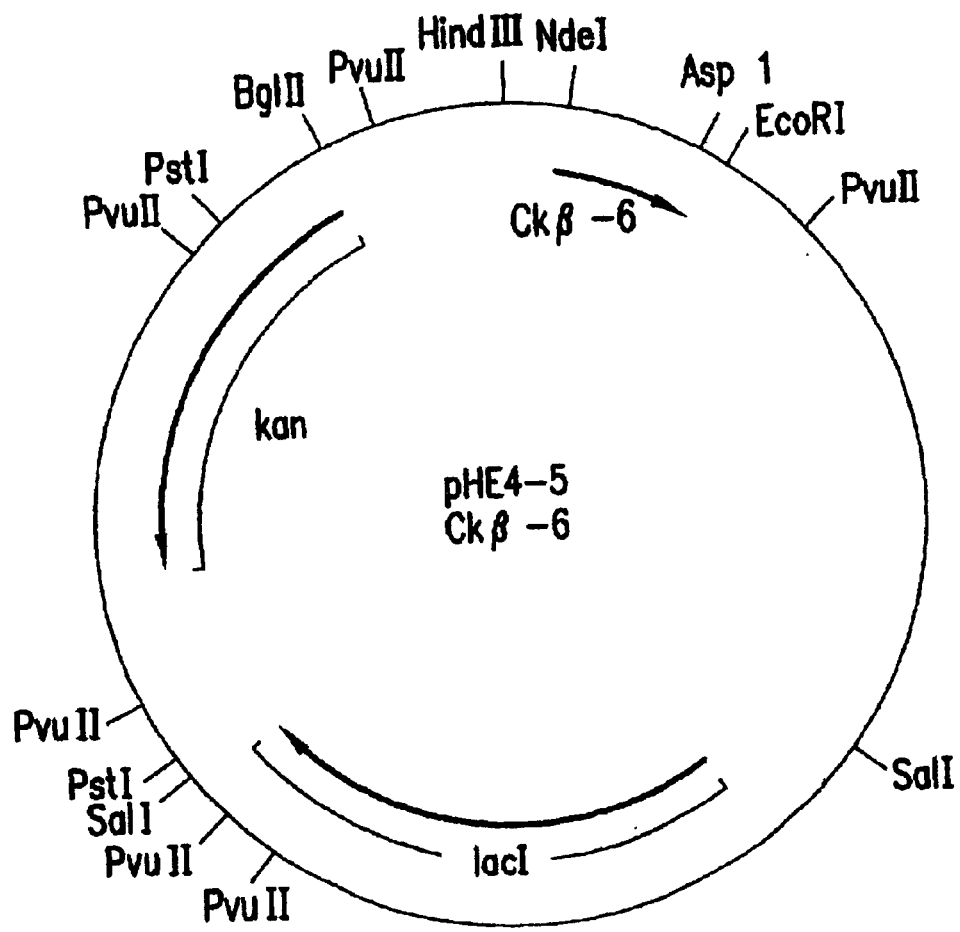

FIG. 21 shows a schematic representation of the pHE4-5 expression vector (SEQ ID NO:21) and the subcloned Ckβ-6 cDNA coding sequence. The locations of the kanamycin resistance marker gene, the Ckβ-6 coding sequence, the oriC sequence, and the lacIq coding sequence are indicated.

FIG. 22 shows the nucleotide sequence of the regulatory elements of the pHE promoter (SEQ ID NO:22). The two lac operator sequences, the Shine-Delgarno sequence (S/D), and the terminal HindIII and NdeI restriction sites (italicized) are indicated.

DETAILED DESCRIPTION OF THE PREFERRED EMBODIMENTS

The present invention provides diagnostic or therapeutic compositions and methods that utilize isolated polynucleotide molecules encoding Ckβ-6 polypeptides, or the Ckβ-6 polypeptides themselves, as well as vectors, host cells and recombinant or synthetic methods for producing such compositions. Other names of Ckβ-6 include MPIF-2 and eotaxin-2.

Nucleic Acids

In accordance with an aspect of the present invention, there is provided an isolated nucleic acid (polynucleotide) which encodes for the full-length or mature polypeptide having the deduced amino acid sequence of FIG. 1 (SEQ ID NO:2) or for the mature polypeptide encoded by the cDNA of the clone deposited at the American Type Culture Collection, 10801 University Boulevard, Manassas, Va. 20110-2209, as ATCC Deposit No. 75703 on Mar. 10, 1994.

The deposit referred to herein will be maintained under the terms of the Budapest Treaty on the International Recognition of the Deposit of Micro-organisms for purposes of Patent Procedure. The deposit is provided merely as convenience to those of skill in the art and is not an admission that a deposit is required under 35 U.S.C. §112. The sequence of the polynucleotide contained in the deposited materials, as well as the amino acid sequence of the polypeptides encoded thereby, are incorporated herein by reference and are controlling in the event of any conflict with any description of sequences herein. A license may be required to make, use or sell the deposited material, and no such license is hereby granted.

The polynucleotide of this invention was discovered from an activated monocyte cDNA library. It contains an open reading frame encoding a protein of approximately 119 amino acids in length of which the first 26 amino residues comprise a putative leader sequence. The mature protein therefore is predicted to be 93 amino acids in length. It is structurally related to mouse monocyte chemotactic protein-1 (MCP-1 or JE, sequence not shown), and human MCP-1 (SEQ ID NO:5) showing 36% identity, and 52% similarity over the entire human MCP-1 protein sequence as determind by the computer program Bestfit (shown in FIG. 2). The polypeptide contains all four cysteine residues that occur in all chemokines in a characteristic motif. The spacing between these cysteines is conserved compared with the human MCP-1 and murine MCP-1/JE which strongly suggests that the new gene is a chemokine.

The polynucleotide of the present invention may be in the form of RNA or in the form of DNA, which DNA includes cDNA, genomic DNA, and synthetic DNA. The DNA may be double-stranded or single-stranded, and if single stranded may be the coding strand or non-coding (anti-sense) strand. The coding sequence which encodes the mature polypeptide may be identical to the coding sequence shown in FIG. 1 (SEQ ID NO: 1) or that of the deposited clone or may be a different coding sequence which coding sequence, as a result of the redundancy or degeneracy of the genetic code, encodes the same mature polypeptide as the DNA of FIG. 1 (SEQ ID NO:1) or the deposited cDNA.

The polynucleotide which encodes for the mature polypeptide of FIG. 1 (SEQ ID NO:2) or for the mature polypeptide encoded by the deposited cDNA may include, but is not limited to: only the coding sequence for the mature polypeptide; the coding sequence for the mature polypeptide and additional coding sequence such as a leader or secretory sequence or a proprotein sequence; the coding sequence for the mature polypeptide (and optionally additional coding sequence) and non-coding sequence, such as introns or non-coding sequence 5' and/or 3' of the coding sequence for the mature polypeptide.

Thus, the term "polynucleotide encoding a polypeptide" encompasses a polynucleotide which includes only coding sequence for the polypeptide as well as a polynucleotide which includes additional coding and/or non-coding sequence.

Unless otherwise indicated, all nucleotide sequences determined by sequencing a DNA molecule herein were determined using an automated DNA sequencer (such as the Model 373 from Applied Biosystems, Inc.), and all amino acid sequences of polypeptides encoded by DNA molecules determined herein were predicted by translation of a DNA sequence determined as above. Therefore, as is known in the art for any DNA sequence determined by this automated approach, any nucleotide sequence determined herein may contain some errors. Nucleotide sequences determined by automation are typically at least about 90% identical, more typically at least about 95% to at least about 99.9% identical to the actual nucleotide sequence of the sequenced DNA molecule. The actual sequence can be more precisely determined by other approaches including manual DNA sequencing methods well known in the art. As is also known in the art, a single insertion or deletion in a determined nucleotide sequence compared to the actual sequence will cause a frame shift in translation of the nucleotide sequence such that the predicted amino acid sequence encoded by a determined nucleotide sequence will be completely different from the amino acid sequence actually encoded by the sequenced DNA molecule, beginning at the point of such an insertion or deletion.

Unless otherwise indicated, each nucleotide sequence set forth herein is presented as a sequence of deoxyribonucleotides (abbreviated A, G, C and T). However, by nucleotide sequence of a nucleic acid molecule or polynucleotide is intended, for a DNA molecule or polynucleotide, a sequence of deoxyribonucleotides, and for an RNA molecule or polynucleotide, the corresponding sequence of ribonucleotides (A, G, C and U), where each thymidine deoxyribonucleotide (T) in the specified deoxyribonucleotide sequence is replaced by the ribonucleotide uridine (U). For instance, reference to an RNA molecule having the sequence of SEQ ID NO:1, as set forth using deoxyribonucleotide abbreviations, is intended to indicate an RNA molecule having a sequence in which each deoxyribonucleotide A, G or C of SEQ ID NO:1 has been replaced by the corresponding ribonucleotide A, G or C, and each deoxyribonucleotide T has been replaced by a ribonucleotide U.

Using the information provided herein, such as the nucleotide sequence in FIG. 1, a nucleic acid molecule of the present invention encoding an Ckβ-6 polypeptide may be obtained using standard cloning and screening procedures, such as those for cloning cDNAs using mRNA as starting material.

The present invention further relates to variants of the hereinabove described polynucleotides which encode for fragments, analogs and derivatives of the polypeptide having the deduced amino acid sequence of FIG. 1 (SEQ ID NO:2) or the polypeptide encoded by the cDNA of the deposited clone. The variant of the polynucleotide may be a naturally occurring allelic variant of the polynucleotide or a non-naturally occurring variant of the polynucleotide.

Thus, the present invention includes polynucleotides encoding the same mature polypeptide as shown in FIG. 1 (SEQ ID NO:2) or the same mature polypeptide encoded by the cDNA of the deposited clone as well as variants of such polynucleotides which variants encode for a fragment, derivative or analog of the polypeptide of FIG. 1 (SEQ ID NO:2) or the polypeptide encoded by the cDNA of the deposited clone. Such nucleotide variants include deletion variants, substitution variants and addition or insertion variants.

As hereinabove indicated, the polynucleotide may have a coding sequence which is a naturally occurring allelic variant of the coding sequence shown in FIG. 1 (SEQ ID NO:1) or of the coding sequence of the deposited clone. As known in the art, an allelic variant is an alternate form of a polynucleotide sequence which may have a substitution, deletion or addition of one or more nucleotides, which does not substantially alter the function of the encoded polypeptide.

The present invention also includes polynucleotides, wherein the coding sequence for the mature polypeptide may be fused in the same reading frame to a polynucleotide sequence which aids in expression and secretion of a polypeptide from a host cell, for example, a leader sequence which functions as a secretory sequence for controlling transport of a polypeptide from the cell. The polypeptide having a leader sequence is a preprotein and may have the leader sequence cleaved by the host cell to form the mature form of the polypeptide. The polynucleotides may also encode for a proprotein which is the mature protein plus additional 5' amino acid residues. A mature protein having a prosequence is a proprotein and is an inactive form of the protein. Once the prosequence is cleaved an active mature protein remains.

Thus, for example, the polynucleotide of the present invention may encode for a mature protein, or for a protein having a prosequence or for a protein having both a prosequence and a presequence (leader sequence).

The polynucleotides of the present invention can also have the coding sequence fused in frame to a marker sequence which allows for purification of the polypeptide of the present invention. The marker sequence can be a hexa-histidine tag supplied by a pQE-9 vector to provide for purification of the mature polypeptide fused to the marker in the case of a bacterial host, or, for example, the marker sequence can be a hemagglutinin (HA) tag when a mammalian host, e.g. COS-7 cells, is used. The HA tag corresponds to an epitope derived from the influenza hemagglutinin protein (Wilson, I., et al., *Cell* 37:767 (1984)).

The term "gene" means the segment of DNA involved in producing a polypeptide chain; it includes regions preceding and following the coding region (leader and trailer) as well as intervening sequences (introns) between individual coding segments (exons).

As indicated, nucleic acid molecules of the present invention may be in the form of RNA, such as mRNA, or in the form of DNA, including, for instance, cDNA and genomic DNA obtained by cloning or produced synthetically. The DNA may be double-stranded or single-stranded. Single-stranded DNA or RNA may be the coding strand, also known as the sense strand, or it may be the non-coding strand, also referred to as the anti-sense strand.

The term "isolated" means that the material is removed from its original environment (e.g., the natural environment if it is naturally occurring). For example, a naturally-occurring polynucleotides or polypeptides present in a living animal is not isolated, but the same polynucleotides or DNA or polypeptides, separated from some or all of the coexisting materials in the natural system, is isolated. Such polynucleotides could be part of a vector and/or such polynucleotides or polypeptides could be part of a composition, and still be isolated in that such vector or composition is not part of its natural environment. Isolated RNA molecules include in vivo or in vitro RNA transcripts of the DNA molecules of the present invention. Isolated nucleic acid molecules according to the present invention further include such molecules produced synthetically.

Isolated nucleic acid molecules of the present invention include DNA molecules comprising an open reading frame (ORF) for an Ckβ-6 cDNA; DNA molecules comprising the coding sequence for a mature Ckβ-6 protein; and DNA molecules which comprise a sequence substantially different from those described above but which, due to the degeneracy of the genetic code, still encode an Ckβ-6 polypeptide. Of course, the genetic code is well known in the art Thus, it would be routine for one skilled in the art to generate the degenerate variants described above.

The present invention further relates to polynucleotides which hybridize to the hereinabove-described sequences if there is at least 70%, preferably at least 90%, and more preferably at least 95% identity between the sequences. The present invention particularly relates to polynucleotides which hybridize under stringent conditions to the hereinabove-described polynucleotides. As herein used, the term "stringent conditions" means hybridization will occur only if there is at least 95% and preferably at least 97% identity between the sequences. The polynucleotides which hybridize to the hereinabove described polynucleotides in a preferred embodiment encode polypeptides which either retain substantially the same biological function or activity as the mature polypeptide encoded by the cDNAs of FIG. 1 (SEQ ID NO:1) or the deposited cDNA(s).

Alternatively, the polynucleotide may have at least 20 bases, preferably 30 bases, and more preferably at least 50 bases which hybridize to a polynucleotide of the present invention and which has an identity thereto, as hereinabove described, and which may or may not retain activity. For example, such polynucleotides may be employed as probes for the polynucleotide of SEQ ID NO: 1, for example, for recovery of the polynucleotide or as a diagnostic probe or as a PCR primer.

In another aspect, the invention provides an isolated nucleic acid molecule comprising a polynucleotide which hybridizes under stringent hybridization conditions to a portion of the polynucleotide in a nucleic acid molecule of the invention described above, for instance, the cDNA clone contained in ATCC Deposit 75703. By "stringent hybridization conditions" is intended overnight incubation at 42° C. in a solution comprising: 50% formamide, 5×SSC (150 mM NaCl, 15 mM trisodium citrate), 50 mM sodium phosphate (pH 7.6), 5× Denhardt's solution, 10% dextran sulfate, and 20 g/ml denatured, sheared salmon sperm DNA, followed by washing the filters in 0.1×SSC at about 65° C.

By a polynucleotide which hybridizes to a "portion" of a polynucleotide is intended a polynucleotide (either DNA or RNA) hybridizing to at least about 15 nucleotides (nt), and more preferably at least about 20 nt, still more preferably at least about 30 nt, and even more preferably about 30–70 nt of the reference polynucleotide. These are useful as diagnostic probes and primers as discussed above and in more detail below.

Of course, polynucleotides hybridizing to a larger portion of the reference polynucleotide (e.g. the deposited cDNA clone), for instance, a portion 50–750 nt in length, or even to the entire of the reference polynucleotide, are also useful as probes according to the present invention, as are polynucleotides corresponding to most, if not all, of the nucleotide sequence of the deposited cDNA or the nucleotide sequence as shown in FIG. 1. By a portion of a polynucleotide of "at least 20 nt in length," for example, is intended 20 or more contiguous nucleotides from the nucleotide sequence of the reference polynucleotide. As indicated, such portions are useful diagnostically either as a probe according to conventional DNA hybridization techniques or as primers for amplification of a target sequence by the polymerase chain reaction (PCR), as described, for instance, in Molecular Cloning, A Laboratory Manual, 2nd. edition, Sambrook, J., Fritsch, E. F. and Maniatis, T., eds., Cold Spring Harbor Laboratory Press, Cold Spring Harbor, N.Y. (1989), the entire disclosure of which is hereby incorporated herein by reference.

Since an Ckβ-6 cDNA clone has been deposited and its determined nucleotide sequence provided, generating polynucleotides which hybridize to a portion of the Ckβ-6 cDNA molecules would be routine to the skilled artisan. For example, restriction endonuclease cleavage or shearing by sonication of an Ckβ-6 cDNA clone could easily be used to generate DNA portions of various sizes which are polynucleotides that hybridize, respectively, to a portion of the Ckβ-6 cDNA molecule.

Alternatively, the hybridizing polynucleotides of the present invention could be generated synthetically according to known techniques. Of course, a polynucleotide which hybridizes only to a poly A sequence (such as the 3. terminal poly(A) tract of a cDNA, or to a complementary stretch of T (or U) residues, would not be included in a polynucleotide of the invention used to hybridize to a portion of a nucleic acid of the invention, since such a polynucleotide would hybridize to any nucleic acid molecule containing a poly (A) stretch or the complement thereof (e.g. practically any double-stranded cDNA clone).

As indicated, nucleic acid molecules of the present invention which encode an Ckβ-6 polypeptide may include, but are not limited to those encoding the amino acid sequence of the mature polypeptide, by itself; the coding sequence for the mature polypeptide and additional sequences, such as those encoding the leader or secretory sequence, such as a pre-, or pro- or prepro-protein sequence; the coding sequence of the mature polypeptide, with or without the aforementioned additional coding sequences, together with additional, non-coding sequences, including for example, but not limited to introns and non-coding 5' and 3' sequences, such as the transcribed, non-translated sequences that play a role in transcription, mRNA processing, including splicing and polyadenylation signals, for example— ribosome binding and stability of mRNA; an additional coding sequence which codes for additional amino acids, such as those which provide additional functionalities. Thus, the sequence encoding the polypeptide may be fused to a marker sequence, such as a sequence encoding a peptide which facilitates purification of the fused polypeptide. In certain preferred embodiments of this aspect of the invention, the marker amino acid sequence is a hexa-histidine peptide, such as the tag provided in a pQE vector (Qiagen, Inc.), among others, many of which are commercially available. As described in Gentz, et al., *Proc. Natl. Acad Sci.* (*USA*) 86:821–824 (1989), for instance, hexa-histidine provides for convenient purification of the fusion protein. The "HA" tag is another peptide useful for purification which corresponds to an epitope derived from the influenza hemagglutinin protein, which has been described by Wilson, et al., *Cell* 37:767 (1984). As discussed below, other such fusion proteins include at least an Ckβ-6 polypeptide or fragment fused to Fc at the N- or C-terminus.

The present invention further relates to variants of the nucleic acid molecules of the present invention, which encode portions, analogs or derivatives of an Ckβ-6 polypeptide. Variants may occur naturally, such as a natural allelic variant By an "allelic variant" is intended one of several alternate forms of a gene occupying a given locus on a chromosome of an organism. Genes V, Lewin, B., ed., Oxford University Press, New York (1994). Non-naturally occurring variants may be produced using art-known mutagenesis techniques.

Such variants include those produced by nucleotide substitutions, deletions or additions. The substitutions, deletions or additions may involve one or more nucleotides. The variants may be altered in coding regoins, non-coding regions, or both. Alterations in the coding regions may produce conservative or non-conservative amino acid substitutions, deletions or additions. Especially preferred among these are silent substitutions, additions and deletions, which do not alter the properties and activities of an Ckβ-6 polypeptide or portions thereof. Also especially preferred in this regard are conservative substitutions. Most highly preferred are nucleic acid molecules encoding the mature protein or the mature amino acid sequence encoded by the deposited cDNA clone, as described herein.

The present invention is further directed to polynucleotides having at least a 70% identity, preferably at least 90% and more preferably at least a 95% identity to a polynucleotide which encodes the polypeptide of SEQ ID NO:2 as well as fragments thereof, which fragments have at least 30 bases and preferably at least 50 bases and to polypeptides encoded by such polynucleotides.

Further embodiments of the invention include isolated nucleic acid molecules comprising a polynucleotide having a nucleotide sequence at least 90% identical, and more preferably at least 95%, 96%, 97%, 98% or 99% identical to (a) a nucleotide sequence encoding an Ckβ-6 polypeptide or fragment, having an amino acid sequence of FIG. 1 (SEQ ID NO:2), including the predicted leader sequence; (b) a nucleotide sequence encoding an Ckβ-6 polypeptide having the amino acid sequence of FIG. 1 (SEQ ID NO:2), including the predicted leader sequence excepting the N-terminal methionine; (c) a nucleotide sequence encoding the mature Ckβ-6 polypeptide (fill-length polypeptide with the leader removed); (d) a nucleotide sequence encoding the full-length polypeptide having the complete amino acid sequence including the leader encoded by the deposited cDNA clone; (e) a nucleotide sequence encoding the full-length polypeptide having the complete amino acid sequence including the leader excepting the N-terminal methionine encoded by the deposited cDNA clone; (f) a nucleotide sequence encoding the mature polypeptide having the amino acid sequence encoded by the deposited cDNA clone; or (g) a nucleotide sequence complementary to any of the nucleotide sequences in (a), (b), (c), (d), (e) or (f).

By a polynucleotide having a nucleotide sequence at least, for example, 95% "identical" to a reference nucleotide sequence encoding an Ckβ-6 polypeptide is intended that the nucleotide sequence of the polynucleotide is identical to the reference sequence except that the polynucleotide sequence may include up to five point mutations per each 100 nucleotides of the reference nucleotide sequence encoding the polypeptide. In other words, to obtain a polynucleotide having a nucleotide sequence at least 95% identical to a reference nucleotide sequence, up to 5% of the nucleotides in the reference sequence may be deleted or substituted with another nucleotide, or a number of nucleotides up to 5% of the total nucleotides in the reference sequence may be inserted into the reference sequence. These mutations of the reference sequence may occur at the 5' or 3' terminal positions of the reference nucleotide sequence or anywhere between those terminal positions, interspersed either individually among nucleotides in the reference sequence or in one or more contiguous groups within the reference sequence.

As a practical matter, whether any particular nucleic acid molecule is at least 90%, 95%, 96%, 97%, 98% or 99% identical to, for instance, the nucleotide sequence shown in FIG. 1, or to the nucleotide sequence of the deposited cDNA clone can be determined conventionally using known computer programs such as the Bestfit program (Wisconsin Sequence Analysis Package, Version 8 for Unix, Genetics Computer Group, University Research Park, 575 Science Drive, Madison, Wis. 53711. Bestfit uses the local homology algorithm of Smith and Waterman, Advances in Applied Mathematics 2: 482–489 (1981), to find the best segment of homology between two sequences. When using Bestfit or any other sequence alignment program to determine whether a particular sequence is, for instance, 95% identical to a reference sequence according to the present invention, the parameters are set, of course, such that the percentage of identity is calculated over the full length of the reference nucleotide sequence and that gaps in homology of up to 5% of the total number of nucleotides in the reference sequence are allowed.

As one of ordinary skill would appreciate, due to the possibilities of sequencing errors discussed above, as well as the variability of cleavage sites for leaders in different known proteins, the actual mature Ckβ-6 polypeptide encoded by the deposited cDNA comprises about 93 amino acids, but may be anywhere in the range of 86–99 amino acids; and the actual leader sequence of this protein is about 26 amino acids, but may be anywhere in the range of about 20 to about 33 amino acids.

Such isolated molecules, particularly DNA molecules, are useful as probes for gene mapping, by in situ hybridization with chromosomes, and for detecting expression of an Ckβ-6 gene in human tissue, for instance, by Northern blot analysis. The present invention is further directed to fragments of the isolated nucleic acid molecules described herein. By a fragment of an isolated nucleic acid molecule having the nucleotide sequence of the deposited Ckβ-6 cDNA, or a nucleotide sequence shown in FIG. 1 (SEQ ID NO:1), is intended fragments at least about 15 nt, and more preferably at least about 20 nt, still more preferably at least about 30 nt, and even more preferably, at least about 40 nt in length which are useful as diagnostic probes and primers as discussed herein. Of course, larger fragments 50–500 nt in length are also useful according to the present invention as are fragments corresponding to most, if not all, of a nucleotide sequence of the deposited Ckβ-6 cDNAs, or as shown in FIG. 1 (SEQ ID NO:1). By a fragment at least 20 nt in length, for example, is intended fragments which include 20 or more contiguous bases from the nucleotide sequence of the deposited cDNA or the nucleotide sequence as shown in FIG. 1 (SEQ ID NO: 1). Since the gene has been deposited and the nucleotide sequences shown in FIG. 1 (SEQ ID NO: 1) is provided, generating such DNA fragments would be routine to the skilled artisan. For example, restriction endonuclease cleavage or shearing by sonication could easily be used to generate fragments of various sizes. Alternatively, such fragments could be generated synthetically.

Fragments of the full length gene of the present invention may be used as a hybridization probe for a cDNA library to isolate the full length cDNA and to isolate other cDNAs which have a high sequence similarity to the gene or similar biological activity. Probes of this type preferably have at least 30 bases and may contain, for example, 50 or more bases. The probe may also be used to identify a cDNA clone corresponding to a full length transcript and a genomic clone or clones that contain the complete gene including regulatory and promotor regions, exons, and introns. An example of a screen comprises isolating the coding region of the gene by using the known DNA sequence to synthesize an oligonucleotide probe. Labeled oligonucleotides having a sequence complementary to that of the gene of the present invention are used to screen a library of human cDNA, genomic DNA or mRNA to determine which members of the library the probe hybridizes to.

Polypeptides and Polypeptide Fragments

The present invention further relates to an isolated polypeptide which has the deduced amino acid sequence of FIG. 1 (SEQ ID NO:2) or which has the amino acid sequence encoded by the deposited cDNA, as well as fragments, analogs and derivatives of such polypeptide. The terms "peptide" and "oligopeptide" are considered synonymous (as is commonly recognized) and each term can be used interchangeably as the context requires to indicate a chain of at least two amino acids coupled by peptidyl linkages. The word "polypeptide" is used herein for chains containing more than ten amino acid residues. All oligopeptide and polypeptide formulas or sequences herein are written from left to right and in the direction from amino terminus to carboxy terminus.

By "a polypeptide having Ckβ-6 activity" is intended polypeptides exhibiting activity similar, but not necessarily identical, to an activity of the Ckβ-6 protein of the invention (either the full-length protein or, preferably, the mature protein), as measured in a particular biological assay. Ckβ-6 protein activity can be measured by the assays set forth in Examples 5, 6, 7 and 8. For example, Ckβ-6 protein activity measured using the in vitro myeloprotection assay disclosed in Example 7, infra.

Briefly, lineage-depleted populations of cells (Lin cells) are isolated from mouse bone marrow and incubated in the presence of multiple cytokines with or without Ckβ-6. After 48 hours, one set of each culture receives 5-Fu and the incubation is then continued for additional 24 hours, at which point the numbers of surviving low proliferative potential colony-forming cells (LPP-CFC) and high proliferative potential colony-forming cells (HPP-CFC) are determined by any suitable clonogenic assay known to those of skill in the art.

Thus, "a polypeptide having Ckβ-6 protein activity" includes polypeptides that exhibit Ckβ-6 activity, in the above-described assay. Although the degree of activity need not be identical to that of the Ckβ-6 protein, preferably, "a polypeptide having Ckβ-6 protein activity" will exhibit substantially similar activity as compared to the Ckβ-6 protein (i.e., the candidate polypeptide will exhibit greater activity or not more than about twenty-fold less and, preferably, not more than about ten-fold less activity relative to the reference Ckβ-6 protein).

The present invention further relates to Ckβ-6 polypeptides which have the amino acid sequence of FIG. 1 (SEQ ID NO:2) or which have the amino acid sequence encoded by the deposited cDNA, as well as fragments, analogs and derivatives of such polypeptide.

The terms "fragment," "derivative" and "analog" when referring to the polypeptide of FIG. 1 (SEQ ID NO:2) or that encoded by the deposited cDNA, means a polypeptide which retains essentially the same biological function or activity as such polypeptide. Thus, an analog includes a proprotein which can be activated by cleavage of the proprotein portion to produce an active mature polypeptide.

The polypeptide of the present invention may be a recombinant polypeptide, a natural polypeptide or a synthetic polypeptide, preferably a recombinant polypeptide.

The fragment, derivative or analog of the polypeptide of FIG. 1 (SEQ ID NO:2) or that encoded by the deposited cDNA may be (i) one in which one or more of the amino acid residues are substituted with a conserved or non-conserved amino acid residue (preferably a conserved amino acid residue) and such substituted amino acid residue may or may not be one encoded by the genetic code, or (ii) one in which one or more of the amino acid residues includes a substituent group, or (iii) one in which the mature polypeptide is fused with another compound, such as a compound to increase the half-life of the polypeptide (for example, polyethylene glycol), or (iv) one in which the additional amino acids are fused to the mature polypeptide, such as a leader or secretory sequence or a sequence which is employed for purification of the mature polypeptide or a proprotein sequence. Such fragments, derivatives and analogs are deemed to be within the scope of those skilled in the art from the teachings herein.

The polypeptides and polynucleotides of the present invention are preferably provided in an isolated form, and preferably are purified to homogeneity.

The polypeptides of the present invention include the polypeptide of SEQ ID NO:2 (in particular the mature polypeptide) as well as polypeptides which have at least 70% similarity (preferably at least 70% identity) to the polypeptide of SEQ ID NO:2 and more preferably at least 90% similarity (more preferably at least 90% identity) to the polypeptide of SEQ ID NO:2 and still more preferably at least 95% similarity (still more preferably at least 95% identity) to the polypeptide of SEQ ID NO:2 and also include portions of such polypeptides with such portion of the polypeptide generally containing at least 30 amino acids and more preferably at least 50 amino acids.

As known in the art "similarity" between two polypeptides is determined by comparing the amino acid sequence and its conserved amino acid substitutes of one polypeptide to the sequence of a second polypeptide.

Of course, due to the degeneracy of the genetic code, one of ordinary skill in the art will immediately recognize that a large number of the nucleic acid molecules having a sequence at least 90%, 95%, 96%, 97%, 98%, or 99% identical to the nucleic acid sequence of the deposited cDNA (ATCC 75703) or the nucleic acid sequence shown in FIG. 1 (SEQ ID NO:1) will encode a polypeptide "having Ckβ-6 protein activity". In fact, since degenerate variants of these nucleotide sequences all encode the same polypeptide, this will be clear to the skilled artisan even without performing the above described comparison assay. It will be further recognized in the art that, for such nucleic acid molecules that are not degenerate variants, a reasonable number will also encode a polypeptide having Ckβ-6 protein activity. This is because the skilled artisan is fully aware of amino acid substitutions that are either less likely or not likely to significantly effect protein function (e.g. replacing one aliphatic amino acid with a second aliphatic amino acid).

For example, guidance concerning how to make phenotypically silent amino acid substitutions is provided in Bowie, J. U., et al., "Deciphering the Message in Protein Sequences: Tolerance to Amino Acid Substitutions," *Science* 247:1306–1310 (1990), wherein the authors indicate that there are two main approaches for studying the tolerance of an amino acid sequence to change. The first method relies on the process of evolution, in which mutations are either accepted or rejected by natural selection. The second approach uses genetic engineering to introduce amino acid changes at specific positions of a cloned gene and selections or screens to identify sequences that maintain functionality. As the authors state, these studies have revealed that proteins are surprisingly tolerant of amino acid substitutions. The authors further indicate which amino acid changes are likely to be permissive at a certain position of the protein. For example, most buried amino acid residues require nonpolar side chains, whereas few features of surface side chains are generally conserved. Other such phenotypically silent substitutions are described in Bowie, J. U. et al., supra, and the references cited therein.

Fragments or portions of the polypeptides of the present invention may be employed for producing the corresponding full-length polypeptide by peptide synthesis; therefore, the fragments may be employed as intermediates for producing the full-length polypeptides. Fragments or portions of the polynucleotides of the present invention may be used to synthesize full-length polynucleotides of the present invention.

For secretion of the translated protein into the lumen of the endoplasmic reticulum, into the periplasmic space or into the extracellular environment, appropriate secretion signals may be incorporated into the expressed polypeptide. The signals may be endogenous to the polypeptide or they may be heterologous signals.

In addition, polypeptides of the invention may also include an initial modified methionine residue, in some cases as a result of host-mediated processes. Thus, it is well known in the art that the N-terminal methionine encoded by the translation initiation codon generally is removed with high efficiency from any protein after translation in all eukaryotic cells. While the N-terminal methionine on most proteins also is efficiently removed in most prokaryotes, for some proteins this prokaryotic removal process is inefficient, depending on the nature of the amino acid to which the N-terminal methionine is covalently linked. Thus, a full-length Ckβ-6 polypeptide lacking the N-terminal methionine is specifically contemplated by the invention. Further, it will be recognized by those of skill in the art that in many cases it may be beneficial to add an N-terminal methionine to an N-terminally truncated Ckβ-6 polypeptide otherwise lacking an amino terminal methionine, for example, to achieve efficient expression by recombinant technology in bacterial such as *E. coli*.

The polypeptide may be expressed in a modified form, such as a fusion protein, and may include not only secretion signals, but also additional heterologous functional regions. For instance, a region of additional amino acids, particularly charged amino acids, may be added to the N-terminus of the polypeptide to improve stability and persistence in the host cell, during purification, or during subsequent handling and storage. Also, peptide moieties may be added to the polypeptide to facilitate purification. Such regions may be removed prior to final preparation of the polypeptide. The addition of peptide moieties to polypeptides to engender secretion or excretion, to improve stability and to facilitate purification, among others, are familiar and routine techniques in the art. A preferred fusion protein comprises a heterologous region from immunoglobulin that is useful to solubilize proteins. For example, EP-A-O 464 533 (Canadian counterpart 2045869) discloses fusion proteins comprising various portions of constant region of immunoglobin molecules together with another human protein or part thereof. In many cases, the Fc part in a fusion protein is thoroughly advantageous for use in therapy and diagnosis and thus results, for example, in improved pharmacokinetic properties (EP-A 0232 262). On the other hand, for some uses it would be desirable to be able to delete the Fe part after the fusion protein has been expressed, detected and purified in the advantageous manner described. This is the case when Fe portion proves to be a hindrance to use in therapy and diagnosis, for example when the fusion protein is to be used as antigen for immunizations. In drug discovery, for example, human proteins, such as, hIL5-has been fused with Fc portions for the purpose of high-throughput screening assays to identify antagonists of hIL-5. See, Bennett, D., et al., *Journal of Molecular Recognition* 8:52–58 (1995) and Johanson, K., et al., *J. Biol. Chem.* 270(16):9459–9471 (1995).

The Ckβ-6 protein can be recovered and purified from recombinant cell cultures by well-known methods including ammonium sulfate or ethanol precipitation, acid extraction, anion or cation exchange chromatography, phosphocellulose chromatography, hydrophobic interaction chromatography, affinity chromatography, hydroxylapatite chromatography and lectin chromatography. Most preferably, high performance liquid chromatography ("HPLC") is employed for purification. Polypeptides of the present invention include naturally purified products, products of chemical synthetic procedures, and products produced by recombinant techniques from a prokaryotic or eukaryotic host, including, for example, bacterial, yeast, higher plant, insect and mammalian cells. Depending upon the host employed in a recombinant production procedure, the polypeptides of the present invention may be glycosylated or may be non-glycosylated. In addition, polypeptides of the invention may also include an initial modified methionine residue, in some cases as a result of host-mediated processes.

It will be recognized in the art that some amino acid sequences of the Ckβ-6 polypeptide can be varied without significant affect on the structure or function of the protein. If such differences in sequence are contemplated, it should be remembered that there will be critical areas on the protein which determine activity. In general, it is possible to replace residues which form the tertiary structure, provided that residues performing a similar function are used. In other instances, the type of residue may be completely unimportant if the alteration occurs at a non-critical region of the protein.

Thus, the invention further includes variations of an Ckβ-6 polypeptide which show substantial Ckβ-6 polypeptide activity or which include regions of an Ckβ-6 protein such as the protein portions discussed below. Such mutants include deletions, insertions, inversions, repeats, and type substitutions (for example, substituting one hydrophilic residue for another, but not strongly hydrophilic for strongly hydrophobic as a rule). Small changes or such "neutral" amino acid substitutions will generally have little effect on activity.

Typically seen as conservative substitutions are the replacements, one for another, among the aliphatic amino acids Ala, Val, Leu and Ile; interchange of the hydroxyl residues Ser and Thr, exchange of the acidic residues Asp and Glu, substitution between the amide residues Asn and Gln, exchange of the basic residues Lys and Arg and replacements among the aromatic residues Phe, Tyr.

Of additional special interest are also substitutions of charged amino acids with another charged amino acid or with neutral amino acids. This may result in proteins with improved characteristics such as less aggregation. Prevention of aggregation is highly desirable. Aggregation of proteins cannot only result in a reduced activity but be problematic when preparing pharmaceutical formulations because they can be immunogenic (Pinckard, et al., *Clin. Exp. Immunol.* 2:331–340 (1967), Robbins, et al., *Diabetes* 36:838–845 (1987), Cleland, et al., *Crit. Rev. Therapeutic Drug Carrier Systems* 10:307–377 (1993).

The replacement of amino acids can also change the selectivity of the binding to cell surface receptors. Ostade, et al., *Nature* 361:266–268 (1993), described certain TNF alpha mutations resulting in selective binding of TNF alpha to only one of the two known TNF receptors.

As indicated in detail above, further guidance concerning which amino acid changes are likely to be phenotypically silent (i.e., are not likely to have a significant deleterious effect on a function) can be found in Bowie, J. U., et al., "Deciphering the Message in Protein Sequences: Tolerance to Amino Acid Substitutions," *Science* 247:1306–1310 (1990) (see Table 1).

As indicated, changes are preferably of a minor nature, such as conservative amino acid-substitutions that do not significantly affect the folding or activity of the protein (see Table 1).

TABLE 1

Conservative Amino Acid Substitutions

| | |
|---|---|
| Aromatic | Phenylalanine |
| | Tryptophan |
| | Tyrosine |
| Hydrophobic | Leucine |
| | Isoleucine |
| | Valine |
| Polar | Glutamine |
| | Asparagine |
| Basic | Arginine |
| | Lysine |
| | Histidine |
| Acidic | Aspartic Acid |
| | Glutamic Acid |
| Small | Alanine |
| | Serine |
| | Threonine |
| | Methionine |
| | Glycine |

Of course, the number of amino acid substitutions a skilled artisan would make depends on many factors, including those described above. Generally speaking, the number of substitutions for any given Ckβ-6 polypeptide will not be more than 50, 40, 30, 25, 20, 15, 10, 5 or 3.

Recombinant DNA technology known to those skilled in the art can be used to create novel proteins. Muteins and deletions or fusion proteins can show, e.g., enhanced activity or increased stability. In addition, they could be purified in higher yields and show better solubility at least under certain purification and storage conditions. Set out below are additional examples of mutations that can be constructed.

Ckβ-6 Amino terminal and carboxy terminal deletions: Interferon gamma shows up to ten times higher activities by deleting 8–10 amino acid residues from the carboxy terminus of the protein (Dšbeli, et al., *J. Biotechnology* 7:199–216 (1988)). Ron, et al., *J. Biol. Chem.* 268(4):2984–2988 (1993), reported modified KGF proteins that had heparin binding activity even if 3, 8, or 27 amino terminal amino acid residues were missing. Many other examples are known to those skilled in the art.

In the present case it has been shown that the Ckβ-6 polypeptide composition, comprising C-terminal Ckβ-6 truncations, produced according to the method of Example 3 retains Ckβ-6 polypeptide activity. Furthermore, since the protein of the invention is a member of the chemokine polypeptide family, deletions of N-terminal amino acids up to the cysteine at position 7 of SEQ ID NO:2 (Cys-7), and deletions of C-terminal amino acids up to the cysteine at position 48 of SEQ ID NO:2 (Cys-48), may retain some biological activity such as receptor binding or modulation of target cell activities. Polypeptides having further N- and C-terminal deletions including Cys-7 or Cys-48 would not be expected to retain such biological activities because it is known that these residues in a chemokine-related polypeptide are required for forming a disulfide bridge to provide structural stability which is needed for receptor binding and signal transduction.

However, even if deletion of one or more amino acids from the N- or C-termini of a protein results in modification of loss of one or more biological functions of the protein, other biological activities may still be retained. Thus, the ability of the shortened protein to induce and/or bind to antibodies which recognize the complete or mature form of the protein generally will be retained when less than the majority of the residues of the complete or mature protein are removed from either termini. Whether a particular polypeptide lacking N- or C-terminal residues of a complete protein retains such immunologic activities can readily be determined by routine methods described herein and otherwise known in the art.

Accordingly, the present invention further provides polypeptides having one or more residues deleted from the amino terminus of the amino acid sequence of the Ckβ-6 polypeptide shown in SEQ ID NO:2 up to the cysteine as position 7. Likewise the present invention provides polypeptides having one or more residues deleted from the carboxy terminus of the amino acid sequence of the Ckβ-6 polypeptide shown in SEQ ID NO:2, up to the cysteine at position 48. In particular, the present invention provides polypeptides having the amino acid sequence of residues n-93 of the amino acid sequence in SEQ ID NO:2, where n is any integer in the range of 1–7. Similarly, the present invention provides polypeptides having the amino acid sequence of residues 1-m of the amino acid sequence in SEQ ID NO:2, where m is any integer in the range of 48–93.

The invention also provides polypeptides having one or more amino acids deleted from both the amino and the carboxyl termini, which may be described generally as having residues x-n-m of SEQ ID NO:2, where n and m are integers as described above, and x may be either $NH_2$ or methionine.

More in particular, the invention provides polypeptides having the amino acid sequence of residues:

| | |
|---|---|
| Val (1) to Cys (93) | Pro (4) to Cys (93) |
| Val (2) to Cys (93) | Ser (5) to Cys (93) |
| Ile (3) to Cys (93) | Pro (6) to Cys (93) |
| Val (1) to Thr (92) | Pro (4) to Thr (92) |
| Val (2) to Thr (92) | Ser (5) to Thr (92) |
| Ile (3) to Thr (92) | Pro (6) to Thr (92) |
| Val (1) to Thr (91) | Pro (4) to Thr (91) |
| Val (2) to Thr (91) | Ser (5) to Thr (91) |
| Ile (3) to Thr (91) | Pro (6) to Thr (91) |
| Val (1) to Gln (90) | Pro (4) to Gln (90) |
| Val (2) to Gln (90) | Ser (5) to Gln (90) |
| Ile (3) to Gln (90) | Pro (6) to Gln (90) |
| Val (1) to Asn (89) | Pro (4) to Asn (89) |
| Val (2) to Asn (89) | Ser (5) to Asn (89) |
| Ile (3) to Asn (89) | Pro (6) to Asn (89) |
| Val (1) to Gly (88) | Pro (4) to Gly (88) |
| Val (2) to Gly (88) | Ser (5) to Gly (88) |
| Ile (3) to Gly (88) | Pro (6) to Gly (88) |
| Val (1) to Pro (87) | Pro (4) to Pro (87) |
| Val (2) to Pro (87) | Ser (5) to Pro (87) |
| Ile (3) to Pro (87) | Pro (6) to Pro (87) |
| Val (1) to Tyr (86) | Pro (4) to Tyr (86) |
| Val (2) to Tyr (86) | Ser (5) to Tyr (86) |
| Ile (3) to Tyr (86) | Pro (6) to Tyr (86) |
| Val (1) to Arg (85) | Pro (4) to Arg (85) |
| Val (2) to Arg (85) | Ser (5) to Arg (85) |
| Ile (3) to Arg (85) | Pro (6) to Arg (85) |
| Val (1) to Gln (84) | Pro (4) to Gln (84) |
| Val (2) to Gln (84) | Ser (5) to Gln (84) |
| Ile (3) to Gln (84) | Pro (6) to Gln (84) |
| Val (1) to Val (83) | Pro (4) to Val (83) |
| Val (2) to Val (83) | Ser (5) to Val (83) |
| Ile (3) to Val (83) | Pro (6) to Val (83) |
| Val (1) to Pro (82) | Pro (4) to Pro (82) |
| Val (2) to Pro (82) | Ser (5) to Pro (82) |
| Ile (3) to Pro (82) | Pro (6) to Pro (82) |
| Val (1) to Gly (81) | Pro (4) to Gly (81) |
| Val (2) to Gly (81) | Ser (5) to Gly (81) |
| Ile (3) to Gly (81) | Pro (6) to Gly (81) |
| Val (1) to Lys (80) | Pro (4) to Lys (80) |

-continued

| | |
|---|---|
| Val (2) to Lys (80) | Ser (5) to Lys (80) |
| Ile (3) to Lys (80) | Pro (6) to Lys (80) |
| Val (1) to Val (79) | Pro (4) to Val (79) |
| Val (2) to Val (79) | Ser (5) to Val (79) |
| Ile (3) to Val (79) | Pro (6) to Val (79) |
| Val (1) to Ala (78) | Pro (4) to Ala (78) |
| Val (2) to Ala (78) | Ser (5) to Ala (78) |
| Ile (3) to Ala (78) | Pro (6) to Ala (78) |
| Val (1) to Val (77) | Pro (4) to Val (77) |
| Val (2) to Val (77) | Ser (5) to Val (77) |
| Ile (3) to Val (77) | Pro (6) to Val (77) |
| Val (1) to Ala (76) | Pro (4) to Ala (76) |
| Val (2) to Ala (76) | Ser (5) to Ala (76) |
| Ile (3) to Ala (76) | Pro (6) to Ala (76) |
| Val (1) to Arg (75) | Pro (4) to Arg (75) |
| Val (2) to Arg (75) | Ser (5) to Arg (75) |
| Ile (3) to Arg (75) | Pro (6) to Arg (75) |
| Val (1) to Ala (74) | Pro (4) to Ala (74) |
| Val (2) to Ala (74) | Ser (5) to Ala (74) |
| Ile (3) to Ala (74) | Pro (6) to Ala (74) |
| Val (1) to Arg (73) | Pro (4) to Arg (73) |
| Val (2) to Arg (73) | Ser (5) to Arg (73) |
| Ile (3) to Arg (73) | Pro (6) to Arg (73) |
| Val (1) to Pro (72) | Pro (4) to Pro (72) |
| Val (2) to Pro (72) | Ser (5) to Pro (72) |
| Ile (3) to Pro (72) | Pro (6) to Pro (72) |
| Val (1) to Ser (71) | Pro (4) to Ser (71) |
| Val (2) to Ser (71) | Ser (5) to Ser (71) |
| Ile (3) to Ser (71) | Pro (6) to Ser (71) |
| Val (1) to Ala (70) | Pro (4) to Ala (70) |
| Val (2) to Ala (70) | Ser (5) to Ala (70) |
| Ile (3) to Ala (70) | Pro (6) to Ala (70) |
| Val (1) to Lys (69) | Pro (4) to Lys (69) |
| Val (2) to Lys (69) | Ser (5) to Lys (69) |
| Ile (3) to Lys (69) | Pro (6) to Lys (69) |
| Val (1) to Lys (68) | Pro (4) to Lys (68) |
| Val (2) to Lys (68) | Ser (5) to Lys (68) |
| Ile (3) to Lys (68) | Pro (6) to Lys (68) |
| Val (1) to Gln (67) | Pro (4) to Gln (67) |
| Val (2) to Gln (67) | Ser (5) to Gln (67) |
| Ile (3) to Gln (67) | Pro (6) to Gln (67) |
| Val (1) to Lys (66) | Pro (4) to Lys (66) |
| Val (2) to Lys (66) | Ser (5) to Lys (66) |
| Ile (3) to Lys (66) | Pro (6) to Lys (66) |
| Val (1) to Ala (65) | Pro (4) to Ala (65) |
| Val (2) to Ala (65) | Ser (5) to Ala (65) |
| Ile (3) to Ala (65) | Pro (6) to Ala (65) |
| Val (1) to Asp (64) | Pro (4) to Asp (64) |
| Val (2) to Asp (64) | Ser (5) to Asp (64) |
| Ile (3) to Asp (64) | Pro (6) to Asp (64) |
| Val (1) to Leu (63) | Pro (4) to Leu (63) |
| Val (2) to Leu (63) | Ser (5) to Leu (63) |
| Ile (3) to Leu (63) | Pro (6) to Leu (63) |
| Val (1) to Asn (62) | Pro (4) to Asn (62) |
| Val (2) to Asn (62) | Ser (5) to Asn (62) |
| Ile (3) to Asn (62) | Pro (6) to Asn (62) |
| Val (1) to Lys (61) | Pro (4) to Lys (61) |
| Val (2) to Lys (61) | Ser (5) to Lys (61) |
| Ile (3) to Lys (61) | Pro (6) to Lys (61) |
| Val (1) to Met (60) | Pro (4) to Met (60) |
| Val (2) to Met (60) | Ser (5) to Met (60) |
| Ile (3) to Met (60) | Pro (6) to Met (60) |
| Val (1) to Tyr (59) | Pro (4) to Tyr (59) |
| Val (2) to Tyr (59) | Ser (5) to Tyr (59) |
| Ile (3) to Tyr (59) | Pro (6) to Tyr (59) |
| Val (1) to Arg (58) | Pro (4) to Arg (58) |
| Val (2) to Arg (58) | Ser (5) to Arg (58) |
| Ile (3) to Arg (58) | Pro (6) to Arg (58) |
| Val (1) to Gln (57) | Pro (4) to Gln (57) |
| Val (2) to Gln (57) | Ser (5) to Gln (57) |
| Ile (3) to Gln (57) | Pro (6) to Gln (57) |
| Val (1) to Val (56) | Pro (4) to Val (56) |
| Val (2) to Val (56) | Ser (5) to Val (56) |
| Ile (3) to Val (56) | Pro (6) to Val (56) |
| Val (1) to Trp (55) | Pro (4) to Trp (55) |
| Val (2) to Trp (55) | Ser (5) to Trp (55) |
| Ile (3) to Trp (55) | Pro (6) to Trp (55) |
| Val (1) to Glu (54) | Pro (4) to Glu (54) |
| Val (2) to Glu (54) | Ser (5) to Glu (54) |

-continued

| | |
|---|---|
| Ile (3) to Glu (54) | Pro (6) to Glu (54) |
| Val (1) to Gln (53) | Pro (4) to Gln (53) |
| Val (2) to Gln (53) | Ser (5) to Gln (53) |
| Ile (3) to Gln (53) | Pro (6) to Gln (53) |
| Val (1) to Lys (52) | Pro (4) to Lys (52) |
| Val (2) to Lys (52) | Ser (5) to Lys (52) |
| Ile (3) to Lys (52) | Pro (6) to Lys (52) |
| Val (1) to Pro (51) | Pro (4) to Pro (51) |
| Val (2) to Pro (51) | Ser (5) to Pro (51) |
| Ile (3) to Pro (51) | Pro (6) to Pro (51) |
| Val (1) to Asp (50) | Pro (4) to Asp (50) |
| Val (2) to Asp (50) | Ser (5) to Asp (50) |
| Ile (3) to Asp (50) | Pro (6) to Asp (50) |
| Val (1) to Gly (49) | Pro (4) to Gly (49) |
| Val (2) to Gly (49) | Ser (5) to Gly (49) |
| Ile (3) to Gly (49) | Pro (6) to Gly (49) |
| Val (1) to Cys (48) | Pro (4) to Cys (48) |
| Val (2) to Cys (48) | Ser (5) to Cys (48) |
| Ile (3) to Cys (48) | Pro (6) to Cys (48) | all of SEQ ID NO:2. The polypeptides described above may also have an N-terminal methionine. Polynucleotides encoding these polypeptides also are provided. Also included are a nucleotide sequence encoding a polypeptide consisting of a portion of the complete Ckβ-6 amino acid sequence encoded by the cDNA clone contained in ATCC Deposit No. 75703, where this portion excludes from 1 to about 6 amino acids from the amino terminus of the mature amino acid sequence encoded by the cDNA clone contained in ATCC Deposit No. 75703, or from 1 to about 45 amino acids from the carboxy terminus, or any combination of the above amino terminal and carboxy terminal deletions, of the complete amino acid sequence encoded by the cDNA clone contained in ATCC Deposit No. 75703. Polynucleotides encoding all of the above deletion mutant polypeptide forms also are provided.

Particularly preferred Ckβ-6 C-terminal truncations are shown below (numbering is as shown in SEQ ID NO:2):

Val(1) to Ala (78);

Val (1) to Ala (76);

Val (1) to Arg (75); and

Val (1) to Arg (73).

Substitution of Amino Acids: A further aspect of the present invention also includes the substitution of amino acids. Of special interest are conservative amino acid substitutions that do not significantly affect the folding of the protein. Examples of conservative amino acid substitutions known to those skilled in the art are set forth Table 1, above.

Of additional special interest are also substitutions of charged amino acids with another charged amino acid or with neutral amino acids. This may result in proteins with improved characteristics such as less aggregation. Prevention of aggregation is highly desirable. Aggregation of proteins cannot only result in a reduced activity but be problematic when preparing pharmaceutical formulations because they can be immunogenic (Pinckard, et al., Clin. Exp. Immunol. 2:331–340 (1967); Robbins, et al., Diabetes 36:838–845 (1987); Cleland, et al., Crit. Rev. Therapeutic Drug Carrier Systems 10:307–377 (1993)).

The Ckβ-6 protein may contain one or several amino acid substitutions, deletions or additions, either from natural mutation or human manipulation. Examples of some preferred mutations are:

Lys (42) to Ser

Lys (43) to Ser

The lysine residues at positions 42 and 43 of SEQ ID NO:2 correspond with a site known to be necessary for heparin binding in other chemokines. These substitutions would be expected to generate Ckβ-6 antagonists by destroying the ability of Ckβ-6 to bind heparin (Graham, G. J. et al., EMBO 15:6506–15 (1996)).

Asp (50) to Ala, Gly, Ser, Thr or Met,

Asp (64) to Ala, Gly, Ser, Thr or Met,

Substitutions of Asp-50 and Asp-64 of SEQ ID NO:2 have been predicted by the inventors herein to increase Ckβ-6 polypeptide activity by improving the dimerization potential of such polypeptides.

Phe (47) to Ser

The polypeptide composition generated in Example 3 is thought to contain a mutation of the codon -TTC- which codes for Phe47 in SEQ ID NO:2. Such mutation has resulted in the codon -TCC- which codes for Ser. This mutation is thought to have been generated by Taq DNA polymerase during the polymerase chain reaction used during the subcloning of the Ckβ-6 cDNA into the expression vector as described in Example 3. Taq polymerase is known by those of skill in the art to possess less than perfect fidelity.

The present invention further provides for a Ckβ-6 agonist polypeptides wherein the amino terminus of said polypeptides is a residue selected from residue 2 or residue 3 of SEQ ID NO:2 and the. carboxy terminus of said polypeptides is residue m, wherein m is any residue from residue 48 to residue 93 of SEQ ID NO:2. Specific Ckβ-6 agonists according to the present invention include: Val(1) to Ala(78); Val(1) to Val(77); Val(1) to Ala(76); Val(1) to Arg(75); Val(1) to Arg(73); Val(2) to Ala(78); Val(2) to Val(77); Val(2) to Ala(76); Val(2) to Arg(75); Val(2) to Arg(73); Ile(3) to Ala(78); Ile(3) to Val (77); Ile(3) to Ala (76); Ile(3) to Arg(75); Ile(3) to Arg(73). The agonist of the present invention may have either NH$_2$ or methionine attached to the N-terminus.

The present invention further relates to Ckβ-6 antagonists. In particular, a deletion of the first three N-terminal amino acid residues of the mature Ckβ-6 protein (i.e., a deletion of Val(1) to Ile(3) in SEQ ID NO:2) results in a polypeptide having antagonistic activity. Thus, according to the present invention, Ckβ-6 antagonists are provided wherein the amino terminus is residue 4 of SEQ ID NO:2 and the carboxyl terminus is residue m, wherein m is any residue of SEQ ID NO:2 from residue 48 to residue 93. Specific Ckβ-6 antagonists according to the present invention include, but are not limited to: Pro(4) to Arg(73); Pro(4) to Arg(75); Pro(4) to Ala(76); Pro(4) to Ala(78). Optionally, the Ckβ-6 antagonists of the present invention can include a Met residue at the N-terminus.

It has been discovered that the present Ckβ-6 antagonist inhibits not only the activity of Ckβ-6 and agonists of Ckβ-6, but also the activity of other chemokines, such as Ckβ-10 and Eotaxin (See Example 13 below where a Ckβ-6 antagonist polypeptide of the present invention was shown to inhibit eosinophil chemotaxis driven by Ckβ-6, Ckβ-10, or Eotaxin. Ckβ-6, Ckβ-10, and Eotaxin all mediate their effects on eosinophils via the CCR3 receptor. Thus, the antagonist polypeptides of the present invention represent dominant antagonists which are capable of inhibiting CCR3 receptor signaling regardless of the chemokine mediating this effect. Accordingly, by the invention, a method is provided for inhibiting the CCR3 receptor signaling pathway comprising administering to cells which express the CCR3 receptor an effective amount of a Ckβ-6 antagonist of the present invention. An "effective amount" of a Ckβ-6 antagonist and several disease conditions due to the activation of eosinophils are discussed below.

It will be appreciated by those of skill in the art that Ckβ-6 polypeptides, including those Ckβ-6 polypeptides having N- and C-terminal deletions, can contain one or more of the above substitutions.

The polypeptides of the present invention are preferably provided in an isolated form, and preferably are substantially purified. A recombinantly produced version of the Ckβ-6 polypeptide can be substantially purified by the one-step method described in Smith and Johnson, Gene 67:31–40 (1988).

The polypeptides of the present invention include the polypeptide encoded by the deposited cDNA including the leader, the polypeptide encoded by the deposited cDNA including the leader excepting the N-terminal methionine, the mature polypeptide encoded by the deposited cDNA minus the leader (i.e., the mature protein), the polypeptide of FIG. 1 (SEQ ID NO:2) including the leader, the polypeptide of FIG. 1 (SEQ ID NO:2) including the leader excepting the N-terminal methionine, the polypeptide of FIG. 1 (SEQ ID NO:2) minus the leader, as well as polypeptides which have at least 90% similarity, more preferably at least 95% similarity, and still more preferably at least 96%, 97%, 98% or 99% similarity to those described above. Further polypeptides of the present invention include polypeptides at least 80% identical, more preferably at least 90% or 95% identical, still more preferably at least 96%, 97%, 98% or 99% identical to the polypeptide encoded by the deposited cDNA, to the polypeptide of FIG. 1 (SEQ ID NO:2) and also include portions of such polypeptides with at least 30 amino acids and more preferably at least 50 amino acids.

By "% similarity" for two polypeptides is intended a similarity score produced by comparing the amino acid sequences of the two polypeptides using the Bestfit program (Wisconsin Sequence Analysis Package, Version 8 for Unix, Genetics Computer Group, University Research Park, 575 Science Drive, Madison, Wis. 53711) and the default settings for determining similarity. Bestfit uses the local homology algorithm of Smith and Waterman (Advances in Applied Mathematics 2:482–489, 1981) to find the best segment of similarity between two sequences.

By a polypeptide having an amino acid sequence at least, for example, 95% "identical" to a reference amino acid sequence of an Ckβ-6 polypeptide is intended that the amino acid sequence of the polypeptide is identical to the reference sequence except that the polypeptide sequence may include up to five amino acid alterations per each 100 amino acids of the reference amino acid of the Ckβ-6 polypeptide. In other words, to obtain a polypeptide having an amino acid sequence at least 95% identical to a reference amino acid sequence, up to 5% of the amino acid residues in the reference sequence may be deleted or substituted with another amino acid, or a number of amino acids up to 5% of the total amino acid residues in the reference sequence may be inserted into the reference sequence. These alterations of the reference sequence may occur at the amino or carboxy terminal positions of the reference amino acid sequence or anywhere between those terminal positions, interspersed either individually among residues in the reference sequence or in one or more contiguous groups within the reference sequence.

As a practical matter, whether any particular polypeptide is at least 90%, 95%, 96%, 97%, 98% or 99% identical to, for instance, the amino acid sequence shown in FIG. 1 (SEQ ID NO:2) or to the amino acid sequence encoded by the deposited cDNA clone can be determined conventionally using known computer programs such the Bestfit program (Wisconsin Sequence Analysis Package, Version 8 for Unix, Genetics Computer Group, University Research Park, 575 Science Drive, Madison, Wis. 53711. When using Bestfit or any other sequence alignment program to determine whether a particular sequence is, for instance, 95% identical to a reference sequence according to the present invention, the parameters are set, of course, such that the percentage of identity is calculated over the full length of the reference amino acid sequence and that gaps in homology of up to 5% of the total number of amino acid residues in the reference sequence are allowed.

The polypeptide of the present invention could be used as a molecular weight marker on SDS-PAGE gels or on molecular sieve gel filtration columns using methods well known to those of skill in the art.

As described in detail below, the polypeptides of the present invention can also be used to raise polyclonal and monoclonal antibodies, which are useful in assays for detecting Ckβ-6 protein expression as described below or as agonists and antagonists capable of enhancing or inhibiting Ckβ-6 protein function. Further, such polypeptides can be used in the yeast two-hybrid system to "capture" Ckβ-6 protein binding proteins which are also candidate agonist and antagonist according to the present invention. The yeast two hybrid system is described in Fields and Song, *Nature* 340:245–246 (1989).

In another aspect, the invention provides a peptide or polypeptide comprising an epitope-bearing portion of a polypeptide of the invention The epitope of this polypeptide portion is an immunogenic or antigenic epitope of a polypeptide of the invention. An "immunogenic epitope" is defined as a part of a protein that elicits an antibody response when the whole protein is the immunogen. These immunogenic epitopes are believed to be confined to a few loci on the molecule. On the other hand, a region of a protein molecule to which an antibody can bind is defined as an "antigenic epitope." The number of immunogenic epitopes of a protein generally is less than the number of antigenic epitopes. See, for instance, Geysen, et al., *Proc. Natl. Acad. Sci. USA* 81:3998–4002 (1983).

As to the selection of peptides or polypeptides bearing an antigenic epitope (i.e., that contain a region of a protein molecule to which an antibody can bind), it is well known in that art that relatively short synthetic peptides that mimic part of a protein sequence are routinely capable of eliciting an antiserum that reacts with the partially mimicked protein. See, e.g., Sutcliffe, J. G., et al., *Science* 219:660–666 (1983).

Peptides capable of eliciting protein-reactive sera are frequently represented in the primary sequence of a protein, can be characterized by a set of simple chemical rules, and are confined neither to immunodominant regions of intact proteins (i.e., immunogenic epitopes) nor to the amino or carboxyl terminals. Peptides that are extremely hydrophobic and those of six or fewer residues generally are ineffective at inducing antibodies that bind to the mimicked protein; longer, peptides, especially those containing proline residues, usually are effective. Sutcliffe et al., supra, at 661. For instance, 18 of 20 peptides designed according to these guidelines, containing 8–39 residues covering 75% of the sequence of the influenza virus hemagglutinin HA1 polypeptide chain, induced antibodies that reacted with the HA1 protein or intact virus; and 12/12 peptides from the MuLV polymerase and 18/18 from the rabies glycoprotein induced antibodies that precipitated the respective proteins.

Antigenic epitope-bearing peptides and polypeptides of the invention are therefore useful to raise antibodies, including monoclonal antibodies, that bind specifically to a polypeptide of the invention. Thus, a high proportion of hybridomas obtained by fusion of spleen cells from donors immunized with an antigen epitope-bearing peptide generally secrete antibody reactive with the native protein. Sutcliffe et al., supra, at 663. The antibodies raised by antigenic epitope-bearing peptides or polypeptides are useful to detect the mimicked protein, and antibodies to different peptides may be used for tracking the fate of various regions of a protein precursor which undergoes post-translational processing. The peptides and anti-peptide antibodies may be used in a variety of qualitative or quantitative assays for the mimicked protein, for instance in competition assays since it has been shown that even short peptides (e.g. about 9 amino acids) can bind and displace the larger peptides in immunoprecipitation assays. See, for instance, Wilson, et al., *Cell* 37:767–778 (1984) at 777. The anti-peptide antibodies of the invention also are useful for purification of the mimicked protein, for instance, by adsorption chromatography using methods well known in the art.

Antigenic epitope-bearing peptides and polypeptides of the invention designed according to the above guidelines preferably contain a sequence of at least seven, more preferably at least nine and most preferably between about 15 to about 30 amino acids contained within the amino acid sequence of a polypeptide of the invention. However, peptides or polypeptides comprising a larger portion of an amino acid sequence of a polypeptide of the invention, containing about 30 to about 50 amino acids, or any length up to and including the entire amino acid sequence of a polypeptide of the invention, also are considered epitope-bearing peptides or polypeptides of the invention and also are useful for inducing antibodies that react with the mimicked protein. Preferably, the amino acid sequence of the epitope-bearing peptide is selected to provide substantial solubility in aqueous solvents (i.e., the sequence includes relatively hydrophilic residues and highly hydrophobic sequences are preferably avoided); and sequences containing proline residues are particularly preferred.

Non-limiting examples of antigenic polypeptides or peptides that can be used to generate Ckβ-6-specific antibodies include: a polypeptide comprising amino acid residues from about Val-12 to about Val-21 in FIG. 1 (SEQ ID NO:2); a polypeptide comprising amino acid residues from about Leu-26 to about Lys-34 in FIG. 1 (SEQ ID NO:2); a polypeptide comprising amino acid residues from about Phe-39 to about Cys-48 in FIG. 1 (SEQ ID NO:2); and a polypeptide comprising amino acid residues from about Asp-50 to about Gln-57 in FIG. 1 (SEQ ID NO:2). As indicated above, the inventors have determined that the above polypeptide fragments are antigenic regions of the Ckβ-6 protein.

The epitope-bearing peptides and polypeptides of the invention may be produced by any conventional means for making peptides or polypeptides including recombinant means using nucleic acid molecules of the invention. For instance, a short epitope-bearing amino acid sequence may be fused to a larger polypeptide which acts as a carrier during recombinant production and purification, as well as during immunization to produce anti-peptide antibodies. Epitope-bearing peptides also may be synthesized using known methods of chemical synthesis. For instance, Houghten has described a simple method for synthesis of large numbers of peptides, such as 10–20 mg of 248 different 13 residue peptides representing single amino acid variants of a segment of the HA1 polypeptide which were prepared and characterized (by ELISA-type binding studies) in less than four weeks. Houghten, R A., "General method for the rapid solid-phase synthesis of large numbers of peptides: specificity of antigen-antibody interaction at the level of individual amino acids," *Proc. Natl. Acad. Sci. (USA)* 82:5131–5135 (1985). This "Simultaneous Multiple Peptide Synthesis (SMPS)" process is further described in U.S. Pat. No. 4,631,211 to Houghten, et al. (1986). In this procedure the individual resins for the solid-phase synthesis of various peptides are contained in separate solvent-permeable packets, enabling the optimal use of the many identical repetitive steps involved in solid-phase methods. A completely manual procedure allows 500–1000 or more syntheses to be conducted simultaneously. Houghten et al, supra, at 5134.

Preferred nucleic acid fragments of the present invention include nucleic acid molecules encoding epitope-bearing portions of the Ckβ-6 protein.

In particular, such nucleic acid fragments of the Ckβ-6 of the present invention include nucleic acid molecules encoding: a polypeptide comprising amino acid residues from about Val-12 to about Val-21 in FIG. 1 (SEQ ID NO:2); a polypeptide comprising amino acid residues from about Leu-26 to about Lys-34 in FIG. 1 (SEQ ID NO:2); a polypeptide comprising amino acid residues from about Phe-39 to about Cys-48 in FIG. 1 (SEQ ID NO:2); and a polypeptide comprising amino acid residues from about Asp-50 to about Gln-57 in FIG. 1 (SEQ ID NO:2); or any range or value in any of the foregoing.

Methods for determining other such epitope-bearing portions of an Ckβ-6 polypeptide are described herein.

Epitope-bearing peptides and polypeptides of the invention are used to induce antibodies according to methods well known in the art. See, for instance, Sutcliffe, et al., supra; Wilson, et al., supra; Chow, M., et al., *Proc. Natl. Acad. Sci. USA* 82:910–914; and Bittle, F. J. et al., *J. Gen. Virol.* 66:2347–2354 (1985). Generally, animals may be immunized with free peptide; however, anti-peptide antibody titer may be boosted by coupling of the peptide to a macromolecular carrier, such as keyhole limpet hemacyanin (KLH) or tetanus toxoid. For instance, peptides containing cysteine may be coupled to carrier using a linker such as m-maleimidobenzoyl-N-hydroxysuccinimide ester (MBS), while other peptides may be coupled to carrier using a more general linking agent such as glutaraldehyde. Animals such as rabbits, rats and mice are immunized with either free or carrier-coupled peptides, for instance, by intraperitoneal and/or intradermal injection of emulsions containing about 100 g peptide or carrier protein and Freund's adjuvant. Several booster injections may be needed, for instance, at intervals of about two weeks, to provide a useful titer of anti-peptide antibody which can be detected, for example, by ELISA assay using free peptide adsorbed to a solid surface. The titer of anti-peptide antibodies in serum from an immunized animal may be increased by selection of anti-peptide antibodies, for instance, by adsorption to the peptide on a solid support and elution of the selected antibodies according to methods well known in the art.

Immunogenic epitope-bearing peptides of the invention, i.e., those parts of a protein that elicit an antibody response when the whole protein is the immunogen, are identified according to methods known in the art. For instance, Geysen et al., supra, discloses a procedure for rapid concurrent synthesis on solid supports of hundreds of peptides of sufficient purity to react in an enzyme-linked immunosorbent assay. Interaction of synthesized peptides with antibodies is then easily detected without removing them from the support In this manner a peptide bearing an immunogenic epitope of a desired protein may be identified routinely by one of ordinary skill in the art. For instance, the immunologically important epitope in the coat protein of foot-and-mouth disease virus was located by Geysen et al. with a resolution of seven amino acids by synthesis of an overlapping set of all 208 possible hexapeptides covering the entire 213 amino acid sequence of the protein. Then, a complete replacement set of peptides in which all 20 amino acids were substituted in turn at every position within the epitope were synthesized, and the particular amino acids conferring specificity for the reaction with antibody were determined. Thus, peptide analogs of the epitope-bearing peptides of the invention can be made routinely by this method. U.S. Pat. No. 4,708,781 to Geysen (1987) further describes this method of identifying a peptide bearing an immunogenic epitope of a desired protein.

Further still, U.S. Pat. No. 5,194,392 to Geysen (1990) describes a general method of detecting or determining the sequence of monomers (amino acids or other compounds) which is a topological equivalent of the epitope (i.e., a "mimotope") which is complementary to a particular paratope (antigen binding site) of an antibody of interest. More generally, U.S. Pat. No. 4,433,092 to Geysen (1989) describes a method of detecting or determining a sequence of monomers which is a topographical equivalent of a ligand which is complementary to the ligand binding site of a particular receptor of interest. Similarly, U.S. Pat. No. 5,480,971 to Houghten, R. A., et al. (1996) on Peralkylated Oligopeptide Mixtures discloses linear C1-C7-alkyl peralkylated oligopeptides and sets and libraries of such peptides, as well as methods for using such oligopeptide sets and libraries for determining the sequence of a peralkylated oligopeptide that preferentially binds to an acceptor molecule of interest. Thus, non-peptide analogs of the epitope-bearing peptides of the invention also can be made routinely by these methods.

The entire disclosure of each document cited in this section on "Polypeptides and Peptides" is hereby incorporated herein by reference.

As one of skill in the art will appreciate, Ckβ-6 polypeptides of the present invention and the epitope-bearing fragments thereof described above can be combined with parts of the constant domain of immunoglobulins (IgG), resulting in chimeric polypeptides. These fusion proteins facilitate purification and show an increased half-life in vivo. This has been shown, e.g. for chimeric proteins consisting of the first two domains of the human CD4-polypeptide and various domains of the constant regions of the heavy or light chains of mammalian immunoglobulins (EPA 394,827; Traunecker, et al., *Nature* 331:84–86 (1988)). Fusion proteins that have a disulfide-linked dimeric structure due to the IgG part can also be more efficient in binding and neutralizing other molecules than the monomeric Ckβ-6 protein or protein fragment alone (Fountoulakis, et al., *J. Biochem.* 270:3958–3964 (1995)).

Vectors and Host Cells

The present invention also relates to vectors which include polynucleotides of the present invention, host cells which are genetically engineered with vectors of the invention and the production of polypeptides of the invention by recombinant techniques.

Host cells are genetically engineered (transduced or transformed or transfected) with the vectors of this invention which may be, for example, a cloning vector or an expression vector. The vector may be, for example, in the form of a plasmid, a viral particle, a phage, etc. The engineered host cells can be cultured in conventional nutrient media modified as appropriate for activating promoters, selecting transformants or amplifying the genes of the present invention. The culture conditions, such as temperature, pH and the like, are those previously used with the host cell selected for expression, and will be apparent to the ordinarily skilled artisan.

The polynucleotides of the present invention may be employed for producing polypeptides by recombinant techniques. Thus, for example, the polynucleotide may be included in any one of a variety of expression vectors for expressing a polypeptide. Such vectors include chromosomal, nonchromosomal and synthetic DNA sequences, e.g., derivatives of SV40; bacterial plasmids; phage DNA; baculovirus; yeast plasmids; vectors derived from combinations of plasmids and phage DNA, viral DNA such as vaccinia, adenovirus, fowl pox virus, and pseudorabies. However, any other vector may be used as long as it is replicable and viable in the host.

The appropriate DNA sequence may be inserted into the vector by a variety of procedures. In general, the DNA sequence is inserted into an appropriate restriction endonuclease site(s) by procedures known in the art. Such procedures and others are deemed to be within the scope of those skilled in the art.

The DNA sequence in the expression vector is operatively linked to an appropriate expression control sequence(s) (promoter) to direct mRNA synthesis. As representative examples of such promoters, there may be mentioned: LTR or SV40 promoter, the *E. coli* lac or trp, the phage lambda $P_L$ promoter and other promoters known to control expression of genes in prokaryotic or eukaryotic cells or their viruses. The expression vector also contains a ribosome binding site for translation initiation and a transcription terminator. The vector may also include appropriate sequences for amplifying expression.

In addition, the expression vectors preferably contain one or more selectable marker genes to provide a phenotypic trait for selection of transformed host cells such as dihydrofolate reductase or neomycin resistance for eukaryotic cell culture, or such as tetracycline or ampicillin resistance in *E. coli*.

The vector containing the appropriate DNA sequence as hereinabove described, as well as an appropriate promoter or control sequence, may be employed to transform an appropriate host to permit the host to express the protein.

As representative examples of appropriate hosts, there may be mentioned: bacterial cells, such as *E. coli*, Streptomyces, *Salmonella typhimurium*; fungal cells, such as yeast; insect cells such as Drosophila S2 and Spodoptera Sf9; animal cells such as CHO, COS or Bowes melanoma; adenoviruses; plant cells, etc. The selection of an appropriate host is deemed to be within the scope of those skilled in the art from the teachings herein.

In addition to the use of expression vectors in the practice of the present invention, the present invention further includes novel expression vectors comprising operator and promoter elements operatively linked to nucleotide sequences encoding a protein of interest. One example of such a vector is pHE4-5 (SEQ ID NO:21) which is described in detail below.

As summarized in FIGS. 21 and 22, components of the pHE4-5 vector (SEQ ID NOs:21 and 22) include: 1). a neomycinphosphotransferase gene as a selection marker, 2). an *E. coli* origin of replication, 3). a T5 phage promoter sequence, 4). two lac operator sequences, 5). a nucleotide sequence encoding a Ckβ-6 polypeptide (for example, SEQ ID NOs:2 or 6), agonist or antagonist thereof, 6). a Shine-Delgarno sequence, 7). the lactose operon repressor gene (lacIq). The origin of replication (oriC) is derived from pUC19 (LTI, Gaithersburg, Md.). The promoter sequence was and operator sequences were made synthetically. Synthetic production of nucleic acid sequences is well known in the art. CLONTECH 95/96 Catalog, pages 215–216, CLONTECH, 1020 East Meadow Circle, Palo Alto, Calif. 94303.

As noted above, the pHE4-5 vector contains a lacIq gene. LacIq is an allele of the lacI gene which confers tight regulation of the lac operator. Amann, E. et al., *Gene* 69:301–315 (1988); Stark, M., *Gene* 51:255–267 (1987). The lacIq gene encodes a repressor protein which binds to lac operator sequences and blocks transcription of down-stream (i.e., 3') sequences. However, the lacIq gene product dissociates from the lac operator in the presence of either lactose or certain lactose analogs, e.g., isopropyl B-D-thiogalactopyranoside (IPTG). The polypeptide of the present invention thus is not produced in appreciable quantities in uninduced host cells containing the pHE4-5 vector. Induction of these host cells by the additional of an agent such as IPTG, however, results in the expression of the coding sequence for a Ckβ-6, agonist or antagonists thereof.

The promoter/operator sequences of the pHE4-5 vector (SEQ ID NO:22) comprise a T5 phage promoter and two lac operator sequences. One operator is located 5' to the transcriptional start site and the other is located 3' to the same site. These operators, when present in combination with the lacIq gene product, confer tight repression of down-stream sequences in the absence of a lac operon inducer, e.g., IPTG. Expression of operatively linked sequences located downstream from the lac operators may be induced by the addition of a lac operon inducer, such as IPTG. Binding of a lac inducer to the lacIq proteins results in their release from the lac operator sequences and the initiation of transcription of operatively linked sequences. Lac operon regulation of gene expression is reviewed in Devlin, T., TEXTBOOK OF BIOCHEMISTRY WITH CLINICAL CORRELATIONS, 4th Edition (1997), pages 802–807.

The pHE4 series of vectors contain all of the components of the pHE4-5 vector except for a coding sequence for a Ckβ-6, agonist or antagonists thereof. Features of the pHE4 vectors include optimize synthetic T5 phage promoter, lac operator, and Shine-Delagarno sequences. Further, these sequences are also optimally spaced so that expression of an inserted gene may be tightly regulated and high level of expression occurs upon induction.

Among known bacterial promoters suitable for use in the production of proteins of the present invention include the *E. coli* lacI and lacZ promoters, the T3 and T7 promoters, the gpt promoter, the lambda PR and PL promoters and the trp promoter. Suitable eukaryotic promoters include the CMV immediate early promoter, the HSV thymidine kinase promoter, the early and late SV40 promoters, the promoters of retroviral LTRs, such as those of the Rous Sarcoma Virus (RSV), and metallothionein promoters, such as the mouse metallothionein-I promoter.

The pHE4-5 vector also contains a Shine-Delgarno sequence 5' to the AUG initiation codon. Shine-Delgarno sequences are short sequences generally located about 10 nucleotides up-stream (i.e., 5') from the AUG initiation codon. These sequences essentially direct prokaryotic ribosomes to the AUG initiation codon.

Thus, the present invention is also directed to expression vector useful for the production of the proteins of the present invention. This aspect of the invention is exemplified by the pHE4-5 vector (SEQ ID NO:21).

In addition, the present invention also includes recombinant constructs comprising one or more of the sequences as broadly described above. The constructs comprise a vector, such as a plasmid or viral vector, into which a sequence of the invention has been inserted, in a forward or reverse orientation. In a preferred aspect of this embodiment, the construct further comprises regulatory sequences, including, for example, a promoter, operably linked to the sequence.

Large numbers of suitable vectors and promoters are known to those of skill in the art, and are commercially available. The following vectors are provided by way of example; Bacterial: pQE70, pQE60, pQE-9 (Qiagen), pBS, pD10, phagescript, psiX174, pbluescript SK, pbsks, pNH8A, pNH16a, pNH18A, pNH46A (Stratagene); ptrc99a, pKK223-3, pKK233-3, pDR540, pRIT5 (Pharmacia); Eukaryotic: pWLNEO, pSV2CAT, pOG44, pXT1, pSG (Stratagene) pSVK3, pBPV, pMSG, pSVL (Pharmacia). However, any other plasmid or vector may be used as long as they are replicable and viable in the host.

Promoter regions can be selected from any desired gene using CAT (chloramphenicol transferase) vectors or other vectors with selectable markers. Two appropriate vectors are pKK232-8 and pCM7. Particular named bacterial promoters include lacI, lacZ, T3, T7, gpt, lambda $P_R$, $P_L$ and trp. Eukaryotic promoters include CMV immediate early, HSV thymidine kinase, early and late SV40, LTRs from retrovirus, and mouse metallothionein-I. Selection of the appropriate vector and promoter is well within the level of ordinary skill in the art In a further embodiment, the present invention relates to host cells containing the above-described constructs. The host cell can be a higher eukaryotic cell, such as a mammalian cell, or a lower eukaryotic cell, such as a yeast cell, or the host cell can be a prokaryotic cell, such as a bacterial cell. Introduction of the construct into the host cell can be effected by calcium phosphate transfection, DEAE-Dextran mediated transfection, or electroporation (Davis, L., et al., *Basic Methods in Molecular Biology* (1986)).

The constructs in host cells can be used in a conventional manner to produce the gene product encoded by the recombinant sequence. Alternatively, the polypeptides of the invention can be synthetically produced by conventional peptide synthesizers.

Mature proteins can be expressed in mammalian cells, yeast, bacteria, or other cells under the control of appropriate promoters. Cell-free translation systems can also be employed to produce such proteins using RNAs derived from the DNA constructs of the present invention. Appropriate cloning and expression vectors for use with prokaryotic and eukaryotic hosts are described by Sambrook, et al., *Molecular Cloning: A Laboratory Manual,* Second Edition, Cold Spring Harbor, N.Y. (1989), the disclosure of which is hereby incorporated by reference.

Transcription of the DNA encoding the polypeptides of the present invention by higher eukaryotes is increased by inserting an enhancer sequence into the vector. Enhancers are cis-acting elements of DNA, usually about from 10 to 300 bp that act on a promoter to increase its transcription Examples include the SV40 enhancer on the late side of the replication origin bp 100 to 270, a cytomegalovirus early promoter enhancer, the polyoma enhancer on the late side of the replication origin, and adenovirus enhancers.

Generally, recombinant expression vectors will include origins of replication and selectable markers permitting transformation of the host cell, e.g., the ampicillin resistance gene of *E. coli* and *S. cerevisiae* TRP1 gene, and a promoter derived from a highly-expressed gene to direct transcription of a downstream structural sequence. Such promoters can be derived from operons encoding glycolytic enzymes such as 3-phosphoglycerate kinase (PGK), a-factor, acid phosphatase, or heat shock proteins, among others. The heterologous structural sequence is assembled in appropriate phase with translation initiation and termination sequences, and preferably, a leader sequence capable of directing secretion of translated protein into the periplasmic space or extracellular medium. Optionally, the heterologous sequence can encode a fusion protein including an N-terminal identification peptide imparting desired characteristics, e.g., stabilization or simplified purification of expressed recombinant product.

Useful expression vectors for bacterial use are constructed by inserting a structural DNA sequence encoding a desired protein together with suitable translation initiation and termination signals in operable reading phase with a functional promoter. The vector will comprise one or more phenotypic selectable markers and an origin of replication to ensure maintenance of the vector and to, if desirable, provide amplification within the host Suitable prokaryotic hosts for transformation include E. coli, Bacillus subtilis, Salmonella typhimurium and various species within the genera Pseudomonas, Streptomyces, and Staphylococcus, although others may also be employed as a matter of choice.

As a representative but nonlimiting example, useful expression vectors for bacterial use can comprise a selectable marker and bacterial origin of replication derived from commercially available plasmids comprising genetic elements of the well known cloning vector pBR322 (ATCC 37017). Such commercial vectors include, for example, pKK223-3 (Pharmacia Fine Chemicals, Uppsala, Sweden) and GEM1 (Promega Biotec, Madison, Wis., USA). These pBR322"backbone" sections are combined with an appropriate promoter and the structural sequence to be expressed.

Following transformation of a suitable host strain and growth of the host strain to an appropriate cell density, the selected promoter is induced by appropriate means (e.g., temperature shift or chemical induction) and cells are cultured for an additional period.

Cells are typically harvested by centrifugation, disrupted by physical or chemical means, and the resulting crude extract retained for further purification.

Microbial cells employed in expression of proteins can be disrupted by any convenient method, including freeze-thaw cycling, sonication, mechanical disruption, or use of cell lysing agents, such methods are well known to those skilled in the art.

Various mammalian cell culture systems can also be employed to express recombinant protein. Examples of mammalian expression systems include the COS-7 lines of monkey kidney fibroblasts, described by Gluzman, *Cell* 23:175 (1981), and other cell lines capable of expressing a compatible vector, for example, the C127, 3T3, CHO, HeLa and BHK cell lines. Mammalian expression vectors will comprise an origin of replication, a suitable promoter and enhancer, and also any necessary ribosome binding sites, polyadenylation site, splice donor and acceptor sites, transcriptional termination sequences, and 5' flanking nontranscribed sequences. DNA sequences derived from the SV40 splice, and polyadenylation sites may be used to provide the required nontranscribed genetic elements.

Polypeptide Purification and Isolation

The polypeptide can be recovered and purified from recombinant cell cultures by methods including ammonium sulfate or ethanol precipitation, acid extraction, anion or cation exchange chromatography, phosphocellulose chromatography, hydrophobic interaction chromatography, affinity chromatography, hydroxylapatite chromatography and lectin chromatography. Protein refolding steps can be used, as necessary, in completing configuration of the mature protein. Finally, high performance liquid chromatography (HPLC) can be employed for final purification steps. A particularly preferred method of purification of Ckβ-6 polypeptides expressed in *E. coli* is described in Example 1, infra.

The polypeptides of the present invention may be a naturally purified product, or a product of chemical synthetic procedures, or produced by recombinant techniques from a prokaryotic or eukaryotic host (for example, by bacterial, yeast, higher plant, insect and mammalian cells in culture). Depending upon the host employed in a recombinant production procedure, the polypeptides of the present invention may be glycosylated or may be non-glycosylated. Polypeptides of the invention may also include an initial methionine amino acid residue.

Therapeutics

The polypeptide of the present invention can be used in a variety of immunoregulatory and inflammatory functions and also in a number of disease conditions. Ckβ-6 is in the chemokine family and therefore is a chemoattractant for leukocytes such as eosinophils, and basophils.

Northern blot analyses has shown that Ckβ-6 is expressed predominantly in tissues of hematopoietic origin.

The polypeptide of the present invention, may be employed for the promotion of wound healing. Since Ckβ-6 is a chemokine, it is a chemo-attractant for leukocytes such as, basophils and eosinophils causing infiltration of target immune cells to a wound area In a similar fashion, the polypeptides of the present invention can enhance host defenses against chronic infections, e.g., mycobacterial, via the attraction and activation of microbicidal leukocytes.

The Ckβ-6 polypeptide may also be employed as an anti-tumor treatment and for treating localized complications of a malignancy, such as pleural effusions or ascites. There is evidence that chemokine expressing cells injected into tumors have caused regression of the tumor, for example, in the treatment of Karposi's sarcoma. Ckβ-6 may induce cells to secret TNF-α, which is a known agent for tumor regression. Ckβ-6 may also induce monocytes to secrete other tumor and cancer inhibiting agents-such as IL-6, IL-1 and G-CSF.

The presence of MCPs in vivo is accompanied by a local increase in the presence of eosinophils which have the distinctive function of killing the larvae of parasites that invade tissues, as in schistosomiasis, trichinosis and ascariasis. Therefore, Ckβ-6 may be employed for combatting parasitic infections.

The polypeptide of the present invention may be employed for mobilizing hematopoietic progenitor cells into the peripheral blood circulation of a non-human and human host, preferably a human host, for subsequent recovery and use thereof in transplantation. The polypeptide of the present invention is administered in an amount effective to mobilize into and increase the amount of hematopoietic progenitor cells in the peripheral blood, in particular, increase the amount of human hematopoietic stem cells in the peripheral blood. Such cells are often referred to as CD34+ cells. For example, the polypeptide is administered in amounts as hereinafter described. The polypeptide of the present invention may be administered alone or in conjunction with other agents, for example, GM-CSF and G-CSF which are known to be effective for increasing such cells in peripheral blood. Mobilization of hematopoietic progenitor cells into the peripheral circulation is important for autologous and heterologous bone marrow transfers which are used, for example for treatment of cancer and hematological disorders.

The polypeptide of the present invention may also be employed to inhibit destruction of hematopoietic progenitor cells in a non-human and human host, preferably a human host, resulting from treatment with chemotherapeutic agents. The polypeptide of the present invention may be administered prior to, during or subsequent to chemotherapy and allows a higher dose of chemotherapy to be employed in the treatment of cancer. The polypeptide of the present invention is administered in an amount effective to inhibit destruction of hematopoietic progenitor cells; for example, the polypeptide is administered in amounts as hereinafter described. The polypeptide may be administered alone or in conjunction with other agents.

The hematopoietic cell protective compositions of the present invention may be used in combination with a variety of chemotherapeutic agents including alkylating agents such as nitrogen mustards, ethylenimines, methylmelamines, alkyl sulfonates, nitrosuoureas, and triazenes; antimetabolites such as folic acid analogs, pyrimindine analogs, in particular fluorocil and cytosine arabinoside, and purine analogs; natural products such as vinca alkaloids, epipodopyllotoxins, antibiotics, enzymes and biological response modifiers; and miscellaneous products such as platinum coordination complexes, antracenedione, substituted urea such as hydroxyurea, methyl hydrazine derivatives, and adrenocorticoid suppresant.

Chemotherapeutic agents can be administered at known concentrations according to known techniques. The protective compositions of the present invention can be co-administered with a chemotherapeutic agent, or administered separately, either before or after chemotherapeutic administration.

The polypeptide of the present invention may also be employed to protect hematopoietic progenitor cells to thereby prevent or inhibit diseases which may result from the destruction thereof; for example, leukopenia, myelodysplastic syndrome, and neutropenia.

The polypeptide of the present invention may also be employed in amounts effective to inhibit the degeneration of neuronal cells in non-human and human hosts, preferably a human host, which results from neuronal-degenerative diseases such as Alzheimer's disease, Parkinson's disease and AIDS-related complex. Neurodegenerative diseases include, but are not limited to, AIDS dementia complex, demyelinating diseases, such as multiple sclerosis and acute transverse myelitis; extrapyramidal and cerebellar disorders' such as lesions of the corticospinal system; disorders of the basal ganglia or cerebellar disorders; hyperkinetic movement disorders such as Huntington's Chorea and senile chorea; drug-induced movement disorders, such as those induced by drugs which block CNS dopamine receptors; hypokinetic movement disorders, such as Parkinson's disease; Progressive supranucleo Palsy; structural lesions of the cerebellum; spinocerebellar degenerations, such as spinal ataxia, Friedreich's ataxia, cerebellar cortical degenerations, multiple systems degenerations (Mencel, Dejerine-Thomas, Shi-Drager, and Machado-Joseph); systemic disorders (Refsum's disease, abetalipoprotemia, ataxia, telangiectasia, and mitochondrial multisystem disorder); demyelinating core disorders, such as multiple sclerosis, acute transverse myelitis; and disorders of the motor unit such as neurogenic muscular atrophies (anterior horn cell degeneration, such as amyotrophic lateral sclerosis, infantile spinal muscular atrophy and juvenile spinal muscular atrophy); Alzheimer's disease; Down's Syndrome in middle age; Diffuse Lewy body disease; Senile Dementia of Lewy body type; Wernicke-Korsakoff syndrome; chronic alcoholism; Creutzfeldt-Jakob disease; Subacute sclerosing panencephalitis Hallerrorden-Spatz disease; and Dementia pugilistica. One preferred neurodegenerative disease is multiple sclerosis. For example, the polypeptide may be employed in amounts as hereinafter described.

In addition, recent demonstration that the MIP-1a receptor serves as a cofactor in facilitating the entry of HIV into human monocytes and T-lymphocytes raises an interesting possibility that Ckβ-6 or its variants might interfere with the process of HIV entry, or the entry of other viruses, particularly retroviruses, into cells. The, Ckβ-6 can be useful as an antiviral agent for viruses and retroviruses whose entry is facilitated by the Ckβ-6 receptor.

TABLE 1

Effect of Ckβ-6 administration to mice on the distribution of the primitive hematopoietic progenitors in peripheral blood, spleen, and bone marrow after two days

| | Numbers of Progenitors per | | | | | | | |
|---|---|---|---|---|---|---|---|---|
| | $10^4$ PB cells | | | $10^4$ Spleen cells | | | $10^4$ BM cells | |
| Treatment | HPP | LPP | IM | HPP | LPP | IM | HPP | LPP |
| Saline | 0.5 ± 0.7 | 38 ± 9.5 | 6.5 ± 1.9 | 0.7 ± 1.5 | 5.5 ± 2.5 | 1.5 ± 2.3 | 53 ± 11 | 484 ± 59 |
| Ckβ-6 (1 mg/kg/day) | 3.5 ± 0.5 | 95 ± 16.9 | 25 ± 13.5 | 2.75 ± 0.9 | 4.2 ± 3.5 | 3.5 ± 2.4 | 27 ± 3.5 | 610 ± 28 |

PB = Peripheral blood, mononuclear cells

Spl. = Low density fraction of spleen cells

BM = Bone marrow fraction that is 6-fold enriched for the primitive cells

HPP = High proliferative potential colony forming cells

LPP = Low proliferative potential colony forming cells

IM = Immature cell, a rare cell type found in the bone marrow, gives rise to a highly refrectile, small (<50 cells/colony) colony in the presence of multiple cytokines; the cells within the colony are stacked in a horizontal plane and they exhibit blast cell like nuclear staining characteristics.

Three mice were injected IP daily with either Ckβ-6 or saline. Forty eight hours after the first injection, blood was collected from each animal by cardiac puncture and mice were then sacrificed to obtain bone marrow and spleen. Indicated numbers of cells from each of the tissues were then plated in duplicates in agar-containing medium in the presence of rmIL-3(5 ng/ml), rmSCF(50 ng/ml), rhM-CSF(5 ng/ml), and rmIL-1a(10 ng/ml) and incubated for 14 days. Data are pooled from three animals in each group and expressed as mean±S.D.

TABLE 2

Effect of Ckβ-6 administration to mice on the distribution of the primitive hematopoietic progenitors in peripheral blood, spleen, and bone marrow after four days

| | Numbers of Progenitors per | | | | | | | |
|---|---|---|---|---|---|---|---|---|
| | $10^4$ PB cells | | | $10^4$ Spleen cells | | | $10^4$ BM cells | |
| Treatment | HPP | LPP | IM | HPP | LPP | IM | HPP | LPP |
| Saline | 0 | 29 ± 5.6 | 1 ± 1.5 | 1 ± 0.6 | 10 ± 4.6 | 0.8 ± 0.7 | 60 ± 8 | 505 ± 45 |
| Ckβ-6 (1 mg/kg/day) | 3.8 ± 1.5 | 84.5 ± 14.5 | 28.6 ± 8.6 | 2.6 ± 0.5 | 10.3 ± 2.1 | 7 ± 1.5 | 26.5 ± 8 | 330 ± 46 |

PB = Peripheral blood, mononuclear cells
Spl. = Low density fraction of spleen cells
BM = Bone marrow fraction that is 6-fold enriched for the primitive cells
HPP = High proliferative potential colony forming cells
LPP = Low proliferative potential colony forming cells
IM = Immature cell, a rare cell type found in the bone marrow, gives rise to a highly refractile, small (<50 cells/colony) colony in the presence of multiple cytokines; the cells within the colony are stacked in a horizontal plane and they exhibit blast cell like nuclear staining characteristics.

Three mice were injected IP daily with either Ckβ-6 or saline. Ninety six hours after the first injection, blood was collected from each animal by cardiac puncture and mice were then sacrificed to obtain bone marrow and spleen. Indicated numbers of cells from each of the tissues were then plated in duplicates in agar-containing medium in the presence of rmIL-3(5 ng/ml), rmSCF(50 ng/ml), rhM-CSF(5 ng/ml), and rmIL-1a(10 ng/ml) and incubated for 14 days. Data are pooled from three animals in each group and expressed as mean ±S.D.

TABLE 3

Analysis of the peripheral blood leukocyte composition by FACSan in mice administered with Ckβ-6 after two days Percent Positive in the Gated the Cell Populations

| Treatment | CD45R + B-Cells | GR.1 + PMN | Mac. 1 + Monocytes | CD8 + T-cells | CD4 + T-cells |
|---|---|---|---|---|---|
| Saline | 40.5 ± 9.2 | 62.5 ± 10.6 | 19.5 ± 2.1 | 29 ± 5.6 | 39 ± 12 |
| Ckβ-6 (mg/Kg/day) | 37 ± 5.6 | 56 ± 11.3 | 18 ± 4.2 | 27 ± 4.3 | 33 ± 7 |

Three C57 Black 6 mice (~20 g weight) were injected (IP) daily with either saline or Ckβ-6. Forty eight hours after the first injection, blood was collected by cardiac puncture and mice were sacrificed to obtain spleen and bone marrow cells. For immunostaining, 0.1 ml of blood from each of the animal was first treated with Gen Trak lysing solution to lyse the red blood cells. Nucleated cells were then sedimented, washed with PBS, and incubated with PE-conjugated monoclonal antibodies against CD45R, Gr. 1, Mac. 1, CD4, & CD8 and processed for flowcytometry. At least 10,000 cells were analyzed. Data are expressed as mean percent positive cells in the appropriate channels ±SD.

The polynucleotides and polypeptides of the present invention may be employed as research reagents for in vitro purposes related to scientific research, synthesis of DNA and manufacture of DNA vectors, and for the purpose of developing therapeutics and for the treatment of human disease. For example, Ckβ-6 may be employed for the expansion of immature hematopoietic progenitor cells, for example, granulocytes, macrophages or monocytes, by temporarily preventing their differentiation. These bone marrow cells may be cultured in vitro.

Receptors

This invention provides a method for identification of the receptor for Ckβ-6. The gene encoding the receptor can be identified by numerous methods known to those of skill in the art, for example, ligand panning and FACS sorting (Coligan, et al., Current Protocols in Immun., 1(2), Chapter 5, (1991)). Preferably, expression cloning is employed wherein polyadenylated RNA is prepared from a cell responsive to Ckβ-6, and a cDNA library created from this RNA is divided into pools and used to transfect COS cells or other cells that are not responsive to Ckβ-6. Transfected cells which are grown on glass slides are exposed to labeled Ckβ-6. Ckβ-6 can be labeled by a variety of means including iodination or inclusion of a recognition site for a site-specific protein kinase. Following fixation and incubation, the slides are subjected to auto-radiographic analysis. Positive pools are identified and sub-pools are prepared and re-transfected using an iterative sub-pooling and re-screening process, eventually yielding a single clone that encodes the putative receptor. As an alternative approach for receptor identification, labeled ligand can be photoaffinity linked with cell membrane or extract preparations that express the receptor molecule. Cross-linked material is resolved by PAGE and exposed to X-ray film. The labeled complex containing the ligand-receptor can be excised, resolved into peptide fragments, and subjected to protein microsequencing. The amino acid sequence obtained from microsequencing would be used to design a set of degenerate oligonucleotide probes to screen a cDNA library to identify the gene encoding the putative receptor.

Chemokine Receptor-3 (CCR3) has been identified as one of the Ckβ-6 receptors herein (see Examples 9, 10 and 11, below). CCR3 is also known to be a receptor for chemokine-β-10 (published as "MCP-4" in Uguccioni, M., et al.,J. Exp. Med. 183:2379–2384 (1996)) and eotaxin. Accordingly, as would be expected by those of skill in the art, Ckβ-6 antagonists which are capable of binding to CCR3 but lack the capacity to induce signal transduction would also be expected to be antagonists of chemokine-β-10 activity and eotaxin activity. Such activities are described below.

Antagonists, Agonists and Methods

This invention also provides a method of screening compounds to identify agonists and antagonists to the polypeptide of the present invention. An agonist is a compound which has similar biological functions, or enhances the functions, of the polypeptides, while antagonists block such functions. As an example, a mammalian cell or membrane preparation expressing an Ckβ-6 receptor would be contacted with a compound of interest. The ability of the compound to generate a the response of a known second messenger system following interaction with the Ckβ-6 receptor is then measured. Such second messenger systems include but are not limited to, calcium release (as described, for example, in Example 9, cAMP guanylate cyclase, ion channels or phosphoinositide hydrolysis. The ability of a compound to bind the Ckβ-6 receptor and elicit a second messenger response identifies that compound as an agonist A compound which binds but does not elicit a second messenger response identifies that compound as an antagonist.

A competitive binding assay, in which the compounds are labeled, for example by radioactivity may also be employed to identify antagonists. Such methods are known in the art.

Antagonists include negative dominant mutants of Ckβ-6. Ckβ-6 is a tetrameric polypeptide wherein one mutated unit will cause the entire polypeptide to be non-functional. A negative dominant mutant of Ckβ-6 binds to the Ckβ-6 receptor but fails to activate cells (leukocytes and eosinophils) to which it binds. An assay to detect negative dominant mutants of Ckβ-6 is an in vitro chemotaxis assay wherein a multiwell chemotaxis chamber equipped with polyvinylpyrrolidone-free polycarbonate membranes is used to measure the chemoattractant ability of Ckβ-6 for leukocytes in the presence and absence of potential antagonist or agonist molecules, such as is described in Example 10, below. A preferred assay is an in-vitro calcium ($Ca^{2+}$) release assay, for example, as described in Example 9, below.

Potential antagonists also include an antibody, or in some cases, an oligopeptide or oligonucleotide, which binds to the polypeptide and prevents it from binding its receptor.

Another potential antagonist is an antisense construct prepared using antisense technology. Antisense technology can be used to control gene expression through triple-helix formation or antisense DNA or RNA, both of which methods are based on binding of a polynucleotide to DNA or RNA. For example, the 5' coding portion of the polynucleotide sequence, which encodes for the mature polypeptides of the present invention, is used to design an antisense RNA oligonucleotide of from about 10 to 40 base pairs in length. A DNA oligonucleotide is designed to be complementary to a region of the gene involved in transcription (triple helix— see Lee, et al., *Nucl. Acids Res.* 6:3073 (1979); Cooney, et al., *Science* 241:456 (1988); and Dervan, et al., Science 251:1360 (1991)), thereby preventing transcription and the production of Ckβ-6. The antisense RNA oligonucleotide hybridizes to the mRNA in vivo and blocks translation of the mRNA molecule into Ckβ-6 polypeptide (Antisense— Okano, *J. Neurochem.* 56:560 (1991); *Oligodeoxynucleotides as Antisense Inhibitors of Gene Expression,* CRC Press, Boca Raton, Fla. (1988)). The oligonucleotides described above can also be delivered to cells such that the antisense RNA or DNA may be expressed in vivo to inhibit production of Ckβ-6.

Potential antagonists include a small molecule which binds to and occupies the active site of the polypeptide thereby making the catalytic site inaccessible to substrate such that normal biological activity is prevented. Examples of small molecules include but are not limited to small peptides or peptide-like molecules.

Another potential antagonist is a peptide derivative of the polypeptides which are naturally or synthetically modified analogs of the polypeptides that have lost biological function yet still recognize and bind to the receptors of the polypeptides to thereby effectively block the receptors. Examples of peptide derivatives include, but-are not limited to small peptides or peptide-like molecules.

The antagonists may be employed to treat disorders which are either Ckβ-6-induced or enhanced, for example, autoimmune and chronic inflammatory and infective diseases. Examples of auto-immune diseases include multiple sclerosis, and insulin-dependent diabetes.

The antagonists may be employed to treat inflammation by preventing the attraction of eosinophils or basophiles to a wound or a site of trauma, and to regulate normal pulmonary macrophage populations, since acute and chronic inflammatory pulmonary diseases are associated with sequestration of mononuclear phagocytes in the lung. They may also be employed to treat rheumatoid arthritis, since MCP levels were found to be significantly elevated in synovial fluid from rheumatoid arthritis patients which suggests that synovial production of Ckβ-6 attracts eosinophils or basophils whose influx and activation are important in the pathogenesis of both degenerative and inflammatory arthropathies.

The antagonists may also be employed to prevent allergies, since it has been shown that MCPs directly induce histamine release by basophils. Related immunological disorders including late phase allergic reactions, chronic urticaria, and atopic dermatitis can be treated by antagonists which are effective to inhibit chemokine-induced mast cell and basophil degranulation and release of histamine. IgE-mediated allergic reactions such as asthma, rhinitis, and eczema may also be treated. Antagonist can also be used to treat adult respiratory distress syndrome as well as airway inflammation.

Antagonists may also be employed to treat idiopathic hyper-eosinophilic syndrome by preventing eosinophil production an migration. Endotoxic shock may also be treated by the antagonists by preventing the migration of macrophages and their production of the chemokine polypeptides of the present invention. The antagonists may be employed in a composition with a pharmaceutically acceptable carrier, e.g., as herein described.

Antagonists may also be employed to treat rheumatoid arthritis by preventing the attraction of eosinophils and basophils into synovial fluid in the joints of patients.

The antagonists may be employed to interfere with the deleterious cascades attributed primarily to IL-1 and TNF, which prevents the biosynthesis of other inflammatory cytokines. In this way, the antagonists may be employed to inhibit prostaglandin-independent fever induced by chemokines.

The antagonists may also be employed to treat bone marrow failure, for example, aplastic anemia and myelodysplastic syndrome. The antagonists may also be employed to treat subepithelial basement membrane fibrosis which is a prominent feature of the asthmatic lung.

Ckβ-6 agonists include any small molecule that has an activity similar to Ckβ-6 polypeptides, as described herein. For example, Ckβ-6 agonists can be used to enhance Ckβ-6 activity. For example, to enhance Ckβ-6 induced myeloprotection in patients undergoing chemotherapy or bone marrow transplantation.

Pharmaceutical Compositions

The Ckβ-6 pharmaceutical composition comprises an effective amount of an isolated Ckβ-6 polypeptide, agonist or antagonist of the invention, particularly a mature form of Ckβ-6, effective to increase the Ckβ-6 activity level in such an individual. Such compositions can be formulated and doses in a fashion consistent with good medical practice, taking into account the clinical condition of the individual patient (especially the side effects of treatment with Ckβ-6 polypeptide alone), the site of delivery of the polypeptide composition, the method of administration, the scheduling of administration, and other factors known to practitioners. The effective amount of Ckβ-6 polypeptide for purposes herein is thus determined by such considerations.

The polypeptides, and agonists and antagonists, of the present invention may be employed in combination with a suitable pharmaceutical carrier. Such compositions comprise a therapeutically effective amount of the polypeptide or agonist or antagonist, and a pharmaceutically acceptable carrier or excipient Such a carrier includes but is not limited to saline, buffered saline, dextrose, water, glycerol, ethanol, and combinations thereof. The formulation should suit the mode of administration.

By "pharmaceutically acceptable carrier" is meant a non-toxic solid, semisolid or liquid filler, diluent, encapsulating material or formulation auxiliary of any type. The term "parenteral" as used herein refers to modes of administration which include intravenous, intramuscular, intraperitoneal, intrasternal, subcutaneous and intraarticular injection and infusion.

The Ckβ-6 polypeptide is also suitably administered by sustained-release systems. Suitable examples of sustained-release compositions include semi-permeable polymer matrices in the form of shaped articles, e.g. films, or miro-capsules. Sustained-release matrices include polylactides (U.S. Pat. No. 3,773,919, EP 58,481), copolymers of L-glutamic acid and gamma-ethyl-L-glutamate (Sidman, U., et al., *Biopolymers* 22:547–556 (1983)), poly (2-hydroxyethyl methacrylate) (R. Langer, et al., *J. Biomed. Mater. Res.* 15:167–277 (1981), and R. Langer, *Chem. Tech* 12:98–105 (1982)), ethylene vinyl acetate (R. Langer, et al., Id.) or poly-D-(–)-3-hydroxybutyic acid (EP 133,988). Sustained-release Ckβ-6 polypeptide compositions also include liposomally entrapped Ckβ-6 polypeptide. Liposomes containing Ckβ-6 polypeptide are prepared by methods known per se: DE 3,218,121; Epstein, et al., *Proc. Natl. Acad. Sci.* (*USA*) 82:3688–3692 (1985); Hwang, et al., *Proc. Natl. Acad. Sci.* (*USA*) 77:4030–4034 (1980); EP 52,322; EP 36,676; EP 88,046; EP 143,949; EP 142,641; Japanese Pat. Appl. 83–118008; U.S. Pat. Nos. 4,485,045 and 4,544,545; and EP 102,324. Ordinarily, the liposomes are of the small (about 200–800 Angstroms) unilamellar type in which the lipid content is greater than about 30 mol. percent cholesterol, the selected proportion being adjusted for the optimal Ckβ-6 polypeptide therapy.

For parenteral administration, in one embodiment, the Ckβ-6 polypeptide is formulated generally by mixing it at the desired degree of purity, in a unit dosage injectable form (solution, suspension, or emulsion), with a pharmaceutically acceptable carrier, i.e., one that is non-toxic to recipients at the dosages and concentrations employed and is compatible with other ingredients of the formulation. For example, the formulation preferably does not include oxidizing agents and other compounds that are known to be deleterious to polypeptides.

Generally, the formulations are prepared by contacting the Ckβ-6 polypeptide uniformly and intimately with liquid carriers or finely divided solid carriers or both. Then, if necessary, the product is shaped into the desired formulation. Preferably the carrier is a parenteral carrier, more preferably a solution that is isotonic with the blood of the recipient Examples of such carrier vehicles include water, saline, Ringer's solution, and dextrose solution. Non-aqueous vehicles such as fixed oils and ethyl oleate are also useful herein, as well as liposomes.

The carrier suitably contains minor amounts of additives such as substances that enhance isotonicity and chemical stability. Such materials are non-toxic to recipients at the dosages and concentrations employed, and include buffers such as phosphate, citrate, succinate, acetic acid, and other organic acids or their salts; antioxidants such as ascorbic acid; low molecular weight (less than about ten residues) polypeptides, e.g. polyarginine or tripeptides; proteins, such as serum albumin, gelatin, or immunoglobulins; hydrophilic polymers such as polyvinylpyrrolidone; amino acids, such as glycine, glutamic acid, aspartic acid, or arginine; monosaccharides, disaccharides, and other carbohydrates including cellulose or its derivatives, glucose, manose, or dextrins; chelating agents such as EDTA; sugar alcohols such as mannitol or sorbitol; counterions such as sodium; and/or nonionic surfactants such as polysorbates, poloxamers, or PEG.

The Ckβ-6 polypeptide is typically formulated in such vehicles at a concentration of about 0.1 mg/ml to 100 mg/ml, preferably 1–10 mg/ml, at a pH of about 3 to 8. It will be-understood that the use of certain of the foregoing excipients, carriers, or stabilizers will result in the formation of Ckβ-6 polypeptide salts.

Ckβ-6 polypeptide to be used for therapeutic administration must be sterile. Sterility is readily accomplished by filtration through sterile filtration membranes (e.g. 0.2 micron membranes). Therapeutic Ckβ-6 polypeptide compositions generally are placed into a container having a sterile access port, for example, an intravenous solution bag or vial having a stopper pierceable by a hypodermic injection needle.

Ckβ-6 polypeptide ordinarily will be stored in unit or multi-dose containers, for example, sealed ampoules or vials, as an aqueous solution or as a lyophilized formulation for reconstitution. As an example of a lyophilized formulation, 10-ml vials are filled with 5 ml of sterile-filtered 1% (w/v) aqueous Ckβ-6 polypeptide solution, and the resulting mixture is lyophilized. The infusion solution is prepared by reconstituting the lyophilized Ckβ-6 polypeptide using bacteriostatic Water-for-Injection.

The invention also provides a pharmaceutical pack or kit comprising one or more containers filled with one or more of the ingredients of the pharmaceutical compositions of the invention. Associated with such container(s) can be a notice in the form prescribed by a governmental agency regulating the manufacture, use or sale of pharmaceuticals or biological products, which notice reflects approval by the agency of manufacture, use or sale for human administration. In addition, the polypeptides, or agonists and antagonists, of the present invention may be employed in conjunction with other therapeutic compounds.

Modes of Administration

It will be appreciated that conditions caused by a decrease in the standard or normal level of Ckβ-6 activity in an individual, can be treated by administration of Ckβ-6 protein. Thus, the invention further provides a method of treating an individual in need of an increased level of Ckβ-6 activity comprising administering to such an individual a pharmaceutical composition comprising an effective amount of an isolated Ckβ-6 polypeptide of the invention, particularly a mature form of the Ckβ-6, effective to increase the Ckβ-6 activity level in such an individual.

The amounts and dosage regimens of Ckβ-6 administered to a subject will depend on a number of factors such as the mode of administration, the nature of the condition being treated and the judgment of the prescribing physician. The pharmaceutical compositions are administered in an amount which is effective for treating and/or prophylaxis of the specific indication. In general, the polypeptides will be administered in an amount of at least about 10 μg/kg body weight and in most cases they will be administered in an amount not in excess of about 10 mg/kg body weight per day and preferably the dosage is from about 10 μg/kg body weight daily, taking into account the routes of administration, symptoms, etc.

As a general proposition, the total pharmaceutically effective amount of Ckβ-6 polypeptide administered parenterally per dose will more preferably be in the range of about 1 μg/kg/day to 10 mg/kg/day of patient body weight, although, as noted above, this will be subject to therapeutic discretion. Even more preferably, this dose is at least 0.01 mg/kg/day, and most preferably for humans between about 0.01 and 1 mg/kg/day. If given continuously, the Ckβ-6 polypeptide is typically administered at a dose rate of about 1 μg/kg/hour to about 50 μg/kg/hour, either by 1–4 injections per day or by continuous subcutaneous infusions, for example, using a mini-pump. An intravenous bag solution may also be employed. The length of treatment needed to observe changes and the interval following treatment for responses to occur appears to vary depending on the desired effect.

The pharmaceutical compositions may be administered in a convenient manner such as by the oral, topical, parenterally, intravenous, intraperitoneal, intramuscular, subcutaneous, intranasal or intradermal routes.

Gene Therapy

The polypeptides and agonists and antagonists which are polypeptides may also be employed in accordance with the present invention by expression of such polypeptides in vivo, which is often referred to as "gene therapy."

Thus, for example, cells from a patient may be engineered with a polynucleotide (DNA or RNA) encoding a polypeptide ex vivo, with the engineered cells then being provided to a patient to be treated with the polypeptide. Such methods are well-known in the art and are apparent from the teachings herein. For example, cells may be engineered by the use of a retroviral plasmid vector containing RNA encoding a polypeptide of the present invention.

Similarly, cells may be engineered in vivo for expression of a polypeptide in vivo by, for example, procedures known in the art. For example, a packaging cell is transduced with a retroviral plasmid vector containing RNA encoding a polypeptide of the present invention such that the packaging cell now produces infectious viral particles containing the gene of interest. These producer cells may be administered to a patient for engineering cells in vivo and expression of the polypeptide in vivo. These and other methods for administering a polypeptide of the present invention by such method should be apparent to those skilled in the art from the teachings of the present invention.

Retroviruses from which the retroviral plasmid vectors hereinabove mentioned may be derived include, but are not limited to, Moloney Murine Leukemia Virus, spleen necrosis virus, retroviruses such as Rous Sarcoma Virus, Harvey Sarcoma Virus, avian leukosis virus, gibbon ape leukemia virus, human immunodeficiency virus, adenovirus, Myeloproliferative Sarcoma Virus, and mammary tumor virus. In one embodiment, the retroviral plasmid vector is derived from Moloney Murine Leukemia Virus.

In a preferred embodiment the retroviral expression vector, pMV-7, is flanked by the long terminal repeats (LTRs) of the Moloney murine sarcoma virus and contains the selectable drug resistance gene neo under the regulation of the herpes simplex vir (HSV) tymidine kinase (tk) promoter. Unique EcoRI and HindIII sites facilitate the introduction of coding sequence (Kirschmeier, P. T., et al., *DNA* 7:219–25 (1988)).

The vector includes one or more promoters. Suitable promoters which may be employed include, but are not limited to, the retroviral LTR; the SV40 promoter; and the human cytomegalovirus (CMV) promoter described in Miller, et al., *Biotechniques* 7(9):980–990 (1989), or any other promoter (e.g., cellular promoters such as eukaryotic cellular promoters including, but not limited to, the histone, pol III, and b-actin promoters). Other viral promoters which may be employed include, but are not limited to, adenovirus promoters, thymidine linase (TK) promoters, and B19 parvovirus promoters. The selection of a suitable promoter will be apparent to those skilled in the art from the teachings contained herein.

The nucleic acid sequence encoding the polypeptide of the present invention is under the control of a suitable promoter. Suitable promoters which may be employed include, but are not limited to, adenoviral promoters, such as the adenoviral major late promoter; or hetorologous promoters, such as the cytomegalovirus (CMV) promoter; the respiratory syncytial virus (RSV) promoter; inducible promoters, such as the MMT promoter, the metallothionein promoter; heat shock promoters; the albumin promoter; the ApoAI promoter; human globin promoters; viral thymidine kinase promoters, such as the Herpes Simplex thymidine kinase promoter; retroviral LTRs (including the modified retroviral LTRs hereinabove described); the b-actin promoter; and human growth hormone promoters. The promoter also may be the native promoter which controls the gene encoding the polypeptide.

The retroviral plasmid vector is employed to transduce packaging cell lines to form producer cell lines. Examples of packaging cells which may be transfected include, but are not limited to, the PE501, PA317, y-2, y-AM, PA12, T19-14X, VT-19-17-H2, yCRE, yCRIP, GP+E-86, GP+envAm12, and DAN cell lines as described in Miller, *Human Gene Therapy*, Vol. 1 (1990), pp. 5–14, which is incorporated herein by reference in its entirety. The vector may transduce the packaging cells through any means known in the art. Such means include, but are not limited to, electroporation, the use of liposomes, and $CaPO_4$ precipitation. In one alternative, the retroviral plasmid vector may be encapsulated into a liposome, or coupled to a lipid, and then administered to a host.

The producer cell line generates infectious retroviral vector particles which include the nucleic acid sequence(s) encoding the polypeptides. Such retroviral vector particles then may be employed, to transduce eukaryotic cells, either in vitro or in vivo. The transduced eukaryotic cells will express the nucleic acid sequence(s) encoding the polypeptide. Eukaryotic cells which may be transduced include, but are not limited to, embryonic stem cells, embryonic carcinoma cells, as well as hematopoietic stem cells, hepatocytes, fibroblasts, myoblasts, keratinocytes, endothelial cells, and bronchial epithelial cells.

Disease Diagnosis and Prognosis

Certain diseases or disorders, as discussed below, may be associated with altered (enhanced or reduced) levels of the Ckβ-6 protein and mRNA encoding the Ckβ-6 protein when compared to a corresponding "standard" mammal, i.e., a mammal of the same species not having the disease or disorder. Further, it is believed that altered levels of the Ckβ-6 protein can be detected in certain body fluids (e.g. sera, plasma, urine, and spinal fluid) from mammals with a disease or disorder when compared to sera from mammals of the same species not having the disease or disorder. Thus, the invention provides a diagnostic method, which involves assaying the expression level of the gene encoding the Ckβ-6 protein in mammalian cells or body fluid and comparing the gene expression level with a standard Ckβ-6 gene expression level, whereby an alteration in the gene expression level compared to the standard is indicative of certain diseases or disorders.

Where a disease or disorder diagnosis has already been made according to conventional methods, the present invention is useful as a prognostic indicator, whereby patients exhibiting altered Ckβ-6 gene expression will experience a worse clinical outcome relative to patients expressing the gene at a level closer to normal.

By "assaying the expression level of the gene encoding the Ckβ-6 protein" is intended qualitatively or quantitatively measuring or estimating the level of the Ckβ-6 protein or the level of the mRNA encoding the Ckβ-6 protein in a first biological sample either directly (e.g. by determining or estimating absolute protein level or mRNA level) or relatively (e.g. by comparing to the Ckβ-6 protein level or mRNA level in a second biological sample).

Preferably, the Ckβ-6 protein level or mRNA level in the first biological sample is measured or estimated and compared to a standard Ckβ-6 protein level or mRNA level, the standard being taken from a second biological sample obtained from an individual not having the disease or disorder. As will be appreciated in the art, once a standard Ckβ-6 protein level or mRNA level is known, it can be used repeatedly as a standard for comparison.

By "biological sample" is intended any biological sample obtained from an individual, cell line, tissue culture, or other source which contains Ckβ-6 protein or mRNA. Biological samples include mammalian body fluids (such as sera, plasma, urine, synovial fluid and spinal fluid) which contain secreted mature Ckβ-6 protein, and haematopoietic tissue. Methods for obtaining tissue biopsies and body fluids from mammals are well known in the art. Where the biological sample is to include mRNA, a tissue biopsy is the preferred source.

The present invention is useful for detecting disease in mammals. In particular the invention is useful during useful for diagnosis or treatment of various immune system-related disorders in mammals, preferably humans. Such disorders include tumors, cancers, and any disregulation of immune cell function including, but not limited to, autoimmunity, arthritis, leukemias, lymphomas, immunosupression, sepsis, wound healing, acute and chronic infection, cell mediated immunity, humoral immunity, inflammatory bowel disease, myelosupression, asthma and the like. Preferred mammals include monkeys, apes, cats, dogs, cows, pigs, horses, rabbits and humans. Particularly preferred are humans.

Total cellular RNA can be isolated from a biological sample using any suitable technique such as the single-step guanidinium-thiocyanate-phenol-chloroform method described in Chomczynski and Sacchi, *Anal. Biochem.* 162:156–159 (1987). Levels of mRNA encoding the Ckβ-6 protein are then assayed using any appropriate method. These include Northern blot analysis, S1 nuclease mapping, the polymerase chain reaction (PCR), reverse transcription in combination with the polymerase chain reaction (RT-PCR), and reverse transcription in combination with the ligase chain reaction (RT-LCR).

Northern blot analysis can be performed as described in Harada, et al., *Cell* 63:303–312 (1990). Briefly, total RNA is prepared from a biological sample as described above. For the Northern blot, the RNA is denatured in an appropriate buffer (such as glyoxal/dimethyl sulfoxide/sodium phosphate buffer), subjected to agarose gel electrophoresis, and transferred onto a nitrocellulose filter. After the RNAs have been linked to the filter by a UV linker, the filter is prehybridized in a solution containing formamide, SSC, Denhardt's solution, denatured salmon sperm, SDS, and sodium phosphate buffer. Ckβ-6 protein cDNA labeled according to any appropriate method (such as the 32P-multiprimed DNA labeling system (Amersham)) is used as probe. After hybridization overnight, the filter is washed and exposed to x-ray film. cDNA for use as probe according to the present invention is described in the sections above and will preferably at least 15 bp in length.

S1 mapping can be performed as described in Fujita, et al., *Cell* 49:357–367 (1987). To prepare probe DNA for use in S1 mapping, the sense strand of above-described cDNA is used as a template to synthesize labeled antisense DNA. The antisense DNA can then be digested using an appropriate restriction endonuclease to generate further DNA probes of a desired length. Such antisense probes are useful for visualizing protected bands corresponding to the target mRNA (i.e., mRNA encoding the Ckβ-6 protein). Northern blot analysis can be performed as described above.

Preferably, levels of mRNA encoding the Ckβ-6 protein are assayed using the RT-PCR method described in Makino, et al., *Technique* 2:295–301 (1990). By this method, the radioactivities of the "amplicons" in the polyacrylamide gel bands are linearly related to the initial concentration of the target mRNA. Briefly, this method involves adding total RNA isolated from a biological sample in a reaction mixture containing a RT primer and appropriate buffer. After incubating for primer annealing, the mixture can be supplemented with a RT buffer, dNTPs, DTT, RNase inhibitor and reverse transcriptase. After incubation to achieve reverse transcription of the RNA, the RT products are then subject to PCR using labeled primers. Alternatively, rather than labeling the primers, a labeled dNTP can be included in the PCR reaction mixture. PCR amplification can be performed in a DNA thermal cycler according to conventional techniques. After a suitable number of rounds to achieve amplification, the PCR reaction mixture is electrophoresed on a polyacrylamide gel. After drying the gel, the radioactivity of the appropriate bands (corresponding to the mRNA encoding the Ckβ-6 protein)) is quantified using an imaging analyzer. RT and PCR reaction ingredients and conditions, reagent and gel concentrations, and labeling methods are well known in the art. Variations on the RT-PCR method will be apparent to the skilled artisan.

Any set of oligonucleotide primers which will amplify reverse transcribed target mRNA can be used and can be designed as described in the sections above.

Assaying Ckβ-6 protein levels in a biological sample can occur using any art-known method. Preferred for assaying Ckβ-6 protein levels in a biological sample are antibody-based techniques. For example, Ckβ-6 protein expression in tissues can be studied with classical immunohistological methods. In these, the specific recognition is provided by the primary antibody (polyclonal or monoclonal) but the secondary detection system can utilize fluorescent, enzyme, or other conjugated secondary antibodies. As a result, an immunohistological staining of tissue section for pathological examination is obtained. Tissues can also be extracted, e.g. with urea and neutral detergent, for the liberation of Ckβ-6 protein for Western-blot or dot/slot assay (Jalkanen, M., et al., *J. Cell. Biol.* 101:976–985 (1985); Jalkanen, M., et al., *J. Cell. Biol.* 105:3087–3096 (1987)). In this technique, which is based on the use of cationic solid phases, quantitation of Ckβ-6 protein can be accomplished using isolated Ckβ-6 protein as a standard. This technique can also be applied to body fluids. With these samples, a molar concentration of Ckβ-6 protein will aid to set standard values of Ckβ-6 protein content for different body fluids, like serum, plasma, urine, spinal fluid, etc. The normal appearance of Ckβ-6 protein amounts can then be set using values from healthy individuals, which can be compared to those obtained from a test subject.

Other antibody-based methods useful for detecting Ckβ-6 protein gene expression include immunoassays, such as the enzyme linked immunosorbent assay (ELISA) and the radio-immunoassay (RIA). For example, an Ckβ-6 protein-specific monoclonal antibodies can be used both as an immunoabsorbent and as an enzyme-labeled probe to detect and quantify the Ckβ-6 protein. The amount of Ckβ-6 protein present in the sample can be calculated by reference to the amount present in a standard preparation using a linear regression computer algorithm. In another ELISA assay, two distinct specific monoclonal antibodies can be used to detect Ckβ-6 protein in a body fluid. In this assay, one of the antibodies is used as the immunoabsorbent and the other as the enzyme-labeled probe.

The above techniques may be conducted essentially as a "one-step" or "two-step" assay. The "one-step" assay involves contacting Ckβ-6 protein with immobilized antibody and, without washing, contacting the mixture with the labeled antibody. The "two-step" assay involves washing before contacting the mixture with the labeled antibody. Other conventional methods may also be employed as suitable. It is usually desirable to immobilize one component of the assay system on a support, thereby allowing other components of the system to be brought into contact with the component and readily removed from the sample.

Suitable enzyme labels include, for example, those from the oxidase group, which catalyze the production of hydrogen peroxide by reacting with substrate. Glucose oxidase is particularly preferred as it has good stability and its substrate (glucose) is readily available. Activity of an oxidase label may be assayed by measuring the concentration of hydrogen peroxide formed by the enzyme-labelled antibody/substrate reaction. Besides enzymes, other suitable labels include radioisotopes, such as iodine ($^{125}I$, $^{121}I$), carbon ($^{14}C$), sulfur ($^{35}S$), tritium ($^{3}H$), indium ($^{112}In$), and technetium ($^{99m}Tc$), and fluorescent labels, such as fluorescein and rhodamine, and biotin.

The polypeptides of the present invention, and polynucleotides encoding such polypeptides, may be employed as research reagents for in vitro purposes related to scientific research, synthesis of DNA and manufacture of DNA vectors, and for the purpose of developing therapeutics and diagnostics for the treatment of human disease. For example, Ckβ-6 may be employed for the expansion of immature hematopoietic progenitor cells, for example, granulocytes, macrophages or monocytes, by temporarily preventing their differentiation. These bone marrow cells may be cultured in vitro.

Fragments of the full length Ckβ-6 genes may be used as a hybridization probe for a cDNA library to isolate the full length gene and to isolate other genes which have a high sequence similarity to the gene or similar biological activity. Preferably, however, the probes have at least 30 bases and may contain, for example, 50 or more bases. The probe may also be used to identify a cDNA clone corresponding to a full length transcript and a genomic clone or clones that contain the complete genes including regulatory and promotor regions, exons, and introns. An example of a screen comprises isolating the coding region of the genes by using the known DNA sequence to synthesize an oligonucleotide probe. Labeled oligonucleotides having a sequence complementary to that of the genes of the present invention are used to screen a library of human cDNA, genomic DNA or mRNA to determine which members of the library the probe hybridizes to.

This invention is also related to the use of the gene of the present invention as a diagnostic. Detection of a mutated form of the gene will allow a diagnosis of a disease or a susceptibility to a disease which results from underexpression of Ckβ-6.

Individuals carrying mutations in the gene of the present invention may be detected at the DNA level by a variety of techniques. Nucleic acids for diagnosis may be obtained from a patient's cells, including but not limited to blood, urine, saliva, tissue biopsy and autopsy material. The genomic DNA may be used directly for detection or may be amplified enzymatically by using PCR (Saiki et al., Nature 324:163–166 (1986)) prior to analysis. RNA or cDNA may also be used for the same purpose. As an example, PCR primers complementary to the nucleic acid encoding Ckβ-6 can be used to identify and analyze mutations. For example, deletions and insertions can be detected by a change in size of the amplified product in comparison to the normal genotype. Point mutations can be identified by hybridizing amplified DNA to radiolabeled RNA or alternatively, radiolabeled antisense DNA sequences. Perfectly matched sequences can be distinguished from mismatched duplexes by RNase A digestion or by differences in melting temperatures.

Sequence differences between the reference gene and genes having mutations may be revealed by the direct DNA sequencing method. In addition, cloned DNA segments may be employed as probes to detect specific DNA segments. The sensitivity of this method is greatly enhanced when combined with PCR For example, a sequencing primer is used with double-stranded PCR product or a single-stranded template molecule generated by a modified PCR. The sequence determination is performed by conventional procedures with radiolabeled nucleotide or by automatic sequencing procedures with fluorescent-tags.

Genetic testing based on DNA sequence differences may be achieved by detection of alteration in electrophoretic mobility of DNA fragments in gels with or without denaturing agents. Small sequence deletions and insertions can be visualized by high resolution gel electrophoresis. DNA fragments of different sequences may be distinguished on denaturing formamide gradient gels in which the mobilities of different DNA fragments are retarded in the gel at different positions according to their specific melting or partial melting temperatures (see, e.g., Myers et al., Science 230:1242 (1985)).

Sequence changes at specific locations. may also be revealed by nuclease protection assays, such as RNase and S1 protection or the chemical cleavage method (e.g., Cotton et al., Proc. Natl. Acad Sci. (USA) 85:4397–4401 (1985)).

Thus, the detection of a specific DNA sequence may be achieved by methods such as hybridization, RNase protection, chemical cleavage, direct DNA sequencing or the use of restriction enzymes, (e.g., Restriction Fragment Length Polymorphisms (RFLP)) and Southern blotting of genomic DNA.

In addition to more conventional gel-electrophoresis and DNA sequencing, mutations can also be detected by in situ analysis.

The present invention also relates to a diagnostic assay for detecting altered levels of the polypeptide of the present invention in various tissues since an over-expression of the proteins compared to normal control tissue samples may detect the presence of a disease or susceptibility to a disease, for example, a tumor. Assays used to detect levels of the polypeptide of the present invention in a sample derived from a host are well-known to those of skill in the art and include radioimmunoassays, competitive-binding assays, Western Blot analysis, ELISA assays and sandwich assays. An ELISA assay (Coligan, et al., *Current Protocols in Immunology* 1(2), Chapter 6, (1991)) initially comprises preparing an antibody specific to the Ckβ-6 antigen, preferably a monoclonal antibody. In addition a reporter antibody is prepared against the monoclonal antibody. To the reporter antibody is attached a detectable reagent such as radioactivity, fluorescence or in this example a horseradish peroxidase enzyme. A sample is now removed from a host and incubated on a solid support, e.g. a polystyrene dish, that binds the proteins in the sample. Any free protein binding sites on the dish are then covered by incubating with a non-specific protein such as bovine serum albumin. Next, the monoclonal antibody is incubated in the dish during which time the monoclonal antibodies attached to any of the polypeptide of the present invention attached to the polystyrene dish. All unbound monoclonal antibody is washed out with buffer. The reporter antibody linked to horseradish peroxidase is now placed in the dish resulting in binding of the reporter antibody to any monoclonal antibody bound to the polypeptide of the present invention. Unattached reporter antibody is then washed out. Peroxidase substrates are then added to the dish and the amount of color developed in a given time period is a measurement of the amount of the polypeptide of the present invention present in a given volume of patient sample when compared against a standard curve.

A competition assay may be employed wherein antibodies specific to the polypeptide of the present invention are attached to a solid support and labeled Ckβ-6 and a sample derived from the host are passed over the solid support and the amount of label detected attached to the solid support can be correlated to a quantity of the polypeptide of the present invention in the sample.

A "sandwich" assay is similar to an ELISA assay. In a "sandwich" assay Ckβ-6 is passed over a solid support and binds to antibody attached to a solid support. A second antibody is then bound to the Ckβ-6. A third antibody which is labeled and specific to the second antibody is then passed over the solid support and binds to the second antibody and an amount can then be quantified.

This invention provides a method for identification of the receptors for the chemokine polypeptides. The gene encoding the receptor can be identified by numerous methods known to those of skill in the art, for example, ligand panning and FACS sorting (Coligan, et al., *Current Protocols in Immun.* 1(2), Chapter 5, (1991)). Preferably, expression cloning is employed wherein polyadenylated RNA is prepared from a cell responsive to the polypeptides, and a cDNA library created from this RNA is divided into pools and used to transfect COS cells or other cells that are not responsive to the polypeptides. Transfected cells which are grown on glass slides are exposed to the labeled polypeptides. The polypeptides can be labeled by a variety of means including iodination or inclusion of a recognition site for a site-specific protein kinase. Following fixation and incubation, the slides are subjected to autoradiographic analysis. Positive pools are identified and sub-pools are prepared and retransfected using an iterative sub-pooling and rescreening process, eventually yielding a single clones that encodes the putative receptor.

As an alternative approach for receptor identification, the labeled polypeptides can be photoaffinity linked with cell membrane or extract preparations that express the receptor molecule. Cross-linked material is resolved by PAGE analysis and exposed to X-ray film. The labeled complex containing the receptors of the polypeptides can be excised, resolved into peptide fragments, and subjected to protein microsequencing. The amino acid sequence obtained from microsequencing would be used to design a set of degenerate oligonucleotide probes to screen a cDNA library to identify the genes encoding the putative receptors.

Chromosome Assays

The nucleic acids of the present invention are also valuable for chromosome identification. The sequence is specifically targeted to and can hybridize with a particular location on an individual human chromosome. Moreover, there is a current need for identifying particular sites on the chromosome. Few chromosome marking reagents based on actual sequence data (repeat polymorphisms) are presently available for marking chromosomal location. The mapping of DNAs to chromosomes according to the present invention is an important first step in correlating those sequences with genes associated with disease.

In certain perferred embodiments in this regard, the cDNA herein disclosed is used to clone genomic DNA of an Ckβ-6 protein gene. This can be accomplished using a variety of well known techniques and libraries, which are generally available commercially. The genomic DNA this is used for in situ chromosome mapping using well known techniques for this purpose. Typically in accordance with routine procedures for chromosome mapping, some trial and error may be necessary to identify a genomic probe that gives a good in situ hybridization signal.

Briefly, sequences can be mapped to chromosomes by preparing PCR primers (preferably 15–25 bp) from the cDNA. Computer analysis of the 3' untranslated region of the gene is used to rapidly select primers that do not span more than one exon in the genomic DNA, thus complicating the amplification process. These primers are then used for PCR screening of somatic cell hybrids containing individual human chromosomes. Only those hybrids containing the human gene corresponding to the primer will yield an amplified fragment.

PCR mapping of somatic cell hybrids is a rapid procedure for assigning a particular DNA to a particular chromosome. Using the present invention with the same oligonucleotide primers, sublocalization can be achieved with panels of fragments from specific chromosomes or pools of large genomic clones in an analogous manner. Other mapping strategies that can similarly be used to map to its chromosome include in situ hybridization, prescreening with labeled flow-sorted chromosomes and preselection by hybridization to construct chromosome specific-cDNA libraries.

Fluorescence in situ hybridization (FISH) of a cDNA clone to a metaphase chromosomal spread can be used to provide a precise chromosomal location in one step. This technique can be used with cDNA having at least 50 or 60 bases. For a review of this technique, see Verma et al., *Human Chromosomes: a Manual of Basic Techniques,* Pergamon Press, New York (1988).

Once a sequence has been mapped to a precise chromosomal location, the physical position of the sequence on the chromosome can be correlated with genetic map data. Such data are found, for example, in V. McKusick, *Mendelian Inheritance in Man* (available on line through Johns Hopkins University Welch Medical Library). The relationship between genes and diseases that have been mapped to the same chromosomal region are then identified through linkage analysis (coinheritance of physically adjacent genes).

Next, it is necessary to determine the differences in the cDNA or genomic sequence between affected and unaffected individuals. If a mutation is observed in some or all of the affected individuals but not in any normal individuals, then the mutation is likely to be the causative agent of the disease.

With current resolution of physical mapping and genetic mapping techniques, a cDNA precisely localized to a chromosomal region associated with the disease could be one of between 50 and 500 potential causative genes. (This assumes 1 megabase mapping resolution and one gene per 20 kb).

Comparison of affected and unaffected individuals generally involves first looking for structural alterations in the chromosomes, such as deletions or translocations that are visible from chromosome spreads or detectable using PCR based on that cDNA sequence. Ultimately, complete sequencing of genes from several individuals is required to confirm the presence of a mutation and to distinguish mutations from polymorphisms.

Antibodies

Ckβ-6-protein specific antibodies for use in the present invention can be raised against the intact Ckβ-6 protein or an antigenic polypeptide fragment thereof, which may presented together with a carrier protein, such as an albumin, to an animal system (such as rabbit or mouse) or, if it is long enough (at least about 25 amino acids), without a carrier.

As used herein, the term "antibody" (Ab) or "monoclonal antibody" (Mab) is meant to include intact molecules as well as antibody fragments (such as, for example, Fab and F(ab')2 fragments) which are capable of specifically binding to MPIF-1, M-CIF or MIP-4 protein. Fab and F(ab')2 fragments lack the Fc fragment of intact antibody, clear more rapidly from the circulation, and may have less non-specific tissue binding of an intact antibody (Wahl et al., *J. Nucl. Med.* 24:316–325 (1983)). Thus, these fragments are preferred.

The polypeptides, their fragments or other derivatives, or analogs thereof, or cells expressing them can be used as an immunogen to produce antibodies thereto. These antibodies can be, for example, polyclonal or monoclonal antibodies. The present invention also includes chimeric, single chain, and humanized antibodies, as well as Fab fragments, or the product of an Fab expression library. Various procedures known in the art may be used for the production of such antibodies and fragments.

Antibodies generated against the polypeptides corresponding to a sequence of the present invention can be obtained by direct injection of the polypeptides into an animal or by administering the polypeptides to an animal, preferably a nonhuman. The antibody so obtained will then bind the polypeptides itself. In this manner, even a sequence encoding only a fragment of the polypeptides can be used to generate antibodies binding the whole native polypeptides. Such antibodies can then be used to isolate the polypeptide from tissue expressing that polypeptide.

For preparation of monoclonal antibodies, any technique which provides antibodies produced by continuous cell line cultures can be used. Examples include the hybridoma technique (Kohler and Milstein, *Nature* 256:495–497 (1975)), the trioma technique, the human B-cell hybridoma technique (Kozbor, et al., *Immunology Today* 4:72 (1983)), and the EBV-hybridoma technique to produce human monoclonal antibodies (Cole, et al., in *Monoclonal Antibodies and Cancer Therapy,* Alan R. Liss, Inc. (1985), pp. 77–96).

Techniques described for the production of single chain antibodies (U.S. Pat. No. 4,946,778) can be adapted to produce single chain antibodies to immunogenic polypeptide products of this invention. Also, transgenic mice may be used to express humanized antibodies to immunogenic polypeptide products of this invention.

The antibodies of the present invention may be prepared by any of a variety of methods. For example, cells expressing the Ckβ-6 protein or an antigenic fragment thereof can be administered to an animal in order to induce the production of sera containing polyclonal antibodies. In a preferred method, a preparation of Ckβ-6 protein is prepared and purified to render it substantially free of natural contaminants. Such a preparation is then introduced into an animal in order to produce polyclonal antisera of greater specific activity.

In the most preferred method, the antibodies of the present invention are monoclonal antibodies (or Ckβ-6 protein binding fragments thereof). Such monoclonal antibodies can be prepared using hybridoma technology (Kohler, et al., *Nature* 256:495 (1975); Kohler, et al., *Eur. J. Immunol.* 6:511 (1976); Kohler, et al., *Eur. J Immunol.* 6:292 (1976); Hammerling, et al., in *Monoclonal Antibodies and T-Cell Hybridomas,* Elsevier, N.Y., (1981), pp. 563–681). In general, such procedures involve immunizing an animal (preferably a mouse) with an Ckβ-6 protein antigen or, more preferably, with an Ckβ-6 protein-expressing cell. Suitable cells can be recognized by their capacity to bind anti-Ckβ-6 protein antibody. Such cells may be cultured in any suitable tissue culture medium; however, it is preferable to culture cells in Earle's modified Eagle's medium supplemented with 10% fetal bovine serum (inactivated at about 56° C.), and supplemented with about 10 g/l of nonessential amino acids, about 1,000 U/ml of penicillin, and about 100 g/ml of streptomycin. The splenocytes of such mice are extracted and fused with a suitable myeloma cell line. Any suitable myeloma cell line may be employed in accordance with the present invention; however, it is preferable to employ the parent myeloma cell line (SP2O), available from the American Type Culture Collection, Rockville, Md. After fusion, the resulting hybridoma cells are selectively maintained in HAT medium, and then cloned by limiting dilution as described by Wands et al., *Gastroenterology* 80:225–232 (1981). The hybridoma cells obtained through such a selection are then assayed to identify clones which secrete antibodies capable of binding the Ckβ-6 protein antigen.

Alternatively, additional antibodies capable of binding to the Ckβ-6 protein antigen may be produced in a two-step procedure through the use of anti-idiotypic antibodies. Such a method makes use of the fact that antibodies are themselves antigens, and that therefore, it is possible to obtain an antibody which binds to a second antibody. In accordance with this method, Ckβ-6-protein specific antibodies are used to immunize an animal, preferably a mouse. The splenocytes of such an animal are then used to produce hybridoma cells, and the hybridoma cells are screened to identify clones which produce an antibody whose ability to bind to the Ckβ-6 protein-specific antibody can be blocked by the Ckβ-6 protein antigen. Such antibodies comprise anti-idiotypic antibodies to the Ckβ-6 protein-specific antibody and can be used to immunize an animal to induce formation of further Ckβ-6 protein-specific antibodies.

It will be appreciated that Fab and F(ab')2 and other fragments of the antibodies of the present invention may be used according to the methods disclosed herein. Such fragments are typically produced by proteolytic cleavage, using enzymes such as papain (to produce Fab fragments) or pepsin (to produce F(ab')2 fragments). Alternatively, Ckβ-6 protein-binding fragments can be produced through the application of recombinant DNA technology or through synthetic chemistry.

It may be preferable to use "humanized" chimeric monoclonal antibodies. Such antibodies can be produced using genetic constructs derived from hybridoma cells producing the monoclonal antibodies described above. Methods for producing chimeric antibodies are known in the art. See, for review, Morrison, *Science* 229:1202 (1985); Oi, et al., *BioTechniques* 4:214 (1986); Cabilly, et al., U.S. Pat. No. 4,816,567; Taniguchi, et al., EP 171496; Morrison, et al., EP 173494; Neuberger, et al., WO 8601533; Robinson, et al., WO 8702671; Boulianne, et al., *Nature* 312:643 (1984); Neuberger, et al., *Nature* 314:268 (1985).

Further suitable labels for the Ckβ-6 protein-specific antibodies of the present invention are provided below. Examples of suitable enzyme labels include malate dehydrogenase, staphylococcal nuclease, delta-5-steroid isomerase, yeast-alcohol dehydrogenase, alpha-glycerol phosphate dehydrogenase, triose phosphate isomerase, peroxidase, alkaline phosphatase, asparaginase, glucose oxidase, beta-galactosidase, ribonuclease, urease, catalase, glucose-6-phosphate dehydrogenase, glucoamylase, and acetylcholine esterase.

Examples of suitable radioisotopic labels include $^{3}H$, $^{111}In$, $^{125}I$, $^{131}I$, $^{32}P$, $^{35}S$, $^{14}C$, $^{51}Cr$, $^{57}To$, $^{58}Co$, $^{59}Fe$, $^{75}Se$, $^{152}Eu$, $^{90}Y$, $^{67}Cu$, $^{217}Ci$, $^{211}At$, $^{212}Pb$, $^{47}Sc$, $^{109}Pd$, etc. $^{111}In$ is a preferred isotope where in vivo imaging is used since its avoids the problem of dehalogenation of the $^{125}I$ or $^{131}I$-labeled monoclonal antibody by the liver. In addition, this radionucleotide has a more favorable gamma emission energy for imaging (Perkins, et al., *Eur. J. Nucl. Med.* 10:296–301 (1985); Carasquillo, et al., *J. Nucl. Med.* 28:281–287 (1987)).

Examples of suitable non-radioactive isotopic labels include $^{157}Gd$, $^{55}Mn$, $^{162}Dy$, $^{52}Tr$, and $^{56}Fe$.

Examples of suitable fluorescent labels include an $^{152}Eu$ label, a fluorescein label, an isothiocyanate label, a rhodamine label, a phycoerythrin label, a phycocyanin label, an allophycocyanin label, an o-phthaldehyde label, and a fluorescamine label.

Examples of suitable toxin labels include diphtheria toxin, ricin, and cholera toxin.

Examples of chemiluminescent labels include a luminal label, an isoluminal label, an aromatic acridinium ester label, an imidazole label, an acridinium salt label, an oxalate ester label, a luciferin label, a luciferase label, and an aequorin label.

Examples of nuclear magnetic resonance contrasting agents include heavy metal nuclei such as Gd, Mn, and iron.

Typical techniques for binding the above-described labels to antibodies are provided by Kennedy, et al., *Clin. Chim. Acta* 70:1–31 (1976), and Schurs, et al., *Clin Chim. Acta* 81:1–40 (1977). Coupling techniques mentioned in the latter are the glutaraldehyde method, the periodate method, the dimaleimide method, the m-maleimidobenzyl-N-hydroxysuccinimide ester method, all of which methods are incorporated by reference herein.

The present invention will be further described with reference to the following examples; however, it is to be understood that the present invention is not limited to such examples. All parts or amounts, unless otherwise specified, are by weight.

In order to facilitate understanding of the following examples certain frequently occurring methods and/or terms will be described.

"Plasmids" are designated by a lower case p preceded and/or followed by capital letters and/or numbers. The starting plasmids herein are either commercially available, publicly available on an unrestricted basis, or can be constructed from available plasmids in accord with published procedures. In addition, equivalent plasmids to those described are known in the art and will be apparent to the ordinarily skilled artisan.

"Digestion" of DNA refers to catalytic cleavage of the DNA with a restriction enzyme that acts only at certain sequences in the DNA. The various restriction enzymes used herein are commercially available and their reaction conditions, cofactors and other requirements were used as would be known to the ordinarily skilled artisan. For analytical purposes, typically 1 mg of plasmid or DNA fragment is used with about 2 units of enzyme in about 20 ml of buffer solution. For the purpose of isolating DNA fragments for plasmid construction, typically 5 to 50 mg of DNA are digested with 20 to 250 units of enzyme in a larger volume. Appropriate buffers and substrate amounts for particular restriction enzymes are specified by the manufacturer. Incubation times of about 1 hour at 37° C. are ordinarily used, but may vary in accordance with the supplier's instructions. After digestion the reaction is electrophoresed directly on a polyacrylamide gel to isolate the desired fragment.

Size separation of the cleaved fragments is performed using 8 percent polyacrylamide gel described by Goeddel, D. et al., *Nucleic Acids Res.* 8:4057 (1980).

"Oligonucleotides" refers to either a single stranded polydeoxynucleotide or two complementary polydeoxynucleotide strands which may be chemically synthesized. Such synthetic oligonucleotides have no 5' phosphate and thus will not ligate to another oligonucleotide without adding a phosphate with an ATP in the presence of a kinase. A synthetic oligonucleotide will ligate to a fragment that has not been dephosphorylated.

"Ligation" refers to the process of forming phosphodiester bonds between two double stranded nucleic acid fragments (Maniatis, T., et al., Id., p. 146). Unless otherwise provided, ligation may be accomplished using known buffers and conditions with 10 units to T4 DNA ligase ("ligase") per 0.5 mg of approximately equimolar amounts of the DNA fragments to be ligated.

Unless otherwise stated, transformation was performed as described in the method of Graham, F. and Van der Eb, A., *Virology* 52:456–457 (1973).

EXAMPLE 1

Bacterial Expression and Purification of Ckβ-6

The DNA sequence encoding for Ckβ-6, ATCC # 75703, is initially amplified using PCR oligonucleotide primers corresponding to the 5' and 3' sequences of the processed Ckβ-6 protein (minus the signal peptide sequence) and the vector sequences 3' to the Ckβ-6 gene. Additional nucleotides corresponding to Ckβ-6 were added to the 5' and 3' sequences respectively. The 5' oligonucleotide primer has the sequence 5' TCAGGATCCCCTACGGGCTCGTGGTC 3' (SEQ ID NO:3) contains a Bam H1 restriction enzyme site followed by 18 nucleotides of Ckβ-6 coding sequence starting from the presumed terminal amino acid of the processed protein codon. The 3' sequence 3' CGCTCTA-GAGTAAAACGACGGCCAGT 5' (SEQ ID NO:4) contains complementary sequences to the XbaI site and to a pBluescript SK-vector sequence located 3' to the Ckβ-6 DNA insert. The restriction enzyme sites correspond to the restriction enzyme sites on the bacterial expression vector pQE-9. (Qiagen, Inc. 9259 Eton Avenue, Chatsworth, Calif., 91311). pQE-9 encodes antibiotic resistance (Amp'), a bacterial origin of replication (ori), an IPTG-regulatable promoter operator (P/O), a ribosome binding site (RBS), a 6-His tag and restriction enzyme sites. pQE-9 was then digested with Bam H1 and Xba I. The amplified sequences were ligated into pQE-9 and were inserted in frame with the sequence encoding for the histidine tag and the RBS. The ligation mixture was then used to transform *E. coli* strain m15/rep4 available from Qiagen under the trademark M15/rep 4 by the procedure described in Sambrook, J. et al, *Molecular Cloning: A Laboratory Manual,* Cold Spring Laboratory Press (1989). M15/rep4 contains multiple copies of the plasmid pREP4, which expresses the lacI repressor and also confers kanamycin resistance (Kan'). Transformants are identified by their ability to grow on LB plates and ampicillin/kanamycin resistant colonies were selected. Plasmid DNA was isolated and confirmed by restriction analysis.

Clones containing the desired constructs were grown overnight (O/N) in liquid culture in LB media supplemented with both Amp (100 µg/ml) and Kan (25 µg/ml). The O/N culture is used to inoculate a large culture at a ratio of 1:100 to 1:250. The cells were grown to an optical density 600 (O.D.$^{600}$) of between 0.4 and 0.6. IPTG ("Isopropyl-B-D-thiogalacto pyranoside") was then added to a final concentration of 1 mM. IPTG induces by inactivating the lacI repressor, clearing the P/O leading to increased gene expression. Cells were grown an extra 3 to 4 hours. Cells were then harvested by centrifugation. The cell pellet was solubilized in the chaotropic agent 6 M Guanidine HCl. After clarification, solubilized Ckβ-6 was purified from this solution by chromatography on a Nickel-Chelate column under conditions that allow for tight binding by proteins containing the 6-His tag. Hochuli, E. et al., *J. Chromatography* 411:177–184 (1984). Ckβ-6 (95% pure) was eluted from the column in 6 M guanidine HCl pH 5.0 and for the purpose of renaturation adjusted to 3 M guanidine HCl, 100 mM sodium phosphate, 10 mM glutathione (reduced) and 2 mM glutathione (oxidized). After incubation in this solution for 12 hours the protein was dialyzed to 10 mM sodium phosphate.

The following preferred alternative method may be used to purify Ckβ-6 expressed in *E coli* when it is present in the form of inclusion bodies. Unless otherwise specified, all of the following steps are conducted at 4–10° C.

Upon completion of the production phase of the *E. coli* fermentation, the cell culture is cooled to 4–10° C. and the cells are harvested by continuous centrifugation at 15,000 rpm (Heraeus Sepatech). On the basis of the expected yield of protein per unit weight of cell paste and the amount of purified protein required, an appropriate amount of cell paste, by weight, is suspended in a buffer solution containing 100 mM Tris, 50 mM EDTA, pH 7.4. The cells are dispersed to a homogeneous suspension using a high shear mixer.

The cells ware then lysed by passing the solution through a microfluidizer (Microfuidics, Corp. or APV Gaulin, Inc.) twice at 4000–6000 psi. The homogenate is then mixed with NaCl solution to a final concentration of 0.5 M NaCl, followed by centrifugation at 7000×g for 15 min. The resultant pellet is washed again using 0.5M NaCl, 100 mM Tris, 50 mM EDTA, pH 7.4.

The resulting washed inclusion bodies are solubilized with 1.5 M guanidine hydrochloride (GuHCl) for 2–4 hours. After 7000×g centrifugation for 15 min., the pellet is discarded and the Ckβ-6 polypeptide-containing supernatant is incubated at 4° C. overnight to allow further GuHCl extraction.

Following high speed centrifugation (30,000×g) to remove insoluble particles, the GuHCl solubilized protein is refolded by quickly mixing the GuHCl extract with 20 volumes of buffer containing 50 mM sodium, pH 4.5, 150 mM NaCl, 2 mM EDTA by vigorous stirring. The refolded diluted protein solution is kept at 4° C. without mixing for 12 hours prior to further purification steps. To clarify the refolded Ckβ-6 polypeptide solution, a previously prepared tangential filtration unit equipped with 0.16 µlm membrane filter with appropriate surface area (e.g., Filtron), equilibrated with 40 mM sodium acetate, pH 6.0 is employed. The filtered sample is loaded onto a cation exchange resin (e.g., Poros HS-50, Perseptive Biosystems). The column is washed with 40 mM sodium acetate, pH 6.0 and eluted with 250 mM, 500 mM, 1000 mM, and 1500 mM NaCl in the same buffer, in a stepwise manner. The absorbance at 280 mm of the effluent is continuously monitored. Fractions are collected and further analyzed by SDS-PAGE.

Fractions containing the Ckβ-6 polypeptide are then pooled and mixed with 4 volumes of water. The diluted sample is then loaded onto a previously prepared set of tandem columns of strong anion (Poros HQ-50, Perseptive Biosystems) and weak anion (Poros CM-20, Perseptive Biosystems) exchange resins. The columns are equilibrated with 40 mM sodium acetate, pH 6.0. Both columns are washed with 40 mM sodium acetate, pH 6.0, 200 mM NaCl. The CM-20 column is then eluted using a 10 column volume linear gradient ranging from 0.2 M NaCl, 50 mM sodium acetate, pH 6.0 to 1.0 M NaCl, 50 mM sodium acetate, pH 6.5. Fractions are collected under constant $A_{280}$ monitoring of the effluent. Fractions containing the Ckβ-6 polypeptide (determined, for instance, by 16% SDS-PAGE) are then pooled.

The resultant Ckβ-6 polypeptide exhibits greater than 95% purity after the above refolding and purification steps. No major contaminant bands are observed from Commassie blue stained 16% SDS-PAGE gel when 5 µg of purified protein is loaded. The purified protein is also tested for endotoxin/LPS contamination, and typically the LPS content is less than 0.1 ng/ml according to LAL assays.

EXAMPLE 2

Expression Pattern of Ckβ-6 in Human Cells

Northern blot analysis was carried out to examine the levels of expression of Ckβ-6 in human cells. Total cellular RNA samples were isolated with RNAzol' B system (Biotecx Laboratories, Inc. 6023 South Loop East, Houston, Tex. 77033). About 10 µg of total RNA isolated from each human tissue specified was separated on 1% agarose gel and blotted onto a nylon filter. (Sambrook, Fritsch, and Maniatis, *Molecular Cloning,* Cold Spring Harbor Press (1989)). The labeling reaction was done according to the Stratagene Prime-It kit with 50 ng DNA fragment. The labeled DNA was purified with a Select-G-50 column. (5 Prime-3 Prime, Inc. 5603 Arapahoe Road, Boulder, Colo. 80303). The filter was then hybridized with radioactive labeled full length Ckβ-6 gene at 1,000,000 cpm/ml in 0.5 M NaPO$_4$, pH 7.4 and 7% SDS overnight at 65° C. After wash twice at room temperature and twice at 60° C. with 0.5×SSC, 0.1% SDS, the filter was then exposed at −70° C. overnight with an intensifying screen. The message RNA for Ckβ-6 is abundant in activated and unactivated T cells, monocytes and T cell lines.

EXAMPLE 3

Cloning and Expression of Ckβ-6 Using the Baculovirus Expression System

The DNA sequence encoding the full length Ckβ-6 protein, ATCC # 75703, is amplified using PCR oligonucleotide primers corresponding to the 5' and 3' sequences of the gene:

The amplified sequences were isolated from a 1% agarose gel using a commercially available kit ("Geneclean," BIO 101 Inc., La Jolla, Calif.). The fragment was then digested with restriction endonucleases corresponding to the amplified products and then purified again on a 1% agarose gel. This fragment is designated F2.

The vector pRG1 (modification of pVL941 vector, discussed below) is used for the expression of the Ckβ-6 protein using the baculovirus expression system (for review see: Summers, M. D. and Smith, G. E. *A manual of methods for baculovirus vectors and insect cell culture procedures,* Texas Agricultural Experimental Station Bulletin No. 1555 (1987)). This expression vector contains the strong polyhedrin promoter of the Autographa californica nuclear polyhedrosis virus (AcMNPV) followed by the recognition sites for the restriction endonucleases used to digest the amplified products. The polyadenylation site of the simian virus (SV) 40 is used for efficient polyadenylation. For an easy selection of recombinant virus the beta-galactosidase gene from *E. coli* is inserted in the same orientation as the polyhedrin promoter followed by the polyadenylation signal of the polyhedrin gene. The polyhedrin sequences are flanked at both sides by viral sequences for the cell-mediated homologous recombination of co-transfected wild-type viral DNA. Many other baculovirus vectors could be used in place of pRG1 such as pAc373, pVL941 and pAcIM1 (Luckow, V. A. and Summers, M. D., *Virology,* 170:31–39).

The plasmid is digested with the restriction enzymes and dephosphorylated using calf intestinal phosphatase by procedures known in the art. The DNA was then isolated from a 1% agarose gel using the commercially available kit ("Geneclean" BIO 101 Inc., La Jolla, Calif.). This vector DNA is designated V2.

Fragment F2 and the dephosphorylated plasmid V2 are ligated with T4 DNA ligase. *E. coli* HB101 cells are then transformed and bacteria identified that contained the plasmid (pBacCkβ-6) with the Ckβ-6 gene using the enzymes. The sequence of the cloned fragment is confirmed by DNA sequencing.

5 mg of the plasmid pBacCkβ-6 is co-transfected with 1.0 mg of a commercially available linearized baculovirus ("BaculoGold baculovirus DNA", Pharmingen, San Diego, Calif.) using the lipofection method (Felgner, et al., *Proc. Natl. Acad. Sci.* (*USA*) 84:7413–7417 (1987)).

1 mg of BaculoGold virus DNA and 5 mg of the plasmid pBacCkβ-6 are mixed in a sterile well of a microtiter plate containing 50 ml of serum free Grace's medium (Life Technologies Inc., Gaithersburg, Md.). Afterwards 10 ml Lipofectin plus 90 ml Grace's medium are added, mixed and incubated for 15 minutes at room temperature. Then the transfection mixture is added drop-wise to the Sf9 insect cells (ATCC CRL 1711) seeded in a 35 mm tissue culture plate with 1 ml Grace's medium without serum. The plate is rocked back and forth to mix the newly added solution. The plate is then incubated for 5 hours at 27° C. After 5 hours the transfection solution is removed from the plate and 1 ml of Grace's insect medium supplemented with 10% fetal calf serum is added. The plate was put back into an incubator and cultivation continued at 27° C. for four days.

After four days the supernatant is collected and a plaque assay performed similar as described by Summers and Smith (supra). As a modification an agarose gel with "Blue Gal" (Life Technologies Inc., Gaithersburg) is used which allows an easy isolation of blue stained plaques. (A detailed description of a "plaque assay" can also be found in the user's guide for insect cell culture and baculovirology distributed by Life Technologies Inc., Gaithersburg, page 9–10).

Four days after the serial dilution, the virus is added to the cells, blue stained plaques are picked with the tip of an Eppendorf pipette. The agar containing the recombinant viruses is then resuspended in an Eppendorf tube containing 200 ml of Grace's medium. The agar is removed by a brief centrifugation and the supernatant containing the recombinant baculovirus is used to infect Sf9 cells seeded in 35 mm dishes. Four days later the supernatants of these culture dishes are harvested and then stored at 4° C.

Sf9 cells are grown in Grace's medium supplemented with 10% heat-inactivated FBS. The cells are infected with the recombinant baculovirus V-Ckβ-6 at a multiplicity of infection (MOI) of 2. Six hours later the medium is removed and replaced with SF900 II medium minus methionine and cysteine (Life Technologies Inc., Gaithersburg). 42 hours later 5 mCi of $^{35}$S-methionine and 5 mCi $^{35}$S cysteine (Amersham) are added. The cells are further incubated for 16 hours before they are harvested by centrifugation and the labelled proteins visualized by SDS-PAGE and autoradiography.

Ckβ-6 produced essentially according to the above procedure was purified from the serum free insect cell supernatent by cation exchange, heparin affinity, and size exclusion chromatography (poros 50 HS, poros 20 HE1, Perseptive Biosystem, and Sephacryl S200 HR; Pharmacia) in the presence of protease inhibitors (20 mg/ml Pefabloc SC; Boehringer Mannheim, 1 mg/ml leupeptin, 1 mg/ml E64, and 1 mM EDTA).

Analysis of the purified protein was performed by laser desorption mass spectrometry (matrix-associated laser desportion ionization-time of flight) and by Edman degradation after partial proteolysis with endoproteinase GluC (Boehringer Mannheim).

EXAMPLE 4

Expression via Gene Therapy

Fibroblasts are obtained from a subject by skin biopsy. The resulting tissue is placed in tissue-culture medium and separated into small pieces. Small chunks of the tissue are placed on a wet surface of a tissue culture flask, approximately ten pieces are placed in each flask. The flask is turned upside down, closed tight and left at room temperature over night. After 24 hours at room temperature, the flask is inverted and the chunks of tissue remain fixed to the bottom of the flask and fresh media (e.g., Ham's F12 media, with 10% FBS, penicillin and streptomycin, is added. This is then incubated at 37° C. for approximately one week. At this time, fresh media is added and subsequently changed every several days. After an additional two weeks in culture, a monolayer of fibroblasts emerge. The monolayer is trypsinized and scaled into larger flasks.

pMV-7 (Kirschmeier, P. T., et al, *DNA* 7:219–25 (1988)) flanked by the long terminal repeats of the Moloney murine sarcoma virus, is digested with EcoRI and HindIII and subsequently treated with calf intestinal phosphatase. The linear vector is fractionated on agarose gel and purified, using glass beads.

The cDNA encoding a polypeptide of the present invention is amplified using PCR primers which correspond to the 5' and 3' end sequences respectively. The 5' primer contains an EcoRI site and the 3' primer further includes a HindIII site. Equal quantities of the Moloney murine sarcoma virus linear backbone and the amplified EcoRI and HindIII fragment are added together, in the presence of T4 DNA ligase. The resulting mixture is maintained under conditions appropriate for ligation of the two fragments. The ligation mixture is used to transform bacteria HB101, which are then plated onto agar-containing kanamycin for the purpose of confirming that the vector had the gene of interest properly inserted.

The amphotropic pA317 or GP+am12 packaging cells are grown in tissue culture to confluent density in Dulbecco's Modified Eagles Medium (DMEM) with 10% calf serum (CS), penicillin and streptomycin. The MSV vector containing the gene is then added to the media and the packaging cells are transduced with the vector. The packaging cells now produce infectious viral particles containing the gene (the packaging cells are now referred to as producer cells).

Fresh media is added to the transduced producer cells, and subsequently, the media is harvested from a 10 cm plate of confluent producer cells. The spent media, containing the infectious viral particles, is filtered through a millipore filter to remove detached producer cells and this media is then used to infect fibroblast cells. Media is removed from a sub-confluent plate of fibroblasts and quickly replaced with the media from the producer cells. This media is removed and replaced with fresh media. If the titer of virus is high, then virtually all fibroblasts will be infected and no selection is required. If the titer is very low, then it is necessary to use a retroviral vector that has a selectable marker, such as neo or his.

The engineered fibroblasts are then injected into the host, either alone or after having been grown to confluence on cytodex 3 microcarrier beads. The fibroblasts now produce the protein product.

EXAMPLE 5

Primary Indication of Ckβ-6 as a Mobilizer of Marrow Stem Cells (Bone Marrow Rescue)

The effect of Ckβ-6 on the distribution of the primitive hematopojetic progenitors in peripheral blood, spleen, and bone marrow was studied in 16 week old C57B 1/6 mice (about 20 g). In the first experiment, 3 mice were injected i.p. daily with 1 mg/kg Ckβ-6 or saline for 2 days and analyzed 24 hours after the last injection. In the second experiment, another 3 mice were injected i.p. daily with 1 mg/kg Ckβ-6 or saline for 4 days and analyzed 24 hours after the last injection. In both the experiments, the blood of each animal was collected by cardiac puncture and the mice were sacrificed to obtain bone marrow and spleens. The indicated number of cells from each of the tissues was then plated in duplicates in agar-containing medium in the presence of 5 ng/ml IL-3, 50 ng/ml SCF, 5 ng/ml M-CSF and 10 ng/ml IL-1a and incubated for 14 days. In the 2 experiments, the data from the different animals were pooled and expressed as mean ±S. D. The results of both experiments shows that Ckβ-6 mobilize stem cells from bone marrow to peripheral blood (Tables 2 and 3). In the first experiment, after 2 days of treatment with CKβ-6, the frequency of HPP-CFC, LPP-CFC and immature cells in peripheral blood increased significantly over the controls. No changes were observed in the spleen and a significant decrement of IIPP-CFC was observed in the bone marrow (Table 2). In the second experiment, after 4 days of treatment with Ckβ-6, the same significant increment of HPP-CFC, LPP-CFC and immature cells frequency was observed in peripheral blood. A significant increment of immature cells frequency was observed in the spleen and a significant decrement of HPP-CFC and LPP-CFC was observed in the bone marrow Table 3. In particular it is important to note the presence of immature hematopoietic cells in the peripheral blood after the injection of Ckβ-6. The effect was observed in the animals treated with Ckβ-6 was not due to toxicity as the FAC Scan profile of the leukocyte composition of both the control and the mice treated with Ckβ-6 is identical Table 4.

EXAMPLE 6

Ckβ-6 as a Myeloprotectant Against Cytosine Arabinoside

Figure 3:
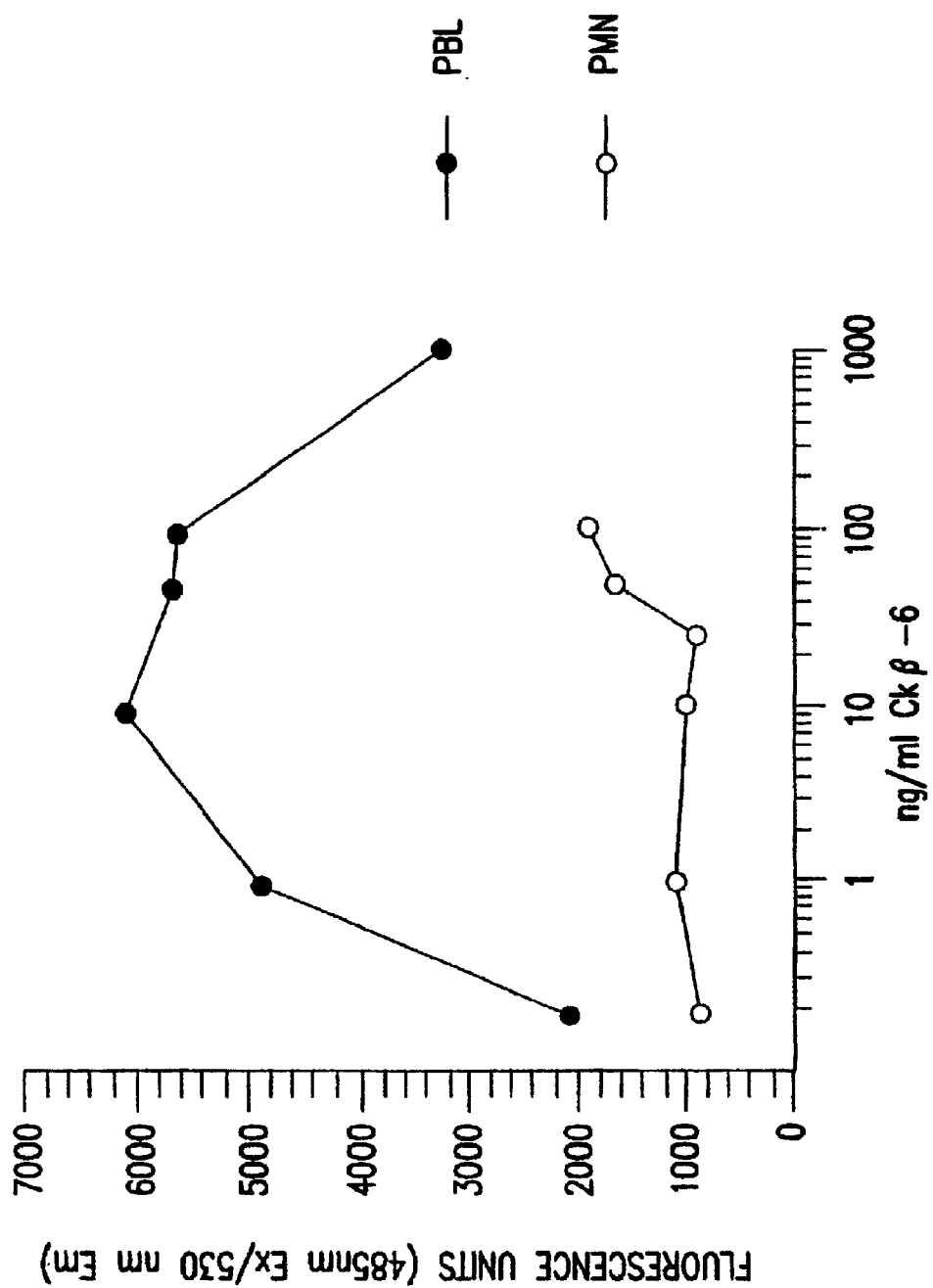
FIG. 3 illustrates the chemotactic activity of the polypeptide of the present invention on neutrophils (PMN) and peripheral blood mononuclear cells (PBMC). Neutrophils and peripheral blood mononuclear cells were isolated from peripheral blood, loaded with calcein-AM and used for chemocaxis in a 96 well, single-use Neuroprobe chemotactic chamber. After 90 minutes incubation with Ckβ-6, the chamber was dismounted, the filter air-dried and the number of cells which migrated through the membrane quantitated in a cytofluor II.
Figure 4A:
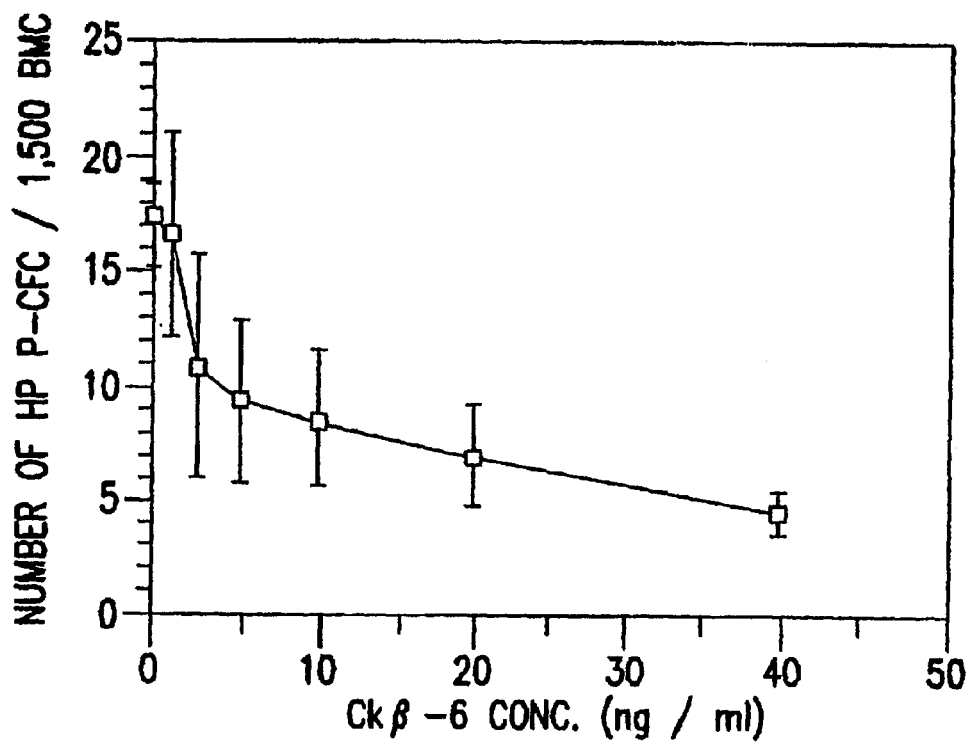
FIG. 4 illustrates that Ckβ-6 inhibits the growth and differentiation of high proliferative potential colony forming cells (HPP-CFC) (A) and is not effective on low proliferative potential colony forming cells (LPP-CFC) (B). In these experiments, 1,500 cells from low density, non-adherent bone marrow cells were plated in agar-medium supplemented with 5 ng/ml mouse IL-3, 100 ng/ml mouse SCF, 10 ng/ml mouse IL-1a, 5 ng/ml human M-CSF, and with or without the indicated concentrations of Ckβ-6. Colonies were scored after 14 days of incubation. Three experiments were performed. The results are presented as mean number of colonies ±SD. An irrelevant protein had no effects.
Figure 4B:
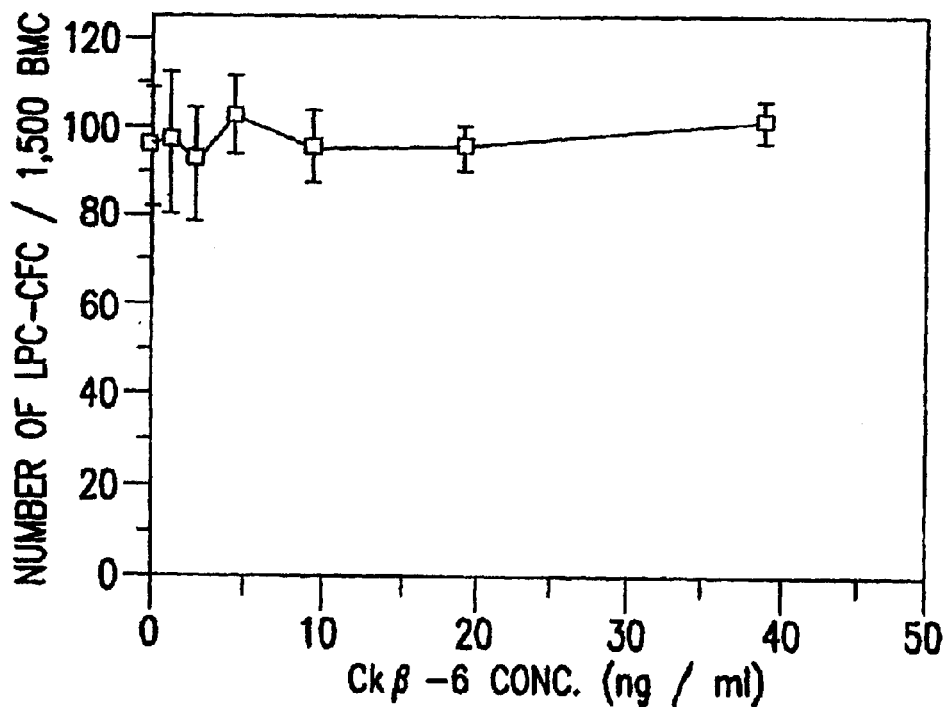

In this experiment, Lin-cells were plated ($1 \times 10^5$ cell/ml) in a growth medium that was supplemented with 5 ng/ml mouse IL-3, 50 ng/ml mouse SCF (column 1); IL-3, SCF and 100 ng/ml Ckβ-6 (column 2); or IL-3, SCF and 100 ng/ml of the irrelevant protein HG200-3-B (column 3). AFter 48 hours of incubation, one set of the above cultures received 50 mg/ml Ara-C and the incubation was then continued for an additional 24 hours. Cells were then harvested, washed three times with HBSS to remove the drug and the cytokines, and assayed for the presence of HPP-CFC and LPP-CFC as described in the legend to FIG. 4. The results are expressed as mean % of protection (±SD). The % of protection was calculated as follows: Percent protection is expressed as number of colonies found in cultures incubated in the presence of Ara-C divided by the number of colonies found in cultures incubated without Ara-C×100. Data from one out of 3 experiments are shown in FIG. 6. All the samples were tested in duplicates.

EXAMPLE 7

Ckβ-6 as a Myeloprotectant Against 5-Fluorouracil

Figure 5A:
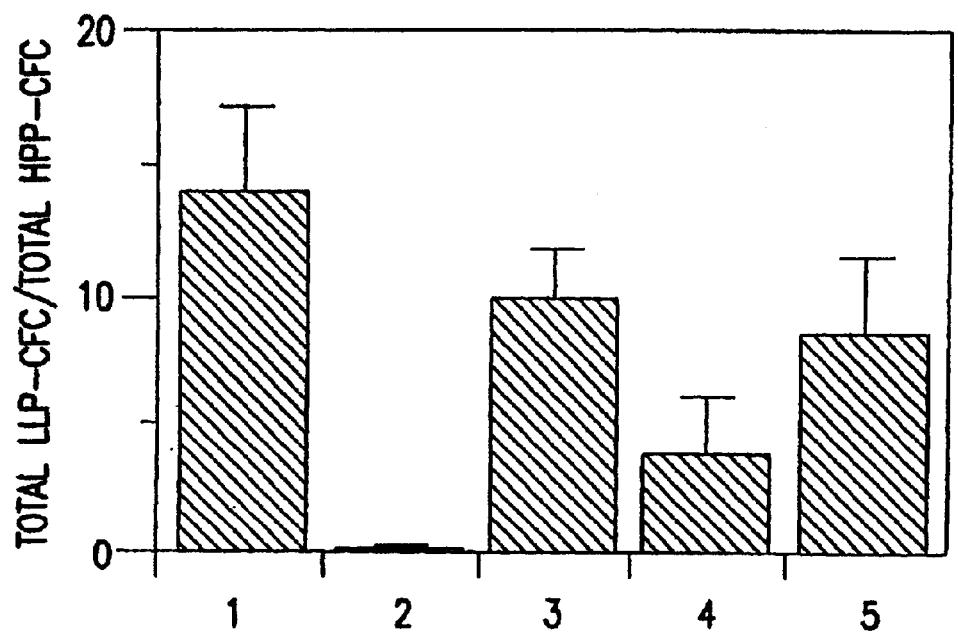
FIG. 5 shows the effect of Ckβ-6 on bone marrow cells which were enriched in the primitive Lin-cells by removing committed precursor cells (antibodies anti-CD11b, CD4, CD8, CD45R and Gr.-1). The panel A shows ratios ±SD of LPP-CFC/HPP-CFC in the bone marrow cells (column 1) or Lin-cells (column 2) plated in agar-medium with 5 ng/ml IL-3, 100 ng/ml SCF, 10 ng/ml IL-1a, 5 ng/ml M-CSF.
Figure 5B:
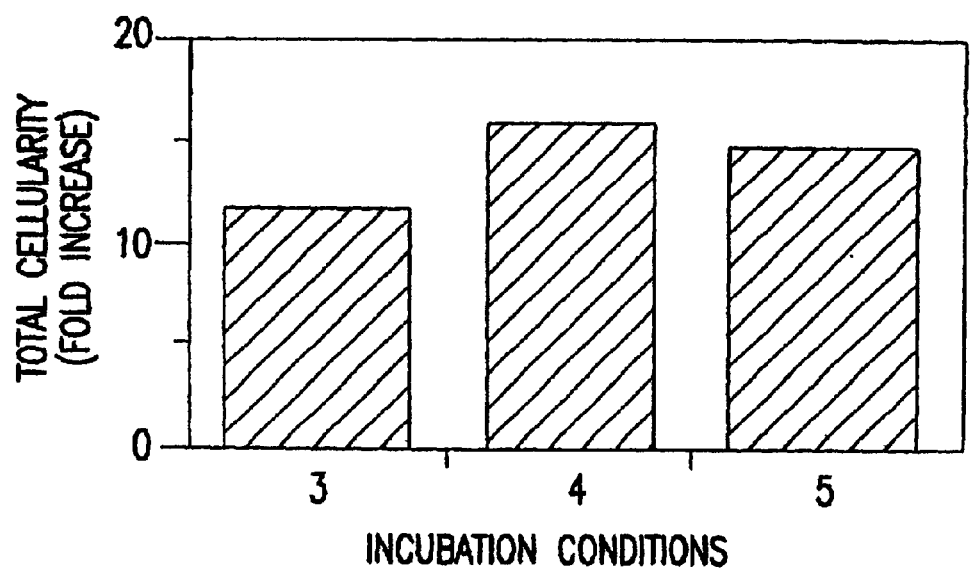

Mononuclear population of mouse bone marrow cells was depleted of lineage-committed cells by negative selection using a panel monoclonal antibodies directed against cell surface antigens. The resulting population of cells (Lin.-cells) were resuspended ($1 \times 10^5$ cells/ml) in a growth medium containing IL-3 (5 ng/ml), SCF (50 ng/l), GM-CSF (5 ng/ml), M-CSF (5 ng/ml) and IL-1a (10 ng/ml) and 1 ml of this cell suspension was dispensed into culture tubes. (1) A set of duplicate cultures received no chemokine; (2) duplicate cultures with Ckβ-6 at 100 ng/ml; and (3) duplicate cultures with an irrelevant protein at 100 ng/ml. All cultures were incubated in a tissue culture incubator for 48 hours, at which point one culture from each set received 5-Fluorouracil at 100 mg/ml and incubation was continued for additional 24 hours. All cultures were then harvested, washed three times with HBSS, and then assayed for the presence of the HPP-CFC & LPP-CFC as described in the legend to FIG. 5. Percent protection is expressed as number of colonies detected in cultures incubated in the presence of 5-FU divided by the number of colonies found in cultures incubated without 5-FU ×100. Data are expressed as Mean ±SD. Two experiments were performed and each assay was in duplicates. See FIG. 7.

EXAMPLE 8

Ckβ-6 Effect on Cortical Neuronal Survival

Sprague-Dawley rats at gestation day 17 were sacrificed and the cortex was removed and the meninges were carefully pealed away from the cortical tissue pieces. Single cell suspensions were prepared and the cells were plated in medium containing 5% horse serum at a density of 20,000 cells/well. After 24 hours the serum containing medium was removed and serum-free medium was added to the cultures. Included in the serum-free cultures was a concentration of Ckβ-6 as shown in FIG. 8. The Ckβ-6 used is an Ckβ-6 polypeptide encoded by the polynucleotide sequence as shown in SEQ ID NO:1 of the application. The medium was changed every other day and Ckβ-6 was added again. The neurons were maintained in culture for 6 days prior to the viability assay.

Cell viability was assessed using the live/dead assay kit from Molecular Probes. This assay is a two-color fluorescence cell viability assay based on the simultaneous determination of live and dead cells. Live cells are distinguished by the presence of ubiquitous intracellular esterase activity, determined by enzymatic conversion of the nearly non-fluorescent cell permeant calcein AM to the intensely fluorescent calcein. The polycationic calcein is well retained by living cells and thus produces an intense uniform green fluorescence in living cells. Thus the emission reading (approximately 530 nm) is a measurement of the total cell number of the cultures. As shown in FIG. 8, the number of live cells increased as the concentration of Ckβ-6 increased.

EXAMPLE 9

Leukocyte Response and Receptor Usage

Monocytes, lymphocytes, and neutrophils were isolated from donor blood buffy coats. Eosinophils and basophils were purified from fresh venous blood of healthy volunteers.

Changes in the cytosolic free $Ca^{2+}$ concentration ($[Ca^{2+}]i$), and enzyme release were monitored in monocytes, eosinophils, lymphocytes and neutrophils loaded with Fura-2 acetoxymethyl ester (0.2 nmol per $10^6$ cells) by incubation for 20 min. at 37° C. in medium containing 136 mM NaCl, 4.8 mM Kcl, 1 mM $CaCl_2$, 5 mM glucose, and 20 mM Hepes, pH 7.4 and 1 to 1,000 nM Ckβ-6 in comparison with IL-8, MCP-1 and MCP-3. Loaded cells were washed and resuspended in the same medium ($10^6$ cells/ml) and $[Ca^{2+}]i$-related fluorescence changes were recorded. Receptor desensitization was tested by monitoring $[Ca^{2+}]i$ changes after sequential chemokine stimulation.

In three independent experiments no effects of Ckβ-6 were observed on neutrophils, monocytes and T-lymphocytes, but considerable activity was found on eosinophils. In these cells, cross-desensitization between Ckβ-6 on the one hand and eotaxin, MCP-3, RANTES or MIP-1α on the other was studied by monitoring $[Ca^{2+}]i$ changes. As shown in FIG. 9, stimulation of eosinophils with Ckβ-6 abrogated the response to eotaxin, attenuated the responses to MCP-3 and RANTES, but did not appreciably affect the response to MIP-1α. In agreement with these results the $[Ca^{2+}]i$ rise induced by Ckβ-6 was abrogated by prior stimulation with eotaxin, decreased by stimulation with RANTES or MCP-3, but not affected by MIP-1α. The complete cross-desensitization with eotaxin suggests that Ckβ-6 also acts via CCR3.

EXAMPLE 10

In-vitro Chemotaxis

Chemotaxis was assessed in 48-well chambers (Neuro Probe, Cabin John, Md.) using polyvinylpyrrolidone-free polycarbonate membranes (Nucleopore) with 5-μm pores for eosinophils and basophils, and 3-μm pores for lymphocytes. RPMI 1640 supplemented with 20 mM Hepes, pH 7.4, and 1% pasteurized plasmaprotein solution (the Central Laboratory of the Swiss Red Cross) was used for the cell suspensions and chemokine dilutions. After an incubation of 60 min. at 37° C. in 5% CO2, the membrane was removed, washed on the upper side with PBS, fixed, and stained. All assays were done in triplicate, and the migrated cells were counted in five randomly selected fields at 1,000-fold magnification. Spontaneous migration was determined in the absence of chemoattractant.

Results. In vitro chemotaxis was tested with human blood monocytes, T lymphocytes, eosinophil and basophil leukocytes. No activity was found toward monocytes and lymphocytes, which agrees with the lack of $[Ca^{2+}]i$ changes, but marked migration was obtained with eosinophils and basophils. As shown in FIG. 10, Ckβ-6 is a very effective attractant for both types of cells. When the assay was performed in the presence of anti-CCR3, eosinophil and basophil chemotaxis toward Ckβ-6 was completely prevented.

EXAMPLE 11

Histamine and Leukotriene $C_4$ (LTC4) Release

Basophils (0.1 to $0.3\times10^6$ cells/ml) in 20 mM Hepes, pH 7.4 containing 125 mM glucose and 0.025% BSA were warmed to 37° C., exposed to IL-3 (10 ng/ml) with or without anti-CCR3 (10 μg/ml) and then challenged with a chemokine. After 20 min. the reaction was stopped by placing the tubes on ice and histamine and $LTC_4$ were measured in the supernatant. Histamine release was expressed as percent of the total content of the sample (determined after cell lysis).

$LTC_4$ generation was expressed in nanogram per $10^6$ basophils, as shown in FIG. 11. On IL-3 pretreated basophils from several unselected donors both Ckβ-6 and eotaxin induced similar release of histamine and peptido leukotrines at maximum effective concentrations. The curves relating effect to concentration shown that eotaxin was slightly more potent than Ckβ-6 in particular as inducer of $LTC_4$ release. In both assays, Ckβ-6 was approximately as potent as RANTES and MIP-1α (data not shown). As expected, in consideration of effects on chemotaxis, above, the release responses to Ckβ-6 was markedly inhibited by pretreatment with anti-CCR3.

EXAMPLE 12

In-vivo Activity

Since human eotaxin is active in monkeys and induces the local accumulation of eosinophils after intradermal injection, its effect in rhesus monkey was compared with Ckβ-6.

A male rhesus monkey of 7.5 kg was anesthetized by i.m. injection of 10 mg/kg Ketamine (Ketolar, Parke Davis) and i.v. injection of 15 mg/kg Na Thiopental (Pentotal, Abbott). Chemokines in 100 μl pyrogen-free isotonic saline (100 pmol eotaxin, 100 and 1,000 pmol Ckβ-6) were then injected intradermally on the back and fill skin thickness punch biopsies of 8 mm diameter were taken from the injection sites after 4 h. The biopsies were fixed in formalin, embedded in parafin, and 5 μm sections were prepared. The sections were stained with hematoxylin and eosin, and the infiltrates were evaluated by two independent observers. Eosinophil counting was performed at a magnification of 630× in five randomly selected fields per section next to and including a postcapillary venule of the superficial vascular plexus using a counting grid of 0.19×0.19 mm, and the number of eosinophils per $mm^2$ was calculated.

As shown in FIG. 12, 4 hours after injection of 100 pmol per site both chemokines induced a similar, marked eosinophil infiltration as compared to the vehicle alone, which had no effect. A 50% higher number of infiltrating eosinophils was counted when 1000 pmol Ckβ-6 were applied. The effect was remarkable because the monkey used in this experiment had a low blood eosinophil count (0.7% of total leukocytes).

EXAMPLE 13

Ckβ-6 Agonists and Antagonists

Several deletion Ckβ-6 mutants were constructed and assayed for activity using a [$Ca^{+2}$]i flux assay and a chemotaxis assay. These mutants were constructed based upon a Ckβ-6 nucleotide sequence wherein the codons were optimized for expression in *E. coli*. The constructs were made as follows:

Codon Optimized Construct for Ckβ-6 Expression in *E. coli*

The initial PCR was done using primers 1, 2, 3 and 4 (below) and further amplified with primers 5 and 6 (below). The product was digested with Nde I and Asp I and cloned into pHE4 for *E. coli* expression. (See, FIG. 21). The resulting codon optimized sequence for expression of Ckβ-6 is shown in SEQ ID NO: 6.

```
Primer #1:
5' GAC TCC ATG GTG GTT ATA CCT TCT CCG TGC TGC
ATG TTC TTT GTT AGC AAG CGC ATT CCT GAA AAC CGT GTG
GTC A GCT ACC AGC TGT CCA GCC GC 3'
(SEQ ID NO:7).

Primer #2:
5' GTT TCG GGT CGC CAC AGA ACT GCT GGC CCT TTT
TGG TGG TGA AGA TCA CGC CAG CTT TCA GGC AGG TGC TGC
GGC TGG ACA GCT GGT AGC TGA CCA C 3'
(SEQ ID NO:8).

Primer #3:
5' AAG GGC CAG CAG TTC TGT GGC GAC CCG AAA CAA
GAG TGG GTC CAG CGT TAC ATG AAA AAC CTG GAC GCC AAA
CAG AAG AAA GCT TCC CCT CGT GCC CG 3'
(SEQ ID NO:9)

Primer #4:
5' AGT CAG ATC TTT AGC AGG TGG TTT GGT TGC CCG
GAT AAC GCT GAA CAG GGC CTT TGA CAG CCA CTG CGC GGG
CAC GAG GGG AAG CTT TCT TCT GTT TGG 3'
(SEQ ID NO:10).

Primer #5:
5' GAC GGAT CCC CAT ATG GTG GTT ATA CCT TCT CCG 3'
(SEQ ID NO:11). (NdeI site in bold)

Primer #6:
5' GAC TGG TAC CTT AGC AGG TGG TTT GGT TGC CC 3'
(SEQ ID NO:12). (Asp I site in bold)
```

Using this *E. coli* optimized codon Ckβ-6 construct, the following deletion mutants, which include a methionine at the N-terminus, were generated using the primers listed below:

ΔC1 amino acids 1 to 73 in SEQ ID NO:2
ΔC1ΔN1 amino acids 2 to 73 in SEQ ID NO:2
ΔC1ΔN2 amino acids 3 to 73 in SEQ ID NO:2
ΔC1ΔN3 amino acids 4 to 73 in SEQ ID NO:2
ΔC1ΔN4 amino acids 5 to 73 in SEQ ID NO:2
ΔC1ΔN5 amino acids 6 to 73 in SEQ ID NO:2
ΔC1ΔN6 amino acids 7 to 73 in SEQ ID NO:2

```
ΔC1:
5' primer: 5' GACGGATCCCCATATGGTGGTTATACCTTCTCCG 3'        (SEQ ID NO:11).

3' primer: 5' GACTGGTACCTTATCAACGAGGGGAAGCTTTCTTCT 3'     (SEQ ID NO:13).

ΔC2:
5' primer: 5' GACGGATCCCCATATGGTGGTTATACCTTCTCCG 3'        (SEQ ID NO:11).

3' primer: 5' GACTGGTACCCTATCAAGCCACTGCGCGGGCACGAGG 3'    (SEQ ID NO:14).

ΔC1ΔN1:
5' primer: 5' GACTCATATGGTTATACCTTCTCCGTGCTGCATG 3'       (SEQ ID NO:15).

3' primer: 5' GACTGGTACCTTATCAACGAGGGGAAGCTTTCTTCT 3'     (SEQ ID NO:13).

ΔC1ΔN2:
5' primer: 5' GACTCATATGATACCTTCTCCGTGCTGCATG 3'          (SEQ ID NO:16).

3' primer: 5' GACTGGTACCTTATCAACGAGGGGAAGCTTTCTTCT 3'     (SEQ ID NO:13).

ΔC1ΔN3:
5' primer: 5' GACTCATATGCCTTCTCCGTGCTGCATGTTC 3'          (SEQ ID NO:17).

3' primer: 5' GACTGGTACCTTATCAACGAGGGGAAGCTTTCTTCT 3'     (SEQ ID NO:13).

ΔC1ΔN4:
5' primer: 5' GACTCATATGTCTCCGTGCTGCATGTTCTTTG 3'         (SEQ ID NO:18).

3' primer: 5' GACTGGTACCTTATCAACGAGGGGAAGCTTTCTTCT 3'     (SEQ ID NO:13).

ΔC1ΔN5:
5' primer: 5' GACTCATATGCCGTGCTGCATGTTCTTTG 3'            (SEQ ID NO:19).

3' primer: 5' GACTGGTACCTTATCAACGAGGGGAAGCTTTCTTCT 3'     (SEQ ID NO:13).
```

-continued

ΔC1ΔN6:
5' primer: 5' GACTCATATGTGCTGCATGTTCTTTGTTAG 3'     (SEQ ID NO:20).

3' primer: 5' GACTGGTACCTTATCAACGAGGGGAAGCTTTCTTCT 3'     (SEQ ID NO:13).

Several of these deletion Ckβ-6 mutants were assayed for activity using a [$Ca^{+2}$]i flux assay and a chemotaxis assay.

Calcium Flux Assay

The calcium flux assay was performed using eosinophils essentially as described in Example 9, above. It should be noted that for the protein preparations assayed, HG00603 and HG00605 retained the N-terminal methionine; HG00606, HG00608 and HG00609 did not have the N-terminal methionine; and in HG00604, about 55% of the protein had the N-terminal methionine.

Results

Four of these mutants (ΔC1ΔN1, ΔC1ΔN2, ΔC1ΔN3, ΔC1ΔN5) were used in calcium flux assays with primary Eosinopils. ΔC1ΔN1 (HG00604) and ΔC1ΔN2 (HG00605) showed activities which were very similar to ΔC1 (HG00603) and Eotaxin whereas ΔC1ΔN3 (HG00606) and ΔC1ΔN5 (HG00608) showed no activity in this assay even at 1000 ng/ml (see, FIGS. 14A and 14B).

Figure 15B:
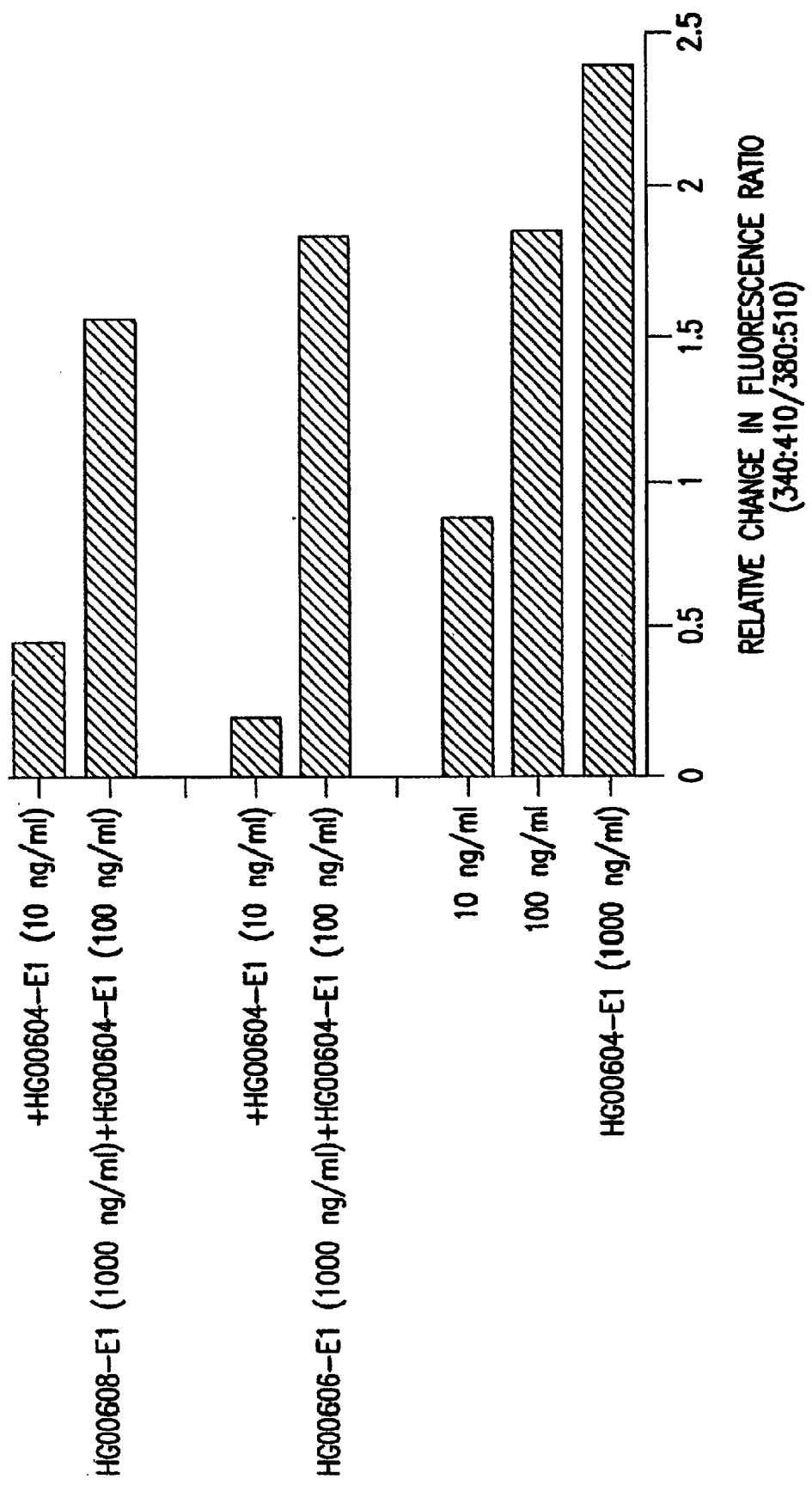

When combined with ΔC1ΔN1 (HG00604), ΔC1ΔN3 (HG00606) was able to inhibit the activity of ΔC1ΔN1 (HG00604) whereas ΔC1ΔN5 (HG00608) was not (see FIGS. 15A and 15B). In addition, when combined with ΔC1ΔN1, Ckβ-10 or Eotaxin, ΔC1ΔN3 (HG00606) was able to inhibit the activity of all three of these chemokines (see FIGS. 16A and 16B). ΔC1ΔN3 (HG00606) is an efficient antagonist of all three of these chemokines due to the fact that these chemokines have all been shown to signal through the same receptor, CCR3.

In Vitro Chemotaxis Assay

Cells were washed and labeled with calcein-AM and distributed into the upper chamber of a 96 well disposable chemotaxis plate (NeuroProbe, Cabin John, Md.) separated by a polycarbonate filter (5–8 μm pore size; PVP free; NeuroProbe, Inc.) Cells were allowed to migrate for 90 minutes (lymphocytes) or 3 hours (eosinophils) and then the number of migrated cells (both attached to the filter as well as in the bottom chamber) were quantitated using a Cytofluor II fluorescence plate reader (PerSeptive Biosystems). Values for the chemotaxis assay are reported as the chemotatic index which refers to the fold induction above background observed with the various factors used. It should be noted that, for the protein preparations assayed, HG00603 and HG00605 retained the N-terminal methionine; HG00606, HG00608 and HG00609 did not retain the N-terminal methionine; and in HG00604, about 55% of the protein retained the N-terminal methionine.

Results

Chemotaxis assays using mutant ΔC1ΔN3 (HG00606) show that this truncated protein is no longer active (FIG. 17). To determine if this protein could serve as an antagonist of eosinophil chemotaxis, experiments were performed with ΔC1 (HG00603), Ckβ-10 or Eotaxin with and without ΔC1ΔN3 (HG00606). ΔC1ΔN3 (HG00606) (1000 ng/ml) was added to both the top and bottom wells of the chemotaxis chambers with increasing amounts of the other chemokines in the bottom well. As shown in FIGS. 18A and B, ΔC1ΔN3 (HG00606) was able to inhibit the chemotaxis of eosinophils directed by ΔC1 (HG00603). In addition, ΔC1ΔN3 (HG00606) was able to inhibit both Eotaxin (FIGS. 19A and B) and Ckβ-10 (FIGS. 20A and B) driven chemotaxis. Since all of these chemokines mediate their effects on eosinophils via the CCR3 receptor, ΔC1ΔN3 (HG00606) represents a dominant antagonist which is capable of inhibiting the signalling through this receptor regardless of the chemokine mediating this effect.

Conclusions

These results indicate that ΔC1ΔN3 is an antagonists of the CCR3 receptor-mediated signalling pathway and is useful for the treatment of any condition due to the activation of eosinophils or basophils. This includes most proinflammatory conditions (both acute and chronic) as well as allergic responses including asthma, airway inflammation, adult respiratory distress syndrome and allergies in general. This further includes any disease state due to the over-expression of Ckβ-6, Ckβ-10 or Eotaxin since ΔC1ΔN3 inhibits the activity of all these chemokines. In addition, ΔC1ΔN3 can also be used to treat conditions resulting from the over-expression and/or over activation of the CCR3 receptor.

It will be clear that the invention may be practiced otherwise than as particularly described in the foregoing description and examples.

Numerous modifications and variations of the present invention are possible in light of the above teachings and, therefore, are within the scope of the appended claims.

The entire disclosure of all publications (including patents, patent applications, journal articles, laboratory manuals, books, or other documents) cited herein are hereby incorporated by reference.

What is claimed is:

1. A method of inhibiting the activation or mobilization of eosinophils in an individual in need thereof comprising administering to said individual a therapeutically effective amount of a polypeptide consisting of the amino acid sequence of SEQ ID NO:48.

2. The method of claim 1, wherein said polypeptide is fused to polyethylene glycol.

3. The method of claim 1, wherein said polypeptide is fused to a heterologous polypeptide.

4. A method of inhibiting the activation or mobilization of basophils in an individual in need thereof comprising administering to said individual a therapeutically effective amount of a polypeptide consisting of the amino acid sequence of SEQ ID NO:48.

5. The method of claim 4, wherein said polypeptide is fused to polyethylene glycol.

6. The method of claim 4, wherein said polypeptide is fused to heterologous polypeptide.

7. A method of inhibiting the activation or mobilization of eosinophils in an individual in need thereof comprising administering to said individual a therapeutically effective amount of a polypeptide consisting of an amino acid sequence shown in any one of SEQ ID NOs:50, 51, 52, 94, 96, 97 and 99.

8. The method of claim 7, wherein said polypeptide is fused to polyethylene glycol.

9. The method of claim 7, wherein said polypeptide is fused to a heterologous polypeptide.

10. The method of claim 7, wherein said polypeptide consists of the amino acid sequence of SEQ ID NO:50.

11. The method of claim 7, wherein said polypeptide consists of the amino acid sequence of SEQ ID NO:51.

12. The method of claim 7, wherein said polypeptide consists of the amino acid sequence of SEQ ID NO:53.

13. The method of claim 7, wherein said polypeptide consists of the amino acid sequence of SEQ ID NO:94.

14. The method of claim 7, wherein said polypeptide consists of the amino acid sequence of SEQ ID NO:96.

15. The method of claim 7, wherein said polypeptide consists of the amino acid sequence of SEQ ID NO:97.

16. The method of claim 7, wherein said polypeptide consists of the amino acid sequence of SEQ ID NO:99.

17. A method of inhibiting the activation or mobilization of basophils in an individual in need thereof comprising administering to said individual a therapeutically effective amount of a polypeptide consisting of an amino acid sequence shown in any one of SEQ ID NOs:50, 51, 53, 94, 96, 97 and 99.

18. The method of claim 17, wherein said polypeptide is fused to polyethylene glycol.

19. The method of claim 17, wherein said polypeptide is fused to a heterologous polypeptide.

20. The method of claim 17, wherein said polypeptide consists of the amino acid sequence of SEQ ID NO:50.

21. The method of claim 17, wherein said polypeptide consists of the amino acid sequence of SEQ ID NO:51.

22. The method of claim 17, wherein said polypeptide consists of the amino acid sequence of SEQ ID NO:53.

23. The method of claim 17, wherein said polypeptide consists of the amino acid sequence of SEQ ID NO:94.

24. The method of claim 17, wherein said polypeptide consists of the amino acid sequence of SEQ ID NO:96.

25. The method of claim 17, wherein said polypeptide consists of the amino acid sequence of SEQ ID NO:97.

26. The method of claim 17, wherein said polypeptide consists of the amino acid sequence of SEQ ID NO:99.

* * * * *

UNITED STATES PATENT AND TRADEMARK OFFICE
CERTIFICATE OF CORRECTION

PATENT NO.     : 6,815,420 B2
DATED           : November 9, 2004
INVENTOR(S)  : Kreider et al.

It is certified that error appears in the above-identified patent and that said Letters Patent is hereby corrected as shown below:

Title page,
Item [56], References Cited, insert the following:

-- U.S. PATENT DOCUMENTS

| | | |
|---|---|---|
| 5,179,078 | 01/1993 | Rollins, et al. |
| 5,237,051 | 08/1993 | Garbers, et al. |
| 5,382,658 | 01/1995 | Kronis, et al. |
| 5,866,373 | 02/1999 | Li, et al. |
| 5,880,263 | 03/1999 | Li, et al. |
| 6,028,169 | 02/2000 | Kreider, et al. |
| 6,075,124 | 06/2000 | Li, et al. |
| 6,100,389 | 08/2000 | Li, et al. |
| 6,379,926 | 04/2002 | Kreider, et al. |

FOREIGN PATENT DOCUMENTS

CA 2,152,141 12/1996
EP 0 488 900 06/1992
WO 92/20372 11/1992
WO 95/07985 03/1995
WO 95/31467 11/1995
WO 96/38559 12/1996
WO 96/40762 12/1996
WO 97/15594 05/1997
WO 98/44118 10/1998

UNITED STATES PATENT AND TRADEMARK OFFICE
CERTIFICATE OF CORRECTION

PATENT NO. : 6,815,420 B2
DATED : November 9, 2004
INVENTOR(S) : Kreider et al.

It is certified that error appears in the above-identified patent and that said Letters Patent is hereby corrected as shown below:

Title page, (cont.)

OTHER PUBLICATIONS

Beall, et al., "Conversion of Monocyte Chemoattractant Protein-1 into a Neutrophil Attractant by Substitution of Two Amino Acids," *J. Biol. Chem.* 267:3455-3459 (1992).

Berkhout, et al., "Cloning, *in Vitro* Expression, and Functional Characterization of a Novel Human CC Chemokine of the Monocyte Chemotactic Protein (MCP) Family (MCP-4) That Binds and Signals through the CC Chemokine Receptor 2B," *J. Biol. Chem.* 272:16404-16413 (Jun. 1997).

Bischoff, et al., "Monocyte Chemotactic Protein 1 Is a Potent Activator of Human Basophils," *J. Exp. Med.* 175:1271-1275 (1992).

Bottazzi, et al., "A Chemoattractant Expressed in Human Sarcoma Cells (Tumor-Derived, Chemotactic Factor, TDCF) is Identical to Monocyte Chemoattractant Protein-1/Monocyte Chemotactic and Activating Factor (MCP-1/MCAF)," *Int. J. Cancer* 45:795-797 (1990).

Bowie, et al., "Deciphering the Message in Protein Sequences: Tolerance to Amino Acid Substitutions," *Science* 247:1306-1310 (1990).

Brieland, et al., "Effect of Acute Inflammatory Lung Injury on the Expression of Monocyte Chemoattractant Protein-1 (MCP-1) in Rat Pulmonary Alveolar Macrophages," *Am. J. Respir. Cell Mol. Biol.* 7:134-139 (1992).

Brieland, et al., "Expression of Monocyte Chemoattractant Protein-1 (MCP-1) by Rat Alveolar Macrophages during Chronic Lung Injury," *Am. J. Respir. Cell Mol. Biol.* 9:300-305 (1993).

Brown, et al., "IL-1 Receptor Antagonist Inhibits Monocyte Chemotactic Peptide-1 Generation by Human Mesangial Cells," *Kidney Int.* 42:95-101 (1992).

Broxmeyer, et al., "Effects of CC, CXC, C, and CX3C Chemokines on Proliferation of Myeloid Progenitor Cells, and Insights into SDF-1-Induced Chemotaxis of Progenitors," *Ann. N.Y. Acad. Sci.* 872:142-163 (Apr. 1999).

Colditz, et al., "*In Vivo* Inflammatory Activity of Neutrophil-Activating Factor, a Novel Chemotactic Peptide Derived from Human Monocytes," *Am. J. Pathol.* 134:755-760 (1989).

Daniel, et al., "Mapping of Linear Antigenic Sites on the S Glycoprotein of a Neurotropic Murine Coronavirus with Synthetic Peptides: A Combination of Nine Prediction Alogorithms Fails to Identify Relevant Epitopes and Peptide Immunogenicity is Drastically Influenced by the Nature of the Protein Carrier," *Virology* 202:540-549 (1994).

Decock, et al., "Identification of the Monocyte Chemotactic Protein from Human Osteosarcoma Cells and Monocytes Detection of a Novel N-Terminally Processed Form," *Biochem. Biophys. Res. Commun.* 167:904-909 (1990).

Forssmann, et al., "Eotaxin-2, a Novel CC Chemokine that is Selective for the Chemokine Receptor CCR3, and Acts Like Eotaxin on Human Eosinophil and Basophil Leukocytes," *J. Exp. Med.* 185:2171-2176 (Jun. 1997).

Furutani, et al., "Cloning and Sequencing of the cDNA for Human Monocyte Chemotactic and Activating Factor (MCAF)," *Biochem. Biophys. Res. Commun.* 159:249-255 (1989).

Garcia-Zepeda, et al., "Human Monocyte Chemoattractant Protein (MCP)-4 is a Novel CC Chemokine with Activities on Monocytes, Eosinophils, and Basophils Induced in Allergic and Nonallergic Inflammation that Signals Through the CC Chemokine Receptors (CCR)-2 and -3," *J. Immunol.* 157:5613-5626 (1996).

UNITED STATES PATENT AND TRADEMARK OFFICE
CERTIFICATE OF CORRECTION

PATENT NO.    : 6,815,420 B2
DATED         : November 9, 2004
INVENTOR(S)   : Kreider et al.

It is certified that error appears in the above-identified patent and that said Letters Patent is hereby corrected as shown below:

Title page, (cont.)

George, et al., "Current Methods in Sequence Comparison and Analysis," in *Macromolecular Sequencing and Synthesis, Selected Methods and Applications*, Schlesinger, D.H., ed., Alan R. Liss, Inc., New York, New York, pp. 127-149 (1988).

Gong, et al., "Antagonists of Monocyte Chemoattractant Protein 1 Identified by Modification of Functionally Critical $NH_2$-terminal Residues," *J. Exp. Med. 181*:631-640 (1995).

Gong, "RANTES and MCP-3 Antagonists Bind Multiple Chemokine Receptors," *J. Biol. Chem. 271*:10521-10527 (May 1996).

Gronenborn, et al., "Modeling the Three-Dimensional Structure of the Monocyte Chemo-attractant and Activating Protein MCAF/MCP-1 on the Basis of the Solution Structure of Interleukin-8," *Protein Eng. 4*:263-269 (1991).

Jose, et al., "Eotaxin: A Potent Eosinophil Chemoattractant Cytokine Detected in a Guinea Pig Model of Allergic Airways Inflammation," *J. Exp. Med. 179*:881-887 (1994).

Kao, et al., "Endothelial Monocyte-activating Polypeptide II. A Novel Tumor-Derived Polypeptide That Activates Host-Response Mechanisms," *J. Biol. Chem. 267*:20239-20247 (1992).

Kawahara, et al., "Platelet-derived Growth Factor-inducible Gene *JE* is a Member of a Family of Small Inducible Genes Related to Platelet Factor 4," *J. Biol. Chem. 264*:679-682 (1989).

Koch, et al., "Enhanced Production of Monocyte Chemoattractant Protein-1 in Rheumatoid Arthritis," *J. Clin. Invest. 90*:772-779 (1992).

Kuna, et al., "Monocyte Chemotactic and Activating Factor is a Potent Histamine-releasing Factor for Human Basophils," *J. Exp. Med. 175*:489-493 (1992).

Marston, F.A.O., "The Purification of Eukaryotic Polypeptides Synthesized in *Escherichia coli*," *Biochem J. 240*:1-12 (1986).

Matsushima, et al., "Molecular Cloning of a Human Monocyte-Derived Neutrophil Chemotactic Factor (MDNCF) and the Induction of MDNCF mRNA by Interleukin 1 and Tumor Necrosis Factor," *J. Exp. Med. 167*:1883-1893 (1988).

Matsushima, et al., "Purification and Characterization of a Novel Monocyte Chemotactic and Activating Factor Produced by a Human Myelomonocytic Cell Line," *J. Exp. Med. 169*:1485-1490 (1989).

Mehrabian, et al., "Localization of Monocyte Chemotactic Protein-1 Gene (SCYA2) to Human Chromosome 17q11.2-q21.1," *Genomics 9*:200-203 (1991).

Minty, et al., "Molecular Cloning of the MCP-3 Chemokine Gene and Regulation of its Expression," *Eur. Cytokine Netw. 4*:99-110 (1993).

Morgan, et al., "Cloning of the cDNA for the Serine Protease Homolog CAP37/Azurocidin, a Microbicidal and Chemotactic Protein from Human Granulocytes," *J. Immunol. 147*:3210-3214 (1991).

Nelken, et al., "Monocyte Chemoattractant Protein-1 in Human Atheromatous Plaques," *J. Clin. Invest. 88*:1121-1127 (1991).

Ngo, et al., "Computational Complexity, Protein Structure Prediction, and the Levinthal Paradox," In: *The Protein Folding Problem and Tertiary Structure Prediction*, Merz, Jr., K. and Le Grand, S., eds., Birkhauser, Boston, Massachusetts, pp. 491-495 (1994).

UNITED STATES PATENT AND TRADEMARK OFFICE
CERTIFICATE OF CORRECTION

PATENT NO. : 6,815,420 B2
DATED : November 9, 2004
INVENTOR(S) : Kreider et al.

It is certified that error appears in the above-identified patent and that said Letters Patent is hereby corrected as shown below:

Title page, (cont.)

Opdenakker, et al., "Human Monocyte Chemotactic Protein-3 (MCP-3): Molecular Cloning of the cDNA and Comparison With Other Chemokines," *Biochem. Biophys. Res. Comm. 191*:535-542 (1993).

Patel, et al., "Molecular and Functional Characterization of Two Novel Human C-C Chemokines as Inhibitors of Two Distinct Classes of Myeloid Progenitors," *J. Exp. Med. 185*:1163-1172 (Apr. 1997).

Pereira, et al., "CAP37, a Human Neutrophil-Derived Chemotactic Factor with Monocyte Specific Activity," *J. Clin. Invest. 85*:1468-1476 (1990).

Ransohoff, et al., "Astrocyte Expression of mRNA Encoding Cytokines IP-10 and JE/MCP-1 in Experimental Autoimmune Encephalomyelitis," *FASEB J. 7*:592-600 (1993).

Robinson, et al., "Complete Amino Acid Sequence of a Human Monocyte Chemoattractant, a Putative Mediator of Cellular Immune Reactions," *Proc. Natl. Acad. Sci. USA 86*:1850-1854 (1989).

Rolfe, et al., "Expression and Regulation of Human Pulmonary Fibroblast-Derived Monocyte Chemotactic Peptide-1," *Am. J. Physiology 263*:L536-L545 (1992).

Rollins, et al., "Cloning and Expression of *JE*, a Gene Inducible by Platelet-Derived Growth Factor and Whose Product Has Cytokine-Like Properties," *Proc. Natl. Acad. Sci. USA 85*:3738-3742 (1988).

Rollins, et al., "The Human Homolog of the *JE* Gene Encodes a Monocyte Secretory Protein,"*Mol. Cell. Biol. 9*:4687-4695 (1989).

Rudinger, J., "Characteristics of the Amino Acids as Components of a Peptide Hormone Sequence," In: *Peptide Hormones,* Parsons, J.A., ed., University Park Press, Baltimore, Maryland, pp. 1-7 (1976).

Russell, et al., "Early and Persistent Induction of Monocyte Chemoattractant Protein 1 in Rat Cardiac Allografts," *Proc. Natl. Acad. Sci. USA 90*:6086-6090 (1993).

Sacerdote, et al., "Cholecystokinin and the Immune System: Receptor-Mediated Chemotaxis of Human and Rat Monocytes," *Peptides 9*:29-34 (1988).

Salcedo, et al., "Structure-Function Analysis of Eotaxin-2/CKβ-6/MPIF-2," *FASEB J. 13*:A317, Abstract No. 252.17, Federation of American Societies for Experimental Biology (Mar. 1999).

Schall, T.J., "Biology of the RANTES/SIS Cytokine Family," *Cytokines 3*:165-183 (1991).

Schulz, et al., "Empirical Similarities Between Amino Acid Residues," In: *Principles of Protein Structure,* Springer-Verlag, New York, New York, pp. 14-16 (1979).

Shyy, et al., "Structure of Human Monocyte Chemotactic Protein Gene and its Regulation by TPA," *Biochem. Biophys. Res. Commun. 169*:346-351 (1990).

Strieter, et al., "Disparate Gene Expression of Chemotactic Cytokines by Human Mononuclear Phagocytes," *Biochem. Biophys. Res. Commun. 166*:886-891 (1990).

Uguccioni, et al., "Monocyte Chemotactic Protein 4 (MCP-4), a Novel Structural and Functional Analogue of MCP-3 and Eotaxin," *J. Exp. Med. 183*:2379-2384 (1996).

Van Damme, et al., "Production and Identification of Natural Monocyte Chemotactic Protein From Virally Infected Murine Fibroblasts: Relationship With the Product of the Mouse Competence (JE) Gene," *Eur. J. Biochem. 199*:223-229 (1991).

UNITED STATES PATENT AND TRADEMARK OFFICE
CERTIFICATE OF CORRECTION

PATENT NO. : 6,815,420 B2
DATED : November 9, 2004
INVENTOR(S) : Kreider et al.

It is certified that error appears in the above-identified patent and that said Letters Patent is hereby corrected as shown below:

Title page, (cont.)

Van Damme, et al., "Structural and Functional Identification of Two Human, Tumor-Derived Monocyte Chemotactic Proteins (MCP-2 and MCP-3) Belonging to the Chemokine Family," *J. Exp. Med. 176*:59-65 (1992).

Villiger, et al., "Monocyte Chemoattractant Protein-1 (MCP-1) Expression in Human Articular Cartilage," *J. Clin. Invest. 90*:488-496 (1992).

Wells, J.A., "Additivity of Mutational Effects in Proteins," *Biochem. 29*:8509-8517 (1990).

Wempe, et al., "Gene Expression and cDNA Cloning Identified a Major Basic Protein Constituent of Bovine Seminal Plasma as Bovine Monocyte-Chemoattractant Protein-1 (MCP-1)," *DNA and Cell Biol. 10*:671-679 (1991).

Yoshimura, et al., "Human Monocyte Chemoattractant Protein-1 (MCP-1): Full-length cDNA Cloning, Expression in Mitogen-stimulated Blood Mononuclear Leukocytes, and Sequence Similarity to Mouse Competence Gene JE," *FEBS Letters 244*:487-493 (1989).

Yoshimura, et al., "Molecular Cloning of Rat Monocyte Chemoattractant Protein-1 (MCP-1) and its Expression in Rat Spleen Cells and Tumor Cell Lines," *Biochem. Biophys. Res. Commun. 174*:504-509 (1991).

Yoshimura and Yuhki, "Neutrophil Attractant/Activation Protein-1 and Monocyte Chemoattractant Protein-1 in Rabbit," *J. Immunol. 146*:3483-3488 (1991).

WPI Accession No. 92-185765, English Language Abstract of EP 0 488 900.

Supplementary European Search Report for Application No. EP 94 91 7388, March 26, 1997.

International Search Report for Application No. PCT/US98/06401, July 31, 1998.--

Column 36,
Line 24, delete the header "TABLE 1" and insert -- TABLE 2 --;

Columns 37-38,
Line 1, delete the header "TABLE 2" and insert -- TABLE 3 --;

Column 37,
Line 33, delete the header "TABLE 3" and insert -- TABLE 4 --;

UNITED STATES PATENT AND TRADEMARK OFFICE
CERTIFICATE OF CORRECTION

PATENT NO. : 6,815,420 B2
DATED : November 9, 2004
INVENTOR(S) : Kreider et al.

It is certified that error appears in the above-identified patent and that said Letters Patent is hereby corrected as shown below:

Column 141,
Lines 56-57, delete "SEQ ID NOs:50,51, 52, 94, 96, 97 and 99." and insert
-- SEQ ID" NOs:50, 51, 53, 94, 96, 97 and 99. --.

Signed and Sealed this

Tenth Day of May, 2005

JON W. DUDAS
*Director of the United States Patent and Trademark Office*